United States Patent
Romagne et al.

(10) Patent No.: US 9,067,997 B2
(45) Date of Patent: Jun. 30, 2015

(54) ANTI-KIR ANTIBODIES FOR THE TREATMENT OF INFLAMMATORY AND AUTOIMMUNE DISORDERS

(75) Inventors: Francois Romagne, Marseilles (FR); Pascale Andre, Marseilles (FR)

(73) Assignee: INNATE PHARMA SA, Marseilles (FR)

( * ) Notice: Subject to any disclaimer, the term of this patent is extended or adjusted under 35 U.S.C. 154(b) by 0 days.

(21) Appl. No.: 13/481,161

(22) Filed: May 25, 2012

(65) Prior Publication Data

US 2012/0328615 A1 Dec. 27, 2012

Related U.S. Application Data

(60) Provisional application No. 61/489,806, filed on May 25, 2011.

(51) Int. Cl.
*C07K 16/28* (2006.01)
*A61K 39/395* (2006.01)
*A61K 39/00* (2006.01)

(52) U.S. Cl.
CPC ....... *C07K 16/2803* (2013.01); *A61K 2039/505* (2013.01)

(58) Field of Classification Search
CPC .......... C07K 16/2803; C07K 16/2896; C07K 2316/96; A61K 2039/505; A61K 39/3955
See application file for complete search history.

(56) References Cited

U.S. PATENT DOCUMENTS 6,632,927 B2 * 10/2003 Adair et al. ................. 530/387.3
2008/0274047 A1 11/2008 Romagne et al. ............ 424/1.49
2011/0256121 A1 * 10/2011 Richardson ................. 424/130.1

FOREIGN PATENT DOCUMENTS

WO WO 2007/042573 4/2007

OTHER PUBLICATIONS

Huang Z., Pharmacology and Therapeutics, 2000, 86: 201-215.*
Rudikoff et al. 1982, Proc. Natl. Acad. Sci. USA, 79: 1979-1983.*
Panka et al., 1988, Proc. Natl. Acad. Sci. USA, 85: 3080-3084.*
Perricone et al. (Autoimmunity Reviews 2008, 7: 384-390).*
Flodstrom et al. (Current Opinion in Immunology 2009, 21: 634-640).*
Mayo et al. (Immunol Rev. 2012; 248(1): 170-187).*
Tian et al., Journal of Autoimmunity 2012, 39: 206-215.*
Momot et al., Arthritis and rheumatism 2004; 50: 1561-1565.*
Romagne et al. (Blood 2009, 114: 2667-2677).*
Amino acid sequences #3 of WO 2008/084106 and #25 of U.S. Appl. No. 13/481,161; 2014, 4 pages.*
C. Sola, et al. "Genetic and antibody-mediated reprogramming of natural killer cell missing-self recognition in vivo," Proceedings of the National Academy of Sciences, vol. 106, No. 31, Aug. 4, 2009, pp. 12879-12884.
Gaelle David, et al. "Discrimination between the main activating and inhibitory killer cell immunoglobulin-like receptor positive natural killer cell subsets using newly characterized monoclonal antibodies," Immunology, vol. 128, No. 2, Oct. 1, 2009, pp. 172-184.
Eric Vivier, et al., "Natural Killer Cells: From Basic Research to Treatments," Frontiers in Immunology, vol. 2, Jan. 1, 2011, pp. 1-4.
Eric Vivier, et al. "Targeting natural killer cells and natural killer T cells in cancer," Nature Reviews Immunology, vol. 12, No. 4, Jan. 1, 2012, pp. 239-252.
Nicolas Schleinitz, et al. "Natural killer cells in human autoimmune diseases," Immunology, vol. 131, No. 4, Dec. 1, 2010, pp. 451-458.

* cited by examiner

*Primary Examiner* — Ilia Ouspenski
(74) *Attorney, Agent, or Firm* — Robin L. Teskin; LeClairRyan a Professional Corporation

(57) ABSTRACT

This invention relates to compounds that inhibit KIR2DL1, 2 and/or 3 polypeptide comprising compounds (e.g., anti-KIR2DL1, 2, and/or 3 antibodies) that neutralize NK cell inhibitory receptors and methods of using such compounds and compositions containing in the treatment and prevention of inflammatory or autoimmune disorders.

35 Claims, 3 Drawing Sheets

Rejection of KbDb -/- cw3 ConA blast cells in
KIR2DL3tg B6 mice injected with 300μg of 1-7F9 monoclonal antibody

ANTI-KIR ANTIBODIES FOR THE TREATMENT OF INFLAMMATORY AND AUTOIMMUNE DISORDERS

CROSS-REFERENCE TO RELATED APPLICATIONS

This application claims priority to U.S. Provisional Application No. 61/489,806, filed on May 25, 2011, the disclosure of which is incorporated in its entirety.

The sequence listing in the file named "43271o3602.txt" having a size of 65,081 bytes that was created Dec. 3, 2013 is hereby incorporated by reference in its entirety.

FIELD OF THE INVENTION

This invention relates to the modulation of NK cell activity using immunomodulatory anti-KIR antibodies to treat or prevent inflammatory diseases and autoimmune diseases, particularly diseases mediated, at least in part, by proinflammatory T cells.

BACKGROUND OF THE INVENTION

Natural killer (NK) cells are a subset of large granular lymphocytes that act as cytotoxic immune cells. The cytotoxic activity mediated by NK cells naturally against target cells (e.g., cancer cells, virally infected cells) is generally expressed a being the result of a "balance" of positive and negative signals transmitted respectively by activating and inhibitory cell surface receptors.

NK cells can be identified by any number of known cell surface markers which vary between species (e.g., in humans CD56, CD16, NKp44, NKp46, and NKp30 are often used; in mice NK1.1, Ly49A-W, CD49b are often used). In an active state, NK cells are capable of killing certain autologous, allogeneic, and even xenogeneic tumor cells, virus-infected cells, certain bacteria (e.g., *Salmonella typhi*), and other target cells. NK cells appear to preferentially kill target cells that express little or no Major Histocompatibility Class I (MHCI or MHC-I) molecules on their surface. NK cells also kill target cells to which antibody molecules have attached, a mechanism known as antibody-dependent cellular cytotoxicity (ADCC). In action against target cells, NK cells can release pore-forming proteins called perforins, proteolytic enzymes called granzymes, and cytokines/chemokines (e.g., TNFα, IFNγ) that directly lead to target cell apoptosis or lysis, or that regulate other immune responses. Upon activation, NK cells also may express Fas ligand (FasL), enabling these cells to induce apoptosis in cells that express Fas.

Sufficient NK cell activity and NK cell count typically are both necessary to mounting an adequate NK cell-mediated immune response. NK cells may be present in normal numbers in an individual, but if not activated these cells will be ineffective in performing vital immune system functions, such as eliminating abnormal cells. Decreased NK cell activity is linked to the development and progression of many diseases. For example, research has demonstrated that low NK cell activity causes greater susceptibility to diseases such as chronic fatigue syndrome (CFS), viral infections, and the development of cancers.

NK cell activity is regulated by NK cell activity-modulating receptors (NKCAMRs), which may be specific for various ligands such as MHC-I molecules, MHC-I homologs, or other biological molecules expressed on target cells. NK cells in an individual typically present a number of activating and inhibitory receptors. The activity of NK cells is regulated by a balance of signals transduced through these activating and inhibitory receptors. Most NK cell activity-modulating receptors appear to belong to one of two classes of proteins: the immunoglobulin (Ig)-like receptor superfamily (IgSF) or the C-type lectin-like receptor (CTLR) super family. See, e.g., Radaev and Sun (2003) Annu. Rev. Biomol. Struct. 32: 93-114). However, other forms of NKCAMRs are known.

Many NK cell activating receptors belong to the Ig superfamily (IgSF) (such receptors also may be referred to as Ig-like receptors or "ILRs" herein). Activating ILR NK receptors (AILRs) include, e.g., CD2, CD16, CD69, DNAX accessory molecule-1 (DNAM-1), 2B4, NK1.1; killer immunoglobulin (Ig)-like activating receptors (KARs); ILTs/LIRs; and natural cytotoxicity receptors (NCRs), such as NKp44, NKp46, and NKp30. Several other activating receptors belong to the CLTR superfamily (e.g., NKRP-1, CD69; CD94/NKG2C and CD94/NKG2E heterodimers, NKG2D homodimer, and in mice, activating isoforms of Ly49, such as Ly49A-D). Still other activating receptors (e.g., LFA-1 and VLA-4) belong to the integrin protein superfamily and other activating receptors may have even other distinguishable structures. Many activating receptors possess extracellular domains that bind to MHC-I molecules, and cytoplasmic domains that are relatively short and lack the immunoreceptor tyrosine-based inhibition motif (ITIM) signaling motifs characteristic of inhibitory NK receptors. The transmembrane domains of these receptors typically include a charged amino acid residue that facilitates their association with signal transduction-associated molecules, e.g., CD3zeta, FcεRIγ, DAP12, and DAP10 (2B4, however, appears to be an exception to this general rule), which contain short amino acid sequences termed an "immunoreceptor tyrosine-based activating motif" (ITAMs) that propagate NK cell-activating signals. Receptor 2B4 contains 4 Immunoreceptor Tyrosine-based Switch Motifs (ITSMs) in its cytoplasmic tail. ITSM motifs can also be found in NKCARs CS1/CRACC and NTB-A. The cytoplasmic domains of 2B4 and SLAM contain two or more unique tyrosine-based motifs that resemble motifs presents in activating and inhibitory receptors and can recruit the SH2-domain containing proteins SHP-2 and SLAM-associated protein (SAP).

Stress-induced molecules, e.g., MIC-A, MIC-B, and ULBPs (in humans), and Rae-1 and H-60 (in mice), can serve as ligands for activating receptors, such as the NKG2D homodimer. Cellular carbohydrates, pathogenic antigens, and antibodies can also be activating receptors ligands. For example, NKR-P1 may bind to carbohydrate ligands and trigger NK cell activation, particularly against tumor cells which exhibit aberrant glycosylation patterns. Viral hemagglutinins may serve as ligands for natural cytotoxic receptors (NCRs), such as ILR NKCARs NKp30, NKp44, NKp46, and NKp80.

Activating receptors can either directly transduce activating signals or can act in connection with adaptor molecules or other receptors, either in the context of a coordinated response between receptors that are sometimes singularly effective or in the context of coreceptor-receptor pairings. For example, NCRs typically lack ITAMs and, accordingly, bind to adaptor molecules through a charged residue in their transmembrane domains (e.g., NKp30 associates with the CD3 zeta chain; NKp44 associates with DAP12 and/or KARAP; NKp46 is coupled to the CD3 zeta chain and FcεRIγ chain), which are, in turn, able to recruit protein tyrosine kinases (PTKs) in order to propagate NK cell-activating signals. CD16, which is an activating receptor important to NK cell-mediated ADCC and cytokine production, associates with homodimers or heterodimers formed of CD3 zeta and/or gamma chains. NKG2D appears to play a complementary and/or synergistic role with NCRs and activating receptors in NK cell activation. Activation of NK cells against particular targets may require coordinated activation of multiple activating receptors or NCRs, or only action of a single receptor. Other triggering surface molecules including 2B4 and NKp80 appear to function as coreceptors for NK cell activation.

Activating isoforms of human killer immunoglobulin-like receptors (KIRs) (e.g., KIR2DS and KIR3DS) and murine Ly-49 proteins (e.g., Ly-49D and Ly-49H) are expressed by some NK cells. Stimulation or tolerance of natural killer (NK) cells is achieved through a cross-talk of signals derived from cell surface activating and inhibitory receptors. Killer cell immunoglobulin-like receptors (KIR) are a family of highly polymorphic activating and inhibitory receptors that serve as key regulators of human NK cell function. Distinct structural domains in different KIR family members determine function by providing docking sites for ligands or signalling proteins. See Campbell & Purdy (2011) *Immunology* 132(3): 315-25. These molecules differ from their inhibitory counterparts, which are discussed below, by lacking ITIMs in their relatively shorter cytoplasmic domains, and possessing a charged transmembrane region that associates with signal-transducing polypeptides, such as disulfide-linked dimers of DAP12.

ILR (IgSF) NK cell inhibitory receptors include a number of different human KIRs specific for HLA-A, -B, or -C allotypes, KIRs may recognize multiple alleles within a particular allotype, e.g., KIR2DL1 recognizes HLA-Cw2, Cw4, and Cw6 allotypes. CTLR superfamily inhibitory receptors include members of the CD94/NKG2 protein family, which comprise receptors formed by lectin-like CD94 with various members of the NKG2 family, such as NKG2A, and recognize the nonclassical MCH-I molecules HLA-E and Qa-1 (in humans and mice, respectively), and the murine Ly49 molecules that recognize the classical MHC-I molecules in mice. In even further contrast, NKRP1A, Nkrp1f and Nkrp1d are inhibitory receptors whose ligands are not MHC-related, but are CTLR family members expressed on various cell types, such as dendritic cells, macrophages, and lymphocytes.

MHC class I-specific NKCIRs include CTLR Ly-49 receptors (in mice); the IgSF receptors Leukocyte Immunoglobulin-like Receptor (LIRs) (in humans), KIRs (e.g., p58 and p70 Killer-cell Immunoglobulin-like Receptors) (in humans), and CTLR CD94/NKG2 receptors (in mice and humans). All MHC-1-specific NKCIRs appear to use a common inhibitory mechanism apparently involving phosphorylation of ITIMs in their cytoplasmic domains in the course of MHC-I binding, and recruitment of tyrosine phosphatases (e.g., SHP-1 and SHP-2) to the phosphorylated ITIMs, resulting in the inhibition of proximal protein tyrosine kinases (PTKs) involved in NK activation through NKCARs. Antibodies against activity-modulating receptors, such as KIR, have been previously described. There also has been at least some suggestion of combining anti-NK receptor antibodies, such as anti-KIR antibodies, with other anti-cancer agents in the prior art. For example, WO 2004/056392 describes anti-NKp30 and/or anti-NKp46 antibodies used in admixture with interleukin-2 (IL-2). WO 2008/084106 describes anti-KIR formulations, dosages and dose regimens. WO 2005/079766 also describes combinations of antibodies (e.g., anti-tissue factor antibodies) including anti-KIR antibodies for use in cancer therapies. WO 2005/003168 and WO 2005/003172 describe combinations of a number of anti-KIR antibodies with a variety of agents, including IL-2 and interleukin-21 (IL-21). WO 2005/037306 similarly describes combinations of IL-21, IL-21 derivatives, and IL-21 analogues in combination with anti-KIR antibodies. WO 2005/009465 describes the combination of a therapeutic antibody (e.g., Rituxan) in combination with a compound that blocks an inhibitory receptor or stimulates an activating receptor of an NK cell (e.g., an anti-KIR monoclonal antibody, such as the monoclonal antibody DF200, or an anti-NKp30 monoclonal antibody) in order to enhance the efficiency of the treatment with therapeutic antibodies in human subjects.

Autoimmune Disease

An autoimmune disorder is a condition that occurs when the immune system mistakenly attacks and destroys healthy body tissue. There are more than 80 different types of autoimmune disorders. Normally the immune system's white blood cells help protect the body from harmful substances, called antigens. Examples of antigens include bacteria, viruses, toxins, cancer cells, and blood or tissues from another person or species. The immune system produces antibodies that destroy these harmful substances.

However, in patients with an autoimmune disorder, the immune system can not distinguish between self and non-self (e.g., healthy tissue and foreign antigens). The result is an immune response that destroys normal body tissues. This response is a hypersensitivity reaction similar to the response in allergic conditions.

In allergies, the immune system reacts to an outside substance that it normally would ignore. With autoimmune disorders, the immune system reacts to normal body tissues that it would normally ignore.

What causes the immune system to no longer tell the difference between healthy body tissues and antigens is unknown. One theory is that some microorganisms (such as bacteria or viruses) or drugs may trigger some of these changes, especially in people who have genes that make them more likely to get autoimmune disorders.

An autoimmune disorder may result in the destruction of one or more types of body tissue, abnormal growth of an organ, and changes in organ function. An autoimmune disorder may affect one or more organ or tissue types. Organs and tissues commonly affected by autoimmune disorders include blood vessels, connective tissues, endocrine glands (e.g., thyroid or pancreas), joints, muscles, red blood cells, and skin. A person may have more than one autoimmune disorder at the same time.

Symptoms of an autoimmune disease vary based on the disease and location of the abnormal immune response. Common symptoms that often occur with autoimmune diseases include fatigue, fever, and a general ill-feeling (malaise). Tests that may be done to diagnose an autoimmune disorder may include: antinuclear antibody tests, autoantibody tests, CBC, C-reactive protein (CRP), and erythrocyte sedimentation rate (ESR).

Medicines are often prescribed to control or reduce the immune system's response. They are often called immunosuppressive medicines. Such medicines may include corticosteroids (such as prednisone) and nonsteroid drugs such as azathioprine, cyclophosphamide, mycophenolate, sirolimus, or tacrolimus.

Complications are common and depend on the disease. Side effects of medications used to suppress the immune system can be severe, such as infections that can be hard to control. "Autoimmune disorders." MedlinePlus—U.S. National Library of Medicine (Apr. 19, 2012).

Inflammatory Conditions

Inflammation is part of the complex biological response of vascular tissues to harmful stimuli, such as pathogens, damaged cells, or irritants. Inflammation is a protective attempt by the organism to remove the injurious stimuli and to initiate the healing process. Without inflammation, wounds and infections would never heal. Similarly, progressive destruction of the tissue would compromise the survival of the organism. However, chronic inflammation can also lead to a host of diseases, such as hay fever, periodontitis, atherosclerosis, rheumatoid arthritis, and even cancer (e.g., gallbladder carcinoma). It is for that reason that inflammation is normally closely regulated by the body.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process. Kindt, et al. (2006) Kuby Immunology [$6^{th}$ Ed.]

T-cells are involved in the promulgation of inflammation. Differentiation of naïve T cells leads to the generation of T-cell subsets, each possessing distinct cytokine expression profiles for serving different immune functions. Through the activation of separate signaling pathways, this process results in both differentiated helper T (Th) cells, termed Th1, Th2 and Th17, and induced regulatory T cells, which suppress Th cells. These different cells are important for combating infectious diseases and cancers; however, when aberrant, they can be responsible for chronic inflammatory diseases. One such disease is inflammatory bowel disease (IBD), in which each T-cell subset can have a role in disease. Zenewicz, et al. (2009) Trends in Molecular Medicine 15(5): 199-207.

While NK cells have received a great deal of attention in the scientific literature for their potential contribution to anti-tumor and anti-viral responses, few studies have been directed to examining the role of NK cells in inflammation and autoimmunity, particularly the KIR2DL1, 2 and/or 3-expressing subsets. The approach toward these NK cells, if anything, has been to seek to eliminate or inhibit NK cells on the basis that they may contribute to inflammation and autoimmunity. The effect of KIR2DL1, 2 and/or 3-mediated potentiating of NK cell cytotoxicity in inflammatory settings has to date not been addressed.

Consequently, there is a need in the art for methods of using NK cell modulation to provide improved benefit to patients.

SUMMARY OF THE INVENTION

In vivo models (mice transgenic for both KIR2DL3 and their HLA ligands) developed specifically to study human KIR2DL1, 2 and 3 blockade showed that administration of an anti-KIR2DL1, 2, or 3 antibody is capable of inducing NK cells to efficiently reduce or eliminate concanavalin A (con A) blasts. Con A principally acts on T-lymphocytes and results in growing and dividing lymphocytes, and has therefore often been used as a model of inflammation. The results suggest that rather than seeking to reduce or eliminate KIR2DL1, 2 and/or 3-positive NK cells in inflammation and autoimmunity, it can be beneficial to potentiate their activity as they can contribute to removal of pro-inflammatory T cells, including but not limited to T cells in circulation, without inducing auto-reactivity-related toxicity.

The present invention provides methods for treating an individual having an inflammatory or autoimmune disorder. The methods may comprise administering to the individual an effective amount of a compound that inhibits a KIR2DL1, 2 and/or 3 polypeptide. The individual may have an inflammatory or autoimmune disorder mediated by T cells, e.g., a disorder involving pro-inflammatory, activated and/or proliferating T cells (e.g., in circulation or in a diseased or inflamed tissue), CD4+ T cells, infiltrating T cells, and/or T cells expressing HLA-cw3 and/or HLA-cw4. In one embodiment, the individual may have an inflammatory or autoimmune disorder selected from the group consisting of systemic lupus erythematosus, Wegener's granulomatosis, autoimmune hepatitis, Crohn's disease, scleroderma, ulcerative colitis, Sjögren's syndrome, Type 1 diabetes mellitus, uveitis, myocarditis, rheumatic fever, ankylosing spondylitis, rheumatoid arthritis, multiple sclerosis, and psoriasis.

In one embodiment, anti-KIR2DL1, 2 and/or 3 antibodies may be characterized on the basis of their ability to block or neutralize KIR2DL1, 2 and/or 3-mediated NK inhibition and thereby potentiate NK cell activity against otherwise blocked target cells.

In one embodiment, the antibody may be a single anti-KIR antibody or combination of anti-KIR antibodies. In another embodiment, the antibody may be a combination of an anti-KIR2DL1 antibody and an anti-KIR2DL2 antibody, or an anti-KIR2DL1 antibody and an anti-KIR2DL3 antibody, or an anti-KIR2DL1 antibody and an anti-KIR2DL2 antibody and an anti-KIR2DL3 antibody, or an anti-KIR antibody that binds at least two different human inhibitory KIR receptor gene products selected from the group consisting of KIR2DL1, 2 and/or 3, or an anti-KIR antibody binds each of KIR2DL1, 2 and 3, wherein said antibody may be capable of neutralizing KIR-mediated inhibition of NK cell cytotoxicity in NK cells expressing the particular KIR2DL1, 2 and/or 3 receptors.

In one embodiment, an effective amount of one or more KIR2DL1, 2 and/or 3 antibodies may be an amount of such antibody that results in substantially complete saturation (90%, optionally 95% receptor occupancy) of the KIR2DL1, 2 and/or 3 on NK cells for a period of at least about 1 week, optionally about 2 weeks, optionally about 3 weeks, optionally about one month, following administration of the antibody.

In one embodiment, antibody may be dosed in amount and at a frequency that results in substantially complete saturation (90%, optionally 95% receptor occupancy) of the KIR2DL1, 2 and/or 3 on NK cells for a period of at least about 1 week without a significant "de-saturation" during the treatment period. In one embodiment, an effective amount of one or more KIR2DL1, 2 and/or 3 antibodies may be an amount of such antibody that results in substantially complete KIR2DL1, 2 and/or 3 saturation (90% KIR2DL1, 2 and/or 3 occupancy, optionally 95% KIR2DL1, 2 and/or 3 occupancy) on circulating NK cells for a period of at least about 2 weeks, optionally about 3 weeks, optionally about one month, following administration of the antibody, and the antibody may be dosed at least twice, wherein dosing occurs about once every 2 weeks, once every 3 weeks, or once per month (subsequent doses are separated by about 2 weeks, 3 weeks or one month).

In one embodiment, the anti-KIR2DL1, 2, and/or 3 antibody may be dosed in amount and at a frequency that results in substantially complete saturation (90%, optionally 95% receptor occupancy) of the KIR2DL1, 2 and/or 3 on NK cells for a period of at least about 1 week and that permits a significant "de-saturation" during the treatment period. In one embodiment, an effective amount of one or more KIR2DL1, 2 and/or 3 antibodies may be an amount of such antibody that results in substantially complete KIR2DL1, 2 and/or 3 saturation (90% KIR2DL1, 2 and/or 3 occupancy, optionally 95% KIR2DL1, 2 and/or 3 occupancy) on circulating NK cells for a period of at least about 2 weeks, optionally about 3 weeks, optionally about one month, following administration of the antibody, and the antibody may be dosed at least twice, wherein dosing occurs about once every two months (subsequent doses are separated by about two months).

In one embodiment, a method for producing an antibody may comprise: (a) immunizing a non-human mammal with an immunogen comprising a KIR2DL1, 2 and/or 3 polypeptide; (b) selecting antibodies from said immunized mammal, wherein said antibodies bind said KIR2DL1, 2 and/or 3 polypeptide, and (c) selecting antibodies of (b) that potentiate NK cells' elimination of T cells, particularly activated CD4+ T cells. In another embodiment, an antibody selected in step (c) may be determined to be suitable for the treatment of an inflammatory or autoimmune disorder. In a further embodiment, the method of producing an antibody may comprise providing a library of antibodies, optionally by phage display techniques. In one embodiment, a method for producing an antibody may comprise: (a) providing a library of antibodies by phage display techniques; (b) selecting antibodies from said library, wherein said antibodies bind said KIR2DL1, 2 and/or 3 polypeptide, and (c) selecting antibodies of (b) that potentiate NK cells' elimination of T cells, particularly activated CD4+ T cells. Preferably, an antibody selected in step (c) will be determined to be suitable for the treatment of an inflammatory or autoimmune disorder.

In one embodiment, a method for reducing or eliminating a T cell in vitro or in vivo may comprise contacting a T cell with a compound that inhibits a KIR2DL1, 2 and/or 3 polypeptide, in the presence of cells (e.g., NK cells) that express a KIR2DL1, 2 and/or 3 polypeptide. In another embodiment, the T cells may be pro-inflammatory, activated and/or proliferating T cells, CD4+ T cells, infiltrating T cells, and/or T cells expressing HLA-cw3 and/or HLA-cw4.

In one embodiment, a method for reducing or eliminating T cells in vivo may comprise administering to an individual having an inflammatory or autoimmune disorder, preferably a disease mediated at least in part by said T cells, an effective amount of a compound that inhibits a KIR2DL1, 2 and/or 3 polypeptide. In another embodiment, the T cells may be activated and/or proliferating T cells, CD4+ T cells, pro-inflammatory T cells (e.g. in circulation or in a diseased or inflamed tissue), T cells expressing HLA-cw3 and/or HLA-cw4, or infiltrating T cells. In a further embodiment, the infiltrating T cells may infiltrate into disease tissues including but not limited to synovial joint tissues or synovial fluid, into the central nervous system, colon, or dermal tissue. In one embodiment, a method for reducing or eliminating T cells comprising administering to an individual having an inflammatory or autoimmune disorder an effective amount of a compound that inhibits a KIR2DL1, 2 and/or 3 polypeptide. In another embodiment, said T cells are activated and/or proliferating T cells, CD4+ T cells, pro-inflammatory T cells (e.g. in circulation or in a diseased or inflamed tissue), infiltrating T cells (infiltration into disease tissues, e.g. synovial joint tissues or synovial fluid, into the central nervous system, colon, dermal tissue), and/or T cells expressing HLA-cw3 and/or HLA-cw4. In another embodiment, said patient may have a disease mediated at least in part by said T cells. In a further embodiment, an effective amount may be an amount of a compound that inhibits a KIR2DL1, 2 and/or 3 polypeptide effective to reduce the number of said T cells.

In one embodiment, a method for activated and/or proliferating T cells may comprise administering to an individual having an inflammatory or autoimmune disorder, preferably a disease mediated at least in part by said T cells, an effective amount of a compound that inhibits a KIR2DL1, 2 and/or 3 polypeptide. In one embodiment, a method for reducing or eliminating T cells CD4+ T cells comprising administering to an individual having an inflammatory or autoimmune disorder, preferably a disease mediated at least in part by said T cells, an effective amount of a compound that inhibits a KIR2DL1, 2 and/or 3 polypeptide. In one embodiment, a method for pro-inflammatory T cells (e.g. in circulation or in a diseased or inflamed tissue) may comprise administering to an individual having an inflammatory or autoimmune disorder, preferably a disease mediated at least in part by said T cells, an effective amount of a compound that inhibits a KIR2DL1, 2 and/or 3 polypeptide. In one embodiment, a method for reducing or eliminating infiltrating T cells (infiltration into disease tissues, e.g. synovial joint tissues or synovial fluid, into the central nervous system, colon, dermal tissue) may comprise administering to an individual having an inflammatory or autoimmune disorder, preferably a disease mediated at least in part by said T cells, an effective amount of a compound that inhibits a KIR2DL1, 2 and/or 3 polypeptide. In a further embodiment, said compound that inhibits a KIR2DL1, 2 and/or 3 polypeptide is an antibody, an antibody fragment, a peptide, a glycoalkoid, an antisense nucleic acid, a ribozyme, a retinoid, an avemir, a small molecule, or any combination thereof. In a further embodiment, said compound is a chimeric, humanized, anti-idiotypic, single-chain, bifunctional, or co-specific antibody or antibody fragment thereof.

In one embodiment, a method for reducing or eliminating T cells expressing HLA-cw3 and/or HLA-cw4, may comprise administering to an individual having an inflammatory or autoimmune disorder, preferably a disease mediated at least in part by said T cells, an effective amount of a compound that inhibits a KIR2DL1, 2 and/or 3 polypeptide. In a further embodiment, said compound that inhibits a KIR2DL1, 2 and/or 3 polypeptide is an antibody, an antibody fragment, a peptide, a glycoalkoid, an antisense nucleic acid, a ribozyme, a retinoid, an avemir, a small molecule, or any combination thereof. In a further embodiment, said compound is a chimeric, humanized, anti-idiotypic, single-chain, bifunctional, or co-specific antibody or antibody fragment thereof.

In a further embodiment, said compound that inhibits a KIR2DL1, 2 and/or 3 polypeptide is an antibody, an antibody fragment, a peptide, a glycoalkoid, an antisense nucleic acid, a ribozyme, a retinoid, an avemir, a small molecule, or any combination thereof. In a further embodiment, said compound is a chimeric, humanized, anti-idiotypic, single-chain, bifunctional, or co-specific antibody or antibody fragment thereof.

In a further embodiment, said compound that inhibits a KIR2DL1, 2 and/or 3 polypeptide is an antibody, an antibody fragment, a peptide, a glycoalkoid, an antisense nucleic acid, a ribozyme, a retinoid, an avemir, a small molecule, or any combination thereof. In a further embodiment, said compound is a chimeric, humanized, anti-idiotypic, single-chain, bifunctional, or co-specific antibody or antibody fragment thereof.

In one embodiment, a method for treating an inflammatory disorder may comprise: (a) determining whether an individual has an inflammatory or autoimmune disorder; and (b) if the individual has an inflammatory or autoimmune disorder, treating the individual with an effective amount of a compound that inhibits a KIR2DL1, 2 and/or 3 polypeptide. In another embodiment, a method for treating an autoimmune disorder may comprise: (a) determining whether an individual has an inflammatory or autoimmune disorder; and (b) if the individual has an inflammatory or autoimmune disorder, treating the individual with an effective amount of a compound that inhibits a KIR2DL1, 2 and/or 3 polypeptide. In a further embodiment, said compound that inhibits a KIR2DL1, 2 and/or 3 polypeptide is an antibody, an antibody fragment, a peptide, a glycoalkoid, an antisense nucleic acid, a ribozyme, a retinoid, an avemir, a small molecule, or any combination thereof. In a further embodiment, said compound is a chimeric, humanized, anti-idiotypic, single-chain, bifunctional, or co-specific antibody or antibody fragment thereof.

In one embodiment, a method for treating an inflammatory disorder may comprise: (a) determining whether an individual has an inflammatory disorder mediated at least in part by T cells, e.g., pro-inflammatory, activated and/or proliferating T cells (e.g. in circulation or in a diseased or inflamed tissue), CD4+ T cells, infiltrating T cells, and/or T cells expressing HLA-cw3 and/or HLA-cw4; and (b) if the individual has an inflammatory disorder mediated at least in part by said T cells, treating the individual with an effective amount of a compound that inhibits a KIR2DL1, 2 and/or 3 polypeptide. In a further embodiment, said compound that inhibits a KIR2DL1, 2 and/or 3 polypeptide is an antibody, an antibody fragment, a peptide, a glycoalkoid, an antisense nucleic acid, a ribozyme, a retinoid, an avemir, a small molecule, or any combination thereof. In a further embodiment, said compound is a chimeric, humanized, anti-idiotypic, single-chain, bifunctional, or co-specific antibody or antibody fragment thereof.

In one embodiment, a method for treating an autoimmune disorder may comprise: (a) determining whether an individual has an autoimmune disorder mediated at least in part by T cells, e.g., pro-inflammatory, activated and/or proliferating T cells (e.g. in circulation or in a diseased or inflamed tissue), CD4+ T cells, infiltrating T cells, and/or T cells expressing HLA-cw3 and/or HLA-cw4; and (b) if the individual has an autoimmune disorder mediated at least in part by said T cells, treating the individual with an effective amount of a compound that inhibits a KIR2DL1, 2 and/or 3 polypeptide. In a further embodiment, said compound that inhibits a KIR2DL1, 2 and/or 3 polypeptide is an antibody, an antibody fragment, a peptide, a glycoalkoid, an antisense nucleic acid, a ribozyme, a retinoid, an avemir, a small molecule, or any combination thereof. In a further embodiment, said compound is a chimeric, humanized, anti-idiotypic, single-chain, bifunctional, or co-specific antibody or antibody fragment thereof.

In one embodiment, a method for the treatment of an inflammatory disease in an individual may comprise: (a) evaluating the presence, stage and/or evolution of inflammatory disease in an individual; and (b) administering to said individual an effective dose of a compound that inhibits a KIR2DL1, 2 and/or 3 polypeptide. Optionally, evaluating the presence, stage and/or evolution of disease in an individual may comprise analyzing levels of autoantibodies, CRP, or any proteolytic enzyme, inflammatory mediator or marker of ongoing inflammation. If said individual is determined to be suitable for treatment with a compound that inhibits a KIR2DL1, 2 and/or 3 polypeptide (e.g. the individual has arthritis, an exacerbation), administering to said individual an effective dose of a compound that inhibits a KIR2DL1, 2 and/or 3 polypeptide. In a further embodiment, said compound that inhibits a KIR2DL1, 2 and/or 3 polypeptide is an antibody, an antibody fragment, a peptide, a glycoalkoid, an antisense nucleic acid, a ribozyme, a retinoid, an avemir, a small molecule, or any combination thereof. In a further embodiment, said compound is a chimeric, humanized, anti-idiotypic, single-chain, bifunctional, or co-specific antibody or antibody fragment thereof.

In one embodiment, a method for the treatment of an autoimmune disease in an individual may comprise: (a) evaluating the presence, stage and/or evolution of autoimmune disease in an individual; and (b) administering to said individual an effective dose of a compound that inhibits a KIR2DL1, 2 and/or 3 polypeptide. Optionally, evaluating the presence, stage and/or evolution of disease in an individual may comprise analyzing levels of autoantibodies, CRP, or any proteolytic enzyme, inflammatory mediator or marker of ongoing inflammation. If said individual is determined to be suitable for treatment with a compound that inhibits a KIR2DL1, 2 and/or 3 polypeptide (e.g. the individual has arthritis, an exacerbation), administering to said individual an effective dose of a compound that inhibits a KIR2DL1, 2 and/or 3 polypeptide. In a further embodiment, said compound that inhibits a KIR2DL1, 2 and/or 3 polypeptide is an antibody, an antibody fragment, a peptide, a glycoalkoid, an antisense nucleic acid, a ribozyme, a retinoid, an avemir, a small molecule, or any combination thereof. In a further embodiment, said compound is a chimeric, humanized, anti-idiotypic, single-chain, bifunctional, or co-specific antibody or antibody fragment thereof.

In one embodiment, a method for the treatment of an inflammatory disease in an individual may comprise: (a) determining whether said individual has an established inflammatory disease; and (b) if said individual has an established inflammatory disease, administering to said patient an effective dose of a compound that inhibits a KIR2DL1, 2 and/or 3 polypeptide. In one embodiment, a method for the treatment of an autoimmune disease in an individual may comprise: (a) determining whether said individual has an established autoimmune disease; and (b) if said individual has an established autoimmune disease, administering to said patient an effective dose of a compound that inhibits a KIR2DL1, 2 and/or 3 polypeptide. In one embodiment, said compound is an anti-KIR2DL1, 2 and/or 3 antibody.

In one embodiment, a method for the treatment of an inflammatory disease in an individual may comprise: (a) determining whether said individual has an established inflammatory disease; and (b) if said individual has an established inflammatory disease, administering to said patient an effective dose of a compound that inhibits a KIR2DL1, 2 and/or 3 polypeptide. In one embodiment, a method for the treatment of an autoimmune disease in an individual may comprise: (a) determining whether said individual has an established autoimmune disease; and (b) if said individual has an established autoimmune disease, administering to said patient an effective dose of a compound that inhibits a KIR2DL1, 2 and/or 3 polypeptide. In one embodiment, said compound is an anti-KIR2DL1, 2 and/or 3 antibody.

In one embodiment, a method for the treatment an inflammatory disease in an individual may comprise (a) determining whether said individual is experiencing an attack, crisis, exacerbation or flare of an inflammatory disease; and (b) if said individual experiences an attack, crisis, exacerbation or flare of an inflammatory disease, administering to said individual an effective dose of a compound that inhibits a KIR2DL1, 2 and/or 3 polypeptide. In one embodiment, said compound is an anti-KIR2DL1, 2 and/or 3 antibody. In one embodiment, a method for the treatment an autoimmune disease in an individual may comprise (a) determining whether said individual is experiencing an attack, crisis, exacerbation or flare of an autoimmune disease; and (b) if said individual experiences an attack, crisis, exacerbation or flare of an autoimmune disease, administering to said individual an effective dose of a compound that inhibits a KIR2DL1, 2 and/or 3 polypeptide. In one embodiment, said compound is an anti-KIR2DL1, 2 and/or 3 antibody.

In one embodiment, a method for the treatment of an inflammatory disease in an individual may comprise (a) determining whether said individual has an inflammatory disease characterized by the presence of T cells; and (b) if said individual has an inflammatory disease characterized by the presence of T said cells, administering to said patient an effective dose of a compound that inhibits a KIR2DL1, 2 and/or 3 polypeptide. In another embodiment, said T cells may be activated and/or proliferating T cells, CD4+ T cells, pro-inflammatory T cells, infiltrating T cells, and/or T cells expressing HLA-cw3 and/or HLA-cw4. In one embodiment, said compound is an anti-KIR2DL1, 2 and/or 3 antibody. In one embodiment, a method for the treatment of an autoimmune disease in an individual may comprise (a) determining whether said individual has autoimmune disease characterized by the presence of T cells; and (b) if said individual has an autoimmune disease characterized by the presence of T said cells, administering to said patient an effective dose of a compound that inhibits a KIR2DL1, 2 and/or 3 polypeptide. In another embodiment, said T cells may be activated and/or proliferating T cells, CD4+ T cells, pro-inflammatory T cells, infiltrating T cells, and/or T cells expressing HLA-cw3 and/or HLA-cw4. In one embodiment, said compound is an anti-KIR2DL1, 2 and/or 3 antibody.

In one embodiment, a method for the treatment of an individual having an inflammatory disease, particularly an established inflammatory disease, or experiencing an attack, crisis, exacerbation or flare of an inflammatory disease, may comprise administering to the individual a compound that inhibits a KIR2DL1, 2 and/or 3 polypeptide. In one embodiment, a method for the treatment of an individual having an autoimmune disease, particularly an established autoimmune disease, or experiencing an attack, crisis, exacerbation or flare of an autoimmune disease, comprises administering to the individual a compound that inhibits a KIR2DL1, 2 and/or 3 polypeptide. In one embodiment, said compound is an anti-KIR2DL1, 2 and/or 3 antibody.

In one embodiment, a method for treating an inflammatory disease may comprise administering a compound that inhibits a KIR2DL1, 2 and/or 3 polypeptide. In one embodiment, said compound is an anti-KIR2DL1, 2 and/or 3 antibody. In one embodiment, a method for treating an autoimmune disease may comprise administering a compound that inhibits a KIR2DL1, 2 and/or 3 polypeptide. In one embodiment, said compound is an anti-KIR2DL1, 2 and/or 3 antibody.

In one embodiment, a method of treating an individual may comprise: (a) determining whether an individual has an inflammatory or autoimmune disorder; and (b) if the individual has an inflammatory or autoimmune disorder, treating the individual with an effective amount of a compound that inhibits a KIR2DL1, 2 and/or 3 polypeptide.

In one embodiment, a method of treating an individual may comprise: (a) determining whether an individual has an inflammatory or autoimmune disorder mediated at least in part by T cells; and (b) if the individual has an inflammatory or autoimmune disorder mediated at least in part by said T cells, treating the individual with an effective amount of a compound that inhibits a KIR2DL1, 2 and/or 3 polypeptide.

In one embodiment, a method of treating an individual may comprise: (a) evaluating the presence, stage and/or evolution of inflammatory or autoimmune disease in an individual; and (b) administering to said individual an effective dose of a compound that inhibits a KIR2DL1, 2 and/or 3 polypeptide.

In one embodiment, a method of treating an individual may comprise: (a) determining whether said individual has an established inflammatory or autoimmune disease; and (b) if said individual has an established inflammatory or autoimmune disease, administering to said patient an effective dose of a compound that inhibits a KIR2DL1, 2 and/or 3 polypeptide.

In one embodiment, a method of treating an individual may comprise: (a) determining whether said individual is experiencing an attack, crisis, exacerbation or flare of an inflammatory or autoimmune disease; and (b) if said individual experiences an attack, crisis, exacerbation or flare of an inflammatory or autoimmune disease, administering to said individual an effective dose of a compound that inhibits a KIR2DL1, 2 and/or 3 polypeptide.

In one embodiment, the compound that inhibits a KIR2DL1, 2 and/or 3 polypeptide is administered as a monotherapy, i.e., used in treatment as a single agent. For example, the medicament may comprise the compound that inhibits a KIR2DL1, 2 and/or 3 polypeptide is free of any other pharmaceutically active agents and/or no additional pharmaceutically active agents are used to treat the individual for the particular disease condition. In in vitro methods, the compound that inhibits a KIR2DL1, 2 and/or 3 polypeptide can be used without the addition or presence of other active agents.

In one embodiment of the treatment methods of the invention, compounds that inhibits a KIR2DL1, 2 and/or 3 polypeptide may be administered in combination with, i.e., before, concomitantly with, or after, a second therapeutic agent.

In one embodiment, the compound that inhibits a KIR2DL1, 2 and/or 3 polypeptide may be administered in combination with a second therapeutic agent, optionally any agent typically used in the context of the particular disease condition. Preferably, the second agent may be an agent other than a therapeutic antibody that induces, via ADCC, the death of a cell expressing an antigen to which the second agent binds. Preferably, the second therapeutic agent may be an agent other than an antibody having an IgG1 or IgG3 isotype, whose mode of action involves induction of ADCC toward a cell to which the antibody binds. In one embodiment, the second agent may be an antibody having a constant region of IgG4 isotype or an antibody fragment (e.g., Fab or F(ab)'2 fragment). In one embodiment, the second agent may be an antibody linked to a cytotoxic moiety. In one embodiment, the second agent may be a non-antibody polypeptide. In one embodiment, the second therapeutic agent may be an synthetic small molecule agent. In another embodiment, the second therapeutic agent may be an small molecule chemotherapeutic agent. In yet another embodiment, the second therapeutic agent may be a DMARD. In a further embodiment, the second therapeutic agent is Optionally, in any methods of treatment, the methods may further comprise administering to the individual a DMARD. In one embodiment, provided may be a method of treating an individual having an autoimmune or inflammatory disease may comprise administering to the individual (a) an effective amount of a compound that inhibits a KIR2DL1, 2 and/or 3 polypeptide, and (b) a DMARD.

Preferably the compound inhibits a KIR2DL1, 2 and/or 3 polypeptide and modulates NK cell cytotoxicity as a result of inhibiting said a KIR2DL1, 2 and/or 3 polypeptide. Preferably the compound may comprise an antibody that binds a KIR2DL1, 2 and/or 3 polypeptide.

In one embodiment, a method for determining the suitability of treatment with a compound that inhibits a KIR2DL1, 2 and/or 3 polypeptide for a patient, may comprise determining whether said patient has an established inflammatory disease, whether said patient may be experiencing an attack, crisis, exacerbation or flare, and/or whether said patient has a disease characterized by the presence of T cells, e.g., activated and/or proliferating T cells, CD4+ T cells, pro-inflammatory T cells, infiltrating T cells, and/or T cells expressing HLA-cw3 and/or HLA-cw4. In one embodiment, a method for determining the suitability of treatment with a compound that inhibits a KIR2DL1, 2 and/or 3 polypeptide for a patient, may comprise determining whether said patient has an established autoimmune disease, whether said patient may be experiencing an attack, crisis, exacerbation or flare, and/or whether said patient has a disease characterized by the presence of T cells, e.g., activated and/or proliferating T cells, CD4+ T cells, pro-inflammatory T cells, infiltrating T cells, and/or T cells expressing HLA-cw3 and/or HLA-cw4.

In one embodiment, a method for treating an autoimmune disorder may comprise administration of a compound that inhibits a KIR2DL1, 2 and/or 3 polypeptide. In another embodiment, said compound is an antibody, an antibody fragment, a peptide, a glycoalkoid, an antisense nucleic acid, a ribozyme, a retinoid, an avemir, a small molecule, or any combination thereof. In another embodiment, the compound is an anti-KIR2DL1, 2 and/or 3 antibody. In one embodiment, the individual has having an autoimmune disorder mediated by T cells. In a further embodiment, the autoimmune disorder is Acquired Immune Deficiency Syndrome (AIDS), acquired splenic atrophy, acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis (including large vessel vasculitis (including polymyalgia rheumatica and giant cell (Takayasu's) arthritis), allergic conditions, allergic contact dermatitis, allergic dermatitis, allergic granulomatous angiitis, allergic hypersensitivity disorders, allergic neuritis, allergic reaction, alopecia areata, alopecia totalis, Alport's syndrome, alveolitis (e.g., allergic alveolitis and fibrosing alveolitis), Alzheimer's disease, amyloidosis, amylotrophic lateral sclerosis (ALS; Lou Gehrig's disease), an eosinophil-related disorder (e.g., eosinophilia), anaphylaxis, ankylosing spondylitis, antgiectasis, antibody-mediated nephritis, Anti-GBM/Anti-TBM nephritis, antigen-antibody complex-mediated diseases, antiglomerular basement membrane disease, antiphospholipid antibody syndrome, antiphospholipid syndrome (APS), aphthae, aphthous stomatitis, aplastic anemia, arrhythmia, arteriosclerosis, arteriosclerotic disorders, arthritis (e.g., rheumatoid arthritis such as acute arthritis, chronic rheumatoid arthritis), arthritis chronica progrediente, arthritis deformans, ascariasis, aspergilloma (or granulomas containing eosinophils), aspergillosis, aspermiogenese, asthma (e.g., asthma bronchiale, bronchial asthma, and auto-immune asthma), ataxia telangiectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease (e.g., autoimmune inner ear disease (AGED)), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies (e.g., epilepsy), channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy (e.g., IgM polyneuropathies or IgM-mediated neuropathy), chronic obstructive airway disease, chronic pulmonary inflammatory disease, Chronic recurrent multifocal ostomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogans syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis (e.g., chronic cyclitis, heterochronic cyclitis, iridocyclitis, or Fuch's cyclitis), cystic fibrosis, cytokine-induced toxicity, deafness, degenerative arthritis, demyelinating diseases (e.g., autoimmune demyelinating diseases), demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis (e.g., allergic encephalomyelitis or encephalomyelitis allergica and experimental allergic encephalomyelitis (EAE)), endarterial hyperplasia, endocarditis, endocrine ophthamopathy, endometriosis. endomyocardial fibrosis, endophthalmia phacoanaphylactica, endophthalmitis, enteritis allergica, eosinophilia-myalgia syndrome, eosinophilic faciitis, epidemic keratoconjunctivitis, epidermolisis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, flariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, haemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schonlein purpura, Herpes gestationis, human immunodeficiency virus (HIV) infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenic purpura (ITP), IgA nephropathy, IgE-mediated diseases (e.g., anaphylaxis and allergic and atopic rhinitis), IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antobodies, inflammation of all or part of the uvea, inflammatory bowel disease (IBD) inflammatory hyperproliferative skin diseases, inflammatory myopathy, insulin-dependent diabetes (type 1), insulitis, Interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis nodosa), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes (e.g., Lambert-Eaton myasthenic syndrome or Eaton-Lambert syndrome), parasitic diseases such as Lesihmania, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including pemphigus vulgaris), pemphigus erythematosus, pemphigus foliaceus, pemphigus mucusmembrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis nodosa, Type I, II, & III, polyarthritis chronica primaria, polychondritis (e.g., refractory or relapsed polychondritis), polyendocrine autoimmune disease, polyendocrine failure, polyglandular syndromes (e.g., autoimmune polyglandular syndromes (or polyglandular endocrinopathy syndromes)), polymyalgia rheumatica, polymyositis, polymyositis/dermatomyositis, polyneuropathies, polyradiculitis acuta, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis (e.g., benign monoclonal gammopathy and monoclonal gammopathy of undetermined significance, MGUS), primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyreoiditis, Raynauds phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma (including systemic scleroderma), sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjogren's syndrome, sperm & testicular autoimmunity, sphenoid sinusitis, Stevens-Johnson syndrome, stiff-man (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes (e.g., cutaneous SLE), systemic necrotizing vasculitis, and ANCA-associated vasculitis, such as Churg-Strauss vasculitis or syndrome (CSS)), tabes dorsalis, Takayasu's arteritis, telangiectasia, temporal arteritis/Giant cell arteritis, thromboangitis ubiterans, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, thrombocytopenic purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria (e.g., chronic allergic urticaria and chronic idiopathic urticaria, including chronic autoimmune urticaria), uveitis (e.g., anterior uveitis), uveoretinitis, valvulitis, vascular dysfunction, vasculitis, vertebral arthritis, vesiculobullous dermatosis, vitiligo, Wegener's granulomatosis (now termed Granulomatosis with Polyangiitis (GPA), Wiskott-Aldrich syndrome, or x-linked hyper IgM syndrome.

In one embodiment, a method for treating an inflammatory disorder may comprise administration of a compound that inhibits a KIR2DL1, 2 and/or 3 polypeptide. In another embodiment, said compound is an antibody, an antibody fragment, a peptide, a glycoalkoid, an antisense nucleic acid, a ribozyme, a retinoid, an avemir, a small molecule, or any combination thereof. In another embodiment, the compound is an anti-KIR2DL1, 2 and/or 3 antibody. In one embodiment, the individual has having an inflammatory disorder mediated by T cells.

In a further embodiment, the inflammatory disorder is rheumatic diseases (e.g., rheumatoid arthritis, osteoarthritis, psoriatic arthritis) spondyloarthropathies (e.g., ankylosing spondylitis, reactive arthritis, Reiter's syndrome), crystal arthropathies (e.g., gout, pseudogout, calcium pyrophosphate deposition disease), multiple sclerosis, Lyme disease, polymyalgia rheumatica; connective tissue diseases (e.g., systemic lupus erythematosus, systemic sclerosis, polymyositis, dermatomyositis, Sjogren's syndrome); vasculitides (e.g., polyarteritis nodosa, Wegener's granulomatosis, Churg-Strauss syndrome); inflammatory conditions including consequences of trauma or ischaemia, sarcoidosis; vascular diseases including atherosclerotic vascular disease, atherosclerosis, and vascular occlusive disease (e.g., atherosclerosis, ischaemic heart disease, myocardial infarction, stroke, peripheral vascular disease), vascular stent restenosis; ocular diseases including uveitis, corneal disease, iritis, iridocyclitis, cataracts, acid Reflux/Heartburn, Acne, Acne Vulgaris, Allergies and Sensitivities, Alzheimer's Disease, Asthma, Atherosclerosis and Vascular Occlusive Disease (e.g., Atherosclerosis, Ischaemic Heart Disease, Myocardial Infarction, Stroke, Peripheral Vascular Disease) and Vascular Stent Restenosis, Autoimmune Diseases, Bronchitis, Cancer, Carditis, Cataracts, Celiac Disease, Chronic Pain, Chronic Prostatitis, Cirrhosis, Colitis, Connective Tissue Diseases (e.g., Systemic Lupus Erythematosus, Systemic Sclerosis, Polymyositis, Dermatomyositis, Sjogren's Syndrome), Corneal Disease, Crohn's Disease, Crystal Arthropathies (e.g., Gout, Pseudogout, Calcium Pyrophosphate Deposition Disease), Dementia, Dermatitis, Diabetes, Dry Eyes, Eczema, Edema, Emphysema, Fibromyalgia, Gastroenteritis, Gingivitis, Glomerulonephritis, Heart Disease, Hepatitis, High Blood Pressure, Hypersensitivities, Inflammatory Bowel Diseases, Inflammatory Conditions including Consequences of Trauma or Ischaemia, Insulin Resistance, Interstitial Cystitis, Iridocyclitis, Iritis, Joint Pain/Arthritis/Rheumatoid Arthritis, Lyme Disease, Metabolic Syndrome (Syndrome X), Multiple Sclerosis, Myositis, Nephritis, Obesity, Ocular Diseases including Uveitis, Osteopenia, Osteoporosis, Parkinson's Disease, Pelvic Inflammatory Disease, Periodontal Disease, Polyarteritis, Polychondritis, Polymyalgia Rheumatica, Psoriasis, Reperfusion Injury, Rheumatic Arthritis, Rheumatic Diseases (e.g., Rheumatoid Arthritis, Osteoarthritis, Psoriatic Arthritis), Rheumatoid Arthritis, Sarcoidosis, Scleroderma, Sinusitis, Sjögren's Syndrome, Spastic Colon, Spondyloarthropathies (e.g., Ankylosing Spondylitis, Reactive Arthritis, Reiter's Syndrome), Systemic Candidiasis, Tendonitis, Transplant Rejection, UTI's, Vaginitis, Vascular Diseases including Atherosclerotic Vascular Disease, Vasculitides (e.g., Polyarteritis Nodosa, Wegener's Granulomatosis, Churg-Strauss Syndrome), and Vasculitis.

In another embodiment, the compound may be an anti-KIR2DL1, 2 and/or 3 antibody. In one embodiment, the antibody may be chimeric, humanized, anti-idiotypic, single-chain, bifunctional, or co-specific. In one embodiment, the antibody may comprise an amino acid sequence of the VL of the amino acid sequence of SEQ ID NO: 1, 3, or 5. In one embodiment, residues 3, 4, 9, 24, 32, 41, 47, 50, 55, 71, and 74 of SEQ ID NO: 3 may be Q, L, S, R, A, G, L, D, E, F, and A, respectively. In one embodiment, the antibody may comprise an amino acid sequence of the VH of the amino acid sequence of SEQ ID NO: 2, 4, or 6. In another embodiment, residues 3, 4, 9, 24, 32, 41, 47, 50, 55, 71, and 74 of SEQ ID NO: 3 may be R, M, F, W, Y, A, F, Y, Q, Y, and T, respectively.

In one embodiment, the anti-KIR2DL1, 2 and/or 3 antibody may comprise the light chain CDR1 amino acid sequence corresponds to residues 24-34 of SEQ ID NO: 1; the light chain CDR2 amino acid sequence corresponds to residues 50-56 of SEQ ID NO: 1; the light chain CDR3 amino acid sequence corresponds to residues 89-97 of SEQ ID NO: 1; the heavy chain CDR1 amino acid sequence corresponds to residues 31-35 of SEQ ID NO: 2; the heavy chain CDR2 amino acid sequence corresponds to residues 50-65 of SEQ ID NO: 2; or the heavy chain CDR3 amino acid sequence corresponds to residues 99-112 of SEQ ID NO: 2.

In one embodiment, the anti-KIR2DL1, 2 and/or 3 antibody may comprise the light chain CDR1 amino acid sequence corresponds to residues 24-34 of SEQ ID NO:3; the light chain CDR2 amino acid sequence corresponds to residues 50-56 of SEQ ID NO:3; the light chain CDR3 amino acid sequence corresponds to residues 89-97 of SEQ ID NO:3; the heavy chain CDR1 amino acid sequence corresponds to residues 31-35 of SEQ ID NO:4; the heavy chain CDR2 amino acid sequence corresponds to residues 50-66 of SEQ ID NO:4; or the heavy chain CDR3 amino acid sequence corresponds to residues 99-113 of SEQ ID NO:4.

In one embodiment, the anti-KIR2DL1, 2 and/or 3 antibody may comprise a VL and a VH sequence comprising the amino acid sequence of SEQ ID NO:1 and SEQ ID NO:2, respectively, SEQ ID NO:3 and SEQ ID NO:4, respectively, or SEQ ID NO: 5 and 6, respectively.

In one embodiment, the anti-KIR2DL1, 2 and/or 3 antibody used in the inventive treatment methods may comprise CDR regions as follows: a light chain CDR1 amino acid sequence corresponding to about residues 24-34 of SEQ ID NO:1; the light chain CDR2 amino acid sequence corresponding to about residues 50-56 of SEQ ID NO:1; the light chain CDR3 amino acid sequence corresponding to about residues 89-97 of SEQ ID NO:1; the heavy chain CDR1 amino acid sequence corresponding to about residues 31-35 of SEQ ID NO:2; the heavy chain CDR2 amino acid sequence corresponding to about to residues 50-65 of SEQ ID NO:2; or the heavy chain CDR3 amino acid sequence corresponding to about residues 99-112 of SEQ ID NO:2.

In one embodiment, the anti-KIR2DL1, 2 and/or 3 antibody used in the inventive treatment methods may comprise CDR regions as follows: a light chain CDR1 amino acid sequence corresponding to about residues 24-34 of SEQ ID NO:3; a light chain CDR2 amino acid sequence corresponding to about residues 50-56 of SEQ ID NO:3; a light chain CDR3 amino acid sequence corresponding to about residues 89-97 of SEQ ID NO:3; a heavy chain CDR1 amino acid sequence corresponding to about residues 31-35 of SEQ ID NO:4; a heavy chain CDR2 amino acid sequence corresponding to about residues 50-66 of SEQ ID NO:4; or a heavy chain CDR3 amino acid sequence corresponding to about residues 99-113 of SEQ ID NO:4.

In one embodiment, the anti-KIR2DL1, 2 and/or 3 antibody used in the inventive treatment methods may comprise a light chain CDR1 amino acid sequence consisting essentially of residues 24-34 of SEQ ID NO:1; a light chain CDR2 amino acid sequence consisting essentially of residues 50-56 of SEQ ID NO:1; a light chain CDR3 amino acid sequence consisting essentially of residues 89-97 of SEQ ID NO:1; a heavy chain CDR1 amino acid sequence consisting essentially of residues 31-35 of SEQ ID NO:2; a heavy chain CDR2 amino acid sequence consisting essentially of residues 50-65 of SEQ ID NO:2; or a heavy chain CDR3 amino acid sequence consisting essentially of residues 99-112 of SEQ ID NO:2.

In one embodiment, the anti-KIR2DL1, 2 and/or 3 antibody used in the inventive treatment methods may comprise CDR regions as follows: a light chain CDR1 amino acid sequence consisting essentially of residues 24-34 of SEQ ID NO:3; a light chain CDR2 amino acid sequence consisting essentially of residues 50-56 of SEQ ID NO:3; a light chain CDR3 amino acid sequence consisting essentially of residues 89-97 of SEQ ID NO:3; a heavy chain CDR1 amino acid sequence consisting essentially of residues 31-35 of SEQ ID NO:4; a heavy chain CDR2 amino acid sequence consisting essentially of residues 50-66 of SEQ ID NO:4; or a heavy chain CDR3 amino acid sequence consisting essentially of residues 99-113 of SEQ ID NO:4.

In one embodiment, the anti-KIR2DL1, 2 and/or 3 antibody used in the inventive treatment methods may bind an epitope within the amino acid sequence of SEQ ID NO: 7, 8, 9, or 10. In one embodiment, the anti-KIR2DL1, 2 and/or 3 antibody may bind KIR2DL1 within a region defined by at least one of the amino acid residues selected from the group consisting of 105, 106, 107, 108, 109, 110, 111, 127, 129, 130, 131, 132, 133, 134, 135, 152, 153, 154, 155, 156, 157, 158, 159, 160, 161, 162, 163, 181, and 192. In one embodiment, the anti-KIR2DL1, 2 and/or 3 antibody may bind KIR2DL1 and KIR2DL2/3 within a region defined by at least one of the amino acid residues selected from the group consisting of 105, 106, 107, 108, 109, 110, 111, 127, 129, 130, 131, 132, 133, 134, 135, 152, 153, 154, 155, 156, 157, 158, 159, 160, 161, 162, 163, 181, and 192.

In one embodiment, the anti-KIR2DL1, 2 and/or 3 antibody or antibody fragment thereof used in the inventive treatment methods may be directly or indirectly conjugated to a label, cytotoxic agent, therapeutic agent, or an immunosuppressive agent. In one embodiment, the label may be a chemiluminescent label, paramagnetic label, an MRI contrast agent, fluorescent label, bioluminescent label, or radioactive label. In one embodiment, the paramagnetic label may be aluminum, manganese, platinum, oxygen, lanthanum, lutetium, scandium, yttrium, or gallium. In one embodiment, the cytotoxic agent may be a moiety that inhibits DNA, RNA, or protein synthesis, a radionuclide, or ribosomal inhibiting protein. In one embodiment, the cytotoxic agent may be $^{212}$Bi, $^{131}$I, $^{188}$Re, $^{90}$Y, vindesine, methotrexate, adriamycin, cisplatin, pokeweed antiviral protein, *Pseudomonas* exotoxin A, ricin, diphtheria toxin, ricin A chain, or cytotoxic phospholipase enzyme.

In one embodiment, the anti-KIR2DL1, 2, or 3 antibody used in the inventive treatment methods blocks or neutralizing NK inhibition. In one embodiment, the anti-KIR2DL1, 2, or 3 antibody may bind to at least one of KIR2DL1, 2 or 3 and neutralizing KIR2DL1, 2 and/or 3-mediated inhibition of NK cell cytotoxicity. In one embodiment, the anti-KIR2DL1, 2, or 3 antibody may neutralize may comprise at least about 20% increase in NK cell-mediated specific lysis of NK target cells.

In one embodiment, the anti-KIR2DL1, 2, or 3 antibody used in the inventive treatment methods may compete for binding with the same antigenic determinant region of monoclonal antibody 1-7F9, DF200, and/or NKVSF1. In one embodiment, the anti-KIR2DL1, 2, or 3 antibody used in the inventive treatment methods may bind to at least two inhibitory KIR receptors at the surface of NK cells. In one embodiment, the anti-KIR2DL1, 2, or 3 antibody used in the inventive treatment methods may bind a common antigenic determinant region of human KIR2DL receptors. In one embodiment, the anti-KIR2DL1, 2, or 3 antibody used in the inventive treatment methods may bind to KIR2DL1, 2 and/or 3 receptors. In one embodiment, the anti-KIR2DL1, 2, or 3 antibody used in the inventive treatment methods has an affinity for KIR2DL1, 2 and/or 3 of at least about $10^4$ to about $10^{10}$ $M^{-1}$. In one embodiment, the anti-KIR2DL1, 2, or 3 antibody used in the inventive treatment methods may have an affinity for KIR2DL1, 2 and/or 3 of at least about $10^7$ to about $10^9$ $M^{-1}$. In one embodiment, the anti-KIR2DL1, 2, or 3 antibody used in the inventive treatment methods may exhibit KIR binding with a disassociation constant of less than about 100 nM. In one embodiment, the anti-KIR2DL1, 2, or 3 antibody may cross-react with KIRs 2DL1 plus 2DL2/3, 3DL1 plus 3DL2, 2DL1 (and 2DL2/3) plus 2DS4, and 2DL1 (and 2DL2/3) but not 2D24. In one embodiment, the anti-KIR2DL1, 2, or 3 antibody may be DF200, 1-7F9, or NKVSF1 antibody.

In one embodiment, the compound that inhibits a KIR2DL1, 2 and/or 3 polypeptide used in the inventive treatment methods may be administered as a monotherapy. In one embodiment, the compound that inhibits a KIR2DL1, 2 and/or 3 polypeptide used in the inventive treatment methods may be administered in combination with a second therapeutic agent. In one embodiment, the second therapeutic agent may be an agent that decreases inflammation. In one embodiment, the second therapeutic agent may be a small molecule chemical agent. In one embodiment, the second therapeutic agent may be a DMARD, optionally an anti-TNFα antibody, a small molecule tyrosine kinase inhibitor, or methotrexate (MTX). In one embodiment, the second therapeutic agent may be an agent other than an antibody having an IgG1 or IgG3 isotype.

In one embodiment, the compound that inhibits a KIR2DL1, 2 and/or 3 used in the inventive treatment methods may be an anti-KIR2DL1, 2 and/or 3 antibody having the ability to block or neutralize KIR2DL1, 2 and/or 3-mediated NK inhibition and thereby potentiate NK cell activity against otherwise blocked target cells. In one embodiment, the antibody may be an anti-KIR antibody that may bind KIR2DL1 and KIR2DL2/3. In one embodiment, the anti-KIR antibody may compete with 1-7F9 for binding to KIR2DL1, 2 and/or 3.

In one embodiment, the antibody may be 1-7F9. In one embodiment, the antibody may comprise the VL and VH domains of 1-7F9. In one embodiment, the antibody may comprise the VL and VH CDRs of 1-7F9. In one embodiment, the anti-KIR2DL1, 2 and/or 3 antibody may be administered as a pharmaceutically acceptable composition may comprise an effective amount of the anti-KIR2DL1, 2 and/or 3 antibody. In one embodiment, the composition may be free of any other pharmaceutically active agents.

In one embodiment, the anti-KIR2DL1, 2 and/or 3 antibody may be administered in an amount resulting in substantially complete saturation of the KIR2DL1, 2 and/or 3 on NK cells for a period of at least about 1 week. In one embodiment, the anti-KIR2DL1, 2, and/or 3 antibody may be administered in an amount resulting in substantially complete saturation of the KIR2DL1, 2 and/or 3 on NK cells for a period of at least about 2 weeks. In one embodiment, the anti-KIR2DL1, 2, and/or 3 antibody may be administered in an amount resulting in substantially complete saturation of the KIR2DL1, 2, and/or 3 on NK cells for a period of at least about 1 month. In one embodiment, the anti-KIR2DL1, 2, and/or 3 antibody may be administered several times at a dosing frequency of once about every 2 weeks. In one embodiment, the anti-KIR2DL1, 2, and/or 3 antibody may be administered several times at a dosing frequency of once about every 1 month. In one embodiment, the anti-KIR2DL1, 2 and/or 3 antibody may be administered several times at a dosing frequency of once about every 2 months or once every period of more than 2 months.

In one embodiment, the invention provides for a composition for treatment of an autoimmune or inflammatory disorder that may comprise an anti-KIR2DL1 antibody and optionally another active agent. In another embodiment, a composition may comprise an anti-KIR2DL2 antibody. In another embodiment, a composition for use in the invention may comprise an anti-KIR2DL3 antibody and optionally another active agent. In a further embodiment, a composition may comprise an anti-KIR2DL1, 2 and/or 3 antibody and optionally another active agent.

In one embodiment, a composition for use in the treatment of an autoimmune disorder may comprise an effective amount of an anti-KIR2DL1 antibody. In one embodiment, a composition for use in the treatment of an autoimmune disorder according to the invention may comprise an effective amount of an anti-KIR2DL2 antibody. In one embodiment, a composition for use in the treatment of an autoimmune disorder according to the invention may comprise administering an effective amount of an anti-KIR2DL3 antibody. In a further embodiment, a composition for use in the treatment of an autoimmune disorder may comprise administering an effective amount of an anti-KIR2DL1, 2 and/or 3 antibody.

In one embodiment, a composition for use in the treatment of an inflammatory disorder according to the invention may comprise an anti-KIR2DL1 antibody. In one embodiment, a composition for use in the treatment of an inflammatory disorder according to the invention may comprise an anti-KIR2DL2 antibody. In one embodiment, a composition for use in the treatment of an inflammatory disorder according to the invention may comprise an anti-KIR2DL3 antibody. In a further embodiment, a composition for use in the treatment of an inflammatory disorder according to the invention may comprise an anti-KIR2DL1, 2 and/or 3 antibody.

In one embodiment, the invention provides for a method of making antibodies comprising (a) immunizing an animal with a KIR2DL1, 2 and/or 3 polypeptide; (b) removing said animal's spleen and prepare a single cell suspension; (c) fusing a spleen cell with a myeloma cell; (d) culturing post-fusion cells in hybridoma selection medium; (e) culturing the resultant hybridomas; (f) screening for specific antibody production; and (g) selecting hybridomas which produce the desired antibody.

In one embodiment, the invention provides for a method for producing an antibody for the treatment of an inflammatory or autoimmune disorder comprising (a) immunizing a non-human mammal with an immunogen comprising a KIR2DL1, 2 and/or 3 polypeptide; (b) selecting antibodies from said immunized mammal, wherein said antibodies bind said KIR2DL1, 2 and/or 3 polypeptide, and (c) selecting antibodies of (b) that potentiate NK cells' elimination of T cells.

In one embodiment, the invention provides for a method for producing an antibody for the treatment of an inflammatory or autoimmune disorder comprising (a) providing a library of antibodies by phage display technology; (b) library, wherein said antibodies bind said KIR2DL1, 2 and/or 3 polypeptide, and (c) selecting antibodies of (b) that potentiate NK cells' elimination of T cells.

In another embodiment, any one of the various above-described methods may further optionally be modified by application of a treatment with one or more additional therapeutic agents, e.g. small molecule agents, DMARDS (preferably other than antibodies whose primary mode of action may be to induce ADCC).

In one embodiment the invention provides a method for treating an autoimmune disorder may comprise administering an effective amount of a compound that inhibits a KIR2DL1, 2, and/or 3 polypeptide. In another embodiment, a method for treating an inflammatory disorder may comprise administering an effective amount of a compound that inhibits a KIR2DL1, 2, and/or 3 polypeptide. In another embodiment, a method for eliminating or reducing the number of T cells involved in a disease condition may comprise contacting said T cells with a compound that inhibits a KIR2DL1, 2 and/or 3 polypeptide, in the presence of cells that express a KIR2DL1, 2 and/or 3 polypeptide. In one embodiment, the cells that express a KIR2DL1, 2 and/or 3 polypeptide are NK cells. In one embodiment, the it is effected ex vivo. In one embodiment, the it is effected in vivo. In one embodiment, the T cells include one or more of pro-inflammatory, activated and/or proliferating T cells, CD4+ T cell, infiltrating T cells, and/or a T cells which expresses HLA-cw3 and/or HLA-cw4.

In another embodiment, a method for eliminating or reducing the number of T cells that are involved in the pathology of an inflammatory disorder may comprise administering to an individual having an inflammatory disorder, an amount of a compound that inhibits a KIR2DL1, 2 and/or 3 polypeptide effective to reduce the number of said T cells. In another embodiment, a method for eliminating or reducing the number of T cells that are involved in the pathology of an autoimmune disorder may comprise administering to an individual having an autoimmune disorder an amount of a compound that inhibits a KIR2DL1, 2 and/or 3 polypeptide effective to reduce the number of said T cells. In one embodiment, the T cells comprise activated and/or proliferating T cells, CD4+ T cells, pro-inflammatory T cells, and/or T cells expressing HLA-cw3 and/or HLA-cw4. In one embodiment, the T cells include one or more of the following: are in circulation, are comprised in a diseased or inflamed tissue, are infiltrating T cells, are T cells that have infiltrated into disease tissues, are comprised in synovial joint tissues or synovial fluid, or are comprised in the central nervous system, colon, or dermal tissue. In one embodiment, the individual has a disease mediated at least in part by said T cells.

In another embodiment, a method for eliminating or reducing the number of activated and/or proliferating T cells that are involved in the pathology of an inflammatory or autoimmune disorder in vivo may comprise administering to an individual having an inflammatory or autoimmune disorder an amount of a compound that inhibits a KIR2DL1, 2 and/or 3 polypeptide effective to reduce the number of said T cells. In another embodiment, a method for eliminating or reducing the number of CD4+ T cells that are involved in the pathology of an inflammatory or autoimmune disorder may comprise administering to an individual having an inflammatory or autoimmune disorder an amount of a compound that inhibits a KIR2DL1, 2 and/or 3 polypeptide effective to reduce the number of said T cells. In another embodiment, a method for eliminating or reducing the number of pro-inflammatory T cells may comprise administering to an individual having an inflammatory or autoimmune disorder, an amount of a compound that inhibits a KIR2DL1, 2 and/or 3 polypeptide effective to reduce the number of said T cells. In one embodiment, the disease is mediated at least in part by said T cells.

In another embodiment, a method for eliminating or reducing the number of infiltrating T cells may comprise administering to an individual having an inflammatory or autoimmune disorder an amount of a compound that inhibits a KIR2DL1, 2 and/or 3 polypeptide effective to reduce the number of said T cells. In one embodiment, the disease is mediated at least in part by said T cells. In one embodiment, the infiltrating T cells include one or more of the following: cells that have infiltrated into disease tissues, cells that have infiltrated into synovial joint tissues or synovial fluid, or cells that have infiltrated into the central nervous system, colon, or dermal tissue.

In another embodiment, a method for eliminating or reducing the number of T cells expressing HLA-cw3 and/or HLA-cw4 may comprise administering to an individual having an inflammatory or autoimmune disorder an amount of a compound that inhibits a KIR2DL1, 2 and/or 3 polypeptide effective to reduce the number of said T cells. In one embodiment, the T cells, at least in part, mediate said disorder.

In another embodiment, a method for treating an inflammatory disorder may comprise: (a) determining whether an individual has an inflammatory or autoimmune disorder; and (b) if the individual has an inflammatory or autoimmune disorder, treating the individual with an effective amount of a compound that inhibits a KIR2DL1, 2 and/or 3 polypeptide.

In another embodiment, a method for treating an autoimmune disorder may comprise: (a) determining whether an individual has an inflammatory or autoimmune disorder; and (b) if the individual has an inflammatory or autoimmune disorder, treating the individual with an effective amount of a compound that inhibits a KIR2DL1, 2 and/or 3 polypeptide.

In another embodiment, a method for treating an inflammatory disorder may comprise: (a) determining whether an individual has an inflammatory disorder mediated at least in part by T cells, and (b) if the individual has an inflammatory disorder mediated at least in part by said T cells, treating the individual with an effective amount of a compound that inhibits a KIR2DL1, 2 and/or 3 polypeptide. In one embodiment, the T cells include one or more of the following: are pro-inflammatory, activated and/or proliferating T cells, are in circulation or in a diseased or inflamed tissue, CD4+ T cells, are infiltrating T cells, and/or express HLA-cw3 and/or HLA-cw4.

In another embodiment, a method for treating an autoimmune disorder may comprise: (a) determining whether an individual has an autoimmune disorder mediated at least in part by T cells; and (b) if the individual has an autoimmune disorder mediated at least in part by said T cells, treating the individual with an effective amount of a compound that inhibits a KIR2DL1, 2 and/or 3 polypeptide. In one embodiment, the T cells include one or more of the following, are pro-inflammatory, activated and/or proliferating T cells, are in circulation or are in a diseased or inflamed tissue, are CD4+ T cells, are infiltrating T cells, and/or express HLA-cw3 and/or HLA-cw4.

In another embodiment, a method for the treatment of an inflammatory disease in an individual may comprise: (a) evaluating the presence, stage and/or evolution of inflammatory disease in an individual; and (b) administering to said individual an effective amount of a compound that inhibits a KIR2DL1, 2 and/or 3 polypeptide. In another embodiment, a method for the treatment of an autoimmune disease in an individual may comprise: (a) evaluating the presence, stage and/or evolution of autoimmune disease in an individual; and (b) administering to said individual an effective amount of a compound that inhibits a KIR2DL1, 2 and/or 3 polypeptide. In one embodiment, the method may comprise evaluating the presence, stage and/or evolution of disease in an individual may comprise analyzing levels of autoantibodies, CRP, any proteolytic enzyme, inflammatory mediator, or marker of ongoing inflammation. In one embodiment, the individual is determined to be suitable for treatment with a compound that inhibits a KIR2DL1, 2 and/or 3 polypeptide, administering to said individual an effective amount of a compound that inhibits a KIR2DL1, 2 and/or 3 polypeptide. In another embodiment, a method for the treatment of an inflammatory disease in an individual may comprise: (a) determining whether said individual has an established inflammatory disease; and (b) if said individual has an established inflammatory disease, administering to said patient an effective amount of a compound that inhibits a KIR2DL1, 2 and/or 3 polypeptide. In another embodiment, a method for the treatment of an autoimmune disease in an individual may comprise: (a) determining whether said individual has an established autoimmune disease; and (b) if said individual has an established autoimmune disease, administering to said patient an effective amount of a compound that inhibits a KIR2DL1, 2 and/or 3 polypeptide. In another embodiment, a method for the treatment an inflammatory disease in an individual may comprise (a) determining whether said individual is experiencing an attack, crisis, exacerbation or flare of an inflammatory disease; and (b) if said individual experiences an attack, crisis, exacerbation or flare of an inflammatory disease, administering to said individual an effective amount of a compound that inhibits a KIR2DL1, 2 and/or 3 polypeptide. In another embodiment, a method for the treatment an autoimmune disease in an individual may comprise (a) determining whether said individual is experiencing an attack, crisis, exacerbation or flare of an autoimmune disease; and (b) if said individual experiences an attack, crisis, exacerbation or flare of an autoimmune disease, administering to said individual an effective amount of a compound that inhibits a KIR2DL1, 2 and/or 3 polypeptide. In another embodiment, a method for the treatment of an inflammatory disease in an individual may comprise (a) determining whether said individual has an inflammatory disease characterized by the presence of T cells; and (b) if said individual has an inflammatory disease characterized by the presence of T said cells, administering to said patient an effective amount of a compound that inhibits a KIR2DL1, 2 and/or 3 polypeptide. In another embodiment, a method for the treatment of an autoimmune disease in an individual may comprise (a) determining whether said individual has autoimmune disease characterized by the presence of T cells; and (b) if said individual has an autoimmune disease characterized by the presence of T said cells, administering to said patient an effective amount of a compound that inhibits a KIR2DL1, 2 and/or 3 polypeptide.

In one embodiment, the T cells may be activated and/or proliferating T cells, CD4+ T cells, pro-inflammatory T cells, infiltrating T cells, and/or T cells expressing HLA-cw3 and/or HLA-cw4.

In one embodiment, the invention provides a method for the treatment of an individual experiencing an attack, crisis, exacerbation or flare of an inflammatory disease, may comprise administering to the individual an effective amount of a compound that inhibits a KIR2DL1, 2 and/or 3 polypeptide. In one embodiment, the individual has an established inflammatory disease. In another embodiment, a method for the treatment of an individual experiencing an attack, crisis, exacerbation or flare of an autoimmune disease, may comprise administering to the individual an effective amount of a compound that inhibits a KIR2DL1, 2 and/or 3 polypeptide. In one embodiment, the individual has an autoimmune inflammatory disease. In another embodiment, a method of treating an individual may comprise: (a) determining whether an individual has an inflammatory or autoimmune disorder; and (b) if the individual has an inflammatory or autoimmune disorder, treating the individual with an effective amount of a compound that inhibits a KIR2DL1, 2 and/or 3 polypeptide. In another embodiment, a method of treating an individual may comprise: (a) determining whether an individual has an inflammatory or autoimmune disorder mediated at least in part by T cells; and (b) if the individual has an inflammatory or autoimmune disorder mediated at least in part by said T cells, treating the individual with an effective amount of a compound that inhibits a KIR2DL1, 2 and/or 3 polypeptide. In another embodiment, a method of treating an individual may comprise: (a) evaluating the presence, stage and/or evolution of inflammatory or autoimmune disease in an individual; and (b) administering to said individual an effective amount of a compound that inhibits a KIR2DL1, 2 and/or 3 polypeptide. In another embodiment, a method of treating an individual may comprise: (a) determining whether said individual has an established inflammatory or autoimmune disease; and (b) if said individual has an established inflammatory or autoimmune disease, administering to said patient an effective amount of a compound that inhibits a KIR2DL1, 2 and/or 3 polypeptide.

In another embodiment, a method of treating an individual may comprise: (a) determining whether said individual is experiencing an attack, crisis, exacerbation or flare of an inflammatory or autoimmune disease; and (b) if said individual experiences an attack, crisis, exacerbation or flare of an inflammatory or autoimmune disease, administering to said individual an effective amount of a compound that inhibits a KIR2DL1, 2 and/or 3 polypeptide. In one embodiment, the compound is an antibody, an antibody fragment, a peptide, a glycoalkoid, an antisense nucleic acid, a ribozyme, a retinoid, an avemir, a small molecule, or any combination thereof. In one embodiment, the individual has an inflammatory or autoimmune disorder mediated by T cells. In one embodiment, the autoimmune disorder is Acquired Immune Deficiency Syndrome (AIDS), acquired spenic atrophy, acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis (including large vessel vasculitis (including polymyalgia rheumatica and giant cell (Takayasu's) arthritis), allergic conditions, allergic contact dermatitis, allergic dermatitis, allergic granulomatous angiitis, allergic hypersensitivity disorders, allergic neuritis, allergic reaction, alopecia areata, alopecia totalis, Alport's syndrome, alveolitis (e.g., allergic alveolitis and fibrosing alveolitis), Alzheimer's disease, amyloidosis, amylotrophic lateral sclerosis (ALS; Lou Gehrig's disease), an eosinophil-related disorder (e.g., eosinophilia), anaphylaxis, ankylosing spondylitis, antgiectasis, antibody-mediated nephritis, Anti-GBM/Anti-TBM nephritis, antigen-antibody complex-mediated diseases, antiglomerular basement membrane disease, antiphospholipid antibody syndrome, antiphospholipid syndrome (APS), aphthae, aphthous stomatitis, aplastic anemia, arrhythmia, arteriosclerosis, arteriosclerotic disorders, arthritis (e.g., rheumatoid arthritis such as acute arthritis, chronic rheumatoid arthritis), arthritis chronica progrediente, arthritis deformans, ascariasis, aspergilloma (or granulomas containing eosinophils), aspergillosis, aspermiogenese, asthma (e.g., asthma bronchiale, bronchial asthma, and auto-immune asthma), ataxia telangiectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease (e.g., autoimmune inner ear disease (AGED)), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies (e.g., epilepsy), channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy (e.g., IgM polyneuropathies or IgM-mediated neuropathy), chronic obstructive airway disease, chronic pulmonary inflammatory disease, Chronic recurrent multifocal ostomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogans syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis (e.g., chronic cyclitis, heterochronic cyclitis, iridocyclitis, or Fuch's cyclitis), cystic fibrosis, cytokine-induced toxicity, deafness, degenerative arthritis, demyelinating diseases (e.g., autoimmune demyelinating diseases), demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis (e.g., allergic encephalomyelitis or encephalomyelitis allergica and experimental allergic encephalomyelitis (EAE)), endarterial hyperplasia, endocarditis, endocrine ophthamopathy, endometriosis. endomyocardial fibrosis, endophthalmia phacoanaphylactica, endophthalmitis, enteritis allergica, eosinophilia-myalgia syndrome, eosinophilic faciitis, epidemic keratoconjunctivitis, epidermolisis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, flariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, haemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schonlein purpura, Herpes gestationis, human immunodeficiency virus (HIV) infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenic purpura (ITP), IgA nephropathy, IgE-mediated diseases (e.g., anaphylaxis and allergic and atopic rhinitis), IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antobodies, inflammation of all or part of the uvea, inflammatory bowel disease (IBD) inflammatory hyperproliferative skin diseases, inflammatory myopathy, insulin-dependent diabetes (type 1), insulitis, Interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis nodosa), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes (e.g., Lambert-Eaton myasthenic syndrome or Eaton-Lambert syndrome), parasitic diseases such as Lesihmania, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including pemphigus vulgaris), pemphigus erythematosus, pemphigus foliaceus, pemphigus mucusmembrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis nodosa, Type I, II, & III, polyarthritis chronica primaria, polychondritis (e.g., refractory or relapsed polychondritis), polyendocrine autoimmune disease, polyendocrine failure, polyglandular syndromes (e.g., autoimmune polyglandular syndromes (or polyglandular endocrinopathy syndromes)), polymyalgia rheumatica, polymyositis, polymyositis/dermatomyositis, polyneuropathies, polyradiculitis acuta, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis (e.g., benign monoclonal gammopathy and monoclonal gammopathy of undetermined significance, MGUS), primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyreoiditis, Raynauds phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma (including systemic scleroderma), sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjogren's syndrome, sperm & testicular autoimmunity, sphenoid sinusitis, Stevens-Johnson syndrome, stiff-man (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes (e.g., cutaneous SLE), systemic necrotizing vasculitis, and ANCA-associated vasculitis, such as Churg-Strauss vasculitis or syndrome (CSS)), tabes dorsalis, Takayasu's arteritis, telangiectasia, temporal arteritis/Giant cell arteritis, thromboangitis ubiterans, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, thrombocytopenic purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria (e.g., chronic allergic urticaria and chronic idiopathic urticaria, including chronic autoimmune urticaria), uveitis (e.g., anterior uveitis), uveoretinitis, valvulitis, vascular dysfunction, vasculitis, vertebral arthritis, vesiculobullous dermatosis, vitiligo, Wegener's granulomatosis (now termed Granulomatosis with Polyangiitis (GPA), Wiskott-Aldrich syndrome, or x-linked hyper IgM syndrome.

In one embodiment, the inflammatory disorder is rheumatic diseases (e.g., rheumatoid arthritis, osteoarthritis, psoriatic arthritis) spondyloarthropathies (e.g., ankylosing spondylitis, reactive arthritis, Reiter's syndrome), crystal arthropathies (e.g., gout, pseudogout, calcium pyrophosphate deposition disease), multiple sclerosis, Lyme disease, polymyalgia rheumatica; connective tissue diseases (e.g., systemic lupus erythematosus, systemic sclerosis, polymyositis, dermatomyositis, Sjogren's syndrome); vasculitides (e.g., polyarteritis nodosa, Wegener's granulomatosis, Churg-Strauss syndrome); inflammatory conditions including consequences of trauma or ischaemia, sarcoidosis; vascular diseases including atherosclerotic vascular disease, atherosclerosis, and vascular occlusive disease (e.g., atherosclerosis, ischaemic heart disease, myocardial infarction, stroke, peripheral vascular disease), vascular stent restenosis; ocular diseases including uveitis, corneal disease, iritis, iridocyclitis, cataracts, acid Reflux/Heartburn, Acne, Acne Vulgaris, Allergies and Sensitivities, Alzheimer's Disease, Asthma, Atherosclerosis and Vascular Occlusive Disease (e.g., Atherosclerosis, Ischaemic Heart Disease, Myocardial Infarction, Stroke, Peripheral Vascular Disease) and Vascular Stent Restenosis, Autoimmune Diseases, Bronchitis, Cancer, Carditis, Cataracts, Celiac Disease, Chronic Pain, Chronic Prostatitis, Cirrhosis, Colitis, Connective Tissue Diseases (e.g., Systemic Lupus Erythematosus, Systemic Sclerosis, Polymyositis, Dermatomyositis, Sjogren's Syndrome), Corneal Disease, Crohn's Disease, Crystal Arthropathies (e.g., Gout, Pseudogout, Calcium Pyrophosphate Deposition Disease), Dementia, Dermatitis, Diabetes, Dry Eyes, Eczema, Edema, Emphysema, Fibromyalgia, Gastroenteritis, Gingivitis, Glomerulonephritis, Heart Disease, Hepatitis, High Blood Pressure, Hypersensitivities, Inflammatory Bowel Diseases, Inflammatory Conditions including Consequences of Trauma or Ischaemia, Insulin Resistance, Interstitial Cystitis, Iridocyclitis, Iritis, Joint Pain/Arthritis/Rheumatoid Arthritis, Lyme Disease, Metabolic Syndrome (Syndrome X), Multiple Sclerosis, Myositis, Nephritis, Obesity, Ocular Diseases including Uveitis, Osteopenia, Osteoporosis, Parkinson's Disease, Pelvic Inflammatory Disease, Periodontal Disease, Polyarteritis, Polychondritis, Polymyalgia Rheumatica, Psoriasis, Reperfusion Injury, Rheumatic Arthritis, Rheumatic Diseases (e.g., Rheumatoid Arthritis, Osteoarthritis, Psoriatic Arthritis), Rheumatoid Arthritis, Sarcoidosis, Scleroderma, Sinusitis, Sjögren's Syndrome, Spastic Colon, Spondyloarthropathies (e.g., Ankylosing Spondylitis, Reactive Arthritis, Reiter's Syndrome), Systemic Candidiasis, Tendonitis, Transplant Rejection, UTI's, Vaginitis, Vascular Diseases including Atherosclerotic Vascular Disease, Vasculitides (e.g., Polyarteritis Nodosa, Wegener's Granulomatosis, Churg-Strauss Syndrome), and Vasculitis.

In one embodiment, the compound may be an anti-KIR2DL1, 2 and/or 3 antibody. In one embodiment, the antibody may be chimeric, humanized, anti-idiotypic, single-chain, bifunctional, or co-specific.

In one embodiment, the light chain of said antibody may comprise the amino acid sequence of SEQ ID NO: 1, 3, or 5. In one embodiment, the residues 3, 4, 9, 24, 32, 41, 47, 50, 55, 71, and 74 of the amino acid sequence of SEQ ID NO: 3 are Q, L, S, R, A, G, L, D, E, F, and A, respectively. In one embodiment, the residues 3, 4, 9, 24, 32, 41, 47, 50, 55, 71, and 74 of the amino acid sequence of SEQ ID NO: 3 are R, M, F, W, Y, A, F, Y, Q, Y, and T, respectively. In one embodiment, the heavy chain of said antibody may comprise the amino acid sequence of SEQ ID NO: 2, 4, or 6. In one embodiment, the antibody may comprise the light chain CDR1 amino acid sequence corresponds to residues 24-34 of the amino acid sequence of SEQ ID NO: 1; the light chain CDR2 amino acid sequence corresponds to residues 50-56 of the amino acid sequence of SEQ ID NO: 1; or the light chain CDR3 amino acid sequence corresponds to residues 89-97 of the amino acid sequence of SEQ ID NO: 1. In one embodiment, the antibody may comprise the light chain CDR1 amino acid sequence corresponds to residues 24-34 of the amino acid sequence of SEQ ID NO: 3; the light chain CDR2 amino acid sequence corresponds to residues 50-56 of the amino acid sequence of SEQ ID NO: 3; or the light chain CDR3 amino acid sequence corresponds to residues 89-97 of the amino acid sequence of SEQ ID NO: 3.

In one embodiment, the antibody may comprise the heavy chain CDR1 amino acid sequence corresponds to residues 31-35 of the amino acid sequence of SEQ ID NO: 2, the heavy chain CDR2 amino acid sequence corresponds to residues 50-65 of the amino acid sequence of SEQ ID NO: 2, or the heavy chain CDR3 amino acid sequence corresponds to residues 99-112 of the amino acid sequence of SEQ ID NO: 2. In one embodiment, the antibody may comprise the heavy chain CDR1 amino acid sequence corresponds to residues 31-35 of the amino acid sequence of SEQ ID NO: 4, the heavy chain CDR2 amino acid sequence corresponds to residues 50-66 of the amino acid sequence of SEQ ID NO: 4, or the heavy chain CDR3 amino acid sequence corresponds to residues 99-113 of the amino acid sequence of SEQ ID NO: 4.

In one embodiment, the antibody may comprise a variable light chain and a variable heavy chain sequence may comprise SEQ ID NO:1 and SEQ ID NO:2, respectively. In one embodiment, the antibody may comprise a variable light chain and a variable heavy chain sequence may comprise the amino acid sequence of SEQ ID NO:3 and SEQ ID NO:4, respectively. In one embodiment, the antibody may comprise a variable light chain and a variable heavy chain sequence may comprise the amino acid sequence of SEQ ID NO:5 and SEQ ID NO:6, respectively. In one embodiment, the antibody binds an epitope within the amino acid sequence of SEQ ID NO: 7, 8, 9, 10, 11, 12, 13, 14, 14, 15, 16, 17, 18, 19, 20, 21, 22, 23, or 24. In one embodiment, the antibody may bind KIR2DL1 within a region defined by at least one of the amino acid residues selected from the group consisting of 105, 106, 107, 108, 109, 110, 111, 127, 129, 130, 131, 132, 133, 134, 135, 152, 153, 154, 155, 156, 157, 158, 159, 160, 161, 162, 163, 181, and 192. In one embodiment, the antibody may bind KIR2DL1 and KIR2DL2/3 within a region defined by at least one of the amino acid residues selected from the group consisting of 105, 106, 107, 108, 109, 110, 111, 127, 129, 130, 131, 132, 133, 134, 135, 152, 153, 154, 155, 156, 157, 158, 159, 160, 161, 162, 163, 181, and 192.

In one embodiment, the antibody or fragment may be directly or indirectly conjugated to a label, cytotoxic agent, therapeutic agent, or an immunosuppressive agent. In one embodiment, the label may be a chemiluminescent label, paramagnetic label, an MRI contrast agent, fluorescent label, bioluminescent label, or radioactive label. In one embodiment, the paramagnetic label may be aluminum, manganese, platinum, oxygen, lanthanum, lutetium, scandium, yttrium, or gallium. In one embodiment, the cytotoxic agent may be a moiety that inhibits DNA, RNA, or protein synthesis, a radionuclide, or ribosomal inhibiting protein. In one embodiment, the cytotoxic agent may be $^{212}$Bi, $^{131}$I, $^{188}$Re, $^{90}$Y, vindesine, methotrexate, adriamycin, cisplatin, pokeweed antiviral protein, *Pseudomonas* exotoxin A, ricin, *diphtheria* toxin, ricin A chain, or cytotoxic phospholipase enzyme.

In one embodiment, the antibody blocks or neutralizing NK inhibition. In one embodiment, the antibody bind to at least one of KIR2DL1, 2 or 3 and neutralizes KIR2DL1, 2 and/or 3-mediated inhibition of NK cell cytotoxicity. In one embodiment, the antibody neutralizing may comprise at least about 20% increase in NK cell-mediated specific lysis of NK target cells.

In one embodiment, the antibody competes for binding with the same antigenic determinant region of monoclonal antibody 1-7F9, DF200, and/or NKVSF1. In one embodiment, the antibody binds to at least two inhibitory KIR receptors at the surface of NK cells. In one embodiment, the antibody binds a common antigenic determinant region of human KIR2DL receptors. In one embodiment, the antibody binds to KIR2DL1, 2 and/or 3 receptors.

In one embodiment, the antibody has an affinity for KIR2DL1, 2 and/or 3 of at least about $10^4$ to about $10^{10}$ M$^{-1}$. In one embodiment, the antibody has an affinity for KIR2DL1, 2 and/or 3 of at least about $10^7$ to about $10^9$ M$^{-1}$. In one embodiment, the antibody exhibits KIR binding with a disassociation constant of less than about 100 nM.

In one embodiment, the antibody cross-reacts with KIRs 2DL1 plus 2DL2/3, 3DL1 plus 3DL2, 2DL1 (and 2DL2/3) plus 2DS4, and 2DL1 (and 2DL2/3) but not 2D24.

In one embodiment, the antibody may be DF200, 1-7F9, or NKVSF1 antibody.

In one embodiment, the compound that inhibits a KIR2DL1, 2 and/or 3 polypeptide may be administered as a monotherapy. In one embodiment, the compound that inhibits a KIR2DL1, 2 and/or 3 polypeptide may be administered in combination with a second therapeutic agent. In one embodiment, the second therapeutic agent may be an agent that decreases inflammation. In one embodiment, the second therapeutic agent may be a small molecule chemical agent. In one embodiment, the second therapeutic agent may be a DMARD, optionally an anti-TNFα antibody, a small molecule tyrosine kinase inhibitor, or methotrexate (MTX). In one embodiment, the second therapeutic agent may be an agent other than an antibody having an IgG1 or IgG3 isotype.

In one embodiment, the compound that inhibits a KIR2DL1, 2 and/or 3 may be an anti-KIR2DL1, 2 and/or 3 antibody having the ability to block or neutralize KIR2DL1, 2 and/or 3-mediated NK inhibition and thereby potentiate NK cell activity against otherwise blocked target cells. In one embodiment, the antibody may be an anti-KIR antibody that binds KIR2DL1 and KIR2DL2/3. In one embodiment, the anti-KIR antibody competes with 1-7F9 for binding to KIR2DL1, 2 and/or 3. In one embodiment, the antibody may be 1-7F9. In one embodiment, the antibody may comprise the VL and VH domains of 1-7F9. In one embodiment, the antibody may comprise the VL and VH CDRs of 1-7F9.

In one embodiment, the anti-KIR2DL1, 2 and/or 3 antibody may be administered as a pharmaceutically acceptable composition may comprise an effective amount of the anti-KIR2DL1, 2 and/or 3 antibody. In one embodiment, the composition may be free of any other pharmaceutically active agents.

In one embodiment, the anti-KIR2DL1, 2 and/or 3 antibody may be administered in an amount resulting in substantially complete saturation of the KIR2DL1, 2 and/or 3 on NK cells for a period of at least about 1 week. In one embodiment, the anti-KIR2DL1, 2 and/or 3 antibody may be administered in an amount resulting in substantially complete saturation of the KIR2DL1, 2 and/or 3 on NK cells for a period of at least about 2 weeks. In one embodiment, the anti-KIR2DL1, 2 and/or 3 antibody may be administered in an amount resulting in substantially complete saturation of the KIR2DL1, 2 and/or 3 on NK cells for a period of at least about 1 month. In one embodiment, the anti-KIR2DL1, 2 and/or 3 antibody may be administered several times at a dosing frequency of once about every 2 weeks. In one embodiment, the anti-KIR2DL1, 2 and/or 3 antibody may be administered several times at a dosing frequency of once about every 1 month. In one embodiment, the anti-KIR2DL1, 2 and/or 3 antibody may be administered several times at a dosing frequency of once about every 2 months or once every period of more than 2 months.

The invention also provides for a composition use in for the treatment of an autoimmune disorder may comprise an anti-KIR2DL1 antibody. In another embodiment, a composition use in for the treatment of an autoimmune disorder may comprise an anti-KIR2DL2 antibody. In another embodiment, a composition for use in the treatment of an autoimmune disorder may comprise an anti-KIR2DL3 antibody. In another embodiment, a composition for use in the treatment of an inflammatory disorder may comprise an anti-KIR2DL1 antibody. In another embodiment, a composition for use in the treatment of an inflammatory disorder may comprise an anti-KIR2DL2 antibody. In another embodiment, a composition for use in the treatment of an inflammatory disorder may comprise an anti-KIR2DL3 antibody.

In a further embodiment, the invention provides for a use of an anti-KIR2DL1 antibody in the preparation of a medicament for the treatment of an autoimmune disorder. In one embodiment, the invention provides for a use of an anti-KIR2DL2 antibody in the preparation of a medicament for the treatment of an autoimmune disorder. In one embodiment, the invention provides for a use of an anti-KIR2DL3 antibody in the preparation of a medicament for the treatment of an autoimmune disorder. In one embodiment, the invention provides for a use of an anti-KIR2DL1 antibody in the preparation of a medicament for the treatment of an inflammatory disorder. In one embodiment, the invention provides for a use of an anti-KIR2DL2 antibody in the preparation of a medicament for the treatment of an inflammatory disorder. In one embodiment, the invention provides for a use of an anti-KIR2DL3 antibody in the preparation of a medicament for the treatment of an inflammatory disorder.

In one embodiment, the invention provides for a method for producing an antibody for the treatment of an inflammatory or autoimmune disorder, said method may comprise the steps of: (a) immunizing a non-human mammal with an immunogen may comprise a KIR2DL1, 2 and/or 3 polypeptide; (b) selecting antibodies from said immunized mammal, wherein said antibodies bind said KIR2DL1, 2 and/or 3 polypeptide, and (c) selecting antibodies of (b) that potentiate NK cells' elimination of T cells.

In one embodiment, the invention provides for a method for producing an antibody for the treatment of an inflammatory or autoimmune disorder may comprise providing a library of antibodies by phage display technology, wherein said antibodies bind said KIR2DL1, 2 and/or 3 polypeptide, and selecting antibodies that potentiate the elimination or depletion of T cells by NK cells.

These aspects are more fully described in, and additional aspects, features, and advantages of the invention will be apparent from, the description of the invention provided herein.

DESCRIPTION OF THE INVENTION

Figure 1A:
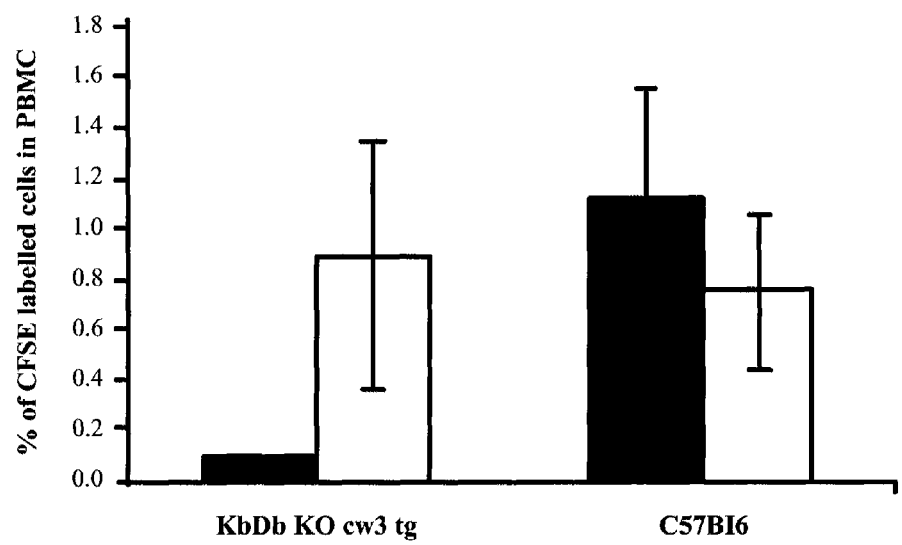
FIG. 1A depicts a decrease in percentage of CSFE-labelled cells (Con A blasts) in PBMC in KIR2DL3tg B6 mice when treated with antibody 1-7F9, compared to both untreated KIR2DL3tg B6 mice and treated and untreated C57Bl6 mice.

In order that the invention herein described may be fully understood, the following detailed description is set forth. Various embodiments of the invention are described in detail and may be further illustrated by the provided examples.

Definitions

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting.

As used in the description herein and throughout the claims that follow, the meaning of "a," "an," and "the" includes plural reference unless the context clearly dictates otherwise.

"Antigen presenting cell," as used herein, refers broadly to professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

"Amino acid," as used herein refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified (e.g., hydroxyproline, γ-carboxyglutamate, and O-phosphoserine.) Amino acid analogs refers to compounds that have the same basic chemical structure as a naturally occurring amino acid (i.e., an a carbon that is bound to a hydrogen, a carboxyl group, an amino group), and an R group (e.g., homoserine, norleucine, methionine sulfoxide, methionine methyl sulfonium.) Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Anergy" or "tolerance," as used herein, refers broadly to refractivity to activating receptor-mediated stimulation. Such refractivity is generally antigen-specific and persists after exposure to the tolerizing antigen has ceased.

"Antibody", as used herein, refers broadly to an "antigen-binding portion" of an antibody (also used interchangeably with "antibody portion," "antigen-binding fragment," "antibody fragment"), as well as whole antibody molecules. The term "antigen-binding portion", as used herein, refers to one or more fragments of an antibody that retain the ability to specifically bind to an antigen (e.g., KIR2DL1, 2 and/or 3). It has been shown that the antigen-binding function of an antibody can be performed by fragments of a full-length antibody. Examples of antigen-binding fragments encompassed within the term "antigen-binding portion" of an antibody include (a) a Fab fragment, a monovalent fragment consisting of the VL, VH, CL and CH1 domains; (b) a F(ab')2 fragment, a bivalent fragment comprising two Fab fragments linked by a disulfide bridge at the hinge region; (c) a Fd fragment consisting of the VH and CH1 domains; (d) a Fv fragment consisting of the VL and VH domains of a single arm of an antibody; (e) a dAb fragment (Ward, et al. (1989) Nature 341: 544-546), which consists of a VH domain; and (f) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See e.g., Bird, et al. (1988) Science 242: 423-426; Huston, et al. (1988) Proc Natl. Acad. Sci. USA 85: 5879-5883; and Osbourn, et al. (1998) Nat. Biotechnol. 16: 778. Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and VL can also be used in the generation of Fab, Fv, or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. See e.g., Holliger, et al. (1993) Proc Natl. Acad. Sci. USA 90: 6444-6448; Poljak, et al. (1994) Structure 2: 1121-1123.

Still further, an antibody or antigen-binding portion thereof (antigen-binding fragment, antibody fragment, antibody portion) may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, et al. (1995) Hum. Antibodies Hybridomas 6: 93-101) and use of a cysteine residue, a marker peptide and a C-terminal polyhistidine tag to make bivalent and biotinylated scFv molecules. Kipriyanov, et al. (1994) Mol Immunol. 31: 1047-1058. Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Antibodies may be polyclonal, monoclonal, xenogeneic, allogeneic, syngeneic, or modified forms thereof, e.g., humanized, chimeric. Preferably, antibodies of the invention bind specifically or substantially specifically to KIR2DL1, 2 and/or 3 polypeptides. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens. In the case of a desired enhanced immune response to particular antigens of interest, such antigens include, but are not limited to, infectious disease antigens for which a protective immune response may be elicited are exemplary.

"Antisense nucleic acid molecule," as used herein, refers broadly to a nucleotide sequence which is complementary to a "sense" nucleic acid encoding a protein (e.g., complementary to the coding strand of a double-stranded cDNA molecule) complementary to an mRNA sequence or complementary to the coding strand of a gene. Accordingly, an antisense nucleic acid molecule can hydrogen bond to a sense nucleic acid molecule.

"Apoptosis," as used herein, refers broadly to programmed cell death which can be characterized using techniques which are known in the art. Apoptotic cell death can be characterized by cell shrinkage, membrane blebbing, and chromatin condensation culminating in cell fragmentation. Cells undergoing apoptosis also display a characteristic pattern of internucleosomal DNA cleavage.

"Autoimmunity" or "autoimmune disease or condition," as used herein, refers broadly to a disease or disorder arising from and directed against an individual's own tissues or a co-segregate or manifestation thereof or resulting condition therefrom.

"Chimeric antibody," as used herein, refers broadly to an antibody molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, the variable region or a portion thereof, is altered, replaced or exchanged with a variable region having a different or altered antigen specificity.

"Coding region," as used herein, refers broadly to regions of a nucleotide sequence comprising codons which are translated into amino acid residues, whereas the term "noncoding region" refers to regions of a nucleotide sequence that are not translated into amino acids (e.g., 5' and 3' untranslated regions).

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. Such nucleic acid variations are "silent variations," which are one species of conservatively modified variations.

Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) "Sequences of Proteins of Immunological Interest" National Institutes of Health, Bethesda, Md. These expressions include the hypervariable regions as defined by Kabat, et al. (1983) "Sequences of Proteins of Immunological Interest" U.S. Dept. of Health and Human Services or the hypervariable loops in 3-dimensional structures of antibodies. Chothia and Lesk (1987) J Mol. Biol. 196: 901-917. The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction. Kashmiri (2005) Methods 36: 25-34.

"Control amount," as used herein, refers broadly to a marker can be any amount or a range of amounts to be compared against a test amount of a marker. For example, a control amount of a marker may be the amount of a marker in a patient with a particular disease or condition or a person without such a disease or condition. A control amount can be either in absolute amount (e.g., microgram/ml) or a relative amount (e.g., relative intensity of signals).

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," as used herein refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Effective amount," as used herein, refers broadly to the amount of a compound, antibody, antigen, or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this invention.

"Extracellular domain," as used herein refers broadly to the portion of a protein that extend from the surface of a cell.

"Expression vector," as used herein, refers broadly to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Fc receptor" (FcRs) as used herein, refers broadly to cell surface receptors for the Fc portion of immunoglobulin molecules (Ig's). Fc receptors are found on many cells which participate in immune responses. Among the human FcRs that have been identified so far are those which recognize IgG (designated FcγR), IgE (FcεR1), IgA (FcαR), and polymerized IgM/A (FcμαR). FcRs are found in the following cell types: FcεRI (mast cells), FcεRII (many leukocytes), FcαR (neutrophils), and FcμαR (glandular epithelium, hepatocytes). Hogg (1988) Immunol. Today 9: 185-86. The widely studied FcγRs are central in cellular immune defenses, and are responsible for stimulating the release of mediators of inflammation and hydrolytic enzymes involved in the pathogenesis of autoimmune disease. Unkeless (1988) Annu. Rev. Immunol. 6: 251-87. The FcγRs provide a crucial link between effector cells and the lymphocytes that secrete Ig, since the macrophage/monocyte, polymorphonuclear leukocyte, and natural killer (NK) cell Fc gamma Rs confer an element of specific recognition mediated by IgG. Human leukocytes have at least three different receptors for IgG: hFcγRI (found on monocytes/macrophages), hFc gamma RII (on monocytes, neutrophils, eosinophils, platelets, possibly B cells, and the K562 cell line), and FcgammaIII (on NK cells, neutrophils, eosinophils, and macrophages).

With respect to T cells, transmission of a costimulatory signal to a T cell involves a signaling pathway that is not inhibited by cyclosporin A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

"Framework region" or "FR," as used herein, refers broadly to one or more of the framework regions within the variable regions of the light and heavy chains of an antibody. See Kabat, et al. (1987) "Sequences of Proteins of Immunological Interest" National Institutes of Health, Bethesda, Md. These expressions include those amino acid sequence regions interposed between the CDRs within the variable regions of the light and heavy chains of an antibody.

"Heterologous," as used herein, refers broadly to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid (e.g., a promoter from one source and a coding region from another source.) Similarly, a heterologous protein indicates that the protein comprises two or more subsequences that are not found in the same relationship to each other in nature (e.g., a fusion protein).

"High affinity," as used herein, refers broadly to an antibody having a KD of at least $10^{-8}$ M, more preferably at least $10^{-9}$ M and even more preferably at least $10^{-10}$ M for a target antigen. However, "high affinity" binding can vary for other antibody isotypes. For example, "high affinity" binding for an IgM isotype refers to an antibody having a KD of at least $10^{-7}$ M, more preferably at least $10^{-8}$ M.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison. The term "sequence identity" may be used interchangeably with "homology."

"Host cell," as used herein, refers broadly to refer to a cell into which a nucleic acid molecule of the invention, such as a recombinant expression vector of the invention, has been introduced. Host cells may be prokaryotic cells such as E. coli, or eukaryotic cells such as yeast, insect (e.g., SF9), amphibian, or mammalian cells such as CHO, HeLa, HEK-293, e.g., cultured cells, explants, and cells in vivo. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Humanized antibody," as used herein, refers broadly to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

"Hybridization," as used herein, refers broadly to the physical interaction of complementary (including partially complementary) polynucleotide strands by the formation of hydrogen bonds between complementary nucleotides when the strands are arranged antiparallel to each other.

"Immune cell," as used herein, refers broadly to cells that are of hematopoietic origin and that play a role in the immune response. Immune cells include lymphocytes, such as B cells and T cells; natural killer cells; and myeloid cells, such as monocytes, macrophages, eosinophils, mast cells, basophils, and granulocytes.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Immune response," as used herein, refers broadly to T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "downmodulation" with reference to the immune response includes a diminution in any one or more immune responses, while the term "upmodulation" with reference to the immune response includes an increase in any one or more immune responses. It will be understood that upmodulation of one type of immune response may lead to a corresponding downmodulation in another type of immune response. For example, upmodulation of the production of certain cytokines (e.g., IL-10) can lead to downmodulation of cellular immune responses.

"Inflammatory conditions or inflammatory disease," as used herein, refers broadly to chronic or acute inflammatory diseases.

"Isolated," as used herein, refers broadly to material removed from its original environment in which it naturally occurs, and thus is altered by the hand of man from its natural environment. Isolated material may be purified so as to be substantially free of other cellular components or other contaminants, e.g., other cellular nucleic acids or proteins, using standard techniques well known in the art. Isolated material may be, for example, exogenous nucleic acid included in a vector system, exogenous nucleic acid contained within a host cell, or any material which has been removed from its original environment and thus altered by the hand of man (e.g., "isolated antibody"). For example, "isolated" or "purified," as used herein, refers broadly to a protein, DNA, antibody, RNA, or biologically active portion thereof, that is substantially free of cellular material or other contaminating proteins from the cell or tissue source from which the biological substance is derived, or substantially free from chemical precursors or other chemicals when chemically synthesized. The language "substantially free of cellular material" includes preparations of KIR2DL1, 2 and/or 3 proteins in which the protein is separated from cellular components of the cells from which it is isolated or recombinantly produced.

"K-assoc" or "Ka", as used herein, refers broadly to the association rate of a particular antibody-antigen interaction, whereas the term "Kdiss" or "Kd," as used herein, refers to the dissociation rate of a particular antibody-antigen interaction. The term "KD", as used herein, is intended to refer to the dissociation constant, which is obtained from the ratio of $K_d$ to Ka (i.e., Kd/Ka) and is expressed as a molar concentration (M). KD values for antibodies can be determined using methods well established in the art.

"Label" or a "detectable moiety" as used herein, refers broadly to a composition detectable by spectroscopic, photochemical, biochemical, immunochemical, chemical, or other physical means.

"Low stringency," "medium stringency," "high stringency," or "very high stringency conditions," as used herein, refers broadly to conditions for nucleic acid hybridization and washing. Guidance for performing hybridization reactions can be found in Ausubel, et al. (2002) Short Protocols in Molecular Biology (5th Ed.) John Wiley & Sons, NY. Exemplary specific hybridization conditions include but are not limited to: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

"Mammal," as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, goats, gorillas, hamsters, horses, humans, lemurs, llamas, mice, non-human primates, pigs, rats, sheep, shrews, squirrels, and tapirs. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C.

"Naturally-occurring nucleic acid molecule," as used herein, refers broadly to refers to an RNA or DNA molecule having a nucleotide sequence that occurs in nature (e.g., encodes a natural protein).

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

"Operatively linked", as used herein, refers broadly to when two DNA fragments are joined such that the amino acid sequences encoded by the two DNA fragments remain in-frame.

"Paratope," as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. Antigens (Chapter 3) Immunology (5th Ed.) New York: W.H. Freeman and Company, pages 57-75.

"Patient," as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient."

"Polypeptide," "peptide" and "protein," are used interchangeably and refer broadly to a polymer of amino acid residues. The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Specifically (or selectively) binds" to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeneous population of proteins and other biologics. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

"Specifically hybridizable" and "complementary" as used herein, refer broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. Determination of binding free energies for nucleic acid molecules is well known in the art. See, e.g., Turner, et al. (1987) CSH Symp. Quant. Biol. LII: 123-33; Frier, et al. (1986) PNAS 83: 9373-77; Turner, et al. (1987) J. Am. Chem. Soc. 109: 3783-85. A percent complementarity indicates the percentage of contiguous residues in a nucleic acid molecule that can form hydrogen bonds (e.g., Watson-Crick base pairing) with a second nucleic acid sequence (e.g., about at least 5, 6, 7, 8, 9, 10 out of 10 being about at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence. "Substantial complementarity" refers to polynucleotide strands exhibiting about at least 90% complementarity, excluding regions of the polynucleotide strands, such as overhangs, that are selected so as to be non-complementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically may differ by at least 5 nucleotides.

"Signs" of disease, as used herein, refers broadly to any abnormality indicative of disease, discoverable on examination of the patient; an objective indication of disease, in contrast to a symptom, which is a subjective indication of disease.

"Solid support," "support," and "substrate," as used herein, refers broadly to any material that provides a solid or semi-solid structure with which another material can be attached including but not limited to smooth supports (e.g., metal, glass, plastic, silicon, and ceramic surfaces) as well as textured and porous materials.

"Subjects" as used herein, refers broadly to anyone suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g., rats and mice), lagomorphs, primates, humans. Any mammalian subject in need of being treated according to the present invention is suitable. Human subjects of both genders and at any stage of development (i.e., neonate, infant, juvenile, adolescent, adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "patients."

"Symptoms" of disease as used herein, refers broadly to any morbid phenomenon or departure from the normal in structure, function, or sensation, experienced by the patient and indicative of disease.

"T cell," as used herein, refers broadly to CD4+ T cells and CD8+ T cells. The term T cell also includes both T helper 1 type T cells and T helper 2 type T cells.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., inflammation, pain). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., inflammation, pain). Therapy encompasses but is not limited to precluding the appearance of signs and/or symptoms anytime as well as reducing existing signs and/or symptoms and reducing or eliminating existing signs and/or symptoms. Therapy includes treating chronic disease ("maintenance") and acute disease. For example, treatment includes treating or preventing relapses or the recurrence of signs and/or symptoms (e.g., inflammation, pain).

"Variable region" or "VR," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

"Vector," as used herein, refers broadly to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. The techniques and procedures are generally performed according to conventional methods well known in the art and as described in various general and more specific references that are cited and discussed throughout the present specification. See, e.g., Sambrook, et al. (2001) Molec. Cloning: Lab. Manual [3$^{rd}$ Ed] Cold Spring Harbor Laboratory Press. Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

The NK Cell Inhibitory Receptors KIR2DL1, 2, and 3

KIRs are cell surface glycoproteins, comprising one to three extracellular immunoglobulin-like domains, which are expressed by some T cells as well as most human NK cells. A number of KIRs are well characterized (See, e.g., Carrington and Norman, The KIR Gene Cluster, May 28, 2003, available through the National Center for Biotechnology Information (NCBI) web site). Human KIRs include KIR2DL and KIR3DL (KIRs also may be referred to by various other names such as CD158e1, CD158k, CD158z, p58 KIR CD158e1 (p70), CD244.) See, e.g., U.S. Patent Application Publication No. 2004/0038894, Radaev et al., Annu. Rev. Biophys. Biomol. Struct., 32:93-114 (2003), Cerweknka et al., Nat. Rev. Immunol. 1:41-49 (2001); Farag et al., Expert Opin. Biol. Ther., 3(2):237-250 (2003); Biassoni et al., J. Cell. Mol. Med., 7(4):376-387 (2003); and Warren et al., British J. Haematology, 121:793-804 (2003), each of which being hereby incorporated in their entirety). The structure of a number of KIRs has been elucidated and reveals remarkable structural similarity between these proteins. See, e.g., Radaev et al., supra.

KIRs can be classified structurally as well as functionally. For example, most KIRs have either two Ig domains (58 kDa KIR2D KIRs), whereas others have three Ig domains (70 kDa KIR3D KIRs) (sometimes respectively referred to as p58 and p70 molecules). KIRs vary also in cytoplasmic tail length. Typically, KIRs with a relatively long cytoplasmic tail (L) deliver an inhibitory signal, whereas KIR with a short cytoplasmic tail (S) can activate NK or T cell responses. Nomenclature for KIRs accordingly can be based upon the number of extracellular domains (KIR2D or KIR3D) and whether the cytoplasmic tail is long (KIR2DL or KIR3DL) or short (KIR2DS or KIR3DS). Additional nomenclature information for KIRs is provided in the following Detailed Description of the Invention. Some members of the "KIR family" are NKCARs, or more particularly "KARs" (e.g., KIR2DS2 and KIR2DS4); they typically comprise one or more charged transmembrane residues (e.g., Lys) that associate with an adapter molecule having an immunostimulatory motif (ITAM) (e.g., DAP12). The intracytoplasmic portion of inhibitory KIRs typically comprises one or more ITIMs that recruit phosphatases. Inhibitory KIRs bind to alpha1/alpha2 domains of HLA molecules. Inhibitory KIRs do not appear to typically require adaptor-molecule association for activity. Unless otherwise stated, terms such as "KIR", "KIRs", and the like refer to KIR2DL1, 2 and/or 3 members of the "KIR family" and terms such as "KAR", "KARs", and the like refer to NKCAR members of the "KIR family."

KIRs can bind MHC-I molecules (e.g., certain HLA class I allotypes), typically resulting in the transmission of a negative signal that counteracts, and may override stimulatory, activating signal(s) to the NK cell, thereby preventing the NK cell from killing the associated potential target cell (apparently via ITIM phosphorylation and tyrosine phosphatase (e.g., SH2-domain containing protein tyrosine phosphatases such as SHP-1 and SHP-2) recruitment, leading to PTK (e.g., Syk, TcR and/or ZAP70) dephosphorylation and/or LAT/PLC complex formation inhibition and associated disruption of ITAM cascade(s)). Because viruses often suppress class I MHC expression in cells they infect, such virus-infected cells become susceptible to killing by NK cells. Because cancer cells also often have reduced or no class I MHC expression, these cells, too, can become susceptible to killing by NK cells. Infected cells can also change the proteins bound in the MHC in terms of glycosylation. If this occurs, the MHC-I: protein complex the cell expresses will be altered. If NK-associated KIRs cannot bind to these "foreign" complexes, no inhibitory signal can be generated, and lysis will proceed.

All confirmed inhibitory KIRs appear to interact with different subsets of HLA/MHC antigens depending upon the KIR subtype. In humans, KIRs having two Ig domains (KIR2D) recognize HLA-C allotypes: KIR2DL2 (formerly designated p58.2) and the closely related gene product KIR2DL3 both recognize an epitope shared by group 1 HLA-C allotypes (Cw1, 3, 7, and 8), whereas KIR2DL1 (p58.1) recognizes an epitope shared by the reciprocal group 2 HLA-C allotypes (Cw2, 4, 5, and 6). The specificity of KIR2DL1 appears to be dictated by the presence of a Lys residue at position 80 of group 2 HLA-C alleles. KIR2DL2 and KIR2DL3 recognition appears to be dictated by the presence of an Asn residue at position 80. A substantial majority of HLA-C alleles have either an Asn or a Lys residue at position 80. One KIR with three Ig domains, KIR3DL1 (p70), recognizes an epitope shared by HLA-Bw4 alleles. Finally, a homodimer of molecules with three Ig domains, KIR3DL2 (p140), recognizes HLA-A3 and -A11.

Individual MHC-1-specific NK cell receptors of either type (activating or inhibitory) typically do not interact with all MHC class I molecules, but specifically bind to certain allotypes (proteins encoded by different variants of a single genetic locus). Also, an individual NK cell may express several different inhibitory and/or activating receptors which function independently of each other. For example, in humans the presence or absence of a given KIR is variable from one NK cell to another within a single individual. There also is relatively high level of polymorphism of KIRs in humans, with certain KIR molecules being present in some, but not all individuals. Although KIRs and other MHC-recognizing inhibitory receptors may be co-expressed by NK cells, in any given individual's NK repertoire there are typically cells that express a single KIR; accordingly, the corresponding NK cell activity in this latter type of NK cells is inhibited only by cells expressing a specific MHC-I allele group. In fact, recent estimates of the extent of KIR genotype diversity within the population suggest that <0.24% of unrelated individuals can expect to have identical genotypes. The most common Caucasian haplotype, the "A" haplotype (frequency of ~47-59%), contains only one activating KIR gene (KIR2DS4) and six inhibitory KIR loci (KIR3DL3, -2DL3, -2DL1, -2DL4, -3DL1, and -3DL2). The remaining "B" haplotypes are very diverse and contain 2-5 activating KIR loci (including KIR2DS1, -2DS2, -2DS3, and -2DS5).

It should be noted that KIRs are known by several aliases, as reflected here in Table 1 and Table 2:

TABLE 1

KIR Nomenclature

| KIR | Full name | Aliases | Accession ID | SEQ ID NO |
|---|---|---|---|---|
| KIR2DL1 | killer cell immunoglobulin-like receptor, two domains, long cytoplasmic tail, 1 | cl-42, nkat1, 47.11, p58.1, CD158a | L41267 | 11 |
| KIR2DL2 | killer cell immunoglobulin-like receptor, two domains, long cytoplasmic tail, 2 | cl-43, nkat6, CD158b1 | L76669 | 12 |
| KIR2DL3 | killer cell immunoglobulin-like receptor, two domains, long cytoplasmic tail, 3 | cl-6, nkat2, nkat2a, nkat2b, p58, CD158b2 | L41268 | 13 |
| KIR2DL4 | killer cell immunoglobulin-like receptor, two domains, long cytoplasmic tail, 4 | 103AS, 15.212, CD158d | X97229 | 14 |
| KIR2DL5A | killer cell immunoglobulin-like receptor, two domains, long cytoplasmic tail, 5A | KIR2DL5.1, CD158f | AF217485 | 15 |
| KIR2DL5B | killer cell immunoglobulin-like receptor, two domains, long cytoplasmic tail, 5B | KIR2DL5.2, KIR2DL5.3, KIR2DL5.4 | AF217486 | |
| KIR2DS1 | killer cell immunoglobulin-like receptor, two domains, short cytoplasmic tail, 1 | EB6ActI, EB6ActII, CD158h | X89892 | 16 |
| KIR2DS2 | killer cell immunoglobulin-like receptor, two domains, short cytoplasmic tail, 2 | cl-49, nkat5, 183ActI, CD158j | L76667 | 17 |
| KIR2DS3 | killer cell immunoglobulin-like receptor, two domains, short cytoplasmic tail, 3 | nkat7 | L76670 | 18 |
| KIR2DS4 | killer cell immunoglobulin-like receptor, two domains, short cytoplasmic tail, 4 | cl-39, KKA3, nkat8, CD158i | L76671 | 19 |
| KIR2DS5 | killer cell immunoglobulin-like receptor, two domains, short cytoplasmic tail, 5 | nkat9, CD158g | L76672 | 20 |
| KIR2DP1 | killer cell immunoglobulin-like receptor, two domains, pseudogene 1 | KIRZ, KIRY, KIR15, KIR2DL6 | AF204908 | |
| KIR3DL1 | killer cell immunoglobulin-like receptor, three domains, long cytoplasmic tail, 1 | cl-2, NKB1, cl-11, nkat3, NKB1B, AMB11, KIR, CD158e1 | L41269 | 21 |
| KIR3DL2 | killer cell immunoglobulin-like receptor, three domains, long cytoplasmic tail, 2 | cl-5, nkat4, nkat4a, nkat4b, CD158k | L41270 | 22 |
| KIR3DL3 | killer cell immunoglobulin-like receptor, three domains, long cytoplasmic tail, 3 | KIRC1, KIR3DL7, KIR44, CD158z | AF352324 | 23 |
| KIR3DS1 | killer cell immunoglobulin-like receptor, three domains, short cytoplasmic tail, 1 | nkat10, CD158e2 | L76661 | 24 |
| KIR3DP1 | killer cell immunoglobulin-like receptor, three domains, pseudogene 1 | KIRX, KIR48, KIR2DS6, KIR3DS2P, CD158c | AF204919, AF204915-AF204917 | |

Obtained from the Hugo Gene Nomenclature Committee web site.

TABLE 2

KIR CD Nomenclature

| Common Name 1 | Common Name 2 | CD Designation |
|---|---|---|
| KIR3DL7 | KIRC1 | CD158z |
| KIR2DL2/L3 | p58.2/p58.3 | CD158b1/b2 |
| KIR2DL1 | p58.1 | CD158z |
| KIR2DS6 | KIRX | CD158b1/b2 |
| KIR2DL4 | — | CD158c |
| KIR3DL1/S1 | p70 | CD158d |
| KIR2DL5 | — | CD158e1/e2 |
| KIR2DS5 | — | CD158f |
| KIR2DS1 | p50.1 | CD158h |
| KIR2DS4 | p50.3 | CD158i |
| KIR2DS2 | p50.2 | CD158j |
| KIR3DL2 | p140 | Cd158k |

Andre, et al. Nature Immunol. 2(8): 661 (2001).

Exemplary KIR2DL1, KIR2DL2, KIR2DL3, and KIR2DS4 molecules comprise the following respective amino acid sequences:

KIR2DL1 extracellular domain:

HEGVHRKPSLLAHPGXLVK-SEETVILQCWSDVMFEHFLLHREGM-FNDTLRLIGEHH DGVSKANFSISRMTQDLAGTYR-CYGSVTHSPYQVSAPSDPLDIVIIGLYEKPSLSAQXGPTVL AGENVTLSCSSRSSYDMYHLSREGEA-HERRLPAGPKVNGTFQADFPLGPATHGGTYRCFGSF HDSPYEWSKSSDPLLVSVTGNPSN-SWPSPTEPSSKTGNPRHLH (SEQ ID NO: 7), where "X" at position 16 is P or R, and where "X" at position 114 is P or L, representing allelic variants.

```
KIR2DL2 extracellular domain:
                                                       (SEQ ID NO: 8)
     HEGVHRKPSLLAHPGRLVKSEETVILQCWSDVRFEHFLLHREGKFKDTLHLIGEHH

DGVSKANFSIGPMMQDLAGTYRCYGSVTHSPYQLSAPSDPLDIVITGLYEKPSLSAQPGPTVL

AGESVTLSCSSRSSYDMYHLSREGEAHECRFSAGPKVNGTFQADFPLGPATHGGTYRCFGSF

RDSPYEWSNSSDPLLVSVIGNPSNSWPSPTEPSSKTGNPRHLH.

KIR2DL3 extracellular domain:
                                                       (SEQ ID NO: 9)
     HEGVHRKPSLLAHPGPLVKSEETVILQCWSDVRFQHFLLHREGKFKDTLHLIGEHH

DGVSKANFSIGPMMQDLAGTYRCYGSVTHSPYQLSAPSDPLDIVITGLYEKPSLSAQPGPTVL

AGESVTLSCSSRSSYDMYHLSREGEAHERRFSAGPKVNGTFQADFPLGPATHGGTYRCFGSF

RDSPYEWSNSSDPLLVSVTGNPSNSWPSPTEPSSETGNPRHLH.

KIR2DS4 extracellular domain:
                                                       (SEQ ID NO: 10)
     QEGVHRKPSFLALPGHLVKSEETVILQCWSDVMFEHFLLHREGKFNNTLHLIGEHH

DGVSKANFSIGPMMPVLAGTYRCYGSVPHSPYQLSAPSDPLDMV.
```

Neutralization of KIR2DL1, 2, and/or 3-Associated NK Cell Inhibition

Anti-KIR2DL1, 2 and/or 3 antibodies can be characterized on the basis of their ability to block or neutralize NK inhibition and thereby potentiate NK cell activity against otherwise blocked target cells (e.g., T cells, CD4+ T cells). As indicated above, anti-KIR2DL1, 2 and/or 3 antibodies that bind to at least one KIR2DL1, 2 and/or 3 for a sufficient amount of time to neutralize KIR2DL1, 2 and/or 3-mediated inhibition of NK cell cytotoxicity in NK cells can be used in the context of this invention. Such Anti-KIR2DL1, 2 and/or 3 antibodies may be used directly as therapeutic agents in a native form. A more particular advantageous feature of the invention is anti-KIR2DL1, 2 and/or 3 antibodies that cross-react with two or more KIR2DL1, 2 and/or 3s and neutralize the inhibitory activity associated with some or all (typically preferably all) of such associated KIR2DL1, 2 and/or 3.

Neutralizing anti-KIR2DL1, 2 and/or 3 antibodies may partially or fully neutralize the KIR2DL1, 2 and/or 3-mediated inhibition of NK cell cytotoxicity. Neutralization refers to any substantial blocking of otherwise present inhibitory signals. Neutralization can be measured by any suitable method. In one aspect, neutralization of inhibition is reflected in that the neutralizing anti-KIR antibody cause an least about 20%, preferably at least about 30%, at least about 40%, at least about 50%, at least about 60%, at least about 75% or more (e.g., about 25-100%) increase in NK cell-mediated specific lysis in a particular mixture of NK and NK target cells compared to the amount of specific lysis that typically occurs in a substantially identical setting without the presence of the anti-KIR2DL1, 2 and/or 3 antibody (ies). The percentage increase in this aspect can be determined when considering anti-KIR2DL1, 2 and/or 3 or other antibodies by, e.g., comparison with the results of chromium release toxicity test assays obtained from a mixture of NK target cells (e.g., T cells, any suitable cell line) and NK cells not blocked their associated KIR2DL1, 2 and/or 3 (100%) and a mixture of NK cells and NK target cells, in which the NK target cells present a ligand for the KIR2DL1, 2 and/or 3 (0%). In the case of anti-KIR antibodies, comparison can be with the results of chromium release toxicity test assays obtained from a mixture of NK target cells and NK cells not blocked their associated KIR (100%) and a mixture of NK cells and NK target cells, in which the NK target cells present the cognate MHC class I molecule for the inhibitory KIR on the NK cells (0%). In an advantageous aspect, the invention provides anti-KIR2DL1, 2 and/or 3 antibodies that induce lysis of cell(s) that would not be effectively lysed without the presence of such anti-KIR2DL1, 2 and/or 3 antibody. Alternatively, neutralization of KIR2DL1, 2 and/or 3 inhibitory activity can be indicated by, e.g., the results of a chromium assay using an NK cell clone or transfectant expressing one or several inhibitory KIR2DL1, 2 and/or 3s (e.g., KIR, NKG2, NKG2A, LIR (e.g. LILRB1, LILRB5) and a target cell expressing only one ligand (e.g. HLA polypeptide or allele, HLA-E) that is recognized by one of the KIR2DL1, 2 and/or 3s on the NK cell, where the level of cytotoxicity obtained with the antibody is at least about 20%, such as at least about 30%, at least about 40%, at least about 50%, at least about 60%, at least about 70% or more (e.g., about 25-100%) of the cytotoxicity observed with a known blocking antibody to the ligand of the KIR2DL1, 2 and/or 3. For example, when testing an anti-KIR antibody, an anti-MHC class I molecule is administered in a substantially identical setting, such as W6/32 anti-MHC class I antibody (which is currently available from, e.g., Research Diagnostics, Flanders, N.J., USA and described in, e.g., Shields et al., Tissue Antigens. 1998 May; 51(5):567-70).

Chromium release assays and other methods of assessing NK cell cytolytic activity are known in the art. Conditions suitable for such assays also are well known. A typical chromium release assay is performed by labeling target cells (e.g., Cw3 and/or Cw4 positive cell lines—at about, e.g., 5000 cells per well in a microtitration plate) with $Na_2{}^{51}CrO_4$ (such that $^{51}Cr$ is taken up and retained by viable target cells), washing to remove excess radioactivity, thereafter exposed to NK cells for a period of about 4 hours in the presence or absence of anti-KIR2DL1, 2 and/or 3 antibody(s) at a suitable effector: target ratio (e.g., about 4:1), and measuring for subsequent $^{51}Cr$ levels reflecting target cell death and lysis. An example of such an assay is described in, e.g., Moretta et al. (1993) J Exp Med 178: 597-604. In a similar assay, proliferating target cells can be labeled with $^3H$-thymidine, which is incorporated into the replicating DNA. Upon cytolytic action by NK cells, the DNA of the target cells is rapidly fragmented and retained in a filtrate, while large, unfragmented DNA can be collected on a filter, such that one can measure either the release of these fragments or the retention of $^3H$-thymidine in cellular DNA.

Other examples and relevant discussion related to such assays can be found in, e.g., WO 2006/072625.

In another aspect, the invention provides Anti-KIR2DL1, 2 and/or 3 Antibodies characterized by the ability to compete with cross-reactive and/or neutralizing anti-KIR2DL1, 2 and/or 3 antibodies for binding to cognate KIR2DL1, 2 and/or 3s and/or to bind to the same antigenic determinant region/epitope as such known antibodies. The phrase "competes with" when referring to a particular monoclonal antibody (e.g. 1-7F9) means that the anti-KIR2DL1, 2 and/or 3 antibody competes with the referenced antibody or other molecule in a binding assay using either recombinant KIR2DL1, 2 and/or 3 molecules or surface expressed KIR2DL1, 2 and/or 3 molecules. For example, if an anti-KIR antibody detectably reduces binding of 1-7F9 to a KIR molecule normally bound by 1-7F9 in a binding assay, the anti-KIR antibody can be said to "compete" with 1-7F9. An anti-KIR Antibody that "competes" with 1-7F9 may compete with 1-7F9 for binding to the KIR2DL1 human receptor, the KIR2DL2/3 human receptor, or both KIR2DL1 and KIR2DL2/3 human receptors.

Although often related, describing a protein in terms of competition with a reference binding protein versus the ability of the protein to bind to the same or substantially similar epitope as a reference protein in some cases imply significantly different biological and physiochemical properties. Competition between binding proteins implies that the test anti-KIR2DL1, 2 and/or 3 antibody binds to an epitope that at least partially overlaps with an epitope bound by an anti-KIR2DL1, 2 and/or 3 antibody or is located near enough to such an epitope so that such an anti-KIR antibody competes with known anti-KIR2DL1, 2 and/or 3 antibodies due to steric hindrance. An anti-KIR2DL1, 2 and/or 3 antibody may compete with a reference anti-KIR2DL1, 2 and/or 3 antibody, without binding to the same or similar epitope due to the large size of the antibodies. Such a competing anti-KIR2DL1, 2 and/or 3 antibody can be useful in blocking interactions associated with the same antigenic determining region as the reference anti-KIR2DL1, 2 and/or 3 antibody even though it binds a different antigenic determinant.

In another exemplary aspect, the invention provides an anti-KIR2DL1, 2 and/or 3 antibody that binds to substantially the same antigenic determinant region as an available anti-KIR antibody, such as 1-7F9, DF200 and/or NKVSF1. See, e.g., WO 2006/003179.

Competition refers to any significant reduction in the propensity for a particular molecule to bind a particular binding partner in the presence of another molecule that binds the binding partner. Typically, competition means an at least about 15% reduction in binding, such as an at least about 20% reduction in binding (e.g., a reduction in binding of about 25% or more, about 30% or more, about 15-35%) between, e.g., an anti-KIR antibody and at least one KIR in the presence of the competing molecule, e.g., an anti-KIR antibody. In certain situations, such as in cases where epitopes belonging to competing antibodies are closely located in an antigen, competition can be marked by greater than about 40% relative inhibition of receptor (e.g., KIR) binding, at least about 50% inhibition, at least about 55% inhibition, at least about 60% inhibition, at least about 75% inhibition, or higher level of inhibition (such as a level of inhibition of about 45-95%).

Assessing competition typically involves an evaluation of relative inhibitory binding using a first amount of a first molecule (e.g., an anti-KIR antibody); a second amount of a second molecule (e.g., a known anti-KIR antibody); and a third amount of a third molecule (e.g., a KIR), wherein the first, second, and third amounts all are sufficient to make a comparison that imparts information about the selectivity and/or specificity of the molecules at issue with respect to the other present molecules. Usually, for ELISA competition assays, about 5-50 µg (e.g., about 10-50 µg, about 20-50 µg, about 5-20 µg, about 10-20 µg) of an anti-KIR antibody, a known anti-KIR antibody, and at least one KIR are used to assess whether competition exists. Conditions also should be suitable for binding of the competing molecules to their putative/known target. Physiological or near-physiological conditions (e.g., temperatures of about 20-40° C., pH of about 7-8) can typically be suitable for Anti-KIR Antibody: KIR.

Determination of competition (or relative inhibition of binding) between two or more molecules can be made by use of immunoassays in which the control KIR2DL1, 2 and/or 3-binding molecule (antibody 1-7F9, for example) and test anti-KIR2DL1, 2 and/or 3 antibody are admixed (or preadsorbed) and applied to a sample containing relevant KIRs, such as both KIR2DL1 and KIR2DL2/3 (each of which is known to be bound by DF200). Protocols based upon ELISAs, radioimmunoassays, Western blotting, and the like are suitable for use in such competition studies. Competition ELISAs are typically performed under conditions suitable for binding of the molecules (e.g., physiological conditions, particularly in the case of antibodies that bind conformational/nonlinear epitopes). Competition also can be assessed by, for example, a flow cytometry test, SPR analysis and other techniques found in, e.g., Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), Ausubel et al., Eds., Short Protocols in Molecular Biology, ($5^{th}$ edition), John Wiley & Sons (2002), and Muller, Meth. Enzymol. 92:589-601 (1983)).

An antigenic determinant region or epitope can be identified by a number of known techniques. For example, an antigenic determinant region can be identified quickly by "foot printing" assays, such as through a chemical modification of the exposed amines/carboxyls in target KIR2DL1, 2, and/or 3 proteins. One specific example of such a foot-printing technique is the use of HXMS (hydrogen-deuterium exchange detected by mass spectrometry), wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) and/or Engen, J. R. and Smith, D. L. (2001) Anal. Chem. 73, 256A-265A.

Another example of a suitable epitope identification technique is nuclear magnetic resonance (NMR) epitope mapping, where typically the position of the signals in two-dimensional NMR spectres of the free antigen and the antigen complexed with the antigen-binding peptide, such as an antibody, are compared. The antigen typically is selectively isotopically labeled with $^{15}N$ so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. See, e.g., Ernst Schering Res Found Workshop. 2004; (44):149-67; Huang, et al, Journal of Molecular Biology 281 (1): 61-67 (1998); and Saito and Patterson, Methods. 1996 June; 9(3):516-24.

Epitope mapping/characterization also can be performed using mass spectrometry methods. See, e.g., Downward, J Mass Spectrom. 2000 April; 35(4):493-503 and Kiselar and Downward, Anal Chem. 1999 May 1; 71(9):1792-801.

Protease digestion techniques also can be useful in the context of epitope mapping and identification. Antigenic determinant-relevant regions/sequences can be determined by protease digestion, e.g. by using trypsin in a ratio of about 1:50 to KIR2DL1, 2 and/or 3 o/n digestion at 37° C. and pH 7-8, followed by mass spectrometry (MS) analysis for peptide identification. The peptides protected from trypsin cleavage by the anti-KIR2DL1, 2 and/or 3-binder can subsequently be identified by comparison of samples subjected to trypsin digestion and samples incubated with antibody and then subjected to digestion by e.g. trypsin (thereby revealing a foot print for the binder). Other enzymes like chymotrypsin, pepsin, also or alternatively can be used in similar epitope characterization methods. Moreover, enzymatic digestion can provide a quick method for analyzing whether a potential antigenic determinant sequence is within a region of the KIR2DL1, 2 and/or 3 in the context of an anti-KIR2DL1, 2 and/or 3 polypeptide that is not surface exposed and, accordingly, most likely not relevant in terms of antigenicity. See, e.g., Manca, Ann Ist Super Sanita. 1991; 27(1):15-9 for a discussion of similar techniques.

Various phage display techniques also can be used to identify epitopes. See, e.g., Wang and Yu, Curr Drug Targets. 2004 January; 5(1):1-15; Burton, Immunotechnology. 1995 August; 1(2):87-94; Cortese et al., Immunotechnology. 1995 August; 1(2):87-94; and Irving et al., Curr Opin Chem Biol. 2001 June; 5(3):314-24. Consensus epitopes also can be identified through modified phage display-related techniques (See, Mumey et al., *J. Comput. Biol.* 10:555-567 and Mumey, *Proceedings of the Sixth Annual International Conference on Computational Molecular Biology* (RECOMB-02), pp. 233-240 (ACM Press, New York)) for discussion (See also Bailey et al., *Protein Science* (2003), 12:2453-2475; Dromey et al., J Immunol. 2004 Apr. 1; 172(7):4084-90; Parker et al., Mol Biotechnol. 2002 January; 20(1):49-62; and Czompoly et al., Biochem Biophys Res Commun. 2003 Aug. 8; 307(4):791-6).

Epitope mapping by competitive binding to a KIR with two KIR-binding molecules where one is biotinylated (e.g., a known anti-KIR antibody) or otherwise similarly labeled is another method for identifying relevant antigenic determinant regions.

Other methods potentially helpful in mapping epitopes include crystallography techniques, X-ray diffraction techniques (such as the X-ray diffraction/sequence study techniques developed by Poljak and others in the 1970s-1980s), and the application of Multipin Peptide Synthesis Technology.

Computer-based methods such as sequence analysis and three dimensional structure analysis and docking also can be used to identify antigenic determinants. For example, an epitope also can be determined by molecular modeling using a structure of a KIR2DL1, 2 and/or 3 or portion thereof with docking of the structure of the Fab fragment of an individual mAb. Where necessary, models of KIR2DL1, 2 and/or 3s can be produced by homology modeling with structure-characterized KIR2DL1, 2 and/or 3s using programs such as MOE (Molecular Operating Environment), which is available from Chemical Computing Group (Montreal, Quebec, Canada—www.chemcomp.com). These and other mapping methods are discussed in Epitope Mapping A Practical Approach (Westwood and Hay Eds.) 2001 Oxford University Press (See also Cason (1994) J Virol Methods. 49(2): 209-19).

Characteristics of Anti-KIR Antibodies

Advantageous Anti-KIR antibodies may be classified based on functional characteristics, particularly with respect to their ability to cross-react or cross-bind more than one KIR, such as more than one type of inhibitory KIR, and/or the ability to effectively neutralize NK inhibitory signals.

Anti-KIR antibodies that effectively bind to more than one type of KIR are a particularly advantageous feature of the invention. In a particular exemplary aspect, the invention provides Anti-KIR Antibodies that bind to at least two inhibitory KIR receptors at the surface of NK cells. In an even more particular illustrative aspect, the invention provides Anti-KIR antibodies that bind a common antigenic determinant region of human KIR2DL receptors. In a yet even further specific aspect, the invention provides an anti-KIR antibody that binds to KIR2DL1, KIR2DL2, and KIR2DL3 receptors.

The term "KIR2DL2/3" can be used to refer to either or both of the KIR2DL2 and KIR2DL3 receptors. These two receptors have a very high homology, are allelic forms of the same gene, and are considered by the art to be interchangeable in many respects. Accordingly, KIR2DL2/3 can be considered in certain respects to be a single inhibitory KIR molecule. While Anti-KIR antibodies that cross-react with KIR2DL2/3 are within the invention, Anti-KIR antibodies that have a KIR-binding profile that only included KIR2DL2 and KIR2DL3 are not considered "cross-reactive."

Because at least one of KIR2DL1 or KID2DL2/3 is present in at least about 90% of the human population, KIR2DL1-KIR2DL2/3 cross-reactive Anti-KIR antibodies can promote or enhance NK activity against most of the HLA-C allotype-associated cells, respectively group 2 HLA-C allotypes and group 1 HLA-C allotypes. A composition comprising a single cross-reacting KIR antibody having such cross-reactivity may be used in treatment and/or diagnosis of most human subjects, thereby eliminating the necessity of genetic profiling of the patient and reducing the amount of different antibodies that need to be administered to a patient to ensure an effective result.

Cross-reacting Anti-KIR antibodies can have any suitable composition and can be obtained by a number of suitable techniques. For example, a cross-reactive Anti-KIR antibody can comprise a number of KIR ligand and/or anti-Anti-KIR antibody sequences that bind to different KIRs, which may be associated by conjugation, multimerization, or (in the case of peptide ligands) by being comprised in a fusion protein. In another aspect, an anti-KIR antibody is provided that comprises anti-Anti-KIR antibody sequences from a cross-reacting anti-Anti-KIR antibody.

Cross-reacting anti-Anti-KIR antibodies, from which KIR-binding sequences can be obtained or derived, are known. An example of such an antibody is antibody NKVSF1 (also referred to as pan2D mAb; recognizing a common epitope of CD158a (KIR2DL1), CD158b (KIR2DL2) and p50.3 (KIR2DS4)) having the variable region and CDR sequences shown in, e.g. FIG. 15, of WO2006/003179 (Innate Pharma; Novo Nordisk; University of Genoa). The monoclonal antibody DF200, which reacts with various members of the KIR family including KIR2DL1 and KIR2DL2/3 is another example of such a cross-reacting antibody. A hybridoma that produces DF200 has been deposited at the CNCM culture collection, as Identification no. "DF200", registration no. CNCM I-3224, registered 10 Jun. 2004, Collection Nationale de Cultures de Microorganismes, Institut Pasteur, 25, Rue du Docteur Roux, F-75724 Paris Cedex 15, France. Several additional monoclonal antibodies can be generated and demonstrated to be cross-reactive anti-Anti-KIR antibodies. Yet other examples are antibodies 1-7F9 and 1-4F1, described in WO2006/003179.

A cross-reactive Anti-KIR antibody can have any suitable affinity and/or avidity for the two or more KIRs to which it binds. Affinity refers to the strength of binding of an anti-KIR antibody or other antigen-binding protein to an epitope or antigenic determinant. Typically, affinity is measured in terms of a dissociation constant $K_d$, defined as $[Ab]\times[Ag]/[Ab-Ag]$ where $[Ab-Ag]$ is the molar concentration of the antibody-antigen complex, $[Ab]$ is the molar concentration of the unbound antibody and $[Ag]$ is the molar concentration of the unbound antigen. The affinity constant $K_a$ is defined by $1/K_d$. Suitable methods for determining binding peptide specificity and affinity by competitive inhibition, equilibrium dialysis, and the like can be found in, e.g., Harlow, et al., Antibodies: A Laboratory Manual, Cold Spring Harbor Laboratory Press, Cold Spring Harbor, N.Y., 1988); Colligan et al., eds., Current Protocols in Immunology, Greene Publishing Assoc. and Wiley Interscience, N.Y., (1992, 1993), and Muller, Meth. Enzymol. 92:589-601 (1983).

Typically, an anti-KIR antibody provided by the invention has an affinity for at least one KIR in the range of about $10^4$ to about $10^{10}$ $M^{-1}$ (e.g., about $10^7$ to about $10^9$ $M^{-1}$). The term immunoreact herein typically refers to binding of an anti-KIR antibody to a KIR with a dissociation constant $K_d$ lower than about $10^{-4}$ M. For example, in a particular aspect the invention provides Anti-KIR antibody that have an average disassociation constant ($K_D$) of about $7\times10^{-9}$M or more with respect to KIR2DL1 and KIR2DL2/3, as determined by, e.g., surface plasmon resonance (SPR) screening (such as by analysis with a BIAcore® SPR analytical device). In a more particular exemplary aspect, the invention provides Anti-KIR antibodies that have a KD of about $2\times10^{-9}$ M (e.g., about $0.1$-$4\times10^{-9}$ M) or more for KIR2DL2/3 and about $11\times10^{-9}$ M (e.g., about $7$-$15\times10^{-9}$ M) or more for KIR2DL1.

Affinity can be determined by any of the methods described elsewhere herein or their known equivalents in the art. An example of one method that can be used to determine affinity is provided in Scatchard analysis of Munson & Pollard, Anal. Biochem. 107:220 (1980). Binding affinity also may be determined by equilibrium methods (e.g. enzyme-linked immunoabsorbent assay (ELISA) or radioimmunoassay (RIA)) or kinetics analysis (e.g. BIAcore® analysis).

Anti-KIR antibodies also or alternatively can be characterized by exhibiting KIR binding with a disassociation constant of less than about 100 nM, less than about 50 nM, less than about 10 nM, about 5 nM or less, about 1 nM or less, about 0.5 nM or less, about 0.1 nM or less, about 0.01 nM or less, or even about 0.001 nM or less.

Avidity refers to the overall strength of the total interactions between a binding protein and antigen (e.g., the total strength of interactions between an anti-KIR antibody and a KIR). Affinity is the strength of the total noncovalent interactions between a single antigen-binding site on an antibody or other binding peptide and a single epitope or antigenic determinant. Avidity typically is governed by three major factors: the intrinsic affinity of the binding protein for the epitope(s) or antigenic determinant(s) to which it binds, the valence of the antibody or binding protein and antigen (e.g., an anti-KIR antibody with a valency of three, four, or more will typically exhibit higher levels of avidity for an antigen than a bivalent antibody and a bivalent antibody can will have a higher avidity for an antigen than a univalent antibody, especially where there are repeated epitopes in the antigen), and/or the geometric arrangement of the interacting components. Avidity typically is measured by the same type of techniques used to assess affinity.

In another aspect, the invention provides an anti-KIR antibody that cross-reacts with KIRs from two or more species. For example, in one aspect, the invention provides an anti-KIR antibody that cross-reacts with KIRs of humans and cynomolgus monkeys. In a particular aspect, the invention provides an anti-KIR antibody that cross-reacts with at least two human KIRs and also binds to NK cells of cynomolgus monkeys. Such an anti-KIR antibody can comprise sequences from or that are derived from antibody NKVSF1, which exhibits such a cross-reactivity profile. Such Anti-KIR antibodies can be subjected to toxicity testing and other useful studies in cynomolgus monkeys, if needed.

Antibodies that are cross-reactive with a variety of KIRs may be used in the combination compositions and methods of the invention. Exemplary cross-reactivity profiles of such antibodies include antibodies that cross-react with KIRs 2DL1 plus 2DL2/3, 3DL1 plus 3DL2, 2DL1 (and 2DL2/3) plus 2DS4, and 2DL1 (and 2DL2/3) but not 2DS4.

Thus, for example, the inventive methods or compositions may comprise an anti-KIR antibody that binds KIR2DL1, KIR2DL2, and KIR2DL3 and reduces or blocks inhibition of KIR-mediated NK cell cytotoxicity, as described in, e.g., WO2005003168.

Exemplary anti-KIR antibodies useful in the combination methods and compositions of the invention include anti-KIR antibodies comprising a VL region that corresponds to that of anti-KIR antibody DF200, or consists essentially of such a VL region (by being substantially similar and retaining a similar binding profile and affinity), or a VL sequence/domain that is highly similar (e.g., at least about 90% identical or 95% identical) to the VL sequence of DF200. The VL sequence of DF200 is shown in WO2006/3179. Such anti-KIR antibodies also may alternatively be defined by comprising the set of light variable CDRs of DF200 (also shown in WO2006/3179). Such an antibody typically also will comprise either the VH domain of DF200 or a highly similar sequence (e.g., a sequence having high identity to the DF200 VH domain or otherwise consisting essentially of such a sequence) or at least the heavy variable CDRs of DF200 (shown in WO2006/3179).

In another exemplary aspect, the combination composition or method of the invention includes an anti-KIR antibody comprising VH and VL sequences that correspond to or are highly similar to (e.g., consists essentially of) the VH and VL sequences of antibody 1-7F9 (shown in WO2006/3179) or at least comprises the VL and VH CDRs of 1-7F9.

Competition with Cross-Reactive and/or Neutralizing Anti-KIR Antibodies

In another aspect, the inventive methods or compositions are characterized by comprising an anti-KIR antibody that competes with one of these antibodies or one of the other anti-KIR antibodies descried in the references incorporated herein (e.g., 1-7F9).

Antibodies that compete with exemplary anti-KIR antibodies, such as DF200, 1-7F9, and/or NKVSF1, can be identified using known screening assays. A number of such assays are routinely practiced and well known in the art (See, e.g., U.S. Pat. No. 5,660,827, which is specifically incorporated herein by reference). Protocols based on, e.g., ELISAs, radioimmunoassays, Western blotting, and the use of BIACORE analysis are suitable for use in such competition studies.

One can, e.g., pre-mix the control antibody (e.g., DF200, NKVSF1, or 1-7F9) with varying amounts of the test antibody (e.g., in ratios of about 1:1, 1:2, 1:10 or about 1:100) for a period of time prior to applying to a KIR antigen sample.

Alternatively, the control and varying amounts of test antibody can simply be added separately and admixed during exposure to the KIR antigen sample. As long as one can distinguish bound from free antibodies (e.g., by using separation or washing techniques to eliminate un-bound antibodies) and control anti-body from the test antibody (e.g., by using species specific or isotype specific secondary antibodies or by specifically labelling the control antibody with a detectable label) one will be able to determine if the test antibody reduce the binding of the control antibody to the different KIR2DL antigens, indicating that the test antibody recognizes substantially the same epitope as the control. The binding of the (labeled) control antibody in the presence of a completely irrelevant antibody (that does not bind KIR) can serve as the control high value. The control low value can be obtained by incubating the labeled control antibody with the same but unlabelled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of control antibody to one or both of KIR2DL1 and KIR2DL3 antigens by at least about 50%, such as at least about 60%, or more preferably at least about 70% (e.g., about 65-100%), at any ratio of control:test antibody between about 1:1 or 1:10 and about 1:100 is considered to be an antibody that competes with the control.

Competition can also be assessed by, for example, flow cytometry. In such a test, cells bearing a given KIR can be incubated first with a control antibody, and then with the test antibody labeled with a fluorochrome or biotin. The antibody is said to compete with control antibody if the binding obtained upon pre-incubation with saturating amount of control antibody is about 80%, preferably about 50%, about 40% or less (e.g., about 30%) of the binding (as measured by mean of fluorescence) obtained by the test antibody without preincubation with control antibody. Alternatively, an antibody is said to compete with the control antibody if the binding obtained with a labeled control antibody (by a fluorochrome or biotin) on cells preincubated with saturating amount of test antibody is about 80%, preferably about 50%, about 40%, or less (e.g., about 30%) of the binding obtained without preincubation with the test antibody.

A simple competition assay in which a test antibody is pre-adsorbed and applied at saturating concentration to a surface onto which either KIR2DL1 or KIR2DL2/3, or both, are immobilized also may be advantageously employed. The surface in the simple competition assay is preferably a BIA-CORE chip (or other media suitable for surface plasmon resonance analysis). The binding of a control antibody to the KIR-coated surface is measured. This binding to the KIR-containing surface of the control antibody alone is compared with the binding of the control antibody in the presence of a test antibody. A significant reduction in binding to the KIR2DL1 and KIR2DL2/3-containing surface by the control antibody in the presence of a test antibody indicates that the test antibody recognizes substantially the same epitope as the control antibody such that the test antibody "competes" with the control antibody. Any test antibody that reduces the binding of control antibody to both of KIR2DL1 and KIR2DL2/3 antigens by at least about 20% or more, at least about 40%, at least about 50%, at least about 70%, or more, can be considered to be an antibody that competes with the control antibody. Preferably, such test antibody will reduce the binding of the control antibody to each of at least the KIR2DL1, 2, and 3 antigens by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the antibody having higher affinity for KIR2DL1 and KIR2DL2/3 antigens is bound to the KIR2DL1 and KIR2DL2/3-containing surface first, as it will be expected that the decrease in binding seen for the second antibody (assuming the antibodies are competing) will be of greater magnitude. Further examples of such assays are provided in the Examples herein, and in e.g., Saunal and Regenmortel, (1995) J. Immunol. Methods 183: 33-41, the disclosure of which is incorporated herein by reference.

In another aspect, the inventive method or composition is characterized by inclusion of only antibodies that are not cross-reactive with more than one KIR. For example, monoclonal antibodies specific only for KIR2DL1 have been shown to block the interactions between KIR2DL1 and HLA-Cw4 allotypes, as well as similar HLA-C allotypes belonging to the same group as Cw4 (Moretta et al., J Exp Med. 1993; 178(2):597-604; the disclosure of which is incorporated herein by reference). In another example, monoclonal antibodies against KIR2DL2/3 have also been described that block the interactions of KIR2DL2/3 with HLACw3 (or the like) allotypes (Moretta et al., 1993, supra). Optionally, the antibody can be selected from the group consisting of GL183 (KIR2DL2/3/S2-specific, available from Immunotech, France and Beckton Dickinson, USA); EB6 (KIR2DL1/s1-specific, available from Immunotech, France and Beckton Dickinson, USA).

Epitopes

In additional aspects, the invention provides anti-KIR Antibodies that are directed to particular antigenic regions and/or epitopes presented on various KIRs. In one exemplary aspect, the invention provides anti-KIR antibodies that specifically bind KIR2DL1 within a region defined by one or more (or all of) of the amino acid residues selected from 105, 106, 107, 108, 109, 110, 111, 127, 129, 130, 131, 132, 133, 134, 135, 152, 153, 154, 155, 156, 157, 158, 159, 160, 161, 162, 163, 181, and 192. In another embodiment the invention provides anti-KIR antibodies that specifically bind to KIR2DL1 and KIR 2DL2/3 in a region defined by one or more (or all of) of amino acid residues 105, 106, 107, 108, 109, 110, 111, 127, 129, 130, 131, 132, 133, 134, 135, 152, 153, 154, 155, 156, 157, 158, 159, 160, 161, 162, 163, 181, and 192 thereof.

In a further aspect, the invention provides anti-KIR antibodies that bind to KIR2DL1, but that bind to a mutant of KIR2DL1 in which R131 is Ala with significantly reduced binding affinity relative thereto (about 20% or less, about 30% or less, about 40% or less, about 50% or less, about 60% or less, about 70% or less, of the affinity exhibited for KIR2DL1). In another aspect, the invention provides anti-KIR Antibodies that bind to KIR2DL1 but that which bind to a mutant of KIR2DL1 in which R157 is Ala with relatively reduced binding affinity (about 20% or less, about 30% or less, about 40% or less, about 50% or less, about 60% or less, about 70% or less, of the affinity exhibited for KIR2DL1). In another aspect, the invention provides anti-KIR Antibodies that bind to KIR2DL1 and which binds a mutant of KIR2DL1 in which R158 is Ala with relatively reduced binding affinity (about 20% or less, about 30% or less, about 40% or less, about 50% or less, about 60% or less, about 70% or less, of the affinity exhibited for KIR2DL1).

The invention provides anti-KIR antibodies that bind to KIR2DL1 residues 131, 157, and 158.

The invention provides anti-KIR antibodies that bind to KIR2DS3(R131W), but not to wild type KIR2DS3. In yet another aspect, the invention provides Anti-KIR antibodies that bind to KIR2DL1 and KIR2DL2/3 as well as KIR2DS4. In still another aspect, the invention provides anti-KIR Antibodies that bind to both KIR2DL1 and KIR2DL2/3, but not to KIR2DS4.

To illustrate the use of anti-KIR antibody sequences in the composition and construction of anti-KIR antibodies, exemplary anti-KIR antibody sequences and antibody sequence variants will be described here. Amino acid and nucleic acid sequences of variable regions and CDRS of exemplary KIR antibodies DF200 and 1-7F9 are also disclosed in WO 2006/003179.

Exemplary anti-KIR mAbs include mAbs 1-7F9 and 1-4F1 which have several advantages over other anti-KIR antibodies. For example, 1-7F9 and 1-4F1 are fully human, thus reducing or minimizing any immune response against the antibody once administered to a subject. Furthermore, both 1-7F9 and 1-4F1 are of suitable isotypes for therapeutic anti-KIR antibodies (IgG4 and IgG2, respectively), as described below. 1-7F9 is also more effective at inducing killing by NK cells that express either KIR2DL1, -2, and/or -3 than murine mAbs EB6, GL183, DF200, and NKVSF1 (Pan2D). 1-7F9 further has a higher affinity for KIR compared to previously known anti-KIR mAbs. For example, 1-7F9 binds to KIR2DL1 and KIR2DL3 with dissociation constants ($K_d$'s) of 0.43 nM and 0.025 nM, respectively, representing a higher affinity for both antigens than, for example, DF200. Particularly preferred antibodies according to the invention therefore have the same or similar antigen-specificities as 1-7F9 and/or 1-4F1. For example, antibodies comprising the same or similar VH and VL regions as 1-7F9 can have the same or similar antigen-binding and/or NK-stimulatory properties as 1-7F9; and antibodies comprising the same or similar VH and VL regions as 1-4F1 can have the same or similar antigen-binding properties as 1-4F1.

An antibody may comprise an amino acid sequence of the VL and/or VH regions of 1-7F9 as follows:

```
1-7F9 VL region (SEQ ID NO: 1):
    EIVLTQSPVTLSLSPGERATLSCRASQSVSSYLAWYQQKPGQAPRLLIYDASNRATGI

PARFSGSGSGTDFTLTISSLEPEDFAVYYCQQRSNWMYTFGQGTKLEIKRT 1-7F9 VH region (SEQ ID NO: 2):
    QVQLVQSGAEVKKPGSSVKVSCKASGGTFSFYAISWVRQAPGQGLEWMGGFIPIFG

AANYAQKFQGRVTITADESTSTAYMELSSLRSDDTAVYYCARIPSGSYYYDYDMDVWGQGT

TVTVSS.
```

The amino acid sequences of the 1-4F1 VL and VH regions are provided in SEQ ID NOS: 3 and 4, respectively. In a particular embodiment, residues 3, 4, 9, 24, 32, 41, 47, 50, 55, 71, and 74 of SEQ ID NO: 3 are Q, L, S, R, A, G, L, D, E, F, and A, respectively. In another particular embodiment, residues 3, 4, 9, 24, 32, 41, 47, 50, 55, 71, and 74 of SEQ ID NO: 3 are R, M, F, W, Y, A, F, Y, Q, Y, and T, respectively.

The amino acid sequences of the 1-7F9 CDRs are as follows: the light chain CDR1 amino acid sequence corresponds to residues 24-34 of SEQ ID NO: 1; the light chain CDR2 amino acid sequence corresponds to residues 50-56 of SEQ ID NO: 1; the light chain CDR3 amino acid sequence corresponds to residues 89-97 of SEQ ID NO: 1; the heavy chain CDR1 amino acid sequence corresponds to residues 31-35 of SEQ ID NO: 2; the heavy chain CDR2 amino acid sequence corresponds to residues 50-65 of SEQ ID NO: 2; and the heavy chain CDR3 amino acid sequence corresponds to residues 99-112 of SEQ ID NO: 2. The amino acid sequences of the 1-4F1 CDRs have been identified as follows: the light chain CDR1 amino acid sequence corresponds to residues 24-34 of SEQ ID NO:3; the light chain CDR2 amino acid sequence corresponds to residues 50-56 of SEQ ID NO:3; the light chain CDR3 amino acid sequence corresponds to residues 89-97 of SEQ ID NO:3; the heavy chain CDR1 amino acid sequence corresponds to residues 31-35 of SEQ ID NO:4; the heavy chain CDR2 amino acid sequence corresponds to residues 50-66 of SEQ ID NO:4; and the heavy chain CDR3 amino acid sequence corresponds to residues 99-113 of SEQ ID NO:4.

Amino acid sequences for the entire 1-7F9 light and heavy chains are provided in SEQ ID NOS:5 and 6, respectively.

Accordingly, additional antibodies of, for example, various human antibody subclasses; antibody fragments, antibody derivatives, and other KIR-binding peptides, can be readily produced by, e.g., recombinant techniques, based upon this information. For example, in one aspect, the invention provides an antibody having a VL and a VH sequence consisting essentially of SEQ ID NO:1 and SEQ ID NO:2, respectively, and/or an antibody having a VL and a VH sequence consisting essentially of SEQ ID NO:3 and SEQ ID NO:4, respectively. In another aspect, the invention provides an antibody comprising CDR regions consisting essentially of the 1-7F9 or 1-4F1 VH CDR1-3 and VL CDR1-3 described above, or an antibody having light and heavy chains consisting essentially of the 1-7F9 light and heavy chains of SEQ ID NOS 5 and 6, respectively. In another aspect, the invention provides an antibody comprising CDR regions as follows: a light chain CDR1 amino acid sequence corresponding to about residues 24-34 of SEQ ID NO:1; the light chain CDR2 amino acid sequence corresponding to about residues 50-56 of SEQ ID NO:1; the light chain CDR3 amino acid sequence corresponding to about residues 89-97 of SEQ ID NO:1; the heavy chain CDR1 amino acid sequence corresponding to about residues 31-35 of SEQ ID NO:2; the heavy chain CDR2 amino acid sequence corresponding to about to residues 50-65 of SEQ ID NO:2; and the heavy chain CDR3 amino acid sequence corresponding to about residues 99-112 of SEQ ID NO:2. In another aspect, the invention provides an antibody comprising CDR regions as follows: a light chain CDR1 amino acid sequence corresponding to about residues 24-34 of SEQ ID NO:3; a light chain CDR2 amino acid sequence corresponding to about residues 50-56 of SEQ ID NO:3; a light chain CDR3 amino acid sequence corresponding to about residues 89-97 of SEQ ID NO:3; a heavy chain CDR1 amino acid sequence corresponding to about residues 31-35 of SEQ ID NO:4; a heavy chain CDR2 amino acid sequence corresponding to about residues 50-66 of SEQ ID NO:4; and a heavy chain CDR3 amino acid sequence corresponding to about residues 99-113 of SEQ ID NO:4. In another aspect, the invention provides an antibody comprising a light chain CDR1 amino acid sequence consisting essentially of residues 24-34 of SEQ ID NO:1; a light chain CDR2 amino acid sequence consisting essentially of residues 50-56 of SEQ ID NO:1; a light chain CDR3 amino acid sequence consisting essentially of residues 89-97 of SEQ ID NO:1; a heavy chain CDR1 amino acid sequence consisting essentially of residues 31-35 of SEQ ID NO:2; a heavy chain CDR2 amino acid sequence consisting essentially of residues 50-65 of SEQ ID NO:2; and a heavy chain CDR3 amino acid sequence consisting essentially of residues 99-112 of SEQ ID NO:2. In another aspect, the invention provides an antibody comprising CDR regions as follows: a light chain CDR1 amino acid sequence consisting essentially of residues 24-34 of SEQ ID NO:3; a light chain CDR2 amino acid sequence consisting essentially of residues 50-56 of SEQ ID NO:3; a light chain CDR3 amino acid sequence consisting essentially of residues 89-97 of SEQ ID NO:3; a heavy chain CDR1 amino acid sequence consisting essentially of residues 31-35 of SEQ ID NO:4; a heavy chain CDR2 amino acid sequence consisting essentially of residues 50-66 of SEQ ID NO:4; and a heavy chain CDR3 amino acid sequence consisting essentially of residues 99-113 of SEQ ID NO:4.

The invention also encompasses use of an anti-KIR antibody, antibody fragment, or antibody derivative, or a KIR-binding polypeptide, comprising at least one variant amino acid sequence substantially identical to the 1-7F9 or 1-4F1 VH or VL sequence, or to a CDR-region therein. A variant amino acid sequence can comprise or consist essentially of an amino acid sequence that is at least about 50, 80, 90, 95, 98, or 99 (e.g., about 50-99, about 65-99, about 75-99, or about 85-99) percent identical to a 1-7F9 or 1-4F1 CDR, VH, or VL region, or heavy or light chain sequence. An antibody can for example comprise 1-7F9 light and heavy chains each having a sequence that is at least about 50, 80, 90, 95, 98, or 99 (e.g., about 50-99, about 65-99, about 75-99, or about 85-99) percent identical to SEQ ID NOS:5 and 6, respectively. A variant amino acid sequence can for example comprise 1, 2, or 3 CDRs that comprise or consist of amino acid sequences that are at least about 80%, at least about 90%, or at least about 95% identical to 1-7F9 or 1-4F1 CDRs. A variant amino acid sequence can also or alternatively comprise 1, 2, or 3 CDRs that comprise or consist of amino acid sequences that are at least about 80%, at least about 90%, or at least about 95% identical to 1-7F9 or 1-4F1 CDRs. Thus, in one aspect, the invention provides a human antibody comprising a light chain CDR1 amino acid sequence at least about 80%, at least about 90%, or at least about 95% identical to residues 24-34 of SEQ ID NO:1 or SEQ ID NO:3; a light chain CDR2 amino acid sequence at least about 80%, at least about 90%, or at least about 95% identical to residues 50-56 of SEQ ID NO:1 or SEQ ID NO:3; a light chain CDR3 amino acid sequence at least about 80%, at least about 90%, or at least about 95% identical to residues 89-97 of SEQ ID NO:1 or SEQ ID NO:3; a heavy chain CDR1 amino acid sequence at least about 80%, at least about 90%, or at least about 95% identical to residues 31-35 of SEQ ID NO:2 or SEQ ID NO:4; a heavy chain CDR2 amino acid sequence at least about 80%, at least about 90%, or at least about 95% identical to residues 50-65 of SEQ ID NO:2 or to residues 50 to 66 of SEQ ID NO:4; and a heavy chain CDR3 amino acid sequence at least about 80%, at least about 90%, or at least about 95% identical to residues 99-112 of SEQ ID NO:2 or to residues 99 to 113 of SEQ ID NO:4. The basic properties of 1-7F9- or 1-4F1-derived KIR-binding amino acid sequences that are retained in such variant amino acid sequences desirably include the specificity and/or avidity of the 1-7F9 or 1-4F1 sequence for one or more KIRs, and may also or alternatively include the capability of 1-7F9 in blocking KIR/HLA-C interaction and potentiating the lytic activity of NK cells.

In another aspect, the invention provides use of an anti-KIR antibody, antibody fragment, or antibody derivative, or a KIR-binding polypeptide, that comprises a KIR-binding amino acid sequence that differs from a 1-7F9 or 1-4F1 KIR-binding sequence in one or more amino acid residues (e.g., at least 2, 3, 5, at least about 10, at least about 15, at least about 20, at least about 25, at least about 30, at least about 35, at least about 40, at least about 50, or more amino acid residues) by way of one or more residue insertions, deletions, and/or substitutions. Such a variant KIR-binding sequence confers greater affinity; greater or different specificity; less immunogenicity (in terms of host response to the sequence); greater in vivo stability; and/or other beneficial properties to the variant sequence over an essentially identical amino acid sequence comprising the native 1-7F9 or 1-4F1 sequence. Suitable sequence variations are further described elsewhere herein. A KIR-binding portion of an anti-KIR antibody, antibody fragment, or antibody derivative, or a KIR-binding polypeptide, can also comprise any suitable number of non-amino acid components or substituents, such as non-amino acid organic moieties, that facilitate KIR binding and/or provide other advantageous physiochemical or immunological properties.

As already mentioned, suitable sequence variants of antigen-binding antibody sequences, such as anti-KIR antibody sequences, can be incorporated into antibodies of the invention. Variations in most types of antibody sequence may be suitable. Thus, for example, an anti-KIR antibody can comprise variant constant sequences and/or variant framework sequences.

The invention provides an anti-KIR antibody that comprises one or more variant CDR sequences (i.e., a CDR sequence that differs from similar wild-type CDR sequence by one or more amino acid insertions, deletions, additions, and/or substitutions that impact the biological and/or physiochemical properties of the sequence with respect to its wild-type relative sequence). See e.g., techniques disclosed in WO 2006/072625. CDR, VH, and VL sequence variants can exhibit any suitable level of identity to one or more "parent" CDR, VH, and VL sequences, respectively, such as the CDR, VH, and VL sequences of anti-KIR mAb DF200 and/or anti-KIR mAb NKVSF1. Typically, a variant sequence that binds to an essentially identical antigenic determinant region as a parent will retain at least about 40% amino acid sequence identity to the parent sequence, such as about 50% or more, about 60% or more, about 70% or more, about 75% or more, about 80% or more, about 85% or more, about 90% or more, or at least about 95% (e.g., about 45-99%, about 55-99%, or about 65-99%) identity to the parent sequence. However, in some cases, particularly with respect to CDR sequences targeted to an essentially identical epitope, variants with even lower levels of identity can be suitable.

CDR, VH, and VL sequence variants that bind to different antigenic determinant regions or a different set (or "profile") of antigenic determinant regions also can be generated by any of the techniques described elsewhere herein (rational design, mutagenesis, directed evolution). In such instances, significantly lower levels of amino acid sequence identity to a parent sequence can be expected. For example, in the context of a CDR-L1, CDR-H1, CDR-H2, or CDR H3 variant having a different epitope binding profile from a parent sequence, as little as about 20-30% amino acid sequence identity to a parent CDR sequence may be exhibited in variants that contribute to binding of NKCAMRs, such as KIRs.

WO 2006/072625 further provides variants of anti-KIR antibody sequences, including specific formulae for CDR and variable region sequences, the disclosures of which are incorporated herein by reference.

Typically, variants differ from "parent" sequences mostly through conservative substitutions; e.g., at least about 35%, about 50% or more, about 60% or more, about 70% or more, about 75% or more, about 80% or more, about 85% or more, about 90% or more, about 95% or more (e.g., about 65-99%) of the substitutions in the variant are conservative amino acid residue replacements. In the context of this invention, conservative substitutions can be defined by substitutions within the classes of amino acids reflected in one or more of tables 4, 5 and 6 of WO 2006/072625 (Novo Nordisk AS and Innate Pharma SA). WO 2006/072625 also describes additional conservative substitutions groupings; making substantial changes in function by selecting substitutions that are less conservative; principles useful in the design and selection of peptide variants; conservation in terms of hydropathic/hydrophilic properties; maintaining a structure of the variant peptide substantially similar to the structure of the parent peptide, including methods for assessing similarity of peptides in terms of conservative substitutions, hydropathic properties, weight conservation, secondary structure comparisons or similarity score, as determined by use of a BLAST program; other points of variation/divergence between a variant and a parent can be acceptable; advantageous sequence changes in CDRs; sequence variations that result in an altered glycosylation; hypervariable region insertions and to generate a variant antibody and more generally, CDR variants.

Identity in the context of amino acid sequences of the invention can be determined by any suitable technique, typically by a Needleman-Wunsch alignment analysis (See Needleman and Wunsch, *J. Mol. Biol*. (1970) 48:443-453), such as is provided via analysis with ALIGN 2.0 using the BLOSUM50 scoring matrix with an initial gap penalty of –12 and an extension penalty of –2 (See Myers and Miller, CABIOS (1989) 4:11-17 for discussion of the global alignment techniques incorporated in the ALIGN program). A copy of the ALIGN 2.0 program is available, e.g., through the San Diego Supercomputer (SDSC) Biology Workbench. Because Needleman-Wunsch alignment provides an overall or global identity measurement between two sequences, it should be recognized that target sequences which may be portions or subsequences of larger peptide sequences may be used in a manner analogous to complete sequences or, alternatively, local alignment values can be used to assess relationships between subsequences, as determined by, e.g., a Smith-Waterman alignment (*J. Mol. Biol*. (1981) 147:195-197), which can be obtained through available programs (other local alignment methods that may be suitable for analyzing identity include programs that apply heuristic local alignment algorithms such as FastA and BLAST programs). Further related methods for assessing identity are described in, e.g., International Patent Application WO 2003/048185. The Gotoh algorithm, which seeks to improve upon the Needleman-Wunsch algorithm, alternatively can be used for global sequence alignments. See, e.g., Gotoh, J. Mol. Biol. 162: 705-708 (1982).

The compounds including antibodies that inhibit a KIR2DL1, 2 and/or 3 polypeptide may be able to enhance elimination of T cells that may be actively contributing to inflammation, which makes these compounds including antibodies suited for use in both chronic settings and acute inflammation, as well as for use in combination with a second therapeutic agent used in inflammatory settings. In particular, the second therapeutic agent decreases inflammation, e.g., agents used in chronic and acute settings, such as disease modifying anti-rheumatic drugs (DMARDs), such as anti-TNFα and MTX, in the case of rheumatoid arthritis and other conditions where such drugs are used. Because mechanisms driving inflammation—particularly acute and chronic inflammation—are believed to often be redundant, the antibodies of the invention will be particularly useful for use in combination with agents that act on an inflammation mechanism other than direct killing (e.g., via ADCC) of T cells, but have a similar biological objective, such as the reduction of pro-inflammatory cytokine production or action, notably the reduction or inhibition of TNFα.

Production of Antibodies

Monoclonal antibodies in particular may be made using the hybridoma method first described by Kohler et al., Nature, 256:495 (1975), or by other well-known, subsequently-developed methods (See, e.g., Goding, Monoclonal Antibodies: Principles and Practice, pages 59-103 (Academic Press, 1986)). Hybridomas and other fusion cells may be formed by chemical fusion, electrical fusion, or any other suitable technique, with any suitable type of myelomas, heteromyelomas, phoblastoid cells, plasmacytomas or similar immortalized cell and any suitable type of antibody-expressing cell(s).

Transformed immortalized B cells also can be used to efficiently produce antibodies. Transformed B cells can be produced by standard techniques, such as transformation with an Epstein Barr Virus, or a transforming gene. (See, e.g., "Continuously Proliferating Human Cell Lines Synthesizing Antibody of Predetermined Specificity," Zurawaki, V. R. et al, in Monoclonal Antibodies, ed. by Kennett R. H. et al, Plenum Press, N.Y. 1980, pages 19-33). Thus, stable and continuous and/or immortalized anti-KIR2DL1, 2 and/or 3 antibody-expressing cells and cell lines are another feature of the invention. A step of a method for producing anti-KIR2DL1, 2 and/or 3 antibodies can include, for example, a step of producing immortalized B cells producing an antibody which are fused to appropriate partners to produce anti-KIR2DL1, 2 and/or 3 antibody (s) or which are sequenced and such sequences used to produce a recombinant anti-KIR2DL1, 2 and/or 3 antibody.

Cell lines available as hosts for recombinant protein expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Other cell lines that may be used are insect cell lines, such as Sf9 cells. When nucleic acids (or nucleic acid-containing vectors) encoding antibody genes are introduced into mammalian host cells, antibodies can be produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Antibodies may also be recovered from host cell lysates when directly expressed without a secretory signal.

The purification of antibodies from cell cultures, cell lysates, and transgenic animals or biological materials obtained therefrom (e.g., from the ascites fluid of a transgenic animal producing antibodies) can be achieved by application of any number of suitable techniques known in the art including, e.g., immunoaffinity column purification; sulfate precipitation; chromatofocusing; preparative SDS-PAGE, and the like.

Anti-KIR2DL1, 2 and/or 3 antibodies also can be produced in bacterial cells and eukaryotic unicellular microorganisms, such as yeast. Bacterial cell produced antibodies lack normal glycosylation and accordingly may be deficient in terms of ADCC functions and other aspects of the immune response that may otherwise be associated with essentially identical antibodies produced in mammalian cells and/or animals.

Suitable methods for purifying, screening and selection of antibodies can be used, including those described in WO 2006/072625. Screening and selection of anti-KIR2DL1, 2 and/or 3 antibodies can be accomplished by any suitable technique or combination of techniques. For example, a variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane, supra. The binding affinity of a monoclonal antibody can, for example, be determined by the Scatchard analysis of Munson et al., Anal. Biochem., 107:220 (1980).

Anti-KIR2DL1, 2 and/or 3 antibodies typically are screened for the ability to modulate NK cell activity, such as by inhibiting KIR2DL1, 2 and/or 3-mediated signals, promoting activation of NK cells through NK activating receptor-mediated signals. A number of NK cell assays have been developed that can be useful in such contexts including, for example, flow cytometric screening methods. See, e.g., McGinnes, et al. (1984) J Immunol Methods 80: 70-85. Methods relevant to culturing NK cells, assessing NK cells, and the like are known in the art. See, e.g., Campbell and Colonna, Natural Killer Cell Protocols (Methods in Molecular Biology Series vol. 121) (2000).

In the context of anti-KIR2DL1, 2, and/or 3 antibodies, NK cell neutralizing activity can be demonstrated by the capacity of an anti-KIR2DL1, 2 and/or 3 Antibody to reconstitute lysis of target cells by KIR2DL1, 2, and/or 3-positive NK cells. Anti-KIR2DL1, 2 and/or 3 antibody-associated NK cell modulation (e.g., KIR inhibition) can also be assessed by various cell based cytotoxicity assays. Redirected killing is one experimental system for determining the capacity of a NK-cell receptor to induce cytotoxicity. NK cells coated with antibody specific for a candidate receptor are assessed for their ability to kill target cells that express an Fc receptor to which the antibody binds. In another variant, the NK cell activity modulation associated with an anti-KIR antibody can be assessed in a cytokine-release assay. Other biological activities associated with various anti-KIR2DL1, 2 and/or 3 antibodies also can be used to evaluate anti-KIR2DL1, 2 and/or 3 antibodies.

Anti-KIR2DL1, 2 and/or 3 antibodies typically are used in and provided in a substantially pure form. A substantially pure molecule is a molecule that is the predominant species in the composition wherein it is found with respect to the class of molecules to which it belongs (e.g., a substantially pure antibody is the predominant protein species in the composition wherein it is found. A substantially pure species makes up at least about 50% of the type of molecule in the composition and typically will make up at least about 70%, at least about 80%, at least about 85%, at least about 90%, at least about 95%, or greater percentage of the species in the composition by weight. Commonly, a composition comprising a anti-KIR2DL1, 2 and/or 3 antibody will exhibit at least about 98%, 98%, or 99% homogeneity for the anti-KIR2DL1, 2 and/or 3 antibody in the context of all present peptide species in the composition or at least with respect to substantially active peptide species in the context of proposed use. For example, a peptide stabilizer/buffer such as an albumin may be intentionally included in a final pharmaceutical formulation, without impeding the activity of the anti-KIR2DL1, 2 and/or 3 antibodies, and, accordingly, may be excluded from such purity calculations. The presence of impurities that do not interfere with the fundamental activity also may be acceptable in the context of a substantially pure composition. Purity can be measured by methods appropriate for the given compound (e.g., chromatographic methods; agarose and/or polyacrylamide gel electrophoresis; HPLC analysis; etc.).

An isolated molecule refers to a molecule that is not associated with significant levels (e.g., more than about 1%, more than about 2%, more than about 3%, or more than about 5%) of any extraneous and undesirable biological molecules, such as non-anti-KIR2DL1, 2 and/or 3 antibody biological molecules contained within a cell, cell culture, chemical media, or animal in which the anti-KIR2DL1, 2 and/or 3 antibody was produced. An isolated molecule also refers to any molecule that has passed through such a stage of purity due to human intervention (whether automatic, manual, or both) for a significant amount of time (e.g., at least about 10 minutes, at least about 20 minutes, at least about one hour, or longer). In many of the various compositions provided by the invention, such as in a composition comprising one or more pharmaceutically acceptable carriers, a anti-KIR2DL1, 2 and/or 3 antibody can be present in relatively small amounts in terms of numbers of total molecular species in the composition (e.g., in the case of a composition comprising a large amount of a pharmaceutically acceptable carrier, stabilizer, and/or preservative). In some cases additional peptides, such as BSA, can be included in such a composition with a previously purified Anti-KIR2DL1, 2 and/or 3 antibody. However, provided that such additional constituents of the composition are acceptable for the intended application of the anti-KIR2DL1, 2 and/or 3 antibody, such a composition can still be described as comprising an isolated anti-KIR2DL1, 2 and/or 3 antibody. In other words, the term "isolated" is not meant to exclude artificial or synthetic mixtures with other compounds or materials, such as may form part of a pharmaceutically acceptable preparation.

Pharmaceutically Acceptable Carriers

An Anti-KIR2DL1, 2 and/or 3 antibody can be combined with one or more carriers (diluents, excipients, and the like) and/or adjuvants appropriate for one or more intended routes of administration to provide compositions that are pharmaceutically acceptable.

Anti-KIR2DL1, 2 and/or 3 antibodies may be, for example, admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and optionally further tabletted or encapsulated for conventional administration. Alternatively, an Anti-KIR2DL1, 2 and/or 3 antibody may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other carriers, adjuvants, and modes of administration are well known in the pharmaceutical arts. A carrier or diluent may include time delay material, such as glyceryl monostearate or glyceryl distearate alone or with a wax, or other functionally similar materials.

Pharmaceutically acceptable carriers generally include any and all suitable solvents, dispersion media, coatings, antibacterial and antifungal agents, isotonic and absorption delaying agents, and the like that are physiologically compatible with an anti-KIR2DL1, 2 and/or 3 antibody. Examples of pharmaceutically acceptable carriers include water, saline, phosphate buffered saline, dextrose, glycerol, ethanol, and the like, as well as combinations of any thereof. In many cases, it can be desirable to include isotonic agents, for example, sugars, polyalcohols such as mannitol, sorbitol, or sodium chloride in such a composition. Pharmaceutically acceptable substances such as wetting agents or minor amounts of auxiliary substances such as wetting agents or emulsifying agents, preservatives or buffers, which desirably can enhance the shelf life or effectiveness of the Anti-KIR antibody, related composition, or combination. Suitability for carriers and other components of pharmaceutical compositions is determined based on the lack of significant negative impact on the desired biological properties of the antibody.

Anti-KIR2DL1, 2 and/or 3 antibody compositions, related compositions, and combinations according to the invention may be in a variety of suitable forms. Such forms include, for example, liquid, semi-solid and solid dosage forms, such as liquid solutions (e.g., injectable and infusible solutions), dispersions or suspensions, emulsions, microemulsions, tablets, pills, powders, liposomes, dendrimers and other nanoparticles (see, e.g., Baek et al., Methods Enzymol. 2003; 362: 240-9; Nigavekar et al., Pharm Res. 2004 March; 21(3):476-83), microparticles, and suppositories. Formulations, salts are further described in WO2006/072625.

Typically, compositions in the form of injectable or infusible solutions, such as compositions similar to those used for passive immunization of humans with other antibodies, are used for delivery of anti-KIR2DL1, 2 and/or 3 antibodies of the invention. A typical mode for delivery of anti-KIR2DL1, 2 and/or 3 antibody compositions is by parenteral administration (e.g., intravenous, subcutaneous, intraperitoneal, and/or intramuscular administration). In one aspect, an anti-KIR2DL1, 2 and/or 3 antibody is administered to a human patient by intravenous infusion or injection.

A composition for pharmaceutical use also can include various diluents, fillers, salts, buffers, detergents (e.g., a non-ionic detergent, such as Tween-80), stabilizers (e.g., sugars or protein-free amino acids), preservatives, tissue fixatives, solubilizers, and/or other materials suitable for inclusion in a composition for pharmaceutical use. Examples of suitable components also are described in, e.g., Berge et al., J. Pharm. Sci., 6661), 1-19 (1977); Wang and Hanson, J. Parenteral. Sci. Tech: 42, S4-S6 (1988);U.S. Pat. Nos. 6,165,779 and 6,225,289. Such a pharmaceutical composition also can include preservatives, antioxidants, or other additives known to those of skill in the art. Additional pharmaceutically acceptable carriers are known in the art. See e.g. references in WO2006/072625.

KIR2DL1, KIR2DL2, and KIR2DL3 Polypeptides

The invention provides KIR2DL1, KIR2DL2, and KIR2DL3 polypeptides and compositions containing compounds that inhibit such polypeptides for use in treating or preventing autoimmune and inflammatory disorders. Exemplary KIR2DL1, KIR2DL2, and KIR2DL3 polypeptides are set forth in the amino acid sequences of SEQ ID NOs: 7, 8, 9, 10, 11, 12, 13, 14, 15, 16, 17, 18, 19, 20, 21, 22, 23, and 24. See Table 1.

Nucleic acids encoding KIR2DL1, KIR2DL2, and KIR2DL3 polypeptides may be modified using standard molecular biological techniques that result in variants polypeptides comprising at least one KIR2DL1, KIR2DL2, and KIR2DL3 including but not limited to deletions, additions and substitutions in the amino acid sequence, that retain the specific antigenicity of the KIR2DL1, KIR2DL2, and KIR2DL3 (e.g., the KIR2DL1, KIR2DL2, and KIR2DL3 polypeptides is bound by an anti-KIR2DL1, KIR2DL2, and KIR2DL3 antibody). Additionally, variant polypeptides comprising at least one KIR2DL1, KIR2DL2, and KIR2DL3 polypeptide may also retain the antigenicity of the KIR2DL1, KIR2DL2, and KIR2DL3 polypeptide (e.g., raise a specific immune response against the KIR2DL1, KIR2DL2, and KIR2DL3 polypeptide and variant KIR2DL1, KIR2DL2, and KIR2DL3 polypeptide, respectively, upon immunization in a subject). The KIR2DL1, KIR2DL2, and KIR2DL3 polypeptides may be formulated with a pharmaceutical carrier to manufacture an antigen composition useful as a "cancer vaccine" (e.g., a pharmaceutical composition that elicits a specific immune response against the KIR2DL1, KIR2DL2, and KIR2DL3 (e.g., the amino acid sequences of SEQ ID NOs: 7, 8, 9, 10, 11, 12, 13, 14, 15, 16, 17, 18, 19, 20, 21, 22, 23, and 24), that produces anti-KIRD2L1, 2, and/or 3 antibodies after immunization in a subject).

Polypeptide Derivatives and Analogs

It will be appreciated that polypeptides described herein may be degradation products, synthetic peptides or recombinant peptides as well as peptidomimetics, synthetic peptides, peptoids, and semipeptoids (e.g., peptide analogs, which may have, for example, modifications rendering the peptides more stable while in a body or more capable of penetrating into cells.) Modifications of the KIR2DL1, KIR2DL2, and KIR2DL3 polypeptides described herein include, but are not limited to N-terminus modification, C-terminus modification, peptide bond modification (e.g., $CH_2$—NH, $CH_2$—S, $CH_2$—S=O, O=C—NH, $CH_2$—O, $CH_2$—$CH_2$, S=C—NH, CH=CH or CF=CH), backbone modifications, and residue modification. Methods for preparing peptidomimetic compounds are well known in the art. Martin, (2010) Quantitative Drug Design: A Critical Introduction [$2^{nd}$ Ed.] CRC Press.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

Natural aromatic amino acids, Trp, Tyr and Phe, may be substituted by synthetic non-natural acid such as phenylglycine, TIC, naphthylelanine (Nol), ring-methylated derivatives of phenylalanine, halogenated derivatives of phenylalanine or o-methyl-tyrosine. In addition to the above, the polypeptides of the present invention may also include one or more modified amino acids or one or more non-amino acid monomers (e.g. fatty acids, complex carbohydrates), for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Since the polypeptides of the present invention are preferably utilized in therapeutics which requires the peptides to be in soluble form, the polypeptides of the present invention may comprise one or more non-natural or natural polar amino acids, including but not limited to serine and threonine which are capable of increasing peptide solubility due to their hydroxyl-containing side chain.

The polypeptides of the present invention may be in a linear form, although it will be appreciated that in cases may also be utilized.

The KIR2DL1, KIR2DL2, and KIR2DL3 polypeptides described herein may be purified from cells that have been altered to express it (e.g., recombinant). DNA sequences encoding the KIR2DL1, KIR2DL2, and KIR2DL3 polypeptides may be inserted into an expression vector and then transformed (or transfected) in an appropriate host cell and/or expressed in a transgenic animal. The KIR2DL1, KIR2DL2, and KIR2DL3 polypeptides (e.g., the amino acid sequences of SEQ ID NOs: 7, 8, 9, 10, 11, 12, 13, 14, 15, 16, 17, 18, 19, 20, 21, 22, 23, and 24) so expressed may then be isolated by methods known in the art. See, e.g., Maniatis, et al. (2001) Molecular Cloning: A Laboratory Manual [$3^{rd}$ Ed.] Cold Spring Harbor Laboratory Press.

The polypeptides of the present invention may be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry. Solid phase peptide synthesis procedures are well known in the art and further described by Stewart (1984) Solid Phase Peptide Syntheses [$2^{nd}$ Ed.] Pierce Chemical Company and Benoiton (2005) Chemistry of Peptide Synthesis CRC Press. Synthetic peptides may be purified by preparative high performance liquid chromatography and the composition of which may be confirmed via amino acid sequencing. See Creighton (1992) [$2^{nd}$ Ed.] Proteins, Structures and Molecular Principles W.H. Freeman and Company; Aguilar (2004) [Ed.] HPLC of Peptides and Proteins: Methods and Protocols Humana Press; Simpson (2002) Protein Sequencing Protocols [$2^{nd}$ Ed.] Humana Press.

In cases where large amounts of the polypeptides of the present invention are desired, the polypeptides of the present invention may be generated using recombinant techniques such as described by Invitrogen (2002) "Guide to Baculovirus Expression Vector Systems (BEVs) and Insect Culture Techniques" Instruction Manual; Hatti-Kaul and Mattiasson (2003) [Eds] Isolation and Purification of Proteins; Ahmed (2004) Principles and Reactions of Protein Extraction, Purification and Characterization CRC Press. Further recombinant techniques such as described by, for example, Bitter, et al. (1987) Methods in Enzymol. 153: 516-544, Studier, et al. (1990) Methods in Enzymol. 185: 60-89, Brisson, et al. (1984) Nature 310: 511-514, Takamatsu, et al. (1987) EMBO J. 6: 307-311, Coruzzi, et al. (1984) EMBO J. 3: 1671-1680 and Brogli, et al. (1984) Science 224: 838-843, Gurley, et al. (1986) Mol. Cell. Biol. 6: 559-565 and Weissbach & Weissbach (1988) Methods for Plant Molecular Biology, Academic Press, NY, Section VIII, pages 421-463.

Polypeptide Sequence Variants

For any KIR2DL1, KIR2DL2, and KIR2DL3 sequence of the amino acid sequences of SEQ ID NOs: 7, 8, 9, 10, 11, 12, 13, 14, 15, 16, 17, 18, 19, 20, 21, 22, 23, and 24, further characterization or optimization may be achieved by systematically either adding or removing amino acid residues to generate longer or shorter peptides, and testing those and sequences generated by walking a window of the longer or shorter size up or down the antigen from that point. Coupling this approach to generating new candidate targets with testing for effectiveness of antigenic molecules based on those sequences in an immunogenicity assay, as known in the art or as described herein, may lead to further manipulation of the antigen. Further still, such optimized sequences may be adjusted by, e.g., the addition, deletions, or other mutations as known in the art and/or discussed herein to further optimize the KIR2DL1, KIR2DL2, and KIR2DL3 (e.g., increasing serum stability or circulating half-life, increasing thermal stability, enhancing delivery, enhance immunogenicity, increasing solubility, targeting to a particular in vivo location or cell type).

The KIR2DL1, KIR2DL2, and KIR2DL3 polypeptides described herein may comprise conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid.

KIR2DL1, KIR2DL2, and KIR2DL3 polypeptide sequences may have at least about 60, 65, 70, 75, 80, 81, 82, 83, 84, 85, 86, 87, 88, 89, 90, 91, 92, 93, 94, 95, 96, 97, 98, 99, or 100% sequence homology to any one or more of the amino acid sequences of SEQ ID NOs: 7, 8, 9, 10, 11, 12, 13, 14, 15, 16, 17, 18, 19, 20, 21, 22, 23, and 24. More preferably, the invention contemplates polypeptide sequences having at least about 95% sequence homology, even more preferably at least about 98% sequence homology, and still more preferably at least about 99% sequence homology to any one or more of the polypeptide sequences of KIR2DL1, KIR2DL2, and KIR2DL3 polypeptide sequences of the amino acid sequences of SEQ ID NOs: 7, 8, 9, 10, 11, 12, 13, 14, 15, 16, 17, 18, 19, 20, 21, 22, 23, and 24. Methods for determining homology between amino acid sequences, as well as nucleic acid sequences, are well known to those of ordinary skill in the art. See, e.g., Nedelkov & Nelson (2006) New and Emerging Proteomic Techniques Humana Press.

Thus, a KIR2DL1, KIR2DL2, and KIR2DL3 polypeptide may have at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with a polypeptide sequence. For example, a KIR2DL1, KIR2DL2, and KIR2DL3 polypeptide may have at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with the amino acid sequences of SEQ ID NOs: 7, 8, 9, 10, 11, 12, 13, 14, 15, 16, 17, 18, 19, 20, 21, 22, 23, and 24.

The term homology, or identity, is understood as meaning the number of agreeing amino acids (identity) with other proteins, expressed in percent. The identity is preferably determined by comparing a given sequence with other proteins with the aid of computer programs. If sequences which are compared with each other are different in length, the identity is to be determined in such a way that the number of amino acids which the short sequence shares with the longer sequence determines the percentage identity. The identity can be determined routinely by means of known computer programs which are publicly available such as, for example, ClustalW. Thompson, et al. (1994) Nucleic Acids Research 22: 4673-4680. ClustalW is publicly available from the European Molecular Biology Laboratory and may be downloaded from various interne pages, inter alia the IGBMC (Institut de Génétique et de Biologie Moléculaire et Cellulaire) and the EBI and all mirrored EBI internet pages (European Bioinformatics Institute). If the ClustalW computer program Version 1.8 is used to determine the identity between, for example, the reference protein of the present application and other proteins, the following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP. See also European Bioinformatics Institute (EBI) toolbox available on-line and Smith (2002) Protein Sequencing Protocols [$2^{nd}$ Ed.] Humana Press.

One possibility of finding similar sequences is to carry out sequence database researches. Here, one or more sequences may be entered as what is known as a query. This query sequence is then compared with sequences present in the selected databases using statistical computer programs. Such database queries (blast searches) are known to the skilled worker and may be carried out at different suppliers. If, for example, such a database query is carried out at the NCBI (National Center for Biotechnology Information), the standard settings for the respective comparison query should be used. For protein sequence comparisons (blastp), these settings are: Limit entrez=not activated; Filter=low complexity activated; Expect value=10; word size=3; Matrix=BLOSUM62; Gap costs: Existence=11, Extension=1. The result of such a query is, among other parameters, the degree of identity between the query sequence and the similar sequences found in the databases.

KIR2DL1, KIR2DL2, and KIR2DL3 polypeptides include functional fragments of said polypeptides. A "functional fragment" of said polypeptide includes a fragment of the gene or cDNA encoding said KIR2DL1, KIR2DL2, and KIR2DL3, which fragment is capable of eliciting an immune response (e.g., humoral or cellular immune response.) Thus, for example, fragments of the KIR2DL1, KIR2DL2, and KIR2DL3 according to the invention which correspond to amino acid residues that contribute to the immunogenicity of the antigen and which fragments may serve to function as antigens to elicit an immune response (e.g., humoral or cellular immune response.) This aspect of the invention also includes differentially spliced isoforms and transcriptional starts of the polypeptides according to the invention. The polypeptides according to the invention also may comprise fragments, derivatives and allelic variants of the KIR2DL1, KIR2DL2, and KIR2DL3 s. Methods and materials for making fragments of KIR2DL1, KIR2DL2, and KIR2DL3 polypeptides are well known in the art. See, e.g., Maniatis, et al. (2001) Molecular Cloning: A Laboratory Manual [$3^{rd}$ Ed.] Cold Spring Harbor Laboratory Press.

Variant KIR2DL1, KIR2DL2, and KIR2DL3 polypeptides may retain their antigenic specificity to bind their respective antibodies (e.g., a variant KIR2DL1, KIR2DL2, or KIR2DL3 polypeptide will be bound by an anti-KIR2DL1, KIR2DL2, or KIR2DL3 antibody.) Fully antigenic variants may contain only conservative variations or variations in non-critical residues or in non-critical regions. Antigenic variants may also contain substitution of similar amino acids that result in no change or an insignificant change in antigenicity. Alternatively, such substitutions may positively or negatively affect antigenicity to some degree. Non-antigenic variants typically contain one or more non-conservative amino acid substitutions, deletions, insertions, inversions, or truncation or a substitution, insertion, inversion, or deletion in a critical residue or critical region of an epitope. Molecular biology and biochemistry techniques for modifying KIR2DL1, KIR2DL2, and KIR2DL3 polypeptides while preserving specific antigenicity of the polypeptides for their respective antibodies are well known in the art. See, e.g., Ho, et al. (1989) Gene 77(1): 51-59; Landt, et al. (1990) Gene 96(1): 125-128; Hopp & Woods (1991) Proc. Natl. Acad. Sci. USA 78(6): 3824-3828; Kolaskar & Tongaonkar (1990) FEBS Letters 276(1-2): 172-174; and Welling, et al. (1985) FEBS Letters 188(2): 215-218.

Variants of the KIR2DL1, KIR2DL2, and KIR2DL3 polypeptides which function as either KIR2DL1, KIR2DL2, or KIR2DL3 agonists (mimetics) or as KIR2DL1, KIR2DL2, or KIR2DL3 antagonists. Variants of the KIR2DL1, KIR2DL2, and KIR2DL3 polypeptides can be generated by mutagenesis, e.g., discrete point mutation or truncation of a KIR2DL1, KIR2DL2, and KIR2DL3 polypeptide. An agonist of the KIR2DL1, KIR2DL2, and KIR2DL3 polypeptides can retain substantially the same, or a subset, of the biological activities of the naturally occurring form of a KIR2DL1, KIR2DL2, and KIR2DL3 polypeptide. An antagonist of a KIR2DL1, KIR2DL2, and KIR2DL3 polypeptide can inhibit one or more of the activities of the naturally occurring form of the KIR2DL1, KIR2DL2, and KIR2DL3 polypeptide by, for example, competitively modulating a KIR2DL1, KIR2DL2, and KIR2DL3-mediated activity of a KIR2DL1, KIR2DL2, and KIR2DL3 polypeptide. Thus, specific biological effects can be elicited by treatment with a variant of limited function. For example, a subject may be treated with a variant having a subset of the biological activities of the naturally occurring form of the polypeptide has fewer side effects in a subject relative to treatment with the naturally occurring form of the KIR2DL1, KIR2DL2, and KIR2DL3 polypeptide.

Variants of a KIR2DL1, KIR2DL2, and KIR2DL3 polypeptide which function as either KIR2DL1, KIR2DL2, and KIR2DL3 agonists (mimetics) or as KIR2DL1, KIR2DL2, and KIR2DL3 antagonists may be identified by screening combinatorial libraries of mutants, e.g., truncation mutants, of a KIR2DL1, KIR2DL2, and KIR2DL3 polypeptide for KIR2DL1, KIR2DL2, and KIR2DL3 polypeptide agonist or antagonist activity.

Peptidomimetics

In addition to KIR2DL1, KIR2DL2, and KIR2DL3 polypeptides consisting only of naturally-occurring amino acids, KIR2DL1, KIR2DL2, and KIR2DL3 peptidomimetics are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere (1986) Adv. Drug Res. 15: 29; Advances in Amino Acid Mimetics and Peptidomimetics (Volume 2) Andrew Abell (Ed.) (1999) JAI Press, Inc. and Evans et al. (1987) J. Med. Chem 30: 1229) and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as human or mouse KIR2DL1, KIR2DL2, and KIR2DL3, but have one or more peptide linkages optionally replaced by a linkage selected from the group consisting of: —$CH_2NH$—, —$CH_2S$—, —$CH_2$—$CH_2$-, —CH=CH— (cis and trans), —$COCH_2$—, —$CH(OH)CH_2$—, and —$CH_2SO$—, by methods known in the art and further described in the following references: Spatola in Chemistry and Biochemistry of Amino Acids, Peptides, and Proteins Weinstein, B., ed., Marcel Dekker, New York, p. 267 (1983); Spatola, Vega Data (March 1983), Vol. 1, Issue 3, "Peptide Backbone Modifications"; Morley (1980) Trends. Pharm. Sci. pp. 463-468; Hudson, et al. (1979) Int. J. Pept. Prot. Res. 14:177-185 (—$CH_2NH$—, $CH_2CH_2$—); Spatola, et al. (1986) Life. Sci. 38:1243-1249 (—$CH_2$—S); Hann, (1982) J. Chem. SoC Perkin. Trans. I 307-314 (—CH—CH—, cis and trans); Almquist, et al. (1980) J. Med. Chem. 23:1392-1398

(—COCH₂—); Jennings-White, et al. (1982) Tetrahedron Lett. 23:2533 (—COCH₂—); (—CH(OH)CH₂—); Holladay, et al. (1983) Tetrahedron. Lett. 24:4401-4404 (—C(OH) CH₂—); and Hruby (1982) Life Sci. 31:189-199 (—CH₂—S—). A particularly preferred non-peptide linkage is —CH₂NH—. Such peptide mimetics may have significant advantages over polypeptide embodiments, including, for example: more economical production, greater chemical stability, enhanced pharmacological properties (half-life, absorption, potency, efficacy), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labeling) of peptidomimetics should not substantially interfere with the desired biological or pharmacological activity of the peptidomimetic.

Systematic substitution of one or more amino acids of a KIR2DL1, KIR2DL2, and KIR2DL3 amino acid sequence with a D-amino acid of the same type (e.g., D-lysine in place of L-lysine) can be used to generate more stable peptides. In addition, constrained peptides comprising a KIR2DL1, KIR2DL2, and KIR2DL3 amino acid sequence or a substantially identical sequence variation can be generated by methods known in the art (Rizo and Gierasch (1992) Annu. Rev. Biochem. 61:387); for example, by adding internal cysteine residues capable of forming intramolecular disulfide bridges which cyclize the peptide. The amino acid sequences of the KIR2DL1, KIR2DL2, and KIR2DL3 polypeptides identified herein will enable those of skill in the art to produce polypeptides corresponding to KIR2DL1, KIR2DL2, and KIR2DL3 peptide sequences and sequence variants thereof. Such polypeptides can be produced in prokaryotic or eukaryotic host cells by expression of polynucleotides encoding a KIR2DL1, KIR2DL2, and KIR2DL3 peptide sequence, frequently as part of a larger polypeptide. Alternatively, such peptides can be synthesized by chemical methods. Methods for expression of heterologous polypeptides in recombinant hosts, chemical synthesis of polypeptides, and in vitro translation are well known in the art. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides can be used therapeutically to treat disease, e.g., by altering costimulation in a patient.

Amino acids that are essential for function may be identified by methods known in the art, such as site-directed mutagenesis or alanine-scanning mutagenesis. Cunningham, et al. (1989) Sci. 244: 1081-85. The latter procedure introduces single alanine mutations at every residue in the molecule. The resulting mutant molecules are then tested for biological activity such as epitope binding or in vitro ADCC activity. Sites that are critical for ligand-receptor binding may also be determined by structural analysis such as crystallography, nuclear magnetic resonance, or photoaffinity labeling. Smith, et al. (1992) J. Mol. Biol. 224: 899-904; de Vos, et al. (1992) Sci. 255: 306-12.

For example, one class of substitutions is conserved amino acid substitutions. Such substitutions are those that substitute a given amino acid in a KIR2DL1, KIR2DL2, and KIR2DL3 polypeptide with another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr. Guidance concerning which amino acid changes are likely to be phenotypically silent is found in, for example, Bowie, et al. (1990) Sci. 247: 1306-10. Hence, one of ordinary skill in the art appreciates that the inventors possess peptide variants without delineation of all the specific variants. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. See, e.g., Creighton (1992) Proteins: Structures and Molecular Properties [$2^{nd}$ Ed.] W.H. Freeman.

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, g-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See Creighton (1992) Proteins: Structure and Molecular Properties [$2^{nd}$ Ed.] and Lundblad (1995) Techniques in Protein Modification [$1^{st}$ Ed.] Many detailed reviews are available on this subject. See, e.g., Wold (1983) Posttranslational Covalent Modification of Proteins Acad. Press, NY; Seifter, et al. (1990) Meth. Enzymol. 182: 626-46; and Rattan, et al. (1992) Ann. NY Acad. Sci. 663: 48-62.

Fragments

A biologically active portion of a KIR2DL1, KIR2DL2, and KIR2DL3 polypeptide includes a fragment of a KIR2DL1, KIR2DL2, and KIR2DL3 polypeptide which participates in an interaction between a KIR2DL1, KIR2DL2, and KIR2DL3 molecule and a non-KIR2DL1, KIR2DL2, and KIR2DL3 molecule, e.g., a natural ligand of KIR2DL1, KIR2DL2, and KIR2DL3. Biologically active portions of a KIR2DL1, KIR2DL2, and KIR2DL3 polypeptide include peptides comprising amino acid sequences sufficiently identical to or derived from the amino acid sequence of the KIR2DL1, KIR2DL2, and KIR2DL3 polypeptide, e.g., the amino acid sequence shown in SEQ ID NO: 2, 4 or 5, which include fewer amino acids than the full length KIR2DL1, KIR2DL2, and KIR2DL3 polypeptides, and exhibit at least one activity of a KIR2DL1, KIR2DL2, and KIR2DL3 polypeptide. Typically, biologically active portions comprise a domain or motif with at least one activity of the KIR2DL1, KIR2DL2, and KIR2DL3 polypeptide, e.g., modulating (suppressing) CD4 T cell proliferative responses to anti-CD3, suppression of the proliferative response of cognate CD4 T cells in an antigen specific manner, effects on the expression of specific cytokines. A biologically active portion of a KIR2DL1, KIR2DL2, and KIR2DL3 polypeptide can be a polypeptide which is, for example, 25, 50, 75, 100, 125, 150, 175, 200, 225 or more amino acids in length of the amino acid sequences of SEQ ID NOs: 7, 8, 9, 10, 11, 12, 13, 14, 15, 16, 17, 18, 19, 20, 21, 22, 23, or 24. Biologically active portions of a KIR2DL1, KIR2DL2, and KIR2DL3 polypeptide can be used as targets for developing agents which modulate a KIR2DL1, KIR2DL2, and KIR2DL3-mediated activity, e.g., immune cell activation.

A biologically active portion of a KIR2DL1, KIR2DL2, and KIR2DL3 polypeptide may comprise at least a portion of an extracellular domain. A biologically active portion of a KIR2DL1, KIR2DL2, and KIR2DL3 polypeptide may contain at least a portion of an extracellular domain and one or more of the following domains: a signal peptide domain, a transmembrane domain, and a cytoplasmic domain. Moreover, other biologically active portions, in which other regions of the polypeptide are deleted, can be prepared by recombinant techniques and evaluated for one or more of the functional activities of a native KIR2DL1, KIR2DL2, and KIR2DL3 polypeptide.

The KIR2DL1, KIR2DL2, and KIR2DL3 polypeptide may have the amino acid sequence shown in the amino acid sequences of SEQ ID NOs: 7, 8, 9, 10, 11, 12, 13, 14, 15, 16, 17, 18, 19, 20, 21, 22, 23, and 24. The KIR2DL1, KIR2DL2, and KIR2DL3 polypeptide may be substantially identical to the amino acid sequences of SEQ ID NOs: 7, 8, 9, 10, 11, 12, 13, 14, 15, 16, 17, 18, 19, 20, 21, 22, 23, and 24, and retains the functional activity of the polypeptide of the amino acid sequences of SEQ ID NOs: 7, 8, 9, 10, 11, 12, 13, 14, 15, 16, 17, 18, 19, 20, 21, 22, 23, and 24, yet differs in amino acid sequence due to natural allelic variation or mutagenesis, as described herein.

Fusion Proteins

Fusions comprising the KIR2DL1, KIR2DL2, and KIR2DL3 polypeptides are also within the scope of the present invention. For example, the fusion protein may be linked to a GST fusion protein in which the KIR2DL1, KIR2DL2, and KIR2DL3 polypeptide sequences are fused to the C-terminus of the GST sequences. Such fusion proteins may facilitate the purification of the recombinant KIR2DL1, KIR2DL2, and KIR2DL3 polypeptides. Alternatively, KIR2DL1, KIR2DL2, and KIR2DL3 polypeptides may be fused with a protein that binds B-cell follicles, thus initiating both a humoral immune response and activation of T cells. Berney, et al. (1999) J. Exp. Med. 190: 851-60. Alternatively, for example, the KIR2DL1, KIR2DL2, and KIR2DL3 polypeptides may be genetically coupled with and anti-dendritic cell antibody to deliver the antigen to the immune system and stimulate a cellular immune response. He, et al. (2004) Clin. Cancer Res. 10: 1920-27. A chimeric or fusion protein of the invention may be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene may be synthesized by conventional techniques including automated DNA synthesizers.

Fusion proteins may include C-terminal or N-terminal translocation sequences. Further, fusion proteins can comprise additional elements, e.g., for protein detection, purification, or other applications. Detection and purification facilitating domains including but not limited to metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAG extension/affinity purification system (Sigma-Aldrich, St. Louis Mo.)

A fusion protein may be prepared from a protein of the invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises CH2 and CH3 domains. Although any IgG subtype may optionally be used, the IgG1 subtype is preferred. The Fc chain may optionally be a known or "wild type" Fc chain, or alternatively may be mutated. See, e.g., U.S. Patent Application Publication No. 2006/0034852. The term "Fc chain" also optionally comprises any type of Fc fragment. Several of the specific amino acid residues that are involved in antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect. See McCafferty, et al. (2002) Antibody Engineering: A Practical Approach (Eds.) Oxford University Press.

The inclusion of a cleavable linker sequences such as Factor Xa (See, e.g., Ottavi, (1998) Biochimie 80: 289-93), subtilisin protease recognition motif (See, e.g., Polyak (1997) Protein Eng. 10: 615-19); enterokinase (Invitrogen, San Diego, Calif.), between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (See, e.g., Williams (1995) Biochemistry 34: 1787-97), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature. See, e.g., Kroll (1993) DNA Cell. Biol. 12: 441-53.

A fusion protein may be a GST-KIR2DL1, KIR2DL2, and KIR2DL3 fusion protein in which the KIR2DL1, KIR2DL2, and KIR2DL3 sequences are fused to the C-terminus of the GST sequences. Such fusion proteins can facilitate the purification of recombinant KIR2DL1, KIR2DL2, and KIR2DL3. In another embodiment, the fusion protein is a KIR2DL1, KIR2DL2, and KIR2DL3 polypeptide containing a heterologous signal sequence at its N-terminus. In certain host cells (e.g., mammalian host cells), expression and/or secretion of KIR2DL1, KIR2DL2, and KIR2DL3 can be increased through use of a heterologous signal sequence. In an embodiment, the fusion protein is an Ig-KIR2DL1, KIR2DL2, and KIR2DL3 fusion protein in which the KIR2DL1, KIR2DL2, and KIR2DL3 sequences are fused to a portion of an Ig molecule. The Ig portion of the fusion protein can include and immunoglobulin constant region, e.g., a human Cgamma1 domain or a C gamma4 domain (e.g., the hinge, CH2, and CH3 regions of human IgC gamma1 or human IgC gamma4 (See, e.g., U.S. Pat. Nos. 5,116,964; 5,580,756; 5,844,095). A resulting fusion protein may have altered KIR2DL1, KIR2DL2, and KIR2DL3 solubility, binding affinity, stability and/or valency (i.e., the number of binding sites per molecule) and may increase the efficiency of protein purification.

Particularly preferred KIR2DL1, KIR2DL2, and KIR2DL3 Ig fusion proteins include an extracellular domain portion of KIR2DL1, KIR2DL2, and KIR2DL3 coupled to an immunoglobulin constant region (e.g., the Fc region). The immunoglobulin constant region may contain genetic modifications which reduce or eliminate effector activity inherent in the immunoglobulin structure. For example, DNA encoding an extracellular portion of a KIR2DL1, KIR2DL2, and KIR2DL3 polypeptide can be joined to DNA encoding the hinge, CH2, and CH3 regions of human IgG gamma1 and/or IgG gamma4 modified by site-directed mutagenesis, e.g., as taught in WO 97/28267. The KIR2DL1, KIR2DL2, and KIR2DL3 fusion proteins of the invention can be incorporated into pharmaceutical compositions and administered to a subject in vivo. The KIR2DL1, KIR2DL2, and KIR2DL3 fusion proteins can be used to affect the bioavailability of a KIR2DL1, KIR2DL2, and KIR2DL3 binding partner. Use of KIR2DL1, KIR2DL2, and KIR2DL3 fusion proteins may be useful therapeutically for the treatment of conditions or disorders that would benefit from modulation of the immune response. Moreover, the KIR2DL1, KIR2DL2, and KIR2DL3-fusion proteins of the invention can be used as immunogens to produce anti-KIR2DL1, KIR2DL2, and KIR2DL3 antibodies in a subject, to purify KIR2DL1, KIR2DL2, and KIR2DL3-binding proteins, and in screening assays to identify molecules which inhibit the interaction of KIR2DL1, KIR2DL2, and KIR2DL3 with its natural binding partner.

Conjugates

The KIR2DL1, KIR2DL2, and KIR2DL3 polypeptides may be conjugated to other moieties. Such conjugates are often used in the preparation of vaccines. The KIR2DL1, KIR2DL2, and KIR2DL3 polypeptide may be conjugated to a carbohydrate (e.g., mannose, fucose, glucose, GlcNAs, maltose), which is recognized by the mannose receptor present on dendritic cells and macrophages. The ensuing binding, aggregation, and receptor-mediated endocytosis and phagocytosis functions provide enhanced innate and adaptive immunity. See Mahnke, et al. (2000) J. Cell Biol. 151: 673-84; Dong, et al. (1999) J. Immonol. 163: 5427-34. Other moieties suitable for conjugation to elicit an immune response includes but not limited to Keyhole Limpit Hemocyannin (KLH), diphtheria toxoid, cholera toxoid, *Pseudomonas* exoprotein A, and microbial outer membrane proteins (OMPS).

Polypeptide Isolation

The present invention also provides methods for isolation of the KIR2DL1, KIR2DL2, and KIR2DL3 polypeptides (e.g., the amino acid sequences of SEQ ID NOs: 7, 8, 9, 10, 11, 12, 13, 14, 15, 16, 17, 18, 19, 20, 21, 22, 23, and 24). For example, relevant cell lines may be obtained from a patient suffering from an autoimmune or inflammatory disorder. After homogenization and solubilization in a detergent, the antigen is chromatographically purified. Size-exclusion or affinity chromatography may be used for this, and may be used in conjunction with anti-KIR2DL1, KIR2DL2, and KIR2DL3 antibodies. For example, anti-KIR2DL1, KIR2DL2, and KIR2DL3 antibody may be immobilized on a solid support (e.g., coupled to resins, magnetic beads) for simple antigen adsorption, washing, and elution from the solid support. The eluted protein is then studied further for antigen presence, characterization, and identification. See Walker (2002) Protein Protocols Handbook [$2^{nd}$ Ed.] Humana Press and Culture (2003) [Ed.] Protein Purification Protocols Humana Press.

The antigen isolated in this way may be used for preparing a pharmaceutical using the conventional pharmaceutical excipient and carrier substance. For example, in-vivo administration of the purified antigen in a physiological NaCl solution.

Additionally, the KIR2DL1, KIR2DL2, and KIR2DL3 polypeptides according to the invention may serve as an antigen in the identification of activities as part of a high-throughput screening. High-throughput screening methods are known to persons skilled in the art. Wells (2002) High Throughout Bioanalytical Sample Preparation Elsevier Health Sciences.

Polynucleotides Encoding KIR2DL1, KIR2DL2, and KIR2DL3

The present invention also provides nucleotides which encode KIR2DL1, KIR2DL2, and KIR2DL3 s. The present invention also provides polynucleotides that encode KIR2DL1, KIR2DL2, and KIR2DL3 polypeptides of the amino acid sequences of SEQ ID NOs: 7, 8, 9, 10, 11, 12, 13, 14, 15, 16, 17, 18, 19, 20, 21, 22, 23, and 24. The present invention also provides for fragments, sequences hybridizable with, and sequences homologous to the polynucleotide sequences described herein which are at least about 80%, 81%, 82%, 83%, 84%, 85%, 86%, 87%, 88%, 89%, 90%, 91%, 92%, 93%, 94%, 95%, 96%, 97%, 98%, 99% or 100%.

The invention also provides polynucleotides comprising at least one KIR2DL1, KIR2DL2, and KIR2DL3 sequence encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (e.g., which form a part of a polynucleotide sequence of the present invention), which include sequence regions unique to the polynucleotides of the present invention.

The present invention also encompasses nucleic acids encoding homologues of KIR2DL1, KIR2DL2, and KIR2DL3 polypeptides, such homologues can be at least about 80%, 81%, 82%, 83%, 84%, 85%, 86%, 87%, 88%, 89%, 90%, 91%, 92%, 93%, 94%, 95%, 96%, 97%, 98%, 99% or 100% identical homologous to the amino acid sequences set forth herein, as may be determined using BlastP software of the National Center of Biotechnology Information (NCBI) using default parameters. The present invention also encompasses fragments of the above described polynucleotides and polypeptides having mutations, such as deletions, insertions or substitutions of one or more nucleic acids, either naturally occurring or man induced, either randomly or in a targeted fashion.

Nucleic acid molecules may encode a KIR2DL1, KIR2DL2, and KIR2DL3, or a functional fragment of said nucleic acid molecule. A "functional fragment" of said nucleic acid includes a fragment of the gene or cDNA encoding said KIR2DL1, KIR2DL2, and KIR2DL3, which fragment is capable of being expressed to produce a KIR2DL1, KIR2DL2, and KIR2DL3 capable of eliciting an immune response (e.g., antibodies which selectively bind the KIR2DL1, KIR2DL2, and KIR2DL3) Thus, for example, fragments of the KIR2DL1, KIR2DL2, and KIR2DL3 according to the invention which correspond to amino acid residues that contribute to the immunogenicity of the antigen and which fragments may serve to function as antigens to elicit an immune response (e.g., humoral or cellular immune response.) This aspect of the invention also includes differentially spliced isoforms and transcriptional starts of the nucleic acids according to the invention. The nucleic acid molecules according to the invention also comprise fragments, derivatives and allelic variants of the nucleic acid molecules described above that encodes a KIR2DL1, KIR2DL2, and KIR2DL3 according to the invention. Methods and materials for making nucleic acids encoding fragments of KIR2DL1, KIR2DL2, and KIR2DL3 are well known in the art. See, e.g., Maniatis, et al. (2001) Molecular Cloning: A Laboratory Manual [$3^{rd}$ Ed.] Cold Spring Harbor Laboratory Press.

A nucleic acid molecule encompassing all or a portion of a polynucleotide that encodes the amino acid sequences of SEQ ID NOs: 7, 8, 9, 10, 11, 12, 13, 14, 15, 16, 17, 18, 19, 20, 21, 22, 23, and 24, or an ortholog or variant can be isolated by the polymerase chain reaction (PCR) using synthetic oligonucleotide primers designed based upon the sequence of a polynucleotide that encodes the amino acid sequences of SEQ ID NOs: 7, 8, 9, 10, 11, 12, 13, 14, 15, 16, 17, 18, 19, 20, 21, 22, 23, and 24.

A nucleic acid molecule of the invention can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to KIR2DL1, KIR2DL2, and KIR2DL3 nucleotide sequences can be prepared by standard synthetic techniques, e.g., using an automated DNA synthesizer.

In an embodiment, an isolated KIR2DL1, KIR2DL2, and KIR2DL3 encoding nucleic acid molecule of the invention comprises the nucleotide sequence shown in SEQ ID NO: 1, or 3, or a fragment thereof. In another embodiment the nucleic acid molecule of the invention comprises a nucleic acid molecule which is a complement of the nucleotide sequence shown in SEQ ID NO: 1, or 3, or a portion of any of these nucleotide sequences. A nucleic acid molecule which is complementary to the a polynucleotide that encodes the amino acid sequences of SEQ ID NOs: 7, 8, 9, 10, 11, 12, 13, 14, 15, 16, 17, 18, 19, 20, 21, 22, 23, and 24, is one which is sufficiently complementary to the nucleotide sequence of a polynucleotide that encodes the amino acid sequences of SEQ ID NOs: 7, 8, 9, 10, 11, 12, 13, 14, 15, 16, 17, 18, 19, 20, 21, 22, 23, and 24 such that it can hybridize to the nucleotide sequence of a polynucleotide that encodes the amino acid sequences of SEQ ID NOs: 7, 8, 9, 10, 11, 12, 13, 14, 15, 16, 17, 18, 19, 20, 21, 22, 23, and 24 respectively, thereby forming a stable duplex.

In still another embodiment, an isolated nucleic acid molecule of the present invention comprises a nucleotide sequence which is at least about 70%, 75%, 80%, 85%, 90%, 91%, 92%, 93%, 94%, 95%, 96%, 97%, 98%, 99%, or 99.5% identical to the entire length of a polynucleotide that encodes the amino acid sequences of SEQ ID NOs: 7, 8, 9, 10, 11, 12, 13, 14, 15, 16, 17, 18, 19, 20, 21, 22, 23, and 24, or a portion of any of these nucleotide sequences.

Moreover, the nucleic acid molecule of the invention can comprise only a portion of a polynucleotide that encodes the amino acid sequences of SEQ ID NOs: 7, 8, 9, 10, 11, 12, 13, 14, 15, 16, 17, 18, 19, 20, 21, 22, 23, and 24, for example, a fragment which can be used as a probe or primer or a fragment which encodes a portion of a KIR2DL1, KIR2DL2, and KIR2DL3 polypeptide, e.g., a biologically active portion of a KIR2DL1, KIR2DL2, and KIR2DL3-polypeptide. The nucleotide sequences determined from the cloning of the human PD-L2 gene allow for the generation of probes and primers designed for use in identifying and/or cloning other PD-L2 family members, as well as KIR2DL1, KIR2DL2, and KIR2DL3 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO: 1, or 3; of an anti-sense sequence of a polynucleotide that encodes the amino acid sequences of SEQ ID NOs: 7, 8, 9, 10, 11, 12, 13, 14, 15, 16, 17, 18, 19, 20, 21, 22, 23, and 24, or a naturally occurring allelic variant or mutant of a polynucleotide that encodes the amino acid sequences of SEQ ID NOs: 7, 8, 9, 10, 11, 12, 13, 14, 15, 16, 17, 18, 19, 20, 21, 22, 23, and 24.

In one embodiment, a nucleic acid molecule of the present invention comprises a nucleotide sequence which is greater than about 50-100, 100-150, 150-200, 200-250, 250-300, 300-350, 350-400, 400-450, 450-500, 500-550, 550-600, 600-650, 650-700, 700-750, 750-800, 800-850, 850-900, 900-950 or more nucleotides in length and hybridizes under stringent hybridization conditions to a polynucleotide that encodes the amino acid sequences of SEQ ID NOs: 7, 8, 9, 10, 11, 12, 13, 14, 15, 16, 17, 18, 19, 20, 21, 22, 23, and 24, or the complement thereof. In a further embodiment, a nucleic acid molecule of the present invention comprises a nucleotide sequence which is greater than about 880-900, 900-950, 950-1000, 1000-1050, 1050-1100, 1100-1150 or more nucleotides in length and hybridizes under stringent hybridization conditions to a polynucleotide that encodes the amino acid sequences of SEQ ID NOs: 7, 8, 9, 10, 11, 12, 13, 14, 15, 16, 17, 18, 19, 20, 21, 22, 23, and 24, or the complement thereof. In yet another embodiment, a nucleic acid molecule of the present invention comprises a nucleotide sequence which is greater than 50-100, 100-150, 150-200, 200-250, 250-300 or more nucleotides in length and hybridizes under stringent hybridization conditions to a nucleic acid molecule comprising the coding region a polynucleotide that encodes the amino acid sequences of SEQ ID NOs: 7, 8, 9, 10, 11, 12, 13, 14, 15, 16, 17, 18, 19, 20, 21, 22, 23, and 24, or a complement thereof. In yet a further embodiment, a nucleic acid molecule of the present invention comprises a nucleotide sequence which is greater than about 50-100, 100-150, 150-200, 200-250, 250-300, 300-350, 350-400, 400-450, 450-500, 500-550, 550-600, 600-650, 650-700, 700-750, 750-800, 850-900, 900-950, or more nucleotides in length, includes at least about 15 (i.e., 15 contiguous) nucleotides of the sequence comprising the coding region of a polynucleotide that encodes the amino acid sequences of SEQ ID NOs: 7, 8, 9, 10, 11, 12, 13, 14, 15, 16, 17, 18, 19, 20, 21, 22, 23, and 24, or a complement thereof, and hybridizes under stringent conditions to a nucleic acid molecule comprising a polynucleotide that encodes the amino acid sequences of SEQ ID NOs: 7, 8, 9, 10, 11, 12, 13, 14, 15, 16, 17, 18, 19, 20, 21, 22, 23, and 24a complement thereof.

Probes based on the KIR2DL1, KIR2DL2, and KIR2DL3 nucleotide sequences can be used to detect transcripts or genomic sequences encoding the same or homologous polypeptides. In embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which mis-express a KIR2DL1, KIR2DL2, and KIR2DL3 polypeptide, such as by measuring a level of a KIR2DL1, KIR2DL2, and KIR2DL3-encoding nucleic acid in a sample of cells from a subject, e.g., detecting KIR2DL1, KIR2DL2, and KIR2DL3 mRNA levels or determining whether a genomic KIR2DL1, KIR2DL2, and KIR2DL3 gene has been mutated or deleted.

In addition to the KIR2DL1, KIR2DL2, and KIR2DL3 nucleotide sequences of a polynucleotide that encodes the amino acid sequences of SEQ ID NOs: 7, 8, 9, 10, 11, 12, 13, 14, 15, 16, 17, 18, 19, 20, 21, 22, 23, and 24, it will be appreciated by those skilled in the art that DNA sequence polymorphisms that lead to changes in the amino acid sequences of the KIR2DL1, KIR2DL2, and KIR2DL3 polypeptides may exist within a population (e.g., the human population). Such genetic polymorphism in the KIR2DL1, KIR2DL2, and KIR2DL3 genes may exist among individuals within a population due to natural allelic variation. As used herein, the terms "gene" and "recombinant gene" refer to nucleic acid molecules which include an open reading frame encoding a KIR2DL1, KIR2DL2, and KIR2DL3 polypeptide, preferably a mammalian KIR2DL1, KIR2DL2, and KIR2DL3 polypeptide, and can further include non-coding regulatory sequences, and introns.

Allelic variants of human or mouse KIR2DL1, KIR2DL2, and KIR2DL3 include both functional and non-functional KIR2DL1, KIR2DL2, and KIR2DL3 polypeptides. Functional allelic variants are naturally occurring amino acid sequence variants of the human or mouse KIR2DL1, KIR2DL2, and KIR2DL3 polypeptide that maintain the ability to bind natural KIR2DL1, KIR2DL2, and KIR2DL3 binding partner(s) and/or modulate CD4+ and CD8+ T cell proliferation and cytokine production and lymphocyte activation. Functional allelic variants will typically contain only conservative substitution of one or more amino acids of the amino acid sequences of SEQ ID NOs: 7, 8, 9, 10, 11, 12, 13, 14, 15, 16, 17, 18, 19, 20, 21, 22, 23, and 24, or substitution, deletion or insertion of non-critical residues in non-critical regions of the polypeptide.

Non-functional allelic variants are naturally occurring amino acid sequence variants of the human or mouse KIR2DL1, KIR2DL2, and KIR2DL3 polypeptide that do not have the ability to either bind natural KIR2DL1, KIR2DL2, and KIR2DL3 binding partners, and/or modulate any of the KIR2DL1, KIR2DL2, and KIR2DL3 activities described herein. Non-functional allelic variants will typically contain a non-conservative substitution, deletion, or insertion or premature truncation of the amino acid sequences of SEQ ID NOs: 7, 8, 9, 10, 11, 12, 13, 14, 15, 16, 17, 18, 19, 20, 21, 22, 23, and 24, or a substitution, insertion or deletion in critical residues or critical regions of the polypeptide.

The present invention further provides non-human, non-mouse orthologs of the human or mouse KIR2DL1, KIR2DL2, and KIR2DL3 polypeptide. Orthologs of the human KIR2DL1, KIR2DL2, and KIR2DL3 polypeptide are polypeptides that are isolated from non-human, non-mouse organisms and possess the same binding activity and/or lymphocyte activation-modulating activity, and ability to modulate CD4+ and CD8+ T cell proliferation and cytokine production as the human and murine KIR2DL1, KIR2DL2, and KIR2DL3 polypeptides disclosed herein.

A mutant KIR2DL1, KIR2DL2, and KIR2DL3 polypeptide may be assayed for the ability to bind to and/or modulate the activity of a natural KIR2DL1, KIR2DL2, and KIR2DL3 binding partner, to modulate intra- or intercellular signaling, modulate activation of T lymphocytes, and/or modulate the immune response of an organism.

Isolated nucleic acid molecules encoding a KIR2DL1, KIR2DL2, and KIR2DL3 or KIR2DL1, KIR2DL2, and KIR2DL3 fusion proteins. Such nucleic acid molecules, comprising at least a first nucleotide sequence encoding a KIR2DL1, KIR2DL2, and KIR2DL3 or KIR2DL1, KIR2DL2, and KIR2DL3 protein, polypeptide or peptide operatively linked to a second nucleotide sequence encoding a non-KIR2DL1, KIR2DL2, and KIR2DL3 protein, polypeptide or peptide, can be prepared by standard recombinant DNA techniques.

Furthermore, identity refers broadly to the that functional and/or structural equivalence that exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. At the same time, the variations may occur naturally, for example they may be sequences from other species, or they may be mutants, wherein these mutants may have occurred in a natural manner or have been introduced by objective mutagenesis. The variations may also be synthetically manufactured sequences. The allelic variants may be both naturally occurring variants and also synthetically manufactured variants or variants produced by recombinant DNA techniques. Nucleic acid molecules, which deviate from nucleic acid molecules according to the invention due to degeneration of the genetic code, constitute a special form of derivatives.

Included also within the scope of the invention is any nucleotide sequence that encodes the amino acid sequence of KIR2DL1, KIR2DL2, and KIR2DL3 thereof. Because the genetic code is degenerate, more than one codon may be used to encode a particular amino acid. Using the genetic code, one or more different nucleotides may be identified, each of which would be capable of encoding the amino acid. The probability that a particular nucleotide will, in fact, constitute the actual codon encoding sequence may be estimated by considering abnormal base pairing relationships and the frequency with which a particular codon is actually used (to encode a particular amino acid) in eukaryotic or prokaryotic cells expressing a KIR2DL1, KIR2DL2, and KIR2DL3 thereof. Such "codon usage rules" are disclosed by Lathe, et al. (1985) J. Molec. Biol. 183: 1-12.

Modified KIR2DL1, KIR2DL2, and KIR2DL3 Polynucleotides

The nucleotides of the present invention may be modified polynucleotides. Unmodified nucleotide are often less optimal in some applications, e.g., prone to degradation by cellular nucleases. Chemical modifications to one or more of the subunits of oligonucleotide may confer improved properties, e.g., may render polynucleotides more stable to nucleases. Typical oligonucleotide modifications are well-known in the art and may include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the ribose sugar, e.g., of the modification or replacement of the 2' hydroxyl on the ribose sugar; (iii) wholesale replacement of the phosphate moiety; (iv) modification or replacement of a naturally occurring base with a non-natural base; (v) replacement or modification of the ribose-phosphate backbone, e.g. with peptide nucleic acid (PNA); (vi) modification of the 3' end or 5' end of the oligonucleotide; and (vii) modification of the sugar, e.g., six membered rings. Polynucleotides used in accordance with this invention may be synthesized by any number of means well-known in the art, or purchased from a variety of commercial vendors (LC Sciences, Houston, Tex.; Promega, Madison, Wis.; Invitrogen, Carlsbad, Calif.).

Antisense

In addition to the nucleic acid molecules encoding KIR2DL1, KIR2DL2, and KIR2DL3 polypeptides described above, another aspect of the invention pertains to isolated nucleic acid molecules which are antisense thereto. An "antisense" nucleic acid comprises a nucleotide sequence which is complementary to a "sense" nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire KIR2DL1, KIR2DL2, and KIR2DL3 coding strand, or to only a portion thereof. In one embodiment, an antisense nucleic acid molecule is antisense to a "coding region" of the coding strand of a nucleotide sequence encoding a KIR2DL1, KIR2DL2, and KIR2DL3. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding PD-L. The term "noncoding region" refers to 5' and 3' sequences which flank the coding region that are not translated into amino acids (also referred to as 5' and 3' untranslated regions). Given the coding strand sequences encoding human or mouse KIR2DL1, KIR2DL2, and KIR2DL3 disclosed herein, antisense nucleic acids of the invention can be designed according to the rules of Watson and Crick base pairing. The antisense nucleic acid molecule can be complementary to the entire coding region of KIR2DL1, KIR2DL2, and KIR2DL3 mRNA, but more preferably is an oligonucleotide which is antisense to only a portion of the coding or noncoding region of KIR2DL1, KIR2DL2, and KIR2DL3 mRNA. For example, the antisense oligonucleotide can be complementary to the region surrounding the translation start site of KIR2DL1, KIR2DL2, and KIR2DL3 or KIR2DL1, KIR2DL2, and KIR2DL3 mRNA. An antisense oligonucleotide can be, for example, about 5, 10, 15, 20, 25, 30, 35, 40, 45 or 50 nucleotides in length. An antisense nucleic acid molecule of the invention can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridin-e, 5-carboxymethylaminom- ethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiour-acil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a KIR2DL1, KIR2DL2, and KIR2DL3 polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

The KIR2DL1, KIR2DL2, and KIR2DL3 antisense nucleic acid molecule may be an α-anomeric nucleic acid molecule. An α-anomeric nucleic acid molecule forms specific double-stranded hybrids with complementary RNA in which, contrary to the usual β-units, the strands run parallel to each other. Gaultier, et al. (1987) Nucleic Acids Res. 15: 6625-6641. The antisense nucleic acid molecule can also comprise a 2'-O-methylribonucleotide (Inoue, et al. (1987) Nucleic Acids Res. 15: 6131-6148) or a chimeric RNA-DNA analogue (Inoue, et al. (1987) FEBS Lett. 215: 327-330).

A KIR2DL1, KIR2DL2, and KIR2DL3 antisense nucleic acid may be a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) Nature 334:585-591)) can be used to catalytically cleave KIR2DL1, KIR2DL2, and KIR2DL3 mRNA transcripts to thereby inhibit translation of KIR2DL1, KIR2DL2, and KIR2DL3 mRNA. A ribozyme having specificity for a KIR2DL1, KIR2DL2, and KIR2DL3-encoding nucleic acid can be designed based upon the nucleotide sequence of a KIR2DL1, KIR2DL2, and KIR2DL3 cDNA disclosed herein. For example, a derivative of a Tetrahymena L-19 IVS RNA can be constructed in which the nucleotide sequence of the active site is complementary to the nucleotide sequence to be cleaved in a KIR2DL1, KIR2DL2, and KIR2DL3-encoding mRNA. See, e.g., U.S. Pat. Nos. 4,987, 071 and 5,116,742. Alternatively, KIR2DL1, KIR2DL2, and KIR2DL3 mRNA can be used to select a catalytic RNA having a specific ribonuclease activity from a pool of RNA molecules. See, e.g., Bartel and Szostak (1993) Science 261: 1411-1418.

Alternatively, KIR2DL1, KIR2DL2, and KIR2DL3 gene expression can be inhibited by targeting nucleotide sequences complementary to the regulatory region of the KIR2DL1, KIR2DL2, and KIR2DL3 (e.g., the KIR2DL1, KIR2DL2, and KIR2DL3 promoter and/or enhancers; to form triple helical structures that prevent transcription of the KIR2DL1, KIR2DL2, and KIR2DL3 gene in target cells. See generally, Helene (1991) Anticancer Drug Des. 6(6):569-84; Helene, et al. (1992) Ann. N.Y. Acad. Sci. 660:27-36; and Maher, L. J. (1992) Bioessays 14(12):807-15.

Peptide Nucleic Acid

In yet another embodiment, the KIR2DL1, KIR2DL2, and KIR2DL3 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids. See Hyrup and Nielsen (1996) Bioorg. Med. Chem. 4(1): 5-23. As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe, et al. (1996) Proc Natl. Acad. Sci. USA 93:14670-675.

PNAs of KIR2DL1, KIR2DL2, and KIR2DL3 nucleic acid molecules can be used in therapeutic and diagnostic applications. For example, PNA scan be used as antisense or antigene agents for sequence-specific modulation of gene expression by, for example, inducing transcription or translation arrest or inhibiting replication. PNAs of KIR2DL1, KIR2DL2, and KIR2DL3 nucleic acid molecules can also be used in the analysis of single base pair mutations in a gene (e.g., by PNA-directed PCR clamping); as 'artificial restriction enzymes' when used in combination with other enzymes (e.g., S1 nucleases (Hyrup and Nielsen (1996) supra)); or as probes or primers for DNA sequencing or hybridization (Hyrup and Nielsen (1996) supra; Perry-O'Keefe et al. (1996) supra).

PNAs of KIR2DL1, KIR2DL2, and KIR2DL3 can be modified (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of KIR2DL1, KIR2DL2, and KIR2DL3 nucleic acid molecules can be generated which may combine the advantageous properties of PNA and DNA. Such chimeras allow DNA recognition enzymes (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn P. J. et al. (1996) Nucleic Acids Res. 24 (17):3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a bridge between the PNA and the 5' end of DNA (Mag, M. et al. (1989) Nucleic Acids Res. 17:5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, et al. (1975) Bioorganic Med. Chem. Lett. 5:1119-11124).

Oligonucleotide

The oligonucleotide may include other appended groups such as peptides (e.g., for targeting host cell receptors in vivo), or agents facilitating transport across the cell membrane (See, e.g., Letsinger et al. (1989) Proc Natl. Acad. Sci. USA 86:6553-6556; Lemaitre et al. (1987) Proc Natl. Acad. Sci. USA 84:648-652; PCT Publication No. WO 88/09810) or the blood-brain barrier (See, e.g., PCT Publication No. WO 89/10134). In addition, oligonucleotides can be modified with hybridization-triggered cleavage agents (See, e.g., Krol et al. (1988) Biotechniques 6:958-976) or intercalating agents (See, e.g., Zon (1988) Pharm. Res. 5:539-549). To this end, the oligonucleotide may be conjugated to another molecule (e.g., a peptide, hybridization triggered cross-linking agent, transport agent, or hybridization-triggered cleavage agent).

Expression

Isolation and expression of the KIR2DL1, KIR2DL2, and KIR2DL3 of the invention may be effected by well-established cloning procedures using probes or primers constructed based on the KIR2DL1, KIR2DL2, and KIR2DL3 nucleic acids sequences disclosed in the application. Related KIR2DL1, KIR2DL2, and KIR2DL3 sequences may also be identified from human or other species genomic databases using the sequences disclosed herein and known computer-based search technologies, e.g., BLAST sequence searching. The pseudogenes disclosed herein may be used to identify functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers) within the vectors of the invention. Any of the known methods described for increasing or decreasing expression or activity can be used.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989)

Proc Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374-379) and the α-fetoprotein promoter (Campes and Tilghman (1989) Genes Dev. 3: 537-546).

The polynucleotide sequences provided herein may be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art. See, e.g., Maniatis, et al. (2001) Molecular Cloning: A Laboratory Manual [3$^{rd}$ Ed.] Cold Spring Harbor Laboratory Press; Swamy (2008) Laboratory Manual on Biotechnology Rastogi Publications; Herdewijn (2005) [Ed.] Methods in Molecular Biolog: Oligonucleotide Synthesis: Methods and Applications Volume 288 Humana Press; and Rapley (2000) [Ed.] The Nucleic Acid Protocols Handbook Humana Press. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization are well described in the scientific and patent literature. See, e.g., Sambrook, et al. (2001) (Eds.) Molecular Cloning: A Laboratory Manual (3$^{rd}$ Ed.) Cold Spring Harbor Laboratory; Ausubel, et al. (2011) Ed., Current Protocols in Molecular Biology, John Wiley & Sons, Inc., New York; Tijssen (1993) [Ed.] Laboratory Techniques in Biochemistry and Molecular Biology: Hybridization With Nucleic Acid Probes, Part I, Theory and Nucleic Acid Preparation, Elsevier, N.Y.

Hybridization and the strength of hybridization (e.g., the strength of the association between polynucleotides) is impacted by many factors well known in the art including the degree of complementarity between the polynucleotides, and the stringency of the conditions involved, which is affected by such conditions as the concentration of salts, the presence of other components (e.g., the presence or absence of polyethylene glycol), the molarity of the hybridizing strands and the G+C content of the polynucleotide strands, all of which results in a characteristic melting temperature ($T_m$) of the formed hybrid. Techniques of nucleic acid hybridization are disclosed by Sambrook, et al. (2001) (Eds.) Molecular Cloning: A Laboratory Manual [3$^{rd}$ Ed.] Cold Spring Harbor Laboratory, and by Hayrnes, et al. (1985) in Nucleic Acid Hybridization, a Practical Approach (IRL Press, DC). Hybridization wash conditions may include wash solution of 0.2×SSC/0.1% SDS and incubation with rotation for 10 minutes at room temperature, (low stringency wash), wash solution of prewarmed (42° C.) 0.2×SSC/0.1% SDS and incubation with rotation for 15 minutes at 42° C. (medium stringency wash) and wash solution of prewarmed (68° C.) 0.1×SSC/0.1% SDS and incubation with rotation for 15 minutes at 68° C. (high stringency wash). See Ausubel, et al. (2011) [Ed.] Current Protocols in Molecular Biology John Wiley & Sons, Inc.

Oligonucleotide primers may be used to amplify nucleic acids encoding a KIR2DL1, KIR2DL2, and KIR2DL3. The nucleic acids described herein can also be cloned or measured quantitatively using amplification techniques. Amplification methods are also well known in the art, and include, e.g., polymerase chain reaction (PCR) (Innis (1990) [Ed.] PCR Protocols, a Guide to Methods and Applications, Academic Press, NY.; Innis (1995) [Ed.] PCR Strategies, Academic Press, Inc., NY.); ligase chain reaction (LCR) (Wu (1989) Genomics 4: 560; Landegren (1988) Science 241: 1077; Barringer (1990) Gene 89: 117); transcription amplification (Kwoh (1989) PNAS 86: 1173); self-sustained sequence replication (Guatelli (1990) PNAS 87: 1874); Q Beta replicase amplification (Smith (1997) J. Clin. Microbiol. 35: 1477-91)); automated Q-beta replicase amplification assay (Burg (1996) Mol. Cell. Probes 10: 257-71); and other RNA polymerase mediated techniques (e.g., NASBA, Cangene, Mississauga, Ontario). See also Berger (1987) Methods Enzymol. 152: 307-16; Sambrook, et al. (2001) (Eds.) Molecular Cloning: A Laboratory Manual (3$^{rd}$ Ed.) Cold Spring Harbor Laboratory; Ausubel, et al. (2011) [Ed.] Current Protocols in Molecular Biology, John Wiley & Sons, Inc., New York; Maniatis, et al. (2001) Molecular Cloning: A Laboratory Manual [3$^{rd}$ Ed.] Cold Spring Harbor Laboratory Press; U.S. Pat. Nos. 4,683,195 and 4,683,202; Sooknanan (1995) Biotechnology 13: 563-64.

Paradigms to design degenerate primer pairs are well known in the art. For example, a COnsensus-DEgenerate Hybrid Oligonucleotide Primer (CODEHOP) strategy computer program is readily accessible and is directly linked from the BlockMaker multiple sequence alignment site for hybrid primer prediction beginning with a set of related protein sequences, such as the KIR2DL1, KIR2DL2, and KIR2DL3 sequences provided herein. See, e.g., Rose (1998) Nucleic Acids Res. 26: 1628-35; Singh (1998) Biotechniques 24: 318-19.

Polymorphic variants, alleles, and interspecies homologs that are substantially identical to KIR2DL1, KIR2DL2, and KIR2DL3 disclosed herein may be isolated using the nucleic acid probes described above. Alternatively, expression libraries can be used to clone KIR2DL1, KIR2DL2, and KIR2DL3 s and polymorphic variants, alleles, and interspecies homologs thereof, by detecting expressed homologs immunologically with antisera or purified antibodies made against a KIR2DL1, KIR2DL2, and KIR2DL3, which also recognize and selectively bind to the KIR2DL1, KIR2DL2, and KIR2DL3 homolog.

Nucleic acids that encode KIR2DL1, KIR2DL2, and KIR2DL3 may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from KIR2DL1, KIR2DL2, and KIR2DL3 expressing cells. Methods for expression of heterologous sequences in host cells are well known in the art. See, e.g., Maniatis, et al. (2001) Molecular Cloning: A Laboratory Manual [3$^{rd}$ Ed.] Cold Spring Harbor Laboratory Press.

Fusion Proteins Comprising a KIR2DL1, KIR2DL2, and KIR2DL3

Hybrid protein-coding sequences comprising nucleic acids encoding KIR2DL1, KIR2DL2, and KIR2DL3 fused to a translocation sequences may be constructed. Also provided are hybrid KIR2DL1, KIR2DL2, and KIR2DL3 comprising the motifs and antigenic regions. These nucleic acid sequences may be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

Fusion proteins may comprise C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Sigma-Aldrich.)

The inclusion of a cleavable linker sequences such as Factor Xa (See, e.g., Ottavi, (1998) Biochimie 80: 289-93), subtilisin protease recognition motif (See, e.g., Polyak (1997) Protein Eng. 10: 615-19); enterokinase (Invitrogen, San Diego, Calif.), between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (See, e.g., Williams (1995) Biochemistry 34: 1787-97), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature. See, e.g., Kroll (1993) DNA Cell. Biol. 12: 441-53.

Systems for Recombinant Expression of the KIR2DL1, KIR2DL2, and KIR2DL3 Polypeptides and Anti-KIR2DL1, KIR2DL2, and KIR2DL3 Antibodies Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Sambrook, et al. (2001) [Eds.] Molecular Cloning: A Laboratory Manual ($3^{rd}$ Ed.) Cold Spring Harbor Laboratory; Ausubel, et al. (2011) [Ed.] Current Protocols in Molecular Biology John Wiley & Sons, Inc.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfurone or Basta) to permit selection of those cells transformed with the desired DNA sequences. See, e.g., Ausubel, et al. (2011) [Ed.] Current Protocols in Molecular Biology John Wiley & Sons, Inc.; and Walker & Papley (2009) Molecular Biology and Biotechnology [$5^{th}$ Ed.] Royal Society of Chemistry. Because selectable marker genes conferring resistance to substrates like neomycin or hygromycin can only be utilized in tissue culture, chemoresistance genes are also used as selectable markers in vitro and in vivo.

To enable cellular expression of the polynucleotides of the present invention, a nucleic acid construct according to the present invention may be used, which includes at least a coding region of one of the above nucleic acid sequences, and further includes at least one cis acting regulatory element. Preferably, the promoter utilized by the nucleic acid construct of the present invention is active in the specific cell population transformed. Examples of cell type-specific and/or tissue-specific promoters are well-known in the art. See Bernardi (2003) [Ed.] Gene Transfer and Expression in Mammalian Cells Volume 38 Elsevier Science B.V. The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (Carlsbad, Calif.) Examples of retroviral vector and packaging systems are those sold by Clontech (San Diego, Calif.), including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5' LTR promoter.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel (1990) Gene Expression Technology: Methods in Enzymology 185, Academic Press, San Diego, Calif. Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired. The expression vectors of the invention can be introduced into host cells to thereby produce proteins or peptides, including fusion proteins or peptides, encoded by nucleic acids as described herein.

The recombinant expression vectors of the invention may be designed for production of variant proteins in prokaryotic or eukaryotic cells. For example, proteins of the invention can be expressed in bacterial cells such as *Escherichia coli*, insect cells (e.g., using baculovirus expression vectors), yeast cells, or mammalian cells. Suitable host cells are discussed further in Goeddel (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase. Typical fusion expression vectors include pGEX (Pharmacia Biotech Inc; Smith and Johnson (1988) *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

The recombinant mammalian expression vector is capable of directing expression of the nucleic acid may be in a particular cell type (e.g., tissue-specific regulatory elements are used to express the nucleic acid). Tissue-specific regulatory elements are known in the art. For efficient production of the protein, it is preferable to place the nucleotide sequences encoding the protein of the invention under the control of expression control sequences optimized for expression in a desired host. For example, the sequences may include optimized transcriptional and/or translational regulatory sequences (e.g., altered Kozak sequences).

One strategy to maximize recombinant protein expression in *E. coli* is to express the protein in a host bacterium with an impaired capacity to proteolytically cleave the recombinant protein. See, e.g., Gottesman (1990) Gene Expression Technology: Methods in Enzymology Academic Press, San Diego, Calif. 185: 119-128. Another strategy is to alter the nucleic acid sequence of the nucleic acid to be inserted into an expression vector so that the individual codons for each amino acid are those preferentially utilized in *E. coli*. See, e.g., Wada, et al. (1992) Nucl. Acids Res. 20: 2111-2118. Such alteration of nucleic acid sequences of the invention can be carried out by standard DNA synthesis techniques. Another strategy to solve codon bias is by using BL21-codon plus bacterial strains (Invitrogen) or Rosetta bacterial strain (Novagen), these strains contain extra copies of rare *E. coli* tRNA genes.

The expression vector encoding for the protein of the invention may be a yeast expression vector. Examples of vectors for expression in yeast *Saccharomyces cerevisiae* include pYepSec1 (Baldari, et al. (1987) EMBO J. 6: 229-234), pMFa (Kurjan and Herskowitz (1982) Cell 30: 933-943), pJRY88 (Schultz, et al. (1987) Gene 54: 113-123), pYES2 (Invitrogen Corporation, San Diego, Calif.), and picZ (Invitrogen Corp, San Diego, Calif.)

Alternatively, polypeptides of the present invention can be produced in insect cells using baculovirus expression vectors. Baculovirus vectors available for expression of proteins in cultured insect cells (e.g., SF9 cells) include the pAc series (Smith, et al. (1983) Mol. Cell. Biol. 3: 2156-2165) and the pVL series (Lucklow and Summers (1989) Virology 170: 31-39). In yet another embodiment, a nucleic acid of the invention is expressed in mammalian cells using a mammalian expression vector. Examples of mammalian expression vectors include pCDM8 (Seed (1987) Nature 329: 840) and pMT2PC (Kaufman, et al. (1987) EMBO J. 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells See, e.g., Sambrook, et al. (2001) (Eds.) Molecular Cloning: A Laboratory Manual ($3^{rd}$ Ed.) Cold Spring Harbor Laboratory.

A host cell can be any prokaryotic or eukaryotic cell. For example, protein of the invention can be produced in bacterial cells such as *E. coli*, insect cells, yeast, plant or mammalian cells (e.g., Chinese hamster ovary cells (CHO), COS, HEK293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (2001) [Eds.] Molecular Cloning: A Laboratory Manual ($3^{rd}$ Ed.) Cold Spring Harbor Laboratory and other laboratory manuals.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. See, e.g., Sambrook, et al. (2001) (Eds.) Molecular Cloning: A Laboratory Manual ($3^{rd}$ Ed.) Cold Spring Harbor Laboratory and Walker & Papley (2009) Molecular Biology and Biotechnology [$5^{th}$ Ed.] Royal Society of Chemistry. It is only necessary that the particular genetic engineering procedure used be capable of successfully introducing at lest one nucleic acid molecule into the host cell capable of expressing the KIR2DL1, KIR2DL2, and KIR2DL3, fragment, or variant of interest.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin and methotrexate. Nucleic acids encoding a selectable marker can be introduced into a host cell on the same vector as that encoding protein of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) protein of the invention. Accordingly, the invention further provides methods for producing proteins of the invention using the host cells of the invention. In one embodiment, the method comprises culturing the host cell of the present invention (into which a recombinant expression vector encoding protein of the invention has been introduced) in a suitable medium such that the protein of the invention is produced. In another embodiment, the method further comprises isolating protein of the invention from the medium or the host cell.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593.

For example, the production of anti-KIR2DL1, KIR2DL2, and KIR2DL3 monoclonal antibodies described herein may be effected using a vector which allows for the insertion of both heavy and light chain genes, with transfection to CHO cells may be used to optimize production. The plasmid vector pRc/CMV that we employed was designed with the intent of achieving high expression of our chimeric monoclonal antibodies. The vector has a cloning site which accepted the heavy and light chain genes, inserting them downstream from the human CMV. The vector allows antibody to be produced at levels greater than 1000 mg/L in bioreactor media, so that therapeutic doses of 250-500 mg may be delivered.

Monoclonal antibodies demonstrating minimal HAMA at doses of 200 mg to 400 mg delivered every two weeks I.V. could be effective in controlling metastatic cancer. At the present time we have chosen a newer vector which allows similar insertion of heavy and light chain genes, but has a potential for production in excess of 1000 mg/L of bioreactor fluid. Both plasmid vectors carry a dhfr expression unit driven by an enhancer-deficient SV40 early promoter. The vector may be inserted into the CHO-D-SFM (dihydrofolate reductase (dhfr)-deficient Chinese hamster ovary) cells in near serum-free medium supplemented with 1.0 µg/ml of methotrexate (MTX). At the end of the production, cells may be adapted to serum free media before final purification of the antibody.

Antibodies which Bind KIR2DL1, KIR2DL2, and KIR2DL3

The present invention also provides antibodies which selectively bind the KIR2DL1, KIR2DL2, and KIR2DL3 including but not limited monoclonal and humanized monoclonal antibodies. The antibodies which selectively bind the KIR2DL1, KIR2DL2, and KIR2DL3 may be admixed in compositions with pharmaceutical carriers and additional agents (e.g., one anti-inflammatory agent, analgesic agent, or disease-modifying antirheumatic drug (DMARD)).

An isolated KIR2DL1, KIR2DL2, and KIR2DL3 polypeptide, or a portion or fragment thereof, can be used as an immunogen to generate antibodies that bind KIR2DL1, KIR2DL2, and KIR2DL3 using standard techniques for polyclonal and monoclonal antibody preparation. A full-length KIR2DL1, KIR2DL2, and KIR2DL3 polypeptide can be used or, alternatively, the invention provides antigenic peptide fragments of KIR2DL1, KIR2DL2, and KIR2DL3 for use as immunogens. In one embodiment, an antigenic peptide of KIR2DL1, KIR2DL2, and KIR2DL3 comprises at least 8 amino acid residues of the amino acid sequence shown in any one of SEQ ID NO: 7-24 and encompasses an epitope of KIR2DL1, KIR2DL2, and KIR2DL3 such that an antibody raised against the peptide forms a specific immune complex with the KIR2DL1, KIR2DL2, and KIR2DL3 polypeptide. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of KIR2DL1, KIR2DL2, and KIR2DL3 that are located in the extracellular domain of the polypeptide, e.g., hydrophilic regions, as well as regions with high antigenicity.

A KIR2DL1, KIR2DL2, and KIR2DL3 immunogen typically is used to prepare antibodies by immunizing a suitable subject (e.g., rabbit, goat, mouse, or other mammal) with the immunogen. An appropriate immunogenic preparation can contain, for example, recombinantly expressed KIR2DL1, KIR2DL2, and KIR2DL3 polypeptide or a chemically synthesized KIR2DL1, KIR2DL2, and KIR2DL3 polypeptide. For example, may comprise the extracellular domain of a KIR2DL1, KIR2DL2, and KIR2DL3 polypeptide (e.g., the amino acid sequence of SEQ ID NO: 7-24). The preparation can further include an adjuvant, such as Freund's complete or incomplete adjuvant, or similar immunostimulatory agent. Immunization of a suitable subject with an immunogenic KIR2DL1, KIR2DL2, and KIR2DL3 preparation induces a polyclonal anti-KIR2DL1, KIR2DL2, and KIR2DL3 antibody response.

Antibodies may comprise of two identical light polypeptide chains of molecular weight approximately 23,000 daltons ("light chain"), and two identical heavy chains of molecular weight 53,000-70,000 ("heavy chain"). See Edelman (1971) Ann. NY. Acad. Sci. 190: 5. The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_c$ region. The amino acid sequence orientation runs from the N-terminal end at the top of the "Y" configuration to the C-terminal end at the bottom of each chain. The N-terminal end possesses the variable region having specificity for the antigen that elicited it, and is about 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (e.g., IgG, IgM, IgA, IgD, and IgE corresponding to γ, µ, α, δ, and ε heavy chain constant regions). The constant region or class determines subsequent effector function of the antibody, including activation of complement (Kabat (1976) Structural Concepts in Immunology and Immunochemistry [$2^{nd}$ Ed.] pages 413-436; Holt, Rinehart, Winston) and other cellular responses (Andrews, et al. (1980) Clinical Immunobiology 1-18; Kohl, et al. (1983) Immunology 48: 187) while the variable region determines the antigen with which it will react. Light chains are classified as either κ (kappa) or λ (lambda). Each heavy chain class may be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein. See, e.g., Harlow & Lane (1998) USING ANTIBODIES: A LABORATORY MANUAL Cold Spring Harbor Laboratory, for a description of immunoassay formats and conditions that can be used to determine specific immunoreactivity. Typically a specific or selective reaction will be at least twice background signal or noise and more typically more than about 10 to 100 times background.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374-379) and the α-fetoprotein promoter (Campes and Tilghman (1989) Genes Dev. 3: 537-546).

Polyclonal Antibody

Polyclonal antibodies are heterogeneous populations of antibody molecules derived from the sera of animals immunized with an antigen. Polyclonal antibodies which selectively bind the KIR2DL1, KIR2DL2, and KIR2DL3 may be made by methods well-known in the art. See, e.g., Howard & Kaser (2007) Making and Using Antibodies: A Practical Handbook CRC Press.

Monoclonal Antibody

A monoclonal antibody contains a substantially homogeneous population of antibodies specific to antigens, which population contains substantially similar epitope binding sites. Monoclonal antibodies may be obtained by methods known to those skilled in the art. See, e.g. Kohler and Milstein (1975) Nature 256: 495-497; U.S. Pat. No. 4,376,110; Ausubel, et al. [Eds.] (2011) CURRENT PROTOCOLS IN MOLECULAR BIOLOGY, Greene Publishing Assoc. and Wiley Interscience, NY.; and Harlow & Lane (1998) USING ANTIBODIES: A LABORATORY MANUAL Cold Spring Harbor Laboratory; Colligan, et al. (2005) [Eds.] Current Protocols in Immunology Greene Publishing Assoc. and Wiley Interscience, NY. Such antibodies may be of any immunoglobulin class including IgG, IgM, IgE, IgA, GILD and any subclass thereof. A hybridoma producing an antibody of the present invention may be cultivated in vitro, in situ, or in vivo.

Chimeric Antibody

Chimeric antibodies are molecules different portions of which are derived from different animal species, such as those having variable region derived from a murine antibody and a human immunoglobulin constant region, which are primarily used to reduce immunogenicity in application and to increase yields in production, for example, where murine monoclonal antibodies have higher yields from hybridomas but higher immunogenicity in humans, such that human murine chimeric monoclonal antibodies are used. Chimeric antibodies and methods for their production are known in the art. See Cabilly, et al. (1984) Proc. Natl. Acad. Sci. USA 81: 3273-3277; Morrison, et al. (1994) Proc. Natl. Acad. Sci. USA 81: 6851-6855, Boulianne, et al. (1984) Nature 312: 643-646; Neuberger, et al. (1985) Nature 314: 268-270; European Patent Application 173494 (1986); WO 86/01533 (1986); European Patent Application 184187 (1986); European Patent Application 73494 (1986); Sahagan, et al. (1986) J. Immunol. 137: 1066-1074; Liu, et al. (1987) Proc. Natl. Acad. Sci. USA 84: 3439-3443; Sun, et al. (1987) Proc. Natl. Acad. Sci. USA 84: 214-218; Better, et al. (1988) Science 240: 1041-1043; and Harlow & Lane (1998) USING ANTIBODIES: A LABORATORY MANUAL Cold Spring Harbor Laboratory; U.S. Pat. No. 5,624,659.

Humanized Antibody

Humanized antibodies are engineered to contain even more human-like immunoglobulin domains, and incorporate only the complementarity-determining regions of the animal-derived antibody. This may be accomplished by examining the sequence of the hyper-variable loops of the variable regions of the monoclonal antibody, and fitting them to the structure of the human antibody chains. See, e.g., U.S. Pat. No. 6,187,287. Likewise, other methods of producing humanized antibodies are now well known in the art. See, e.g., U.S. Pat. Nos. 5,225,539; 5,530,101; 5,585,089; 5,693,762; 6,054,297; 6,180,370; 6,407,213; 6,548,640; 6,632,927; and 6,639,055; Jones, et al. (1986) Nature 321: 522-525; Reichmann, et al. (1988) Nature 332: 323-327; Verhoeyen, et al. (1988) Science 239: 1534-36; and Zhiqiang An (2009) [Ed.] Therapeutic Monoclonal Antibodies: From Bench to Clinic John Wiley & Sons, Inc.

Antibody Fragments

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. Antigen-binding fragments of immunoglobulins include but are not limited to SMIPs (small molecule immunopharmaceuticals), camelbodies, nanobodies, and IgNAR.

Anti-idiotypic Antibody

An anti-idiotypic (anti-Id) antibody is an antibody which recognizes unique determinants generally associated with the antigen-binding site of an antibody. An Id antibody may be prepared by immunizing an animal of the same species and genetic type (e.g., mouse strain) as the source of the antibody with the antibody to which an anti-Id is being prepared. The immunized animal will recognize and respond to the idiotypic determinants of the immunizing antibody by producing an antibody to these idiotypic determinants (the anti-Id antibody). See e.g., U.S. Pat. No. 4,699,880. The anti-Id antibody may also be used as an "immunogen" to induce an immune response in yet another animal, producing a so-called anti-anti-Id antibody. The anti-anti-Id may be epitopically identical to the original antibody which induced the anti-Id. Thus, by using antibodies to the idiotypic determinants of an antibody it is possible to identify other clones expressing antibodies of identical specificity.

Engineered And Modified Antibodies

An antibody of the invention further may be prepared using an antibody having one or more of the VH and/or VL sequences derived from an antibody starting material to engineer a modified antibody, which modified antibody may have altered properties from the starting antibody. An antibody may be engineered by modifying one or more residues within one or both variable regions (i.e., VH and/or VL), for example within one or more CDR regions and/or within one or more framework regions. Additionally or alternatively, an antibody may be engineered by modifying residues within the constant region(s), for example to alter the effector function(s) of the antibody.

One type of variable region engineering that may be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. See, e.g., Riechmann, et al. (1998) Nature 332: 323-327; Jones, et al. (1986) Nature 321: 522-525; Queen, et al. (1989) Proc. Natl. Acad. U.S.A. 86: 10029-10033; U.S. Pat. Nos. 5,225,539; 5,530,101; 5,585,089; 5,693,762; and 6,180,370.

Suitable framework sequences may be obtained from public DNA databases or published references that include germline antibody gene sequences. For example, germline DNA sequences for human heavy and light chain variable region genes may be found in the "VBase" human germline sequence database (available on the Internet), as well as in Kabat, E. A., et al. (1991) Sequences of Proteins of Immunological Interest [5th Ed.]U.S. Department of Health and Human Services, NIH Publication No. 91-3242; Tomlinson, et al. (1992) "The Repertoire of Human Germline VH Sequences Reveals about Fifty Groups of VH Segments with Different Hypervariable Loops" J. Mol. Biol. 227: 776-798; and Cox, et al. (1994) Eur. J Immunol. 24: 827-836.

Another type of variable region modification is to mutate amino acid residues within the VH and/or VL CDR1, CDR2 and/or CDR3 regions to thereby improve one or more binding properties (e.g., affinity) of the antibody of interest. Site-directed mutagenesis or PCR-mediated mutagenesis may be performed to introduce the mutation(s) and the effect on antibody binding, or other functional property of interest, may be evaluated in appropriate in vitro or in vivo assays. Preferably conservative modifications (as discussed herein) may be introduced. The mutations may be amino acid substitutions, additions or deletions, but are preferably substitutions. Moreover, typically no more than one, two, three, four or five residues within a CDR region are altered.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues may be identified by comparing the antibody framework sequences to the germline sequences from which the antibody is derived.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties may be attached to the antibody) or be modified to alter its glycosylation, again to alter one or more functional properties of the antibody. Such embodiments are described further below. The numbering of residues in the Fc region is that of the EU index of Kabat.

The hinge region of CH1 may be modified such that the number of cysteine residues in the hinge region is altered, e.g., increased or decreased. See U.S. Pat. No. 5,677,425. The number of cysteine residues in the hinge region of CH1 may be altered to, for example, facilitate assembly of the light and heavy chains or to increase or decrease the stability of the antibody.

The Fc hinge region of an antibody may be mutated to decrease the biological half life of the antibody. More specifically, one or more amino acid mutations may be introduced into the CH2-CH3 domain interface region of the Fc-hinge fragment such that the antibody has impaired Staphylococcyl protein A (SpA) binding relative to native Fc-hinge domain SpA binding. See, e.g., U.S. Pat. No. 6,165, 745.

The antibody may be modified to increase its biological half life. Various approaches are possible. For example, one or more of the following mutations may be introduced: T252L, T254S, T256F. See U.S. Pat. No. 6,277,375. Alternatively, to increase the biological half life, the antibody may be altered within the CH1 or CL region to contain a salvage receptor binding epitope taken from two loops of a CH2 domain of an Fc region of an IgG. See U.S. Pat. Nos. 5,869, 046 and 6,121,022.

The Fc region may be altered by replacing at least one amino acid residue with a different amino acid residue to alter the effector function(s) of the antibody. For example, one or more amino acids selected from amino acid residues 234, 235, 236, 237, 297, 318, 320 and 322 may be replaced with a different amino acid residue such that the antibody has an altered affinity for an effector ligand but retains the antigen-binding ability of the parent antibody. The effector ligand to which affinity may be altered may be, for example, an Fc receptor or the C1 component of complement. See U.S. Pat. Nos. 5,624,821 and 5,648,260.

The glycosylation of an antibody may be modified. For example, an aglycoslated antibody may be made (i.e., the antibody lacks glycosylation). Glycosylation may be altered to, for example, increase the affinity of the antibody for antigen. Such carbohydrate modifications may be accomplished by, for example, altering one or more sites of glycosylation within the antibody sequence. For example, one or more amino acid substitutions may be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody may be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications may be accomplished by, for example, expressing the antibody in a host cell with altered glycosylation machinery. Cells with altered glycosylation machinery have been described in the art and may be used as host cells in which to express recombinant antibodies of the invention to thereby produce an antibody with altered glycosylation. See U.S. Patent Application Publication No. 2004/0110704 and Yamane-Ohnuki, et al. (2004) Biotechnol Bioeng. 87: 614-22; EP 1,176,195; WO 2003/035835; Shields, et al. (2002) J. Biol. Chem. 277: 26733-26740; WO 99/54342; Umana, et al. (1999) Nat. Biotech. 17: 176-180; and Tarentino, et al. (1975) Biochem. 14: 5516-23.

An antibody may be Pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer).

The invention also provides variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid.

Production of Antibodies

Monoclonal antibodies in particular may be made using the hybridoma method first described by Kohler, et al., Nature, 256:495 (1975), or by other well-known, subsequently-developed methods (See, e.g., Goding, Monoclonal Antibodies: Principles and Practice, pages 59-103 (Academic Press, 1986)). Hybridomas and other fusion cells may be formed by chemical fusion, electrical fusion, or any other suitable technique, with any suitable type of myelomas, heteromyelomas, phoblastoid cells, plasmacytomas or similar immortalized cell and any suitable type of antibody-expressing cell(s).

Transformed immortalized B cells also can be used to efficiently produce antibodies. Transformed B cells can be produced by standard techniques, such as transformation with an Epstein Barr Virus, or a transforming gene. (See, e.g., "Continuously Proliferating Human Cell Lines Synthesizing Antibody of Predetermined Specificity," Zurawaki, V. R. et al, in Monoclonal Antibodies, ed. by Kennett R. H. et al, Plenum Press, N.Y. 1980, pages 19-33). Thus, stable and continuous and/or immortalized anti-KIR2DL1, 2 and/or 3 antibody-expressing cells and cell lines are another feature of the invention. A step of a method for producing anti-KIR2DL1, 2 and/or 3 antibodies can include, for example, a step of producing immortalized B cells producing an antibody which are fused to appropriate partners to produce anti-KIR2DL1, 2 and/or 3 antibody (s) or which are sequenced and such sequences used to produce a recombinant anti-KIR2DL1, 2 and/or 3 antibody.

Cell lines available as hosts for recombinant protein expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Other cell lines that may be used are insect cell lines, such as Sf9 cells. When nucleic acids (or nucleic acid-containing vectors) encoding antibody genes are introduced into mammalian host cells, antibodies can be produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Antibodies may also be recovered from host cell lysates when directly expressed without a secretory signal.

The purification of antibodies from cell cultures, cell lysates, and transgenic animals or biological materials obtained therefrom (e.g., from the ascites fluid of a transgenic animal producing antibodies) can be achieved by application of any number of suitable techniques known in the art including, e.g., immunoaffinity column purification; sulfate precipitation; chromatofocusing; preparative SDS-PAGE, and the like.

Anti-KIR2DL1, 2 and/or 3 antibodies also can be produced in bacterial cells and eukaryotic unicellular microorganisms, such as yeast. Bacterial cell produced antibodies lack normal glycosylation and accordingly may be deficient in terms of ADCC functions and other aspects of the immune response that may otherwise be associated with essentially identical antibodies produced in mammalian cells and/or animals.

Suitable methods for purifying, screening and selection of antibodies can be used, including those described in WO 2006/072625. Screening and selection of anti-KIR2DL1, 2 and/or 3 antibodies can be accomplished by any suitable technique or combination of techniques. For example, a variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane, supra. The binding affinity of a monoclonal antibody can, for example, be determined by the Scatchard analysis of Munson et al., Anal. Biochem., 107:220 (1980).

Anti-KIR2DL1, 2 and/or 3 antibodies typically are screened for the ability to modulate NK cell activity, such as by inhibiting KIR2DL1, 2 and/or 3-mediated signals, promoting activation of NK cells through NK activating receptor-mediated signals. A number of NK cell assays have been developed that can be useful in such contexts including, for example, flow cytometric screening methods. See, e.g., McGinnes, et al. (1984) J Immunol Methods 80: 70-85. Methods relevant to culturing NK cells, assessing NK cells, and the like are known in the art. See, e.g., Campbell and Colonna, Natural Killer Cell Protocols (Methods in Molecular Biology Series vol. 121) (2000).

In the context of anti-KIR2DL1, 2, and/or 3 antibodies, NK cell neutralizing activity can be demonstrated by the capacity of an anti-KIR2DL1, 2 and/or 3 Antibody to reconstitute lysis of target cells by KIR2DL1, 2, and/or 3-positive NK cells. Anti-KIR2DL1, 2 and/or 3 antibody-associated NK cell modulation (e.g., KIR inhibition) can also be assessed by various cell based cytotoxicity assays. Redirected killing is one experimental system for determining the capacity of a NK-cell receptor to induce cytotoxicity. NK cells coated with antibody specific for a candidate receptor are assessed for their ability to kill target cells that express an Fc receptor to which the antibody binds. In another variant, the NK cell activity modulation associated with an anti-KIR antibody can be assessed in a cytokine-release assay. Other biological activities associated with various anti-KIR2DL1, 2 and/or 3 antibodies also can be used to evaluate anti-KIR2DL1, 2 and/or 3 antibodies.

Antibody Conjugates

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include but are not limited to taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Methods of Engineering Antibodies

Antibodies having VH and VL sequences disclosed herein may be used to create new variant antibodies by modifying the VH and/or VL sequences, or the constant region(s) attached thereto. Thus, the structural features of an variant antibody of the invention, are used to create structurally related variant antibodies that retain at least one functional property of the antibodies of the invention, such as binding to KIR2DL1, KIR2DL2, and KIR2DL3. For example, one or more CDR regions of one anti-KIR2DL1, KIR2DL2, and KIR2DL3 variant antibody or mutations thereof, may be combined recombinantly with known framework regions and/or other CDRs to create additional, recombinantly-engineered, anti-KIR2DL1, KIR2DL2, and KIR2DL3 antibodies (e.g., antibodies which bind the KIR2DL1, KIR2DL2, and/or KIR2DL3) of the invention, as discussed herein. The starting material for the engineering method may be one or more of the VH and/or VK sequences provided herein, or one or more CDR regions thereof. To create the engineered antibody, it is not necessary to actually prepare (i.e., express as a protein) an antibody having one or more of the VH and/or VK sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein. Standard molecular biology techniques may be used to prepare and express altered antibody sequence.

The antibody encoded by the altered antibody sequence(s) may retain one, some or all of the functional properties of the anti-KIR2DL1, KIR2DL2, and KIR2DL3 antibodies produced by methods and with sequences provided herein, which functional properties include binding to variant KIR2DL1, KIR2DL2, and KIR2DL3 or variant KIR2DL1, KIR2DL2, and KIR2DL3 conjugate with a specific KD level or less and/or modulating immune cell activity, and/or selectively binding to desired target cells such as, for example, colorectal carcinoma, lung cancer, prostate cancer, pancreas cancer, ovarian cancer, gastric cancer, and liver cancer. The functional properties of the altered antibodies may be assessed using standard assays available in the art and/or described herein.

Mutations may be introduced randomly or selectively along all or part of an anti-KIR2DL1, KIR2DL2, and KIR2DL3 antibody coding sequence and the resulting modified anti-KIR2DL1, KIR2DL2, and KIR2DL3 antibodies may be screened for binding activity and/or other desired functional properties. See WO 2011/120013.

Nucleic Acids Encoding Antibodies that Selectively Bind KIR2DL1, KIR2DL2, and KIR2DL3

Another aspect of the invention pertains to nucleic acid molecules that encode the antibodies of the invention which bind the KIR2DL1, KIR2DL2, and KIR2DL3. The nucleic acids may be present in whole cells, in a cell lysate, or in a partially purified or substantially pure form. A nucleic acid may be isolated by purification away from other cellular components or other contaminants (e.g., other cellular nucleic acids or proteins) by standard techniques, including alkaline/SDS treatment, CsCl banding, column chromatography, agarose gel electrophoresis and others well known in the art. See Ausubel, et al. (2011) Current Protocols in Molecular Biology John Wiley & Sons, Inc. A nucleic acid of the invention may be, for example, DNA or RNA and may or may not contain intronic sequences. The nucleic acid may be a cDNA molecule.

Nucleic acids of the invention may be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma may be obtained by standard PCR amplification or cDNA cloning techniques. For antibodies obtained from an immunoglobulin gene library (e.g., using phage display techniques), nucleic acid encoding the antibody may be recovered from the library.

Specifically, degenerate codon substitutions may be achieved by generating, e.g., sequences in which the third position of one or more selected codons is substituted with mixed-base and/or deoxyinosine residues. Batzer, et al. (1991) Nucleic Acid Res. 19: 5081; Ohtsuka, et al. (1985) J. Biol. Chem. 260: 2605-08; Rossolini, et al. (1994) Mol. Cell. Probes 8: 91-98.

Once DNA fragments encoding VH and VL segments are obtained, these DNA fragments may be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The isolated DNA encoding the VH region may be converted to a full-length heavy chain gene by operatively linking the VH-encoding DNA to another DNA molecule encoding heavy chain constant regions (CH1, CH2 and CH3). The sequences of human heavy chain constant region genes are known in the art (See, e.g., Kabat, et al. (1991) Sequences of Proteins of Immunological Interest, Fifth Edition, U.S. Department of Health and Human Services, NIH Publication No. 91-3242) and DNA fragments encompassing these regions may be obtained by standard PCR amplification. The heavy chain constant region may be an IgG1, IgG2, IgG3, IgG4, IgA, IgE, IgM, or IgD constant region, but most preferably is an IgG1 or IgG4 constant region. For a Fab fragment heavy chain gene, the VH-encoding DNA may be operatively linked to another DNA molecule encoding only the heavy chain CH1 constant region.

The isolated DNA encoding the VL region may be converted to a full-length light chain gene (as well as a Fab light chain gene) by operatively linking the VL-encoding DNA to another DNA molecule encoding the light chain constant region, CL. The sequences of human light chain constant region genes are known in the art (See, e.g., Kabat, et al. (1991) Sequences of Proteins of Immunological Interest Fifth Edition, U.S. Department of Health and Human Services, NIH Publication No. 91-3242) and DNA fragments encompassing these regions may be obtained by standard PCR amplification. The light chain constant region may be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly4-Ser)_3$, such that the VH and VL sequences may be expressed as a contiguous single-chain protein, with the VL and VH regions joined by the flexible linker. See, e.g., Bird, et al. (1988) Science 242: 423-426; Huston, et al. (1988) Proc. Natl. Acad. Sci. USA 85: 5879-5883; McCafferty, et al. (1990) Nature 348: 552-554.

Methods of Producing Antibodies and Fragments Thereof

The present invention also provides methods for producing antibodies and fragments thereof. Methods of producing antibodies are well known to those of ordinary skill in the art. For example, methods of producing chimeric antibodies are now well known in the art. See, e.g., U.S. Pat. No. 4,816,567; Morrison, et al. (1984) PNAS USA 81: 8651-55; Neuberger, et al. (1985) Nature 314: 268-270; Boulianne, et al. (1984) Nature 312: 643-46.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that may be detected by screening with the antigen or immunogen.

Antibodies, and fragments thereof, of the invention may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, while the DNA sequence encoding the remaining parts of the antibody chain is derived from a human cell source. Furthermore, the invention relates to vectors, especially plasmids, cosmids, viruses, bacteriophages and other vectors common in genetic engineering, which contain the above-mentioned nucleic acid molecules of the invention. The nucleic acid molecules contained in the vectors may be linked to regulatory elements that ensure the transcription in prokaryotic and eukaryotic cells.

Vectors contain elements that facilitate manipulation for the expression of a foreign protein within the target host cell. Conveniently, manipulation of sequences and production of DNA for transformation is first performed in a bacterial host (e.g., *E. coli*) and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that confer resistance to antibiotics or other toxins, complement auxotrophic deficiencies, or supply critical nutrients not available from complex media. Exemplary vectors and methods for transformation of yeast are described in the art. See, e.g., Burke, et al. (2000) Methods in Yeast Genetics Cold Spring Harbor Laboratory Press.

The polypeptide coding sequence of interest may be operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included (e.g., a signal sequence).

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" refers broadly to contiguous linked DNA sequences, and, in the case of a secretory leader, contiguous and in reading frame. However, enhancers do not have to be contiguous.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (e.g., that increase levels of transcription in response to absence of a repressor). Inducible promoters may initiate increased levels of transcription from DNA under their control in response to some change in culture conditions (e.g., the presence or absence of a nutrient or a change in temperature.)

A second expression vector may be produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibodies, and fragments thereof, may be either a bacterial cell such as E. coli, or a eukaryotic cell. A mammalian cell of a well-defined type for this purpose, such as a myeloma cell, a Chinese hamster ovary (CHO), a NSO, or a HEK293 cell line may be used.

The general methods by which the vectors may be constructed, transfection methods required to produce the host cell and culturing methods required to produce the antibodies, and fragments thereof, from said host cells all include conventional techniques. Although preferably the cell line used to produce the antibody is a mammalian cell line, any other suitable cell line, such as a bacterial cell line such as an E. coli-derived bacterial strain, or a yeast cell line, may be used.

Similarly, once produced the antibodies may be purified according to standard procedures in the art, such as for example cross-flow filtration, ammonium sulphate precipitation, and affinity column chromatography.

Generation of Anti-KIR2DL1, 2, and 3 Antibodies Using Animals

The antibodies of the invention that selectively bind the KIR2DL1, KIR2DL2, and KIR2DL3 may be human monoclonal antibodies. Such human monoclonal antibodies directed against a KIR2DL1, KIR2DL2, and KIR2DL3 may be generated using transgenic or transchromosomic mice carrying parts of the human immune system rather than the mouse system. These transgenic and transchromosomic mice include mice referred to herein as the HuMAb Mouse® and KM Mouse® respectively, and are collectively referred to herein as "human Ig mice." The HuMAb Mouse® (Medarex. Inc.) contains human immunoglobulin gene miniloci that encode unrearranged human heavy (μ and γ) and κ light chain immunoglobulin sequences, together with targeted mutations that inactivate the endogenous μ and κ chain loci. See, e.g., Lonberg, et al. (1994) Nature 368(6474): 856-859. Accordingly, the mice exhibit reduced expression of mouse IgM or κ, and in response to immunization, the introduced human heavy and light chain transgenes undergo class switching and somatic mutation to generate high affinity human IgGκ monoclonal. Lonberg (1994) Handbook of Experimental Pharmacology 113: 49-101; Lonberg and Huszar (1995) Intern. Rev. Immunol. 13: 65-93, and Harding and Lonberg (1995) Ann. NY. Acad. Sci. 764: 536-546. The preparation and use of the HuMab Mouse®, and the genomic modifications carried by such mice, is further described in Taylor, et al. (1992) Nucleic Acids Research 20: 6287-6295; Chen, et al. (1993) International Immunology 5: 647-656; Tuaillon, et al. (1993) Proc. Natl. Acad. Sci. USA 90: 3720-3724; Choi, et al. (1993) Nature Genetics 4: 117-123; Chen, et al. (1993) EMBO J. 12: 821-830; Tuaillon, et al. (1994) J. Immunol. 152: 2912-2920; Taylor, et al. (1994) International Immunology 6: 579-591; and Fishwild, et al. (1996) Nature Biotechnology 14: 845-851. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; WO 92/03918, WO 93/12227, WO 94/25585; WO 97/13852; WO 98/24884; WO 99/45962; and WO 01/14424.

Human anti-KIR2DL1, KIR2DL2, and KIR2DL3 antibodies (e.g., antibodies which selectively bind KIR2DL1, KIR2DL2, or KIR2DL3) of the invention may be raised using a mouse that carries human immunoglobulin sequences on transgenes and transchromosomes, such as a mouse that carries a human heavy chain transgene and a human light chain transchromosome. Such mice, referred to herein as "KM Mice®", are described in detail in WO 02/43478.

Still further, alternative transgenic animal systems expressing human immunoglobulin genes are available in the art and may be used to raise anti-KIR2DL1, KIR2DL2, and KIR2DL3 antibodies of the invention. For example, an alternative transgenic system referred to as the Xenomouse (Abgenix, Inc.) may be used; such mice are described in, for example, U.S. Pat. Nos. 5,939,598; 6,075,181; 6,114,598; 6,150,584 and 6,162,963.

Moreover, alternative transchromosomic animal systems expressing human immunoglobulin genes are available in the art and may be used to raise anti-KIR2DL1, KIR2DL2, and KIR2DL3 antibodies of the invention. For example, mice carrying both a human heavy chain transchromosome and a human light chain transchromosome, referred to as "TC mice" may be used. See Tomizuka, et al. (2000) Proc. Natl. Acad. Sci. USA 97: 722-727. Furthermore, cows carrying human heavy and light chain transchromosomes have been described in the art (Kuroiwa, et al. (2002) Nature Biotechnology 20: 889-894) and may be used to raise anti-KIR2DL1, KIR2DL2, and/or KIR2DL3 antibodies of the invention.

Human monoclonal antibodies of the invention may also be prepared using phage display methods for screening libraries of human immunoglobulin genes. Such phage display methods for isolating human antibodies are established in the art. See, e.g., U.S. Pat. Nos. 5,223,409; 5,403,484; 5,571,698; 5,427,908 5,580,717; 5,969,108; 6,172,197; 5,885,793; 6,521,404; 6,544,731; 6,555,313; 6,582,915 and 6,593,081.

Human monoclonal antibodies of the invention may also be prepared using SCID mice into which human immune cells have been reconstituted such that a human antibody response may be generated upon immunization. See, e.g., U.S. Pat. Nos. 5,476,996 and 5,698,767.

When human Ig mice are used to raise human antibodies of the invention, such mice may be immunized with a purified or enriched preparation of KIR2DL1, KIR2DL2, and KIR2DL3 polypeptide, as described by Lonberg, et al. (1994) Nature 368(6474): 856-859; Fishwild, et al. (1996) Nature Biotechnology 14: 845-851; WO 98/24884 and WO 01/14424. Preferably, the mice will be 6-16 weeks of age upon the first infusion. For example, a purified or recombinant preparation (5-50 μg) of KIR2DL1, KIR2DL2, and KIR2DL3 may be used to immunize the human Ig mice intraperitoneally.

Prior experience with various antigens by others has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response may be monitored over the course of the immunization protocol with plasma samples being obtained by retroorbital bleeds. The plasma may be screened by ELISA (as described below), and mice with sufficient titers of anti-KIR2DL1, KIR2DL2, and KIR2DL3 human immunoglobulin may be used for fusions. Mice may be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene may be bred together into a single mouse having two different human heavy chain transgenes (HCo7/HCo12). Alternatively or additionally, the KM Mouse® strain may be used.

Generation of Hybridomas Producing Human Monoclonal Antibodies of the Invention

To generate hybridomas producing human monoclonal antibodies of the invention, splenocytes and/or lymph node cells from immunized mice may be isolated and fused to an appropriate immortalized cell line, such as a mouse myeloma cell line. The resulting hybridomas may be screened for the production of antigen-specific antibodies. For example, single cell suspensions of splenic lymphocytes from immunized mice may be fused to one-sixth the number of P3×63-Ag8.653 nonsecreting mouse myeloma cells (ATCC, CRL 1580) with 50% PEG. Cells may be plated at approximately $2 \times 10^{-5}$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells may be cultured in medium in which the HAT is replaced with HT. Individual wells may then be screened by ELISA for human monoclonal IgM and IgG antibodies. Once extensive hybridoma growth occurs, medium may be observed usually after 10-14 days. The antibody secreting hybridomas may be replated, screened again, and if still positive for human IgG, the monoclonal antibodies may be subcloned at least twice by limiting dilution. The stable subclones may then be cultured in vitro to generate small amounts of antibody in tissue culture medium for characterization.

To purify human monoclonal antibodies, selected hybridomas may be grown in two-liter spinner-flasks for monoclonal antibody purification. Supernatants may be filtered and concentrated before affinity chromatography with protein A-Sepharose (Pharmacia, Piscataway, N.J.) Eluted IgG may be checked by gel electrophoresis and high performance liquid chromatography to ensure purity. The buffer solution may be exchanged into PBS, and the concentration may be determined by OD280 using 1.43 extinction coefficient. The monoclonal antibodies may be aliquoted and stored at −80° C.

Labels

The antigens, antibodies and fragments thereof described herein may be modified post-translationally to add effector moieties such as chemical linkers, detectable moieties such as for example fluorescent dyes, enzymes, substrates, biolumi-nescent materials, radioactive materials, chemiluminescent moieties, a cytotoxic agent, radioactive materials, or functional moieties.

A wide variety of entities, e.g., ligands, may be coupled to the oligonucleotides as known in the art. Ligands may include naturally occurring molecules, or recombinant or synthetic molecules. Exemplary ligands include, but are not limited to, avadin, biotin, peptides, peptidomimetics, polylysine (PLL), polyethylene glycol (PEG), mPEG, cationic groups, spermine, spermidine, polyamine, thyrotropin, melanotropin, lectin, glycoprotein, surfactant protein A, mucin, glycosylated polyaminoacids, transferrin, aptamer, immunoglobulins (e.g., antibodies), insulin, transferrin, albumin, sugar, lipophilic molecules (e.g., steroids, bile acids, cholesterol, cholic acid, and fatty acids), vitamin A, vitamin E, vitamin K, vitamin B, folic acid, B12, riboflavin, biotin, pyridoxal, vitamin cofactors, lipopolysaccharide, hormones and hormone receptors, lectins, carbohydrates, multivalent carbohydrates, radiolabeled markers, fluorescent dyes, and derivatives thereof. See, e.g., U.S. Pat. Nos. 6,153,737; 6,172,208; 6,300,319; 6,335,434; 6,335,437; 6,395,437; 6,444,806; 6,486,308; 6,525,031; 6,528,631; and 6,559,279.

Additionally, moieties may be added to the antigen or epitope to increase half-life in vivo (e.g., by lengthening the time to clearance from the blood stream. Such techniques include, for example, adding PEG moieties (also termed pegilation), and are well-known in the art. See U.S. Patent Application Publication No. 2003/0031671.

An antigen, antibody or antigen binding fragment thereof, described herein may be "attached" to a substrate when it is associated with the solid label through a non-random chemical or physical interaction. The attachment may be through a covalent bond. However, attachments need not be covalent or permanent. Materials may be attached to a label through a "spacer molecule" or "linker group." Such spacer molecules are molecules that have a first portion that attaches to the biological material and a second portion that attaches to the label. Thus, when attached to the label, the spacer molecule separates the label and the biological materials, but is attached to both. Methods of attaching biological material (e.g., label) to a label are well known in the art, and include but are not limited to chemical coupling.

Detectable Labels

The anti-KIR2DL1, KIR2DL2, and KIR2DL3 antibodies described herein may be modified post-translationally to add effector labels such as chemical linkers, detectable labels such as for example fluorescent dyes, enzymes, substrates, bioluminescent materials, radioactive materials, and chemiluminescent labels, or functional labels such as for example streptavidin, avidin, biotin, a cytotoxin, a cytotoxic agent, and radioactive materials. Further exemplary enzymes include, but are not limited to, horseradish peroxidase, acetylcholinesterase, alkaline phosphatase, β-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent labels include, but are not limited to, luminol. Further exemplary bioluminescent materials include, but are not limited to, luciferin, luciferase, and aequorin. Further exemplary radioactive materials include, but are not limited to, bismuth-213 ($^{213}$Bs), carbon-14 ($^{14}$C), carbon-11 ($^{11}$C), chlorine-18 (Cl$^{18}$), chromium-51 ($^{51}$Cr), cobalt-57 ($^{57}$Co), cobalt-60 ($^{60}$Co), copper-64 ($^{64}$Cu), copper-67 ($^{67}$Cu), dysprosium-165 ($^{165}$Dy), erbium-169 ($^{169}$Er), fluorine-18 ($^{18}$F), gallium-67 ($^{67}$Ga), gallium-68 ($^{68}$Ga), germanium-68 ($^{68}$Ge), holmium-166 ($^{166}$Ho), indium-111 ($^{111}$In), iodine-125 ($^{125}$I), iodine-123 ($^{124}$I), iodine-124 ($^{124}$I), iodine-131 ($^{131}$I), iridium-192 ($^{192}$Ir), iron-59 ($^{59}$Fe), krypton-81 ($^{81}$Kr), lead-212 ($^{212}$Pb), lutetium-177 ($^{177}$Lu), molybdenum-99 ($^{99}$Mo), nitrogen-13 ($^{13}$N), oxygen-15 ($^{15}$O), palladium-103 ($^{103}$Pd), phosphorus-32 ($^{32}$P), potassium-42 ($^{42}$K), K), rhenium-186 ($^{186}$Re), rhenium-188 ($^{188}$Re), rubidium-81 ($^{81}$Rb), rubidium-82 ($^{82}$Rb), samarium-153 ($^{153}$Sm), selenium-75 ($^{75}$Se), sodium-24 ($^{24}$Na), strontium-82 ($^{82}$Sr), strontium-89 ($^{89}$Sr), sulfur 35 ($^{35}$S), technetium-99m ($^{99}$Tc), thallium-201 ($^{201}$Tl), tritium ($^{3}$H), xenon-133 ($^{133}$Xe), ytterbium-169 ($^{169}$Yb), ytterbium-177 ($^{177}$Yb), and yttrium-90 ($^{90}$Y).

Cytotoxic Agents

The anti-KIR2DL1, KIR2DL2, and KIR2DL3 antibodies described herein may be conjugated to cytotoxic agents including, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, caminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (TAXOL®), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g., IL-12 or IL-2), IL-12R antagonists, Erbitux®, Avastin®, Pertuzumab, anti-CD20 antibodies, Rituxan®, ocrelizumab, ofatumumab, DXL625, Herceptin®, or any combination thereof. Toxic enzymes from plants and bacteria such as ricin, diphtheria toxin and *Pseudomonas* toxin may be conjugated to the humanized antibodies, or binding fragments thereof, to generate cell-type-specific-killing reagents. Youle, et al. (1980) Proc. Nat'l Acad. Sci. USA 77: 5483; Gilliland, et al. (1980) Proc. Nat'l Acad. Sci. USA 77: 4539; Krolick, et al. (1980) Proc. Nat'l Acad. Sci. USA 77: 5419. Other cytotoxic agents include cytotoxic ribonucleases. See U.S. Pat. No. 6,653,104.

The anti-KIR2DL1, KIR2DL2, and KIR2DL3 antibodies described herein may be conjugated to a radionuclide that emits alpha or beta particles (e.g., radioimmunoconjuagtes). Such radioactive isotopes include but are not limited to beta-emitters such as phosphorus-32 ($^{32}$P), scandium-47 ($^{47}$Sc), copper-67 ($^{67}$Cu), gallium-67 ($^{67}$Ga), yttrium-88 ($^{88}$Y), yttrium-90 ($^{90}$Y), iodine-125 ($^{125}$I), iodine-131 ($^{131}$I), samarium-153 ($^{153}$Sm), lutetium-177 ($^{177}$Lu), rhenium-186 ($^{186}$Re), rhenium-188 ($^{188}$Re), and alpha-emitters such as astatine-211 ($^{211}$At), lead-212 ($^{212}$Pb), bismuth-212 ($^{212}$Bi), bismuth-213 ($^{213}$Bi) or actinium-225 ($^{225}$Ac).

Methods are known in the art for conjugating a KIR2DL1, KIR2DL2, and KIR2DL3 described herein to a label, such as those methods described by Hunter, et al (1962) Nature 144: 945; David, et al. (1974) Biochemistry 13: 1014; Pain, et al. (1981) J. Immunol. Meth. 40: 219; and Nygren (1982) Histochem and Cytochem, 30: 407.

Substrates

The anti-KIR2DL1, KIR2DL2, and KIR2DL3 antibodies described herein may be attached to a substrate. A number of substrates (e.g., solid supports) known in the art are suitable for use with The anti-KIR2DL1, KIR2DL2, and KIR2DL3 antibodies described herein. The substrate may be modified to contain channels or other configurations. See Fung (2004) [Ed.] Protein Arrays: Methods and Protocols Humana Press and Kambhampati (2004) [Ed.] Protein Microarray Technology John Wiley & Sons.

Substrate materials include, but are not limited to acrylics, agarose, borosilicate glass, carbon (e.g., carbon nanofiber sheets or pellets), cellulose acetate, cellulose, ceramics, gels, glass (e.g., inorganic, controlled-pore, modified, soda-lime, or functionalized glass), latex, magnetic beads, membranes, metal, metalloids, nitrocellulose, NYLON®, optical fiber bundles, organic polymers, paper, plastics, polyacryloylmorpholide, poly(4-methylbutene), poly(ethylene terephthalate), poly(vinyl butyrate), polyacrylamide, polybutylene, polycarbonate, polyethylene, polyethyleneglycol terephthalate, polyformaldehyde, polymethacrylate, polymethylmethacrylate, polypropylene, polysaccharides, polystyrene, polyurethanes, polyvinylacetate, polyvinylchloride, polyvinylidene difluoride (PVDF), polyvinylpyrrolidinone, rayon, resins, rubbers, semiconductor materials, Sepharose®, silica, silicon, styrene copolymers, TEFLON®, and variety of other polymers.

Substrates need not be flat and can include any type of shape including spherical shapes (e.g., beads) or cylindrical shapes (e.g., fibers). Materials attached to solid supports may be attached to any portion of the solid support (e.g., may be attached to an interior portion of a porous solid support material).

The substrate body may be in the form of a bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial. The substrate may be a singular discrete body (e.g., a single tube, a single bead), any number of a plurality of substrate bodies (e.g., a rack of 10 tubes, several beads), or combinations thereof (e.g., a tray comprises a plurality of microtiter plates, a column filled with beads, a microtiter plate filed with beads).

An anti-KIR2DL1, KIR2DL2, and KIR2DL3 antibody may be "attached" to a substrate when it is associated with the solid substrate through a non-random chemical or physical interaction. The attachment may be through a covalent bond. However, attachments need not be covalent or permanent. Materials may be attached to a substrate through a "spacer molecule" or "linker group." Such spacer molecules are molecules that have a first portion that attaches to the biological material and a second portion that attaches to the substrate. Thus, when attached to the substrate, the spacer molecule separates the substrate and the biological materials, but is attached to both. Methods of attaching biological material (e.g., label) to a substrate are well known in the art, and include but are not limited to chemical coupling.

Plates, such as microtiter plates, which support and contain the solid-phase for solid-phase synthetic reactions may be used. Microtiter plates may house beads that are used as the solid-phase. By "particle" or "microparticle" or "nanoparticle" or "bead" or "microbead" or "microsphere" herein is meant microparticulate matter having any of a variety of shapes or sizes. The shape may be generally spherical but need not be spherical, being, for example, cylindrical or polyhedral. As will be appreciated by those in the art, the particles may comprise a wide variety of materials depending on their use, including, but not limited to, cross-linked starch, dextrans, cellulose, proteins, organic polymers including styrene polymers such as polystyrene and methylstyrene as well as other styrene co-polymers, plastics, glass, ceramics, acrylic polymers, magnetically responsive materials, colloids, thoriasol, carbon graphite, titanium dioxide, nylon, latex, and TEFLON®. See e.g., "Microsphere Detection Guide" from Bangs Laboratories, Fishers, Ind.

The anti-KIR2DL1, KIR2DL2, and KIR2DL3 antibodies described herein may be attached to on any of the forms of substrates described herein (e.g., bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial). In particular, particles or beads may be a component of a gelling material or may be separate components such as latex beads made of a variety of synthetic plastics (e.g., polystyrene). The label (e.g., streptavidin) may be bound to a substrate (e.g., bead).

Pharmaceutical Compositions

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration may occur by means of injection, powder, liquid, gel, drops, or other means of administration.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations may be found, for example, in Grennaro (2005) [Ed.] Remington: The Science and Practice of Pharmacy [$21^{st}$ Ed.]

Pharmaceutical compositions typically must be sterile and stable under the conditions of manufacture and storage. The invention contemplates that the pharmaceutical composition is present in lyophilized form. The composition may be formulated as a solution, microemulsion, liposome, or other ordered structure suitable to high drug concentration. The carrier may be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition.

The anti-KIR2DL1, KIR2DL2, and KIR2DL3 antibodies described herein may be formulated into pharmaceutical compositions of various dosage forms. To prepare the pharmaceutical compositions of the invention, at least one KIR2DL1, KIR2DL2, and KIR2DL3 as the active ingredient may be intimately mixed with appropriate carriers and additives according to techniques well known to those skilled in the art of pharmaceutical formulations. See Grennaro (2005) [Ed.] Remington: The Science and Practice of Pharmacy [$21^{st}$ Ed.] For example, the antibodies described herein may be formulated in phosphate buffered saline pH 7.2 and supplied as a 5.0 mg/mL clear colorless liquid solution.

Similarly, compositions for liquid preparations include solutions, emulsions, dispersions, suspensions, syrups, and elixirs, with suitable carriers and additives including but not limited to water, alcohols, oils, glycols, preservatives, flavoring agents, coloring agents, and suspending agents. Typical preparations for parenteral administration comprise the active ingredient with a carrier such as sterile water or parenterally acceptable oil including but not limited to polyethylene glycol, polyvinyl pyrrolidone, lecithin, arachis oil or sesame oil, with other additives for aiding solubility or preservation may also be included. In the case of a solution, it may be lyophilized to a powder and then reconstituted immediately prior to use. For dispersions and suspensions, appropriate carriers and additives include aqueous gums, celluloses, silicates, or oils.

For each of the recited embodiments, the anti-KIR2DL1, KIR2DL2, and KIR2DL3 antibodies described herein may be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

In many cases, it will be preferable to include isotonic agents, e.g., sugars, polyalcohols such as mannitol, sorbitol, or sodium chloride in the composition. Prolonged absorption of the injectable compositions may be brought about by including in the composition an agent which delays absorption, e.g., monostearate salts and gelatin. Moreover, the compounds described herein may be formulated in a time release formulation, e.g. in a composition that includes a slow release polymer. The anti-KIR2DL1, KIR2DL2, and KIR2DL3 antibodies described herein may be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Supplementary active compounds can also be incorporated into the compositions.

As noted such compositions may additionally comprise a desired antigen, e.g., a tumor antigen or another immune modulatory compounds such as Toll like receptor agonists, type 1 interferon such as alpha and beta interferons and CD40 agonists such as agonistic CD40 antibodies and antibody fragments, preferably anti-human CD40 agonistic antibodies and antibody fragments or other immune enhancers or suppressors such as PD-L1, PD-L2, CTLA4 fusion proteins and antibodies specific thereto.

Compositions comprising The anti-KIR2DL1, KIR2DL2, and KIR2DL3 antibodies described herein may further comprise an antigen or other immune agonist. The antigen may be administered in an amount that, in combination with the other components of the combination, is effective to generate an immune response against the antigen. For example, the antigen may be administered in an amount from about 100 mg/kg to about 100 mg/kg. In some embodiments, the antigen may be administered in an amount from about 10 mg/kg to about 10 mg/kg. In some embodiments, the antigen may be administered in an amount from about 1 mg/kg to about 5 mg/kg. The particular amount of antigen that constitutes an amount effective to generate an immune response, however, depends to some extent upon certain factors such as, for example, the particular antigen being administered; the particular agonist being administered and the amount thereof; the particular agonist being administered and the amount thereof; the state of the immune system; the method and order of administration of the agonist and the antigen; the species to which the formulation is being administered; and the desired therapeutic result. Accordingly, it is not practical to set forth generally the amount that constitutes an effective amount of the antigen. Those of ordinary skill in the art, however, can readily determine the appropriate amount with due consideration of such factors.

Pharmaceutically Acceptable Carriers

An Anti-KIR2DL1, 2 and/or 3 antibody can be combined with one or more carriers (diluents, excipients, and the like) and/or adjuvants appropriate for one or more intended routes of administration to provide compositions that are pharmaceutically acceptable.

Anti-KIR2DL1, 2 and/or 3 antibodies may be, for example, admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and optionally further tabletted or encapsulated for conventional administration. Alternatively, an Anti-KIR2DL1, 2 and/or 3 antibody may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other carriers, adjuvants, and modes of administration are well known in the pharmaceutical arts. A carrier or diluent may include time delay material, such as glyceryl monostearate or glyceryl distearate alone or with a wax, or other functionally similar materials.

Pharmaceutically acceptable carriers generally include any and all suitable solvents, dispersion media, coatings, antibacterial and antifungal agents, isotonic and absorption delaying agents, and the like that are physiologically compatible with an anti-KIR2DL1, 2 and/or 3 antibody. Examples of pharmaceutically acceptable carriers include water, saline, phosphate buffered saline, dextrose, glycerol, ethanol, and the like, as well as combinations of any thereof. In many cases, it can be desirable to include isotonic agents, for example, sugars, polyalcohols such as mannitol, sorbitol, or sodium chloride in such a composition. Pharmaceutically acceptable substances such as wetting agents or minor amounts of auxiliary substances such as wetting agents or emulsifying agents, preservatives or buffers, which desirably can enhance the shelf life or effectiveness of the Anti-KIR antibody, related composition, or combination. Suitability for carriers and other components of pharmaceutical compositions is determined based on the lack of significant negative impact on the desired biological properties of the antibody.

Anti-KIR2DL1, 2 and/or 3 antibody compositions, related compositions, and combinations according to the invention may be in a variety of suitable forms. Such forms include, for example, liquid, semi-solid and solid dosage forms, such as liquid solutions (e.g., injectable and infusible solutions), dispersions or suspensions, emulsions, microemulsions, tablets, pills, powders, liposomes, dendrimers and other nanoparticles (See, e.g., Baek et al., Methods Enzymol. 2003; 362: 240-9; Nigavekar et al., Pharm Res. 2004 March; 21(3):476-83), microparticles, and suppositories. Formulations, salts are further described in WO2006/072625.

Typically, compositions in the form of injectable or infusible solutions, such as compositions similar to those used for passive immunization of humans with other antibodies, are used for delivery of anti-KIR2DL1, 2 and/or 3 antibodies of the invention. A typical mode for delivery of anti-KIR2DL1, 2 and/or 3 antibody compositions is by parenteral administration (e.g., intravenous, subcutaneous, intraperitoneal, and/or intramuscular administration). In one aspect, an anti-KIR2DL1, 2 and/or 3 antibody is administered to a human patient by intravenous infusion or injection.

A composition for pharmaceutical use also can include various diluents, fillers, salts, buffers, detergents (e.g., a non-ionic detergent, such as Tween-80), stabilizers (e.g., sugars or protein-free amino acids), preservatives, tissue fixatives, solubilizers, and/or other materials suitable for inclusion in a composition for pharmaceutical use. Examples of suitable components also are described in, e.g., Berge et al., J. Pharm. Sci., 6661), 1-19 (1977); Wang and Hanson, J. Parenteral. Sci. Tech: 42, S4-S6 (1988);U.S. Pat. Nos. 6,165,779 and 6,225, 289. Such a pharmaceutical composition also can include preservatives, antioxidants, or other additives known to those of skill in the art. Additional pharmaceutically acceptable carriers are known in the art. See, e.g., references in WO 2006/072625.

A person of skill in the art would be able to determine an effective dosage and frequency of administration through routine experimentation, for example guided by the disclosure herein and the teachings in Goodman, et al. (2011) Goodman & Gilman's The Pharmacological Basis of Therapeutics [$12^{th}$ Ed.]; Howland, et al. (2005) Lippincott's Illustrated Reviews: Pharmacology [$2^{nd}$ Ed.]; and Golan, (2008) Principles of Pharmacology: The Pathophysiologic Basis of Drug Therapy [$2^{nd}$ Ed.] See, also, Grennaro (2005) [Ed.] Remington: The Science and Practice of Pharmacy [20 Ed.]

Routes of Administration

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are intravenous injection or infusion. The administration can be local, where the composition is administered directly, close to, in the locality, near, at, about, or in the vicinity of, the site(s) of disease, e.g., localized, or systemic, wherein the composition is given to the patient and passes through the body widely, thereby reaching the site(s) of disease. Local administration (e.g., injection) may be accomplished by administration to the cell, tissue, organ, and/or organ system, which encompasses and/or is affected by the disease, and/or where the disease signs and/or symptoms are active or are likely to occur (e.g., tumor site). Administration can be topical with a local effect, composition is applied directly where its action is desired (e.g., site of inflammation or pain).

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

In further embodiments, the present invention provides kits including one or more containers comprising pharmaceutical dosage units comprising an effective amount of one or more antibodies and fragments thereof of the present invention. Kits may include instructions, directions, labels, marketing information, warnings, or information pamphlets.

Dosages

The amount of the anti-KIR2DL1, KIR2DL2, and KIR2DL3 antibodies described herein in a therapeutic composition according to any embodiments of this invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of antibodies, and fragments thereof, calculated to produce the desired therapeutic effect in association with the required pharmaceutical carrier. The specification for the dosage unit forms of the invention are dictated by and directly dependent on the unique characteristics of the antibodies, and fragments thereof, and the particular therapeutic effect to be achieved, and the limitations inherent in the art of compounding such an antibodies, and fragments thereof, for the treatment of sensitivity in individuals. In therapeutic use for treatment of conditions in mammals (e.g., humans) for which the antibodies and fragments thereof of the present invention or an appropriate pharmaceutical composition thereof are effective, the antibodies and fragments thereof of the present invention may be administered in an effective amount. The dosages as suitable for this invention may be a composition, a pharmaceutical composition or any other compositions described herein.

The dosage may be administered as a single dose, a double dose, a triple dose, a quadruple dose, and/or a quintuple dose. The dosages may be administered singularly, simultaneously, and sequentially.

The dosage form may be any form of release known to persons of ordinary skill in the art. The compositions of the present invention may be formulated to provide immediate release of the active ingredient or sustained or controlled release of the active ingredient. In a sustained release or controlled release preparation, release of the active ingredient may occur at a rate such that blood levels are maintained within a therapeutic range but below toxic levels over an extended period of time (e.g., 4 to 24 hours). The preferred dosage forms include immediate release, extended release, pulse release, variable release, controlled release, timed release, sustained release, delayed release, long acting, and combinations thereof, and are known in the art.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

It will be appreciated that the pharmacological activity of the compositions may be monitored using standard pharmacological models that are known in the art. Furthermore, it will be appreciated that the compositions comprising an anti-KIR2DL1, KIR2DL2, and KIR2DL3, antibody or antigen-binding fragment thereof, may be incorporated or encapsulated in a suitable polymer matrix or membrane for site-specific delivery, or may be functionalized with specific targeting agents capable of effecting site specific delivery. These techniques, as well as other drug delivery techniques are well known in the art. Determination of optimal dosages for a particular situation is within the capabilities of those skilled in the art. See, e.g., Grennaro (2005) [Ed.] Remington: The Science and Practice of Pharmacy [21$^{st}$ Ed.]

Treatment of Inflammatory and Autoimmune Disorders

The invention provides therapeutic methods for treating or preventing an inflammatory or autoimmune disorder in individuals having or susceptible to an inflammatory or autoimmune disorder, wherein the treatment involves anti-KIR2DL1, 2 and/or 3 antibody compositions, and/or related compositions.

For example, elevated levels of expression of KIR2DL2 have been reported in patient suffering from inflammatory bowel disease (IBD) and Crohn's disease. See Wilson, et al. (2010) Human Immunol. 71(3): 293-7.

The KIR2DL1, 2 and/or 3 antibodies described herein may be used in compositions, uses, and methods for the treatment of T cell mediated inflammatory and autoimmune disorders such as of systemic lupus erythematosus, Wegener's granulomatosis, autoimmune hepatitis, Crohn's disease, scleroderma, ulcerative colitis, Sjögren's syndrome, uveitis, Type 1 diabetes mellitus, myocarditis, rheumatic fever, ankylosing spondylitis, rheumatoid arthritis, multiple sclerosis, or psoriasis.

The KIR2DL1, 2 and/or 3 antibodies described herein may be used in compositions, uses, and methods for the treatment of autoimmune diseases or disorders. Examples of autoimmune diseases or disorders include, but are not limited to acquired immune deficiency syndrome (AIDS), acquired spenic atrophy, acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis (including large vessel vasculitis (including polymyalgia rheumatica and giant cell (Takayasu's) arthritis), allergic conditions, allergic contact dermatitis, allergic dermatitis, allergic granulomatous angiitis, allergic hypersensitivity disorders, allergic neuritis, allergic reaction, alopecia areata, alopecia totalis, Alport's syndrome, alveolitis (e.g., allergic alveolitis and fibrosing alveolitis), Alzheimer's disease, amyloidosis, amylotrophic lateral sclerosis (ALS; Lou Gehrig's disease), an eosinophil-related disorder (e.g., eosinophilia), anaphylaxis, ankylosing spondylitis, antgiectasis, antibody-mediated nephritis, Anti-GBM/Anti-TBM nephritis, antigen-antibody complex-mediated diseases, antiglomerular basement membrane disease, antiphospholipid antibody syndrome, antiphospholipid syndrome (APS), aphthae, aphthous stomatitis, aplastic anemia, arrhythmia, arteriosclerosis, arteriosclerotic disorders, arthritis (e.g., rheumatoid arthritis such as acute arthritis, chronic rheumatoid arthritis), arthritis chronica progrediente, arthritis deformans, ascariasis, aspergilloma (or granulomas containing eosinophils), aspergillosis, aspermiogenese, asthma (e.g., asthma bronchiale, bronchial asthma, and auto-immune asthma), ataxia telangiectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease (e.g., autoimmune inner ear disease (AGED)), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies (e.g., epilepsy), channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy (e.g., IgM polyneuropathies or IgM-mediated neuropathy), chronic obstructive airway disease, chronic pulmonary inflammatory disease, Chronic recurrent multifocal ostomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogans syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis (e.g., chronic cyclitis, heterochronic cyclitis, iridocyclitis, or Fuch's cyclitis), cystic fibrosis, cytokine-induced toxicity, deafness, degenerative arthritis, demyelinating diseases (e.g., autoimmune demyelinating diseases), demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis (e.g., allergic encephalomyelitis or encephalomyelitis allergica and experimental allergic encephalomyelitis (EAE)), endarterial hyperplasia, endocarditis, endocrine ophthamopathy, endometriosis. endomyocardial fibrosis, endophthalmia phacoanaphylactica, endophthalmitis, enteritis allergica, eosinophilia-myalgia syndrome, eosinophilic faciitis, epidemic keratoconjunctivitis, epidermolisis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, flariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, haemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schonlein purpura, Herpes gestationis, human immunodeficiency virus (HIV) infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenic purpura (ITP), IgA nephropathy, IgE-mediated diseases (e.g., anaphylaxis and allergic and atopic rhinitis), IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antobodies, inflammation of all or part of the uvea, inflammatory bowel disease (IBD) inflammatory hyperproliferative skin diseases, inflammatory myopathy, insulin-dependent diabetes (type 1), insulitis, Interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis nodosa), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes (e.g., Lambert-Eaton myasthenic syndrome or Eaton-Lambert syndrome), parasitic diseases such as Lesihmania, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including pemphigus vulgaris), pemphigus erythematosus, pemphigus foliaceus, pemphigus mucusmembrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis nodosa, Type I, II, & III, polyarthritis chronica primaria, polychondritis (e.g., refractory or relapsed polychondritis), polyendocrine autoimmune disease, polyendocrine failure, polyglandular syndromes (e.g., autoimmune polyglandular syndromes (or polyglandular endocrinopathy syndromes)), polymyalgia rheumatica, polymyositis, polymyositis/dermatomyositis, polyneuropathies, polyradiculitis acuta, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis (e.g., benign monoclonal gammopathy and monoclonal garnmopathy of undetermined significance, MGUS), primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyreoiditis, Raynauds phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma (including systemic scleroderma), sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjogren's syndrome, sperm & testicular autoimmunity, sphenoid sinusitis, Stevens-Johnson syndrome, stiff-man (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes (e.g., cutaneous SLE), systemic necrotizing vasculitis, and ANCA-associated vasculitis, such as Churg-Strauss vasculitis or syndrome (CSS)), tabes dorsalis, Takayasu's arteritis, telangiectasia, temporal arteritis/Giant cell arteritis, thromboangitis ubiterans, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, thrombocytopenic purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria (e.g., chronic allergic urticaria and chronic idiopathic urticaria, including chronic autoimmune urticaria), uveitis (e.g., anterior uveitis), uveoretinitis, valvulitis, vascular dysfunction, vasculitis, vertebral arthritis, vesiculobullous dermatosis, vitiligo, Wegener's granulomatosis (now termed Granulomatosis with Polyangiitis (GPA), Wiskott-Aldrich syndrome, and x-linked hyper IgM syndrome.

The KIR2DL1, 2 and/or 3 antibodies described herein may be used in compositions, uses, and methods for the treatment of inflammatory conditions and inflammatory disease.

Inflammatory conditions and inflammatory diseases, include but are not limited to rheumatic diseases (e.g., rheumatoid arthritis, osteoarthritis, psoriatic arthritis) spondyloarthropathies (e.g., ankylosing spondylitis, reactive arthritis, Reiter's syndrome), crystal arthropathies (e.g., gout, pseudogout, calcium pyrophosphate deposition disease), multiple sclerosis, Lyme disease, polymyalgia rheumatica; connective tissue diseases (e.g., systemic lupus erythematosus, systemic sclerosis, polymyositis, dermatomyositis, Sjogren's syndrome); vasculitides (e.g., polyarteritis nodosa, Wegener's granulomatosis, Churg-Strauss syndrome); inflammatory conditions including consequences of trauma or ischaemia, sarcoidosis; vascular diseases including atherosclerotic vascular disease, atherosclerosis, and vascular occlusive disease (e.g., atherosclerosis, ischaemic heart disease, myocardial infarction, stroke, peripheral vascular disease), and vascular stent restenosis; ocular diseases including uveitis, corneal disease, iritis, iridocyclitis, and cataracts.

Inflammatory conditions also include, but are not limited to acid Reflux/Heartburn, Acne, Acne Vulgaris, Allergies and Sensitivities, Alzheimer's Disease, Asthma, Atherosclerosis and Vascular Occlusive Disease (e.g., Atherosclerosis, Ischaemic Heart Disease, Myocardial Infarction, Stroke, Peripheral Vascular Disease) and Vascular Stent Restenosis, Autoimmune Diseases, Bronchitis, Cancer, Carditis, Cataracts, Celiac Disease, Chronic Pain, Chronic Prostatitis, Cirrhosis, Colitis, Connective Tissue Diseases (e.g., Systemic Lupus Erythematosus, Systemic Sclerosis, Polymyositis, Dermatomyositis, Sjogren's Syndrome), Corneal Disease, Crohn's Disease, Crystal Arthropathies (e.g., Gout, Pseudogout, Calcium Pyrophosphate Deposition Disease), Dementia, Dermatitis, Diabetes, Dry Eyes, Eczema, Edema, Emphysema, Fibromyalgia, Gastroenteritis, Gingivitis, Glomerulonephritis, Heart Disease, Hepatitis, High Blood Pressure, Hypersensitivities, Inflammatory Bowel Diseases, Inflammatory Conditions including Consequences of Trauma or Ischaemia, Insulin Resistance, Interstitial Cystitis, Iridocyclitis, Iritis, Joint Pain/Arthritis/Rheumatoid Arthritis, Lyme Disease, Metabolic Syndrome (Syndrome X), Multiple Sclerosis, Myositis, Nephritis, Obesity, Ocular Diseases including Uveitis, Osteopenia, Osteoporosis, Parkinson's Disease, Pelvic Inflammatory Disease, Periodontal Disease, Polyarteritis, Polychondritis, Polymyalgia Rheumatica, Psoriasis, Reperfusion Injury, Rheumatic Arthritis, Rheumatic Diseases (e.g., Rheumatoid Arthritis, Osteoarthritis, Psoriatic Arthritis), Rheumatoid Arthritis, Sarcoidosis, Scleroderma, Sinusitis, Sjögren's Syndrome, Spastic Colon, Spondyloarthropathies (e.g., Ankylosing Spondylitis, Reactive Arthritis, Reiter's Syndrome), Systemic Candidiasis, Tendonitis, Transplant Rejection, UTI's, Vaginitis, Vascular Diseases including Atherosclerotic Vascular Disease, Vasculitides (e.g., Polyarteritis Nodosa, Wegener's Granulomatosis, Churg-Strauss Syndrome), and Vasculitis.

The term "treatment" herein refers to the delivery of an effective amount of such a formulation with the purpose of preventing any symptoms or disease state to develop or with the purpose of preventing (e.g. preventing or postponing progression), easing, ameliorating, or eradicating (curing) such symptoms or disease states already developed. The term "treatment" is thus meant to include treatment of minimal or non-detectable disease, e.g., in an individual having experienced a treatment response after a first treatment, or the treatment of an established and/or acute phase.

Delivering anti-KIR2DL1, 2 and/or 3 antibodies to a subject (either by direct administration or expression from a nucleic acid therein, such as from a pox viral gene transfer vector comprising anti-KIR2DL1, 2 and/or 3 antibody-encoding nucleic acid sequence(s)) and practicing the other methods of the invention can be used for the purpose of preventing (e.g. preventing or postponing progression), easing, ameliorating, or eradicating (curing) such symptoms or disease states already developed.

The methods of the invention can be particularly useful in the reduction and/or amelioration of T cell activity, proliferation or number (e.g. number of activated pro-inflammatory T cells (e.g. CD4+ T cells, HLA-cw3 and/or HLA-cw4-positive T cells) in circulation or at a site of inflammation), and any parameter or symptom associated therewith (e.g. inflammation marker levels). Methods that reduce, prevent, or otherwise ameliorate such aspects of inflammatory or autoimmune disorders, independently and collectively, are advantageous features of the invention. As used herein, "T cells" refers to a sub-population of lymphocytes that mature in the thymus, and which display, among other molecules T cell receptors on their surface. T cells can be identified by virtue of certain characteristics and biological properties, such as the expression of specific surface antigens including the TCR, CD4 or CD8, the ability of certain T cells to kill tumor or infected cells, the ability of certain T cells to activate other cells of the immune system, and the ability to release protein molecules called cytokines that stimulate or inhibit the immune response. Any of these characteristics and activities can be used to identify T cells, using methods well known in the art. Within the context of this invention, "active" or "activated" T cells designate biologically active T cells, more particularly T cells having the capacity of cytolysis or of stimulating an immune response by, e.g., secreting cytokines. Active cells can be detected in any of a number of well known methods, including functional assays and expression-based assays such as the expression of cytokines such as TNF-alpha.

Methods for the treatment of an individual having an autoimmune or inflammatory disease, may comprise administering to the individual an anti-KIR2DL1, 2 and/or 3 antibody. In one embodiment, the individual has an autoimmune or inflammatory disease that has is established (e.g. been declared for an extended period of time, for example more than one year), has signs of ongoing or active inflammation, has physical signs of disease (e.g. joint swelling, lesions, neurological symptoms), has chronic disease, has severe disease (as assessed by applicable criteria, e.g. DAS or ACR criteria in rheumatoid arthritis) or has progressing disease.

Methods for the treatment of an individual having an established autoimmune or inflammatory disease, may comprise administering to the individual an anti-KIR2DL1, 2 and/or 3 antibody. The present invention provides methods for the treatment of acute phases, or of an attack, crisis, exacerbation or flare, of autoimmune or inflammatory diseases using an anti-KIR2DL1, 2 and/or 3 antibody (or related compositions), preferably wherein the antibody is administered to an individual during an acute phase or during an attack, crisis, exacerbation or flare of an autoimmune or inflammatory disease. The disease may be selected from the group consisting of rheumatoid arthritis, Juvenile idiopathic arthritis, multiple sclerosis, Crohn disease or rectocolitis, Lupus erythematosus, ankylosing spondylitis and related diseases. In one embodiment, the disease is characterized by the presence of cells expressing anti-KIR2DL1, 2 and/or 3 ligand (e.g. HLA-cw3 or HLA-cw4), preferably by the presence of CD4+ T cells expressing HLA-cw3 and/or HLA-cw4. The disease is characterized by the presence of detectable levels of a proteolytic enzyme, an inflammatory mediator, a marker of ongoing inflammation or a proinflammatory cytokine (e.g. TNF-α and/or interleukin-1 (IL-1)).

Disease diagnosis, evolution and rating (or staging) can be defined by standard medical criteria for the particular type of disease in order to determine whether an individual has disease that is established, is in an acute phase, is progressing, is chronic, has physical symptoms, or is of a certain level of severity. Likewise, attack, crisis, exacerbation or flares can be identified by any suitable medical criteria.

Anti-KIR2DL1, 2 and/or 3 antibodies can advantageously be used to treat established disease. "Established disease" refers to an autoimmune or inflammatory disease which has been declared for an extended period of time, e.g. more than one year. Depending on the specific disease, established disease also means a disease which is not controlled e.g. which is still progressing or for which the patient does not experience remission, in the presence or in the absence of a treatment. In one aspect, the invention provides a method for the treatment of an autoimmune or inflammatory disease in a patient, comprising: (a) determining whether said patient has an established disease; and (b) if said patient has an established diseases, administering to said patient an effective dose of anti-KIR2DL1, 2 and/or 3 antibody.

Anti-KIR2DL1, 2 and/or 3 antibodies can also advantageously be used to treat chronic disease. "Chronic disease" refers to a disease that persists for an extended period of time. For instance, a chronic disease can be a disease lasting 3 months or more, as defined by the U.S. National Center for Health Statistics. In one aspect, the invention provides a method for the treatment of an autoimmune or inflammatory disease in a patient, comprising: (a) determining whether said patient has chronic disease; and (b) if said patient has chronic diseases, administering to said patient an effective dose of anti-KIR2DL1, 2 and/or 3 antibody.

Anti-KIR2DL1, 2 and/or 3 antibodies can also advantageously be used to treat individuals having an attack, crisis, exacerbation or flare. The terms "attack", "crisis", "exacerbation" and "flare", designate a more rapid evolution of new symptoms or worsening of old symptoms related to an inflammatory or an autoimmune disease. Such phases last over a period of hours or days, as opposed to a slow progression of the disease that occurs over months and years. During such attacks, the patient experiences fever, pain, inflammatory syndrome (flu-like syndrome). In RA, the joints of the patient are swollen and painful. The patient can experience flu-like syndromes. A crisis can last from a few hours to many weeks. In Multiple Sclerosis, flare-ups can feature a new symptom or the worsening of an existing symptom but must last at least 24 hours to be considered a true exacerbation, a flare up denotes new lesions forming in the brain or spinal cord that disrupt neural transmission. Most flare-ups last a few days or weeks but can last for several months. Effects can for instance be: movement difficulties or spasms, balance and coordination problems; vision problems, uncoordinated eye movements, blurred vision or double vision, partial blindness during a flare-up; bladder and bowel symptoms; sexual problems, changes in mental function: memory loss, inattention and poor judgment or depression. In Crohn's disease or rectocolitis, a flare up is mainly the exacerbation of usual Crohn's disease symptoms: diarrhea, crampy abdominal pain, fever, loss of appetite. In one aspect, the invention provides a method for the treatment an autoimmune or inflammatory disease in a patient comprising: (a) determining whether said patient is experiencing an attack, crisis, exacerbation or flare; (b) if said patient experiences an attack, crisis, exacerbation or flare, administering to said patient an effective dose of anti-KIR2DL1, 2 and/or 3 antibody.

Anti-KIR2DL1, 2 and/or 3 antibodies can also advantageously be used to treat individuals having a relapse. The term "relapse" refers to improvement or stabilization in a patient's symptoms. A disease is relapsing when the health or condition of the patient improves. In one aspect, the invention provides a method for the treatment an autoimmune or inflammatory disease in a patient comprising: (a) determining whether said patient is experiencing a relapse, crisis, exacerbation or flare; (b) if said patient experiences a relapse, administering to said patient an effective dose of anti-KIR2DL1, 2 and/or 3 antibody.

Optionally, an HLA-cw3 and/or HLA-cw4 detection step can be carried out, comprising detecting the presence of a an HLA-cw3 and/or HLA-cw4 in a patient, prior to treatment with an anti-KIR2DL1, 2 and/or 3 antibody. Generally, in this step, biological sample is taken from a patient, for example a sample of synovial fluid, e.g. in a patient having rheumatoid arthritis. The biological sample is assessed for the presence of HLA-cw3 and/or HLA-cw4 polypeptide or nucleic acid. If the biological sample is positive for the presence of HLA-cw3 and/or HLA-cw4, the patient can then advantageously be treated with the anti-KIR2DL1, 2 and/or 3 antibodies.

The anti-KIR2DL1, 2 and/or 3 antibody is used as monotherapy (the sole therapeutic agent). The treatment methods this invention may further comprise treatment an individual with an anti-KIR2DL1, 2 and/or 3 antibody and a second therapeutic agent, including agents normally utilized for the particular therapeutic purpose for which the antibody is being administered. The anti-KIR2DL1, 2 and/or 3 antibody and second therapeutic agent can be administered separately, together or sequentially, or in a cocktail. The second therapeutic agent will normally be administered in amounts typically used for that agent in a monotherapy for the particular disease or condition being treated. In one embodiment, the second therapeutic agent is administered in a dose less than the generally accepted efficacious dose; for example, in various embodiments, the composition comprises a dosage that is less than about 10% to 75% of the generally accepted efficacious dose is administered. Preferably, the second therapeutic agent is an agent that reduces proteolytic enzymes, an inflammatory mediator, or a proinflammatory cytokine such as TNF-α and/or interleukin-1 (IL-1). Preferably, the second therapeutic agent is DMARD or a DMD, optionally further wherein the second therapeutic agent is methotrexate (Rheumatrex®, Trexall®), hydroxychloroquine (Plaquenil®), sulfasalazine (Azulfidine®), leflunomide (Arava®), a tumor necrosis factor inhibitor (e.g. a soluble TNFα receptor such as etanercept (Enbrel®), a neutralizing (preferably non-depleting) anti-TNFα antibody such as adalimumab (Humira®) or Certolizumab pegol (Cimzia®)), a T-cell costimulatory blocking agent (e.g. abatacept (Orencia®)), an interleukin-1 (IL-1) receptor antagonist therapy (anakinra (Kineret®)), an anti-BlyS antibody (Benlysta®), a proteosome inhibitor (e.g. bortezomib), a tyrosine kinase inhibitor, intramuscular gold, or another immunomodulatory or cytotoxic agent (e.g. azathioprine (Imuran®), cyclophosphamide, cyclosporine A (Neoral®, Sandimmune®)) or a kinase inhibitor (e.g. a SYK kinase inhibitor such as fostimatinib (R788) or a JAK1, JAK2 inhibitors such as INCB28050, tanezumab or tasocitinib (CP-690,550)).

The anti-KIR2DL1, 2 and/or 3 antibody is administered prior to the administration of the second therapeutic agent. For example, an anti-KIR2DL1, 2 and/or 3 antibody can be administered approximately 0 to 30 days prior to the administration of the second therapeutic agent. In some embodiments, an anti-KIR2DL1, 2 and/or 3 antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent. In some embodiments, the anti-KIR2DL1, 2 and/or 3 antibody is administered concurrently with the administration of the therapeutic agents. The anti-KIR2DL1, 2 and/or 3 antibody is administered after the administration of the second therapeutic agent. For example, an anti-KIR2DL1, 2 and/or 3 antibody can be administered approximately 0 to 30 days after the administration of the second therapeutic agent. In some embodiments, an anti-KIR2DL1, 2 and/or 3 antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the second therapeutic agent.

The composition may further comprise at least one anti-inflammatory agent, analgesic agent, or disease-modifying antirheumatic drug (DMARD).

The anti-inflammatory agent may be selected from the group consisting of steroids, Cortisone, Glucocorticoids, prednisone, prednisolone, Hydrocortisone (Cortisol), Cortisone acetate, Methylprednisolone, Dexamethasone, Betamethasone, Triamcinolone, Beclometasone, and Fludrocortisone acetate, non-steroidal anti-inflammatory drug (NSAIDs), ibuprofen, naproxen, meloxicam, etodolac, nabumetone, sulindac, tolementin, choline magnesium salicylate, diclofenac, diflusinal, indomethicin, Ketoprofen, Oxaprozin, piroxicam, and nimesulide, Salicylates, Aspirin (acetylsalicylic acid), Diflunisal, Salsalate, p-amino phenol derivatives, Paracetamol, phenacetin, Propionic acid derivatives, Ibuprofen, Naproxen, Fenoprofen, Ketoprofen, Flurbiprofen, Oxaprozin, Loxoprofen, Acetic acid derivatives, Indomethacin, Sulindac, Etodolac, Ketorolac, Diclofenac, Nabumetone, Enolic acid (Oxicam) derivatives, Piroxicam, Meloxicam, Tenoxicam, Droxicam, Lornoxicam, Isoxicam, Fenamic acid derivatives (Fenamates), Mefenamic acid, Meclofenamic acid, Flufenamic acid, Tolfenamic acid, Selective COX-2 inhibitors (Coxibs), Celecoxib, Rofecoxib, Valdecoxib, Parecoxib, Lumiracoxib, Etoricoxib, Firocoxib, Sulphonanilides, Nimesulide, and Licofelone.

Rheumatoid Arthritis

Rheumatoid arthritis (RA) is a chronic and typically progressive inflammatory disease in which the synovial membrane is the primary site of inflammation. Bone destruction occurs with the progression of inflammation, resulting in deformation or damage of bones and cartilages. Rheumatoid arthritis (RA) progresses in stages. The first stage is the swelling of the synovial lining, causing pain, warmth, stiffness, redness and swelling around the joint. Second is the rapid division and growth of cells, or pannus, which causes the synovium to thicken. In the third stage, the inflamed cells release enzymes that may digest bone and cartilage, often causing the involved joint to lose its shape and alignment, more pain, and loss of movement. A patient affected with the disease can experience a period of remission, without pain, and then a rheumatoid arthritis crisis, also named flare or attack, where the pain will increase. The methods according to the invention propose to treat such patient experiencing a crisis to help them to deal with the pain.

The level of RA disease can be evaluated using different criteria. The most known criteria have been set up by the ACR (American College of Rheumatology). ACR criteria are indicated as ACR 20, ACR 50, and ACR 70. ACR criteria measure improvement in tender or swollen joint counts and improvement in three of the following five parameters: acute phase reactant (such as sedimentation rate), patient assessment, physician assessment, pain scale and disability/functional questionnaire.

The severity of the disease can also be measured by a score known as DAS (Disease Activity Score). DAS is a composite index of RA activity drawn up by EULAR (European League Against Rheumatism) initially developed for 44 joints for the numbers of joints with synovitis and the 53 Ritchie index sites. DAS is calculated according to the following formula:

$$DAS=[0.553938 \sqrt{Richie's\ index}]+[0.06465 \sqrt{(number\ of\ joints\ with\ synovitis)}]+[0.330\ Ln\ (erythrocyte\ sedimentation\ rate)]+0.024$$

Ritchie's index covers 53 joints: temporomandibular, acromioclavicular, sternocostoclavicular, shoulder, elbow, wrist, metacarpophalangeal (MCP), proximal interphalangeal (PIP) in the fingers, hip, knee, ankle, subtalar, transverse tarsal, and metatarsophalangeal (MTP).

Three activity levels have been defined according to the value of DAS: RA with low activity level DAS≤2.4, moderate active RA 2.4<DAS≤3.7, active RA>3.7. Remission threshold value defined for DAS is <1.6.

The primary objective of the methods of treatment according to the invention is to control the activity of the disease and, also, to achieve remission, reduce pain, prevent and control joint destruction, prevent loss of function in everyday activities and at work, and optimise the patient's quality of life.

Current Treatment Options

Current recommendations for treatment of RA include early treatment with disease modifying anti-rheumatic drugs (DMARDs) after the diagnosis has been established. Non-steroidal anti-inflammatory drugs (NSAIDs), and until recently, COX-2 inhibitors have been widely used while waiting to confirm the diagnosis or later in the course of the disease in conjunction with DMARDs. Methotrexate is the most widely used DMARD, but other agents, including hydroxychloroquine, sulfasalazine, gold, minocycline, and leflunomide, are also prescribed. Corticosteroids may be used in combination with DMARDs, but in general, only low doses are used to minimize adverse events (O'Dell, New Engl. J. Med. 350:2591-2603, 2004). In recent years, anti-cytokine therapies targeting inflammatory cytokines have been receiving attention, and novel biopharmaceuticals having effective anti-rheumatic actions, such as infliximab, etanercept, anakinra, and atlizumab, have been developed. However, there is currently no totally effective treatment and there remains a need for an efficient treatment of the disease, and improvement of the patient's comfort and pain relief and alternative therapies are needed to improve patient's daily life. Some of the main treatments are reviewed hereunder.

Non-steroidal anti-inflammatory agents (NSAIDs). These drugs inhibit the generation of prostaglandins by blocking cyclooxygenase enzymes, COX-1 and COX-2. Prostaglandins are mediators of inflammation and pain but also have important roles in maintenance of normal body functions including protection from stomach acid, maintenance of kidney blood flow, and contributing to platelet stickiness and vascular function. COX-2 selective inhibitors selectively block prostaglandins generated via COX-2 which have prominent roles in inflammation. Many different NSAIDS are available, some over the counter including aspirin, ibuprofen (Advil®, Motrin®, Nuprin®) and naproxen (Aleve®) and many others are available by prescription including meloxicam (Mobic®), etodolac (Lodine®), nabumetone (Relafen®), sulindac (Clinoril®), tolementin (Tolectin®), choline magnesium salicylate (Trilasate®), diclofenac (Cataflam®, Voltaren®, Arthrotec®), Diflusinal (Dolobid®), indomethicin (Indocin®), Ketoprofen (Orudis®, Oruvail®), Oxaprozin (Daypro®), and piroxicam (Feldene®). Longer acting NSAIDs that allow daily or twice daily dosing may improve compliance. The NSAID class also includes drugs known as COX-2 inhibitors that are also effective in controlling inflammation (celecoxib, Celebrex®; etoricoxib, Arcoxia®; lumiracoxib, Prexige®).

Corticosteroids (prednisone; methylprenisolone, Medrol®) have both anti-inflammatory and immunoregulatory activity. They can be given orally, intravenously, intramuscularly or can be injected directly into the joint. Corticosteroids are useful in early disease as temporary adjunctive therapy while waiting for DMARDs to exert their anti-inflammatory effects. Corticosteroids are also useful as chronic adjunctive therapy in patients with severe disease that is not well controlled on NSAIDs and DMARDs. The usual dose of prednisone is 5 to 10 mg daily. Although prednisone can be started at higher doses (15 to 20 mg daily), attempts should be made to taper the dose over a few weeks to less than 10 mg daily. Once started, corticosteroid therapy may be very difficult to discontinue and even at low doses. Some patients are very sensitive to the tapering of prednisone which is generally done slowly over a few weeks.

Disease Modifying Anti-rheumatic Drugs (DMARDS): Although both NSAIDs and DMARD agents improve symptoms of active rheumatoid arthritis, only DMARD agents have been shown to alter the disease course and improve radiographic outcomes. DMARDs have an effect upon rheumatoid arthritis that is different and may be more delayed in onset than either NSAIDs or corticosteroids. In most cases, when the diagnosis of rheumatoid arthritis is confirmed, DMARD agents should be started. The presence of erosions or joint space narrowing on x-rays of the involved joints is a clear indication for DMARD therapy, however one should not wait for x-ray changes to occur. The currently available drugs include: Methotrexate (Rheumatrex®, Trexall®), Hydroxychloroquine (Plaquenil®), Sulfasalazine (Azulfidine®), Leflunomide (Arava®), Tumor Necrosis Factor Inhibitors—etanercept (Enbrel®, adalimumab (Humira®), and infliximab (Remicade®), T-cell Costimulatory Blocking Agents—abatacept (Orencia®), B cell Depleting Agents—rituximab (Rituxan®), Interleukin-1 (IL-1) Receptor Antagonist Therapy—anakinra (Kineret®), Intramuscular Gold, Other Immunomodulatory and Cytotoxic agents—azathioprine (Imuran®), cyclophosphamide, and cyclosporine A (Neoral®, Sandimmune®).

Methotrexate is now considered the first-line DMARD agent for most patients with RA. It has a relatively rapid onset of action at therapeutic doses (6-8 weeks), good efficacy, favorable toxicity profile, ease of administration, and relatively low cost. Methotrexate is effective in reducing the signs and symptoms of RA, as well as slowing or halting radiographic damage. Methotrexate is also effective in many other forms of inflammatory arthritis including psoriatic arthritis and other spondyloarthopathies, and is used in many other autoimmune diseases. Dosage: In a study comparing methotrexate to etanercept in early RA, methotrexate was started at a dose of 10 mg per week, and increased to 20 mg per week by week 8. This dosing regimen or regimens that start at even higher doses (up to 15 mg per week) with a dose escalation to 20 mg within the first three months is now fairly well accepted in clinical practice. Maximal dose is usually 25 mg per week but is sometimes increased further. Methotrexate can be given orally or by subcutaneous injection. The latter route of administration can be advantageous for patients who have methotrexate-associated nausea. Patients starting methotrexate should be carefully evaluated for renal insufficiency, acute or chronic liver disease, significant alcohol intake or alcohol abuse, leukopenia (low white blood cell counts), thrombocytopenia (low platelet counts), or untreated folate deficiency. The coadministration of NSAIDS with methotrexate is routine in patients with rheumatoid arthritis and is considered safe by rheumatologists as long as liver function tests are closely monitored. Methotrexate can be combined safely with nearly every other FDA approved DMARDs for RA, including sulfasalazine, hydroxychloroquine, TNF inhibitors, abatacept, rituximab, anakinra, and leflunomide. In all clinical trials combining methotrexate with one of these DMARDs, no unexpected toxicities or synergistic toxicities were observed with the exception of higher liver toxicity with leflunomide which is also metabolized by the liver.

Hydroxychloroquine and chloroquine are antimalarial drugs which are relatively safe and well-tolerated agent for the treatment of rheumatoid arthritis. Because these drugs have limited ability to prevent joint damage on their own, their use should probably be limited to patients with very mild and nonerosive disease. Hydroxychloroquine is sometimes combined with methotrexate for additive benefits for signs and symptoms or as part of a regimen of "triple therapy" with methotrexate and sulfasalazine.

Sulfasalazine (Azulfidine®) is an effective DMARD for the treatment of RA. It is given in conjunction with methotrexate and hydroxychloroquine as part of a regimen of "triple therapy" which has been shown to provide benefits to patients who have had inadequate responses to methotrexate alone. Sulfasalazine is also used in the treatment of inflammatory bowel disease and spondyloarthropathies. Its mechanism of action in RA is unknown. Some of its effects may be due to folate depletion. Dosage: The usual dose is 2-3 grams per day in a twice daily dosing regimen. The dose may be initiated at 1 gram per day and increased as tolerated.

Leflunomide (Arava®) is also an effective DMARD. Its efficacy is similar to methotrexate in terms of signs and symptoms, and is a viable alternative to patients who have failed or are intolerant to methotrexate. Leflunomide has been demonstrated to slow radiographic progression. Studies have demonstrated that it can also be carefully combined with methotrexate in patients with no preexisting liver disease, as long as the liver function tests are carefully monitored. Leflunomide has also been studied in psoriatic arthritis with some efficacy demonstrated. Dosage: The half-life of the active metabolite of leflunomide is very long. Leflunomide and its metabolites are extensively protein bound and undergo further metabolism before excretion. When initially approved, the medication was given using a loading dose of 100 mg daily for three days then followed by 20 mg daily. Due to a significant incidence of GI side effects and diarrhea, most practitioners now use a shorter loading period with lower doses or initiate treatment at 10-20 mg/day with no loading dose. The dose may be reduced to 10 mg daily if not tolerated at the 20 mg dose.

Tumor necrosis factor (TNF) inhibitors. TNF is found in large quantities in the rheumatoid joint and is produced locally in the joint by synovial macrophages and lymphocytes infiltrating the joint synovium. TNF is one of the critical cytokines that mediate joint damage and destruction due to its activities on many cells in the joint as well as effects on other organs and body systems. TNF antagonists were the first of the biological DMARDS to be approved for the treatment of RA and have also been referred to as biological response modifiers or "biologics" to differentiate them from other DMARDS such as methotrexate, leflunomide, or sulfasalazine. Three TNF antagonists are approved for the treatment of RA and additional agents are under investigation. These drugs are similar in their efficacy at decreasing signs and symptoms of RA, slowing or halting radiographic damage, and improving function and quality of life. These agents are also now approved for the treatment of other forms of inflammatory arthritis including psoriatic arthritis, juvenile idiopathic arthritis and ankylosing spondylitis. There are currently three TNF inhibitors FDA approved for the treatment of RA (listed in order of their approval for RA); etanercept (Enbrel®), infliximab (Remicade®), and adalimumab (Humira®).

Etanercept (Enbrel®) is effective in reducing the signs and symptoms of RA, as well as in slowing or halting radiographic damage, when used either as monotherapy or in combination with methotrexate. Etanercept is also approved for the treatment of psoriatic arthritis and for ankylosing spondylitis as well as psoriasis. Etanercept is a fusion protein that combines two extracellular binding domains of the p75 form of the TNF receptor with the Fc portion of a human IgG1 antibody molecule. The components of the protein are entirely human, and anti-etanercept antibodies are relatively uncommon. Dosage: The most common dose currently used is 50 mg self-administered once per week by subcutaneous injection. Both prefilled syringes and an autoinjection system (SureClick®) are available. Etanercept is also available in a 25 mg dose which is administered twice per week at this dose. Intermittent or occasional dosing has not been studied. There is limited information on the safety or efficacy at doses beyond 50 mg per week. Etanercept has a half-life of 70 hours after a 25 mg dose.

Infliximab (Remicade®): in combination with methotrexate, is approved for the treatment of RA, and for the treatment of psoriatic arthritis, and ankylosing spondylitis, as well as psoriasis and Crohn's disease. Infliximab is a chimeric monoclonal antibody that binds TNF with high affinity and specificity. The antibody binding site for TNF is of mouse origin, with the remaining 75% of the infliximab antibody derived from a human IgG1 antibody sequence. Infliximab is effective as monotherapy in reducing the signs and symptoms of RA but anti-infliximab antibodies can develop which can, in turn, reduce the durability of the response. Co-treatment with methotrexate reduces the frequency of these antibodies and is therefore recommended along with infliximab. The combination of infliximab and methotrexate is very effective in reducing clinical manifestations of disease, as well as in slowing or halting radiographic progression of disease in RA. Dosage: Infliximab is administered via the intravenous route. Infusions typically take between 2-3 hours. The recommended starting dose of infliximab is 3 mg/kg for RA given as an intravenous infusion followed by additional dosing at 2 and 6 weeks, then every 8 weeks thereafter. Infliximab should be given in combination with methotrexate. If the clinical response is inadequate at a starting dose, infliximab can be increased incrementally to a maximum dose of 10 mg/kg and the frequency of infusion increased to every 4-6 weeks.

Adalimumab (Humira®) is a fully human anti-TNF monoclonal antibody with high specificity for TNF. Like the other TNF antagonists, it is effective as monotherapy and in combination with methotrexate, at reducing signs and symptoms of RA and in slowing or halting radiographic progression of disease. It is administered by subcutaneous injection every two weeks but can be increased to weekly, if needed. Adalimumab is effective in RA, Psoriatic arthritis, and ankylosing spondylitis, and Crohn's disease. Dosage: Adalimumab is currently available in a 40 mg dose and is given by self-administered subcutaneous (SC) injection every other week. Both prefilled syringes as well as an autoinjector system (Huimira Pen®) are available. If response to this dose is inadequate, the frequency of injections can be increased to weekly. Adalimumab has a half-life of approximately 2 weeks (ranging from 10-20 days) after a standard 40 mg dose.

T-cell Costimulatory blockade: Abatacept (Orencia®): Abatacept is the first of a class of agents known as T-cell costimulatory blockers. These agent interfere with the interactions between antigen-presenting cells and T lymphocytes and affect early stages in the pathogenic cascade of events in rheumatoid arthritis. T lymphocytes become activated due to an unknown stimulus but likely involving the interaction between antigen presented in the context of the Class II Major Histocompatability Complex molecule on the surface of antigen presenting cells. T cells recognize antigens as foreign and if they receive a second stimulus, will become active, proliferate, traffic to inflamed sites, and secrete proinflammatory cytokines including TNF. One of the important second signals for T cell activation is mediated by the molecules CD80 and CD86 found on antigen presenting cells and the CD28 molecule on the T cell surface. Dosage: Abatacept is administered via intravenous infusion once per month after initial doses at baseline, 2 weeks, and 4 weeks. The dose is based on body weight, with patients <60 kg receiving 500 mg, 60-100 kg receiving 750 mg, and >100 kg receiving 1000 mg. The medication is administered over a period of approximately 30 minutes to one hour.

B-Cell Depletion: Rituximab (Rituxan®): B cells are an important inflammatory cell with multiple functions in the immune response. They serve as antigen presenting cells, can secrete cytokines, and differentiate into antibody-forming plasma cells. The depletion of B cells has been shown to be effective in reducing signs and symptoms of RA and in slowing radiographic progression. One B cell depleting agent, Rituximab, is currently available for the treatment of rheumatoid arthritis. Rituximab (Rituxan®) was originally developed to treat non-Hodgkin's lymphoma and has been used to treat this malignant condition of lymphocytes and lymph nodes for several years. Early studies in patients with rheumatoid arthritis showed rituximab caused a rapid and sustained depletion of circulating B cells in the circulation with clinical improvements in many patients as well. Further clinical studies have now demonstrated that rituximab is effective in decreasing signs and symptoms and in slowing radiographic progression in RA patients who have failed other DMARD therapies. The agent is currently approved in the US, however, only in patients who have failed TNF antagonists. Dosage: The currently approved dose is 1000 mg administered intravenously over 3-4 hours with two doses given 2 weeks apart. Patients typically receive intravenous corticosteroids with each infusion and premedication with diphenhydramine and acetaminophen. The optimal time for readministarion is not yet clear. Some have advocated a fixed dosing regimen of every 6 months, while others have advocated waiting until a patient begins to flare before retreating. Studies are ongoing to evaluate redosing schedules. The extent and duration of B cell depletion has not been clearly correlated with efficacy. Nor has the reconstitution of normal levels of B cells been well correlated with loss of efficacy.

Interleukin-1 (IL-1) is another proinflammatory cytokine implicated in the pathogenesis of RA. IL-1 receptor antagonist (IL1ra) is an endogenous blocker of the cytokine. Evidence supporting an anti-inflammatory role of IL-1ra in vivo is demonstrated by the observation that IL-1ra deficient mice spontaneously develop autoimmune diseases similar to rheumatoid arthritis as well as vasculitis. IL1 has effects on cartilage degradation leading to damage as well as inhibiting repair, and is a potent stimulus to osteoclasts leading to bone erosion. One IL1 antagonist, anakinra (Kineret®), is currently approved for the treatment of RA. Other agents have been studied as well in RA.

Anakinra (Kineret®), a human recombinant IL-1 receptor antagonist (hu rIL-1ra) is approved for the treatment of RA. Anakinra can be used alone or in combination with DMARDs other than TNF blocking agents (Etanercept, Infliximab, Adalimumab). Anakinra is not recommended for use in combination with TNF inhibitors because studies have shown increased infections without additive clinical benefit. Dosage: The recommended dose of anakinra is 100 mg/day administered daily by subcutaneous injection. The dose should be administered at approximately the same time each day. An autoinjection system is available for the medication.

Intramuscular Gold is effective in the treatment of rheumatoid arthritis. Intramuscular gold salts were, until the 1990's, the most often used DMARD agents but have been replaced by Methotrexate and other DMARDS as the preferred agents to treat RA. Two injectable compounds are available, (Myochrysine® and Solganal®). Gold compounds are rarely used now due to their numerous side effects and monitoring requirements, their limited efficacy, and very slow onset of action. An oral gold compound (Auranofin®) is also available but its efficacy is even more limited than injectable compounds. Dosage: Myochrysine or Solganal therapy is started at 10 mg intramuscularly, 25 mg is then given the second week, then 50 mg is given weekly until a response has occurred or until a total of 1 g has been given. If there is a favorable response, therapy is tapered to 50 mg every 2 weeks for 3 months, then every 3 weeks for 3 months and then finally to a maintenance monthly dose. No response after a total of 1 g should be considered a treatment failure. Monthly gold should be continued indefinitely.

Other Immunomodulatory and Cytotoxic Agents: The most commonly used cytotoxic drugs are azathioprine (Imuran®), cyclosporin A (Sandimmune®, Neoral®), cyclophosphamide (Cytoxan®) and d-Penicillamine. Because the potential of high toxicity, these agents are typically utilized for life-threatening extra-articular manifestations of RA such as systemic vasculitis or with severe articular disease that is refractory to other therapy.

Azathioprine (Imuran®) has some activity in rheumatoid arthritis but may take 8-12 weeks to see an effect. It is a purine analog that can cause bone marrow suppression and lowering of blood cell counts (white blood cells, red blood cells, and platelets) particularly in patients with renal insufficiency or when used concomitantly with allopurinol or ACE inhibitors. Increased risk of secondary malignancy due to azathioprine is controversial. Screening for levels of the enzyme thiopurine methyltransferase (TPMT) is recommended before initiating therapy with azathioprine. Certain individuals have deficiencies in this enzyme that metabolizes azathioprine with a concomitantly increased risk of toxicity for the medication. Side effects include nausea, and alopecia. Blood tests to monitor blood counts and liver function tests are necessary for patients on azathioprine.

Cyclosporine (Sandimmune®, Neoral®) has some activity as a disease modifying therapy in rheumatoid arthritis. Studies have demonstrated that cyclosporine can be combined with methotrexate in RA patients to capture clinical responses. It is an immunosuppressive agent approved for use in preventing renal and liver transplant rejection and also has activity in psoriasis and other autoimmune diseases. Cyclosporine inhibits T cell function by inhibiting transcription of interleukin-2. Main toxicities include infection and renal insufficiency. Increase in blood pressure is common and may require treatment. Careful monitoring of renal function and blood pressure is needed for the entire time a patient is taking cyclosporine. Numerous medication interactions may affect blood levels of cyclosporine and lead to more toxicity. The package insert contains important information concerning these medication interactions. Cyclosporine increases risks of infection and may also increase the risk of malignancies including lymphoma.

Cyclophosphamide (Cytoxan®) is a potent immunosuppressive agent that is reserved for severe cases of refractory rheumatoid arthritis and those with manifestations such as vasculitis. It is used in the treatment of other autoimmune conditions including lupus and vasculitis. Cyclophosphamide is an alkylating agent with serious toxicities including bone marrow suppression, hemorrhagic cystitis, premature ovarian failure, infection and secondary malignancy particularly an increased risk of bladder cancer. Blood counts must be carefully monitored with this medication.

d-Penicillamine (Cuprimine®, Depen®) historically has some activity as a treatment for rheumatoid arthritis. It is prescribed primarily for patients with persistent aggressive disease who have failed other available DMARDS. Like gold it is a relatively toxic drug that has limited utility due to issues of tolerability and efficacy that is not as robust as other currently available agents. Major side effects include severe rash and effects on renal function. Careful monitoring of kidney function is required with this drug. Patients may develop a lupus like illness or other autoimmune diseases when taking d-Penicillamine.

Other DMARD compounds currently in development are also suitable for a combination in the treatment methods according to the invention, such as VX-702, ocrelizumab, compounds targeting SYK kinase such as fostimatinib (R788) and JAM, JAK2 inhibitors such as INCB28050, tanezumab or tasocitinib (CP-690,550).

The DMARD may be selected from the group consisting of mycophenolate mofetil (CellCept), calcineurin inhibitors, cyclosporine, sirolimus, everolimus, oral retinoids, azathioprine, fumeric acid esters, D-penicillamine, cyclophosphamide, immunoadsorption column, Prosorba(r) column, a gold salt, auranofin, sodium aurothiomalate (Myocrisin), hydroxychloroquine, chloroquine, leflunomide, methotrexate (MTX), minocycline, sulfasalazine (SSZ), tumor necrosis factor alpha (TNFa) blockers, etanercept (Enbrel), infliximab (Remicade), adalimumab (Humira), certolizumab pegol (Cimzia), golimumab (Simponi)), Interleukin 1 (IL-1) blockers, e.g., anakinra (Kineret), monoclonal antibodies against B cells, rituximab (Rituxan)), T cell costimulation blockers, abatacept (Orencia), Interleukin 6 (IL-6) blockers, tocilizumab, RoActemra, and Actemra.

Treatment with an Anti-KIR2DL1, 2 and/or 3 Antibody

A patient having RA can be evaluated to assess the presence, stage, evolution or rating of disease. Optionally a biological sample (e.g. synovial fluid) is obtained and assessed for the presence of proinflammatory mediators or other markers of active inflammation, and/or presence of T cells (e.g. CD4+ T cells). In one embodiment, the presence of autoantibodies is detected, for example detecting rheumatoid factor (RhF), anti-cyclic citrullinated peptide antibodies, anti-ssRNA, anti-dsRNA, anti-Smith, anti-phospholipid, anti-nuclear and/or anti-actin antibodies. In one embodiment, the methods comprise assessing levels of a proteolytic enzyme, an inflammatory mediator, a marker of ongoing inflammation or a proinflammatory cytokine. In one embodiment, the methods comprise determining c-reactive protein (CRP) level and/or erythrocyte sedimentation rate. A determination that a patient has RA, or that pro-inflammatory mediators or other markers of active inflammation, and/or T cells (e.g. infiltrating T cells, HLA-cw3 and/or cw4 positive T cells) are present (e.g. in the inflamed tissue), that disease is acute, chronic, experiencing a flare or progressing indicates that the patient can be treated with an anti-KIR2DL1, 2 and/or 3 antibody.

A patient having RA, and optionally having active inflammation and/or established or chronic RA, and/or experiencing a flare is treated with an anti-KIR2DL1, 2 and/or 3 antibody. Preferably, established RA may be characterized as RA which has been progressing for over a year, or which has been progressing for less than a year but is unresponsive to a first disease modifying anti-rheumatic drug (DMARD). Established RA can also be assessed using the DAS or the CAS criteria. "RA and related diseases" refers to diseases that can cause or derive from the onset or evolution of rheumatoid arthritis such as e.g. episcleritis, pneumothorax, embolism and ischemic skin ulcer.

The antibodies according to the invention are administered in combination with another RA treatment, such as those listed above.

The anti-KIR2DL1, 2 and/or 3 antibody can be injected or infused via subcutaneous, intravenous, intramuscular, intra-articular, intra-synovial, intrasternal, intrathecal, intrahepatic, intralesional and intracranial routes. In an embodiment, an anti-KIR2DL1, 2 and/or 3 antibody is administered intra-articularly, preferably at the site of the inflammation.

Multiple Sclerosis

Multiple sclerosis (MS) is a chronic inflammatory disease of the central nervous system (CNS) in which the fatty myelin sheaths around the axons of the brain and spinal cord are damaged, leading to demyelination and scarring as well as a broad spectrum of signs and symptoms. Pathophysiological cause remains unknown although different theories incriminate genetics or infections. Different environmental risk factors have also been proposed. Clinical manifestations are associated with the infiltration of the central nervous system by immune-competent cells. Specific T cell populations directed towards neuroantigens, such as myelin basic protein, can be demonstrated in the periphery. Almost any neurological symptom can appear with the disease, and often progresses to physical and cognitive disability. MS progresses in two forms: new symptoms occurring either in discrete attacks (relapsing forms) or slowly accumulating over time (progressive forms). Between attacks, symptoms may go away completely, but permanent neurological problems often occur, especially as the disease advances.

Disease Evaluation and Rating

Several subtypes, or patterns of progression, have been described. Subtypes use the past course of the disease in an attempt to predict the future course. They are important not only for prognosis but also for therapeutic decisions. In 1996 the United States National Multiple Sclerosis Society standardized four subtype definitions: relapsing remitting, secondary progressive, primary progressive, and progressive relapsing.

The relapsing-remitting subtype is characterized by unpredictable relapses followed by periods of months to years of remission with no new signs of disease activity. This describes the initial course of 80% of individuals with MS. Secondary progressive MS describes around 65% of those with an initial relapsing-remitting MS, who then begin to have progressive neurologic decline between acute attacks without any definite periods of remission. Occasional relapses and minor remissions may appear. The median time between disease onset and conversion from relapsing-remitting to secondary progressive MS is 19 years. The primary progressive subtype describes the approximately 10-15% of individuals who never have remission after their initial MS symptoms. It is characterized by progression of disability from onset, with no, or only occasional and minor, remissions and improvements. The age of onset for the primary progressive subtype is later than for the relapsing-remitting, but similar to mean age of progression between the relapsing-remitting and the secondary progressive. In both cases it is around 40 years of age. Progressive relapsing MS describes those individuals who, from onset, have a steady neurologic decline but also suffer clear superimposed attacks. This is the least common of all subtypes. Multiple sclerosis evolves either by progressive neurologic decline or by acute attacks, or by a combination of both depending on the MS type. Symptoms of MS include: fatigue, visual problems such as blurred or double vision, tingling, numbing, or burning sensations, muscle weakness, stiffness, tremor, and spasms, walking and gait problems, bladder and bowel dysfunction, sexual dysfunction, cognitive and memory problems, swallowing and speech problem, pain or depression. Those symptoms are exacerbated during an attack whereas the general condition of the patient declines. Typical variants of MS with non-standard behavior have been described; these include Devic's disease, Balo concentric sclerosis, Schilder's diffuse sclerosis and Marburg multiple sclerosis.

The multiple sclerosis diagnostic is established using different criteria. Historically, the Schumacher and Poser criteria were widely used. Currently, the McDonald criteria, established by the National Multiple Sclerosis Society (NMSS) of America, using IMR imaging, tend to replace the older criteria. (McDonald W I, Compston A, Edan G, et al. (2001), Ann. Neurol. 50 (1): 121-7).

Current Treatment Options

There are many issues for the patient and physician to consider in treating multiple sclerosis. Goals may include: improving the speed of recovery from attacks (e.g. treatment with steroid drugs); reducing the number of attacks or the number of MRI lesions; attempting to slow progression of the disease (treatment with disease modifying drugs or DMDs), one additional goal is relief from complications due to the loss of function of affected organs.

Most neurologists will consider treatment with DMDs once the diagnosis of relapsing remitting multiple sclerosis is established. Many will begin treatment at the time of the first multiple sclerosis attack, since clinical trials have suggested that patients in whom treatment is delayed may not benefit as much as patients who are treated early.

Patients receive immunosuppressive therapy including azathioprine and corticosteroids in order to limit the extent of the inflammatory process. Immunosuppressive therapy of multiple sclerosis, however, is only partially effective, and in most cases only offers a delay in disease progression despite anti-inflammatory and immunosuppressive treatment. Current disease-modifying treatments for MS are, inter alia: IFNβ-1a (Avonex®, CinnoVex®, ReciGen®, Rebif®), IFNβ-1b (Betaseron®, Betaferon®), glatiramer acetate (Copaxone®) which is a non-interferon, non-steroidal immunomodulator, mitoxantrone, an immunosuppressant, natalizumab (Tysabri®), fingolimod (Gilenia®). A number of treatments are under investigation. Emerging agents for RRMS that have shown promise in phase 2 trials include alemtuzumab (Campath®), daclizumab (Zenapax®), rituximab, dirucotide, BHT-3009, cladribine, dimethyl fumarate, estriol, fingolimod, laquinimod, minocycline, statins, temsirolimus and teriflunomide.

Treatment with Anti-KIR2DL1, 2 and/or 3 Antibody

Optionally, in a first step a patient's disease can be evaluated. The patient is then treated with an anti-KIR2DL1, 2 and/or 3 antibody in an appropriate manner. A patient having MS can be evaluated to assess the presence, stage, evolution or rating of disease. In one advantageous aspect, a patient determined to have active inflammation, and/or established or chronic MS, and/or experiencing a flare is treated with an anti-KIR2DL1, 2 and/or 3 antibody. Preferably, established MS may be characterized as MS which has progressive neurologic decline, such as secondary progressive, primary progressive or progressive relapsing type disease alternatively, an "established MS" refers to a MS which has been progressing for over a year, or which has been progressing for less than a year but is unresponsive to a first line of treatment. Preferably a flare is defined as an exacerbation of the symptoms related to multiple sclerosis, optionally; such flare leads to a decline in the patient's general condition. Another aspect of the invention is to provide a composition which is able to treat an established MS, or to reduce or abort an MS attack, thereby leading to an improvement of the patient's health and comfort.

In one embodiment, the antibodies according to the invention are administered in combination with another MS treatment, such as those listed above.

The anti-KIR2DL1, 2 and/or 3 antibody can be injected or infused via subcutaneous, intravenous, intramuscular, intraarticular, intra-synovial, intrasternal, intrathecal, intrahepatic, intralesional and intracranial routes.

Chronic Inflammatory Diseases of the Intestine (CIDI)—Crohn's Disease—Rectocolitis Chronic inflammatory diseases of the intestine are a series of diseases affecting the gastrointestinal tractus. Most common CIDI are ulcerative colitis, Crohn's disease, inflammatory bowel disease, regional enteritis, rectocolitis and Granulomatous ileocolitis.

Disease Evaluation and Rating

Diagnosis tests include: noninvasive laboratory tests (anemia and infection, liver function tests to screen for liver and bile duct problems, and stool studies to rule out bacterial, viral and parasitic infections), endoscopy, endoscopic ultrasound (EUS), capsule endoscopy, radiology such as Multiphase CT enterography, MR enterography (MRE).

Chronic inflammatory diseases of the intestine are rather hard to score. In rectocolitis, a coloscopy can provide a quite complete overview of the wounds in the colon, but in Crohn's disease, as wound can appear anywhere from oesophagus to rectum, patient evaluation is much more difficult to obtain. A scoring system has been set up to evaluate Crohn's disease: the Crohn's disease activity index (CDAI, See for review Sandborn W J et al. Gastroenterology 2002; 112:512). Score ranges from 0 to 600. Below 150 points, patients are scored as "very well". Between 150 and 219, the disease is mildly active, between 220 and 449, the disease is moderately active. Above 450 points the disease is rated as very severe. However, such scoring may be patient dependant and more recently, another scoring system, the Crohn Disease Digestive Damage Score ($CD_3S$) or Lémann score has been established to score patients disease through more precise scientific values, such as a score established by tomodensitometry. (Pariente B. et al. Development of the Crohn's Disease Digestive Damage score, the Lémann score Innflamm Bowel Dis 2010; Nov. 28).

Crohn's disease evolves with crisis, also known as flare-ups. Flare-ups can be mild or severe, brief or prolonged. Such flare-ups or attacks can be associated with a CDAI score of more than 150, more than 219, more than 449 points. Severe flare-ups can lead to intense pain, dehydration, and blood loss. Recurrent inflammation tends to appear in the same area of the intestine, but it may spread to adjacent areas after a diseased segment has been removed surgically. When Crohn's disease causes a flare-up of gastrointestinal symptoms, the person may also experience inflammation of the joints (arthritis), inflammation of the whites of the eyes (episcleritis), mouth sores (aphthous stomatitis), inflamed skin nodules on the arms and legs (erythema nodosum), and blue-red skin sores containing pus (pyoderma gangrenosum). Even when Crohn's disease is not causing a flare-up of gastrointestinal symptoms, the person still may experience pyoderma gangrenosum, while inflammation of the spine (ankylosing spondylitis), inflammation of the pelvic joints (sacroiliitis), inflammation inside the eye (uveitis), or inflammation of the bile ducts (primary sclerosing cholangitis) are liable to occur entirely without relation to the clinical activity of the bowel disease.

Current Treatment Options

Current treatment options are restricted to controlling symptoms, maintaining remission, and preventing relapse. Treatment of Crohn's disease involves first treating the acute symptoms of the disease, then maintaining remission. Treatment initially involves the use of medications to eliminate infections, generally antibiotics, and reduce inflammation, generally aminosalicylate anti-inflammatory drugs and corticosteroids. Surgery may be required for complications such as obstructions or abscesses, or if the disease does not respond to drugs within a reasonable time.

Aminosalicylate anti-inflammatory drugs: Mesalazine or mesalamine (Lialda®, Asacol®, Pentasa®, Salofalk®, Dipentum® and Rowasa®), Sulfasalazine, which is converted to 5-ASA and sulfapyridine by intestinal bacteria. The sulfapyridine may have some therapeutic effect in rheumatoid arthritis. However, the sulfapyridine component is often the limiting factor in treatment of Crohn's disease because of high side-effect profile. 5-ASA compounds have been shown to be useful in the treatment of mild-to-moderate Crohn's disease. They are usually considered to be first line therapy for disease in the ileum and right side of the colon particularly due to their lower side effect profile compared to corticosteroids.

Corticosteroid anti-inflammatory drugs: Steroid enemas can be used for treatment of rectal disease symptoms. Corticosteroids are a class of anti-inflammatory drug that are used primarily for treatment of moderate to severe flares or attacks of Crohn's disease. They are used more sparingly due to the availability of effective treatments with less side-effects. The most commonly prescribed oral steroid is prednisone, which is typically dosed at 0.5 mg/kg for induction of remission. Intravenous steroids are used for cases refractory to oral steroids, or where oral steroids cannot be taken. Because corticosteroids reduce the ability to fight infection, care must be used to ensure that there is no active infection, particularly an intra-abdominal abscess before the initiation of steroids. Budesonide is an oral corticosteroid with limited absorption and high level of first-pass metabolism, meaning that less quantities of steroid enter into the bloodstream. It has been shown to be useful in the treatment of mild-to-moderate Crohn's disease and for maintenance of remission in Crohn's disease. Formulated as Entocort®, budesonide is released in the ileum and right colon, and is therefore has a topical effect against disease in that area. Budesonide is also useful when used in combination with antibiotics for active Crohn's disease.

Mercaptopurine immunosuppressing drugs: Azathioprine, shown here in tablet form, is a first line steroid-sparing immunosuppressant. Azathioprine and 6-mercaptopurine (6-MP) are the most used immunosuppressants for maintenance therapy of Crohn's disease. They are purine anti-metabolites, meaning that they interfere with the synthesis of purines required for inflammatory cells. They have a duration of action of months, making it unwieldy to use them for induction of remission. Both drugs are dosed at 1.5 to 2.5 mg/kg, with literature supporting the use of higher doses. Azathioprine and 6-MP have been found to be useful for the following indications: maintenance therapy for people who are dependent on steroids, fistulizing disease, induction of remission in steroid refractory disease, maintenance of remission after surgery for Crohn's disease. Azathioprine is however a particularly dangerous drug, with great potential for inviting a host of potentially fatal infections, and is also listed by the FDA as a human carcinogen.

Infliximab, marketed as Remicade®, is a mouse-human chimeric antibody that targets tumour necrosis factor, a cytokine in the inflammatory response. It is a monoclonal antibody that inhibits the pro-inflammatory cytokine tumour necrosis factor alpha. It is administered intravenously and dosed per weight starting at 5 mg/kg and increasing according to character of disease. Infliximab has found utility as follows: maintenance of remission for people with Crohn's disease, induction of remission for people with Crohn's disease, maintenance for fistulizing Crohn's disease, side effects of infliximab, like other immunosuppressants of the TNF class, can be serious and potentially fatal, and infliximab carries an FDA black-box warning on the label. Listed side effects include hypersensitivity and allergic reactions, risk of re-activation of tuberculosis, serum sickness, and risk of multiple sclerosis.

Adalimumab, marketed as Humira®, like infliximab is an antibody that targets tumour necrosis factor. Adalimumab has been shown to reduce the signs and symptoms of, and is approved for treatment of, moderate to severe Crohn's disease (CD) in adults who have not responded well to conventional treatments and who have lost response to, or are unable to tolerate infliximab.

Natalizumab, marketed as Tysabri®, is an anti-integrin monoclonal antibody that has shown utility as induction and maintenance treatment for moderate to severe Crohn's disease. Natalizumab may be appropriate in patients who do not respond to medications that block tumor necrosis factor-alpha such as infliximab.

Treatment with Anti-KIR2DL1, 2 and/or 3 Antibody

One aspect of the invention is to provide a composition which is able to treat Crohn's disease, optionally an established Crohn's disease. In the present invention "established Crohn's disease" refers to a Crohn's disease which has been declared for more than one year.

Another aspect of the invention is to provide a treatment method to reduce or abort a Crohn's disease attack, thereby leading to an improvement of the patient's health and comfort. A disease attack can refer to a patient who has a CDAI score of more than 150, more than 219, more than 449 points. Thus, the present invention also provides a method for treating a patient having a chronic inflammatory disease of the intestine comprising the step of assessing whether said patient is experiencing a flare-up or an attack, and if said patient is experiencing an attack, treating said patient with an effective amount of an anti-KIR2DL1, 2 and/or 3 antibody.

Still another aspect of the invention is to provide a method for the prophylactic treatment of a patient suffering from a Crohn's disease, thereby avoiding a flare up.

In an embodiment, the antibodies according to the invention are administered in combination with another Crohn's disease treatment, such as those listed above.

Lupus Erythematosus

Four main types of lupus exist—systemic lupus erythematosus, discoid lupus erythematosus, drug-induced lupus erythematosus, and neonatal lupus erythematosus. Of these, systemic lupus erythematosus is the most common and serious form of lupus.

Discoid lupus erythematosus (DLE) is a chronic skin condition of sores with inflammation and scarring favoring the face, ears, and scalp and at times on other body areas. These lesions develop as a red, inflamed patch with a scaling and crusty appearance. The center areas may appear lighter in color with a rim darker than the normal skin.

Drug-induced lupus erythematosus (DIL or DILE) is an autoimmune disorder caused by chronic use of certain drugs. These drugs cause an autoimmune response producing symptoms similar to those of SLE. There are 38 known medications to cause DIL but there are three that report the highest number of cases: hydralazine, procainamide, and isoniazid. While the criteria for diagnosing DIL has not been thoroughly established, symptoms of DIL typically present as myalgia and arthralgia. Generally, the symptoms recede after discontinuing use of the drugs.

Neonatal lupus erythematosus presents in infants, most often girls, born to mothers who carry the Ro/SSA antibody. The infants have no skin lesions at birth, but develop them during the first weeks of life.

Systemic lupus erythematosus is a chronic systemic autoimmune disease that can affect any part of the body. As occurs in other autoimmune diseases, the immune system attacks the body's cells and tissue, resulting in inflammation and tissue damage. SLE most often harms the heart, joints, skin, lungs, blood vessels, liver, kidneys, and nervous system. The course of the disease is unpredictable, with periods of illness (flares) alternating with remissions. The disease occurs nine times more often in women than in men, especially in women in child-bearing years ages 15 to 35, and is more common in those also of non-European descent. SLE is treatable through addressing its symptoms, mainly with cyclophosphamide, corticosteroids and immunosuppressants; there is currently no cure. SLE can be fatal, although with recent medical advances, fatalities are becoming increasingly rare. SLE is considered incurable, but highly treatable. In the 1950s, most people diagnosed with SLE lived fewer than five years. Advances in diagnosis and treatment have improved survival to the point where over 90% now survive for more than ten years, and many can live relatively asymptomatically.

Disease Evaluation and Rating

Steroids should be used at the lowest dose for the shortest possible period, to reduce potential for cardiovascular issues, and other drugs that can reduce symptoms should be used whenever possible. High serum creatinine, hypertension, nephrotic syndrome, anemia and hypoalbuminemia are poor prognostic factors. The ANA is the most sensitive screening test for evaluation, whereas anti-Sm (anti-Smith) is the most specific. The dsDNA antibody is also fairly specific and often fluctuates with disease activity; as such, the dsDNA titer is sometimes useful to monitor disease flares or response to treatment.

Some physicians make a diagnosis on the basis of the American College of Rheumatology (ACR) classification criteria. The criteria, however, were established mainly for use in scientific research including use in randomized controlled trials which require higher confidence levels, so some people with SLE may not pass the full criteria.

The American College of Rheumatology established eleven criteria in 1982, revised in 1997 as a classificatory instrument to operationalise the definition of SLE in clinical trials. For the purpose of identifying patients for clinical studies, a person has SLE if any 4 out of 11 symptoms are present simultaneously or serially on two separate occasions: Serositis: Pleuritis or pericarditis, Oral ulcers, Arthritis: nonerosive arthritis of two or more peripheral joints, with tenderness, swelling, or effusion, photosensitivity, blood (hematologic disorder, hemolytic anemia (low red blood cell count) or leukopenia (white blood cell count<4000/µl), lymphopenia (<1500/µl) or thrombocytopenia (<100000/µl) in the absence of offending drug; renal disorder; antinuclear antibody test positive; immunologic disorder: Positive anti-Smith, anti-ds DNA, antiphospholipid antibody, and/or false positive serological test for syphilis; presence of anti-ss DNA in 70% of cases, neurologic disorder: Seizures or psychosis, Malar rash, Discoid rash.

Current Treatment Options

The treatment of SLE involves preventing flares and reducing their severity and duration when they occur. Treatment can include corticosteroids and anti-malarial drugs. Certain types of lupus nephritis such as diffuse proliferative glomerulonephritis require bouts of cytotoxic drugs. These drugs include cyclophosphamide and mycophenolate.

Disease-modifying antirheumatic drugs (DMARDs) are used preventively to reduce the incidence of flares, the process of the disease, and lower the need for steroid use; when flares occur, they are treated with corticosteroids. DMARDs commonly in use are antimalarials such as plaquenil and immunosuppressants (e.g. methotrexate and azathioprine). Hydroxychloroquine (HCQ) was the last medication approved by the FDA for lupus in 1955. Anti-BlyS antibodies (Benlysta®, Human Genomce Science, Inc.) can also be used as a DMARD. Hydroxychloroquine is an antimalarial used for constitutional, cutaneous, and articular manifestations. Hydroxychloroquine has relatively few side effects, and there is evidence that it improves survival among people who have SLE. Cyclophosphamide is used for severe glomerulonephritis or other organ-damaging complications. Some drugs approved for other diseases are used for SLE 'off-label'; Immunosuppressive drugs are also used to control the disease and prevent recurrence of symptoms (known as flares). Depending on the dosage, people who require steroids may develop Cushing's syndrome, side-effects of which may include obesity, puffy round face, diabetes mellitus, large appetite, difficulty sleeping and osteoporosis. Those side-effects can subside if and when the large initial dosage is reduced, but long-term use of even low doses can cause elevated blood pressure and cataracts. Numerous new immunosuppressive drugs are being actively tested for SLE. Rather than suppressing the immune system nonspecifically, as corticosteroids do, they target the responses of individual immune cells; analgesics, such as indomethacin and diclofenac, may be used if over-the-counter drugs (mainly nonsteroidal anti-inflammatory drugs) do not provide effective relief. Pain is typically treated with prescription. Due to the variety of symptoms and organ system involvement with SLE, its severity in an individual must be assessed in order to successfully treat SLE. Mild or remittent disease can sometimes be safely left untreated.

Treatment with Anti-KIR2DL1, 2 and/or 3 Antibody

The anti-KIR2DL1, 2 and/or 3 antibodies can be used to treat lupus, including but not limited to an established lupus, or to reduce or abort a lupus flare, thereby leading to an improvement of the patient's health and comfort. "Established lupus" refers to a lupus disease which has been progressing for over a year or which has been declared for more than one year. In one embodiment, the antibodies according to the invention are administered in combination with another lupus treatment, such as those listed above.

Other Autoimmune and Inflammatory Disorders

The anti-KIR2DL1, 2 and/or 3 antibodies can be used to treat suitable autoimmune and inflammatory disorders, preferably disorders involved T cells. Autoimmune and inflammatory diseases may, but are not limited to: Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Unknown or Multiple Autoimmune progesterone dermatitis, Autoimmune thrombocytopenic purpura, Autoimmune uveitis, Balo disease/Balo concentric sclerosis, Bechets Syndrome, Berger's disease, Bickerstaff's encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohn's Disease (one of two types of idiopathic inflammatory bowel disease "IBD"), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressive, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barré syndrome (GBS), Hashimoto's encephalitis, Hashimoto's thyroiditis, Haemolytic anaemia, Henoch-Schonlein purpura, Herpes gestationis, Hidradenitis suppurative, Hughes syndrome, Hypogammaglobulinemia, Idiopathic Inflammatory Demyelinating Diseases, Idiopathic pulmonary fibrosis, Idiopathic thrombocytopenic purpura, IgA nephropathy, Inclusion body myositis, Inflammatory demyelinating polyneuopathy, Interstitial cystitis, Irritable Bowel Syndrome (IBS), Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease, Lupoid hepatitis, Lupus erythematosus, Majeed syndrome, Ménière's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica, Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis (SBE), Susac's syndrome, Sweet syndrome, Sydenham Chorea, Sympathetic ophthalmia, Takayasu's arteritis, Temporal arteritis, Tolosa-Hunt syndrome, Transverse Myelitis, Ulcerative Colitis, Undifferentiated connective tissue disease, Undifferentiated spondyloarthropathy, Vasculitis, Vitiligo, Wegener's granulomatosis, Wilson's syndrome and Wiskott-Aldrich syndrome.

Dosing and Dosage Regimens of Anti-KIR2DL1, 2 and/or 3 Antibodies

In one aspect, the methods of treatment of the invention provides comprise administering to an individual a composition comprising an anti-KIR2DL1, 2 and/or 3 antibody in a therapeutically effective amount. A therapeutically effective amount may be for example a dosage of about 0.0003 mg (antibody)/kg (patient weight) to about 3 mg/kg (e.g., about 0.003 mg/kg to about 3 mg/kg, such as about 0.015 to about 3 mg/kg, e.g., any of about 0.075 mg to about 3 mg/kg, about 0.3 mg/kg to about 3 mg/kg, and about 1 mg/kg to about 3 mg/kg, or any of about 0.0003 mg/kg, about 0.003 mg/kg, about 0.015 mg/kg, about 0.075 mg/kg, about 0.3 mg/kg, about 1 mg/kg, and about 3 mg/kg). Doses and formulations of anti-KIR antibodies are described in WO2008/084106, the disclosure of which is incorporated herein by reference. In one embodiment, the method comprises repeating the administration at least once, for example with a dosing frequency in the range of 3 times per day to once per 2 months. The dose may also be administered, e.g., at least 3 times, at least 6 times, or at least 10 times. In one embodiment, the antibody is administered intravenously. In another embodiment, binding of the antibody to an inhibitory KIR on the surface of an NK cell potentiates the cytotoxic activity of the NK cell. In yet another embodiment, the antibody is a cross-reactive anti-KIR antibody. For example, the antibody may be antibody 1-7F9 in a formulation as described in WO2008/084106.

In one preferred embodiment, the dose is selected to provide full saturation (at least 90% occupancy of the targeted KIR2DL1, 2 and/or 3) in human patients. The method optionally includes assessing the patient for NK cell potentiation and/or anti-inflammatory (or anti-T cell) activity (which may be performed by use of any suitable technique, several of which being known in the art, including, e.g., KIR2DL1, 2 and/or 3 occupancy level, CD107a marker, as described herein). The formulation is typically administered by i.v. administration over a suitable period of time, such as about 1 hour.

For example, an anti-KIR2DL1, 2 and/or 3 antibody can be administered at a dose and a dosing frequency achieving at least about 90%, preferably at least about 95% KIR2DL1, 2 and/or 3 occupancy on NK cells in plasma for at least about one, two, three or six months, thereby having sustained saturation for an extended period of time (e.g., at least 3 months, 6 months). In separate embodiments, the dose is in the range from about 0.1 to about 3 mg/kg, from about 0.3 to about 3 mg/kg, from about 0.1 to about 1 mg/kg and from about 1 to about 3 mg/kg, further preferably wherein the antibody is an anti-KIR antibody, further preferably wherein the antibody is 1-7F9. The dosing frequency may be in the range of once per day to once per 2 months, from about once per week to about once per 2 months; or about once per month. Alternatively, the dosing frequency can be selected from about three times, about twice, and about once per day; about five times, about four times, about three times, and about twice per week; and about once every two, four, and six weeks.

In one preferred embodiment, a dose of anti-KIR2DL1, 2 and/or 3 antibody resulting in substantially full receptor saturation (e.g. at least about 90% or 95% receptor occupancy) is administered from about 2 times per week to about once per month, or from about once per month to about once per 2 months. The dose can be, e.g., administered at least 3 times, at least 6 times, or more. For example, the method may comprise administering an anti-KIR2DL1, 2 and/or 3 antibody at a dose and a dosing frequency achieving at least about 90% or 95% KIR2DL1, 2 and/or 3 occupancy on NK cells for at least about two weeks, one month, 6 months, 9 months or 12 months.

In one preferred embodiment, a regimen results in sustained substantially full receptor saturation. A dose of anti-KIR2DL1, 2 and/or 3 antibody resulting in substantially full receptor saturation for a period of at least about 1 week, 2 weeks or 1 month is administered. When the dose results in substantially full receptor saturation (e.g. at least about 90% or 95% receptor occupancy) for about one week, the dose may be administered for example between once per week and once every two weeks; when the dose results in substantially full receptor saturation for about two weeks, the dose may be administered for example between once every two weeks and once per month. When the dose results in substantially full receptor saturation for about two weeks to about one month, the dose may be administered for example about once per month. In each regimen, the dose can be, e.g., administered at least 3 times, at least 6 times, or more. For example, the method may comprise administering an anti-KIR2DL1, 2 and/or 3 antibody at a dose and a dosing frequency achieving at least about 95% KIR occupancy on NK cells for at least about 6 months, 9 months or 12 months.

In another preferred embodiment, a regimen results in intermittent substantially full receptor saturation. A dose of anti-KIR2DL1, 2 and/or 3 antibody resulting in substantially full receptor saturation (e.g. at least about 90% or 95% receptor occupancy) for a period of at least about 1 week, 2 weeks or 1 month is administered. When the dose results in substantially full receptor saturation for about one to two weeks, the dose may be administered for example about once per month or once per period of at least two months (e.g. once every two months). When the dose results in substantially full receptor saturation for about two weeks to about one month, the dose may be administered for example about once per period of at least two months (e.g. once every two months). In separate embodiments, the dose is in the range from about 0.1 to about 0.3 mg/kg, administered about once per month; in one embodiment, the dose is in the range of about 0.1 to about 3 mg/kg, preferably 1 to about 3 mg/kg, administered about once every about two months (or once per period of more than two months, that is, less than once per two month period), further preferably wherein the antibody is an anti-KIR antibody, further preferably wherein the antibody is 1-7F9. The treatment can be repeated such that the treatment regimen results in intermittent substantially full receptor saturation for a period of at least 6 months, 9 months or 12 months.

The antibody is typically administered intravenously, but other suitable administration modes are known, and also described in, e.g., WO2008/084106.

While Anti-KIR (1-7F9) or its S241P variant is a preferred antibody for modulating NK cell activity and/or treatment of disease, other anti-KIR2DL1, 2 and/or 3 and anti-KIR antibodies may also be used in the methods according to the invention. Such antibodies should, however, have similar Kd values, similar clearance in a patient, and a similar volume of distribution, as Anti-KIR (1-7F9), where "similar" means within about 50%, preferably within about 30% of the corresponding Anti-KIR (1-7F9) parameter. Anti-KIR (1-7F9) has a high affinity Kd of about 4 ng/ml, and low affinity Kd of about 20 ng/ml for doses up to 0.015 mg/kg; a clearance of about 0.5 ml/h/kg, and a volume of distribution of about 115 ml/kg (See WO2008/084106). An exemplary anti-KIR2DL1, 2 and/or 3 antibody useful in one or more methods of the invention may have the following properties: (a) reduces or blocks the signalling of an inhibitory KIR2DL1, 2 and/or 3 on NK cells; (b) a high affinity Kd from about 2 to about 6 ng/ml; (c) a low affinity Kd from about 10 to about 30 ng/ml; (d) a clearance of from about 0.25 to about 0.75 ml/h/kg, (e) a volume of distribution of from about 50 ml/kg to about 175 ml/kg. Anti-KIR2DL1, 2 and/or 3 antibodies' receptor occupancy can be determined using assays as described in the present invention adapted to the particular KIR2DL1, 2 and/or 3 bound by the antibody. See, e.g., Example 2. Anti-KIR2DL1, 2 and/or 3 antibodies' pharmacokinetic properties can be determined using assays as described in the present invention adapted to the particular anti-KIR2DL1, 2 and/or 3 antibody. See, e.g., Example 1.

Autoimmune Diseases

The and anti-KIR2DL1, KIR2DL2, and KIR2DL3 antibodies described herein may be used in compositions, uses, and methods for the treatment of autoimmune diseases.

Examples of autoimmune diseases or disorders include, but are not limited to acquired immune deficiency syndrome (AIDS), acquired spenic atrophy, acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis (including large vessel vasculitis (including polymyalgia rheumatica and giant cell (Takayasu's) arthritis), allergic conditions, allergic contact dermatitis, allergic dermatitis, allergic granulomatous angiitis, allergic hypersensitivity disorders, allergic neuritis, allergic reaction, alopecia areata, alopecia totalis, Alport's syndrome, alveolitis (e.g., allergic alveolitis and fibrosing alveolitis), Alzheimer's disease, amyloidosis, amylotrophic lateral sclerosis (ALS; Lou Gehrig's disease), an eosinophil-related disorder (e.g., eosinophilia), anaphylaxis, ankylosing spondylitis, antgiectasis, antibody-mediated nephritis, Anti-GBM/Anti-TBM nephritis, antigen-antibody complex-mediated diseases, antiglomerular basement membrane disease, anti-phospholipid antibody syndrome, antiphospholipid syndrome (APS), aphthae, aphthous stomatitis, aplastic anemia, arrhythmia, arteriosclerosis, arteriosclerotic disorders, arthritis (e.g., rheumatoid arthritis such as acute arthritis, chronic rheumatoid arthritis), arthritis chronica progrediente, arthritis deformans, ascariasis, aspergilloma (or granulomas containing eosinophils), aspergillosis, aspermiogenese, asthma (e.g., asthma bronchiale, bronchial asthma, and auto-immune asthma), ataxia telangiectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease (e.g., autoimmune inner ear disease (AGED)), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies (e.g., epilepsy), channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy (e.g., IgM polyneuropathies or IgM-mediated neuropathy), chronic obstructive airway disease, chronic pulmonary inflammatory disease, Chronic recurrent multifocal ostomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogans syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis (e.g., chronic cyclitis, heterochronic cyclitis, iridocyclitis, or Fuch's cyclitis), cystic fibrosis, cytokine-induced toxicity, deafness, degenerative arthritis, demyelinating diseases (e.g., autoimmune demyelinating diseases), demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis (e.g., allergic encephalomyelitis or encephalomyelitis allergica and experimental allergic encephalomyelitis (EAE)), endarterial hyperplasia, endocarditis, endocrine ophthamopathy, endometriosis. endomyocardial fibrosis, endophthalmia phacoanaphylactica, endophthalmitis, enteritis allergica, eosinophilia-myalgia syndrome, eosinophilic faciitis, epidemic keratoconjunctivitis, epidermolisis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, flariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, haemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schonlein purpura, Herpes gestationis, human immunodeficiency virus (HIV) infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenic purpura (ITP), IgA nephropathy, IgE-mediated diseases (e.g., anaphylaxis and allergic and atopic rhinitis), IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antibodies, inflammation of all or part of the uvea, inflammatory bowel disease (IBD) inflammatory hyperproliferative skin diseases, inflammatory myopathy, insulin-dependent diabetes (type 1), insulitis, Interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis nodosa), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes (e.g., Lambert-Eaton myasthenic syndrome or Eaton-Lambert syndrome), parasitic diseases such as Lesihmania, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including pemphigus vulgaris), pemphigus erythematosus, pemphigus foliaceus, pemphigus mucus-membrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis nodosa, Type I, II, & III, polyarthritis chronica primaria, polychondritis (e.g., refractory or relapsed polychondritis), polyendocrine autoimmune disease, polyendocrine failure, polyglandular syndromes (e.g., autoimmune polyglandular syndromes (or polyglandular endocrinopathy syndromes)), polymyalgia rheumatica, polymyositis, polymyositis/dermatomyositis, polyneuropathies, polyradiculitis acuta, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis (e.g., benign monoclonal gammopathy and monoclonal garnmopathy of undetermined significance, MGUS), primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyreoiditis, Raynauds phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma (including systemic scleroderma), sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjogren's syndrome, sperm & testicular autoimmunity, sphenoid sinusitis, Stevens-Johnson syndrome, stiff-man (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes (e.g., cutaneous SLE), systemic necrotizing vasculitis, and ANCA-associated vasculitis, such as Churg-Strauss vasculitis or syndrome (CSS)), tabes dorsalis, Takayasu's arteritis, telangiectasia, temporal arteritis/Giant cell arteritis, thromboangitis ubiterans, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, thrombocytopenic purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria (e.g., chronic allergic urticaria and chronic idiopathic urticaria, including chronic autoimmune urticaria), uveitis (e.g., anterior uveitis), uveoretinitis, valvulitis, vascular dysfunction, vasculitis, vertebral arthritis, vesiculobullous dermatosis, vitiligo, Wegener's granulomatosis (now termed Granulomatosis with Polyangiitis (GPA), Wiskott-Aldrich syndrome, and x-linked hyper IgM syndrome.

Treatment of Cancer

The anti-KIR2DL1, KIR2DL2, and KIR2DL3 antibodies described herein may be used in compositions, uses, and methods for the treatment of cancer (e.g., tumors).

Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; multiple myeloma and post-transplant lymphoproliferative disorder (PTLD).

The term cancer amenable for treatment by the present invention include, but not limited to, carcinoma, lymphoma, blastoma, sarcoma, and leukemia or lymphoid malignancies. More particular examples of such cancers include bladder, ovarian, melanoma, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma. In an exemplary embodiment (See working examples) the cancer is an early advanced (including metastatic) bladder, ovarian or melanoma. In another embodiment the cancer is colorectal cancer. The cancerous conditions amenable for treatment of the invention include metastatic cancers wherein KIR2DL1, KIR2DL2, and KIR2DL3 expression by myeloid derived suppressor cells suppress anti-tumor responses and anti-invasive immune responses. The method of the present invention is particularly suitable for the treatment of vascularized tumors.

The invention is also suitable for treating cancers in combination with chemotherapy or radiotherapy or other biologics and for enhancing the activity thereof, i.e., in individuals wherein KIR2DL1, KIR2DL2, and KIR2DL3 expression by myeloid derived suppressor cells suppress antitumor responses and the efficacy of chemotherapy or radiotherapy or biologic efficacy. Any chemotherapeutic agent exhibiting anticancer activity can be used according to the present invention. Preferably, the chemotherapeutic agent may be selected from the group consisting of alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. More preferably, the chemotherapeutic agent may be selected from the group consisting of 5-fluorouracil (5-FU), leucovorin (LV), irenotecan, oxaliplatin, capecitabine, paclitaxel and doxetaxel. Two or more chemotherapeutic agents can be used in a cocktail to be administered in combination with administration of the anti-VEGF antibody. One preferred combination chemotherapy is fluorouracil-based, comprising 5-FU and one or more other chemotherapeutic agent(s). Suitable dosing regimens of combination chemotherapies are known in the art and described in, for example, Saltz, et al. (1999) Proc ASCO 18:233a and Douillard, et al. (2000) Lancet 355: 1041-7. The bilogic may be another immune potentiators such as antibodies to PD-L1, PD-L2, CTLA-4 and PD-L1, PD-L2, CTLA-4 fusion proteins as well as cytokines, growth factor antagonists and agonists, hormones and anti-cytokine antibodies.

Allergies

The anti-KIR2DL1, KIR2DL2, and KIR2DL3 antibodies described herein may be used in compositions, uses, and methods for the treatment of allergies (e.g., allergic reactions to allergens).

Examples of allergens include mite antigens and pollen antigens.

Representative allergic diseases include bronchial asthma, allergic rhinitis, atopic dermatitis, and pollen and insect allergies. Allergic diathesis is a genetic factor that can be inherited by the children of allergic parents. Familial allergic diseases are also called atopic diseases, and the causative, genetically transmitted factor is atopic diathesis. "Atopic dermatitis" is a general term for an atopic disease, especially diseases accompanied by dermatitis symptoms. Preferred examples include allergic condition is selected from the group consisting of eczema, allergic rhinitis, hay fever, urticaria, and food allergies. Allergic conditions include eczema, allergic rhinitis or coryza, hay fever, bronchial asthma, urticaria (hives) and food allergies, and other atopic conditions.

Inflammatory Conditions and Inflammatory Diseases

The anti-KIR2DL1, KIR2DL2, and KIR2DL3 antibodies described herein may be used in compositions, uses, and methods for the treatment of inflammatory conditions and inflammatory disease.

Inflammatory conditions and inflammatory diseases, include but are not limited to rheumatic diseases (e.g., rheumatoid arthritis, osteoarthritis, psoriatic arthritis) spondyloarthropathies (e.g., ankylosing spondylitis, reactive arthritis, Reiter's syndrome), crystal arthropathies (e.g., gout, pseudo-gout, calcium pyrophosphate deposition disease), multiple sclerosis, Lyme disease, polymyalgia rheumatica; connective tissue diseases (e.g., systemic lupus erythematosus, systemic sclerosis, polymyositis, dermatomyositis, Sjogren's syndrome); vasculitides (e.g., polyarteritis nodosa, Wegener's granulomatosis, Churg-Strauss syndrome); inflammatory conditions including consequences of trauma or ischaemia, sarcoidosis; vascular diseases including atherosclerotic vascular disease, atherosclerosis, and vascular occlusive disease (e.g., atherosclerosis, ischaemic heart disease, myocardial infarction, stroke, peripheral vascular disease), and vascular stent restenosis; ocular diseases including uveitis, corneal disease, iritis, iridocyclitis, and cataracts.

Inflammatory conditions also include, but are not limited to acid Reflux/Heartburn, Acne, Acne Vulgaris, Allergies and Sensitivities, Alzheimer's Disease, Asthma, Atherosclerosis and Vascular Occlusive Disease (e.g., Atherosclerosis, Ischaemic Heart Disease, Myocardial Infarction, Stroke, Peripheral Vascular Disease) and Vascular Stent Restenosis, Autoimmune Diseases, Bronchitis, Cancer, Carditis, Cataracts, Celiac Disease, Chronic Pain, Chronic Prostatitis, Cirrhosis, Colitis, Connective Tissue Diseases (e.g., Systemic Lupus Erythematosus, Systemic Sclerosis, Polymyositis, Dermatomyositis, Sjogren's Syndrome), Corneal Disease, Crohn's Disease, Crystal Arthropathies (e.g., Gout, Pseudo-gout, Calcium Pyrophosphate Deposition Disease), Dementia, Dermatitis, Diabetes, Dry Eyes, Eczema, Edema, Emphysema, Fibromyalgia, Gastroenteritis, Gingivitis, Glomerulonephritis, Heart Disease, Hepatitis, High Blood Pressure, Hypersensitivities, Inflammatory Bowel Diseases, Inflammatory Conditions including Consequences of Trauma or Ischaemia, Insulin Resistance, Interstitial Cystitis, Iridocyclitis, Iritis, Joint Pain/Arthritis/Rheumatoid Arthritis, Lyme Disease, Metabolic Syndrome (Syndrome X), Multiple Sclerosis, Myositis, Nephritis, Obesity, Ocular Diseases including Uveitis, Osteopenia, Osteoporosis, Parkinson's Disease, Pelvic Inflammatory Disease, Periodontal Disease, Polyarteritis, Polychondritis, Polymyalgia Rheumatica, Psoriasis, Reperfusion Injury, Rheumatic Arthritis, Rheumatic Diseases (e.g., Rheumatoid Arthritis, Osteoarthritis, Psoriatic Arthritis), Rheumatoid Arthritis, Sarcoidosis, Scleroderma, Sinusitis, Sjögren's Syndrome, Spastic Colon, Spondyloarthropathies (e.g., Ankylosing Spondylitis, Reactive Arthritis, Reiter's Syndrome), Systemic Candidiasis, Tendonitis, Transplant Rejection, UTI's, Vaginitis, Vascular Diseases including Atherosclerotic Vascular Disease, Vasculitides (e.g., Polyarteritis Nodosa, Wegener's Granulomatosis, Churg-Strauss Syndrome), and Vasculitis.

Diagnostic Methods

The anti-KIR2DL1, KIR2DL2, and KIR2DL3 and anti-KIR2DL1, KIR2DL2, and KIR2DL3 antibodies which selectively bind the KIR2DL1, KIR2DL2, and KIR2DL3, and antigen-binding fragments thereof, may be used in diagnostic methods for detecting the presence or absence of an KIR2DL1, KIR2DL2, and KIR2DL3 polypeptides. Anti-KIR2DL1, KIR2DL2, and KIR2DL3 and anti-KIR2DL1, KIR2DL2, and KIR2DL3 antibodies may be used in methods comprising (a) contacting a test sample with an antibody, or fragment thereof, that binds a KIR2DL1, KIR2DL2, and KIR2DL3 or KIR2DL1, KIR2DL2, and KIR2DL3, and (b) assaying for antibody-epitope complexes. The antibody-epitope complex may be detected by Western blot, radioimmunoassay, ELISA (enzyme linked immunosorbent assay), "sandwich" immunoassay, immunoprecipitation assay, precipitation reaction, gel diffusion precipitation reaction, immunodiffusion assay, agglutination assay, complement-fixation assay, immunohistochemical assay, fluorescent immunoassay, and protein A immunoassay. The sample may be sample is a tissue biopsy, lymph, urine, cerebrospinal fluid, amniotic fluid, inflammatory exudate, blood, serum, stool, or liquid collected from the colorectal tract.

The antibodies which selectively bind a KIR2DL1, KIR2DL2, and KIR2DL3 may be recombinant. The fragments of antibodies which selectively bind a KIR2DL1, KIR2DL2, and KIR2DL3 may be a Fab, Fab', F(ab')2, Fv, CDR, paratope, or portion of an antibody that is capable of binding the antigen. The antibodies which selectively bind a KIR2DL1, KIR2DL2, and KIR2DL3 may be chimeric, humanized, anti-idiotypic, single-chain, bifunctional, or co-specific. The antibodies which selectively bind a KIR2DL1, KIR2DL2, and KIR2DL3 may be or fragment is conjugated to a label, including but not limited to a chemiluminescent label, paramagnetic label (e.g., aluminum, manganese, platinum, oxygen, lanthanum, lutetium, scandium, yttrium, or gallium), an MRI contrast agent, fluorescent label, bioluminescent label, or radioactive label.

Additionally, KIR2DL1, KIR2DL2, and KIR2DL3, antibody which selectively bind a KIR2DL1, KIR2DL2, and KIR2DL3, and antigen-binding fragments thereof, may be attached to a solid support (e.g., bead, test tube, sheet, culture dish, or test strip) such as an array.

The method may comprise imaging a KIR2DL1, KIR2DL2, and KIR2DL3 polypeptide by positron emission tomography (PET), CCD low-light monitoring system, x-ray, CT scanning, scintigraphy, photo acoustic imaging, single photon emission computed tomography (SPECT), magnetic resonance imaging (MRI), ultrasound, paramagnetic imaging, and endoscopic optical coherence tomography.

The invention may comprises a step of conducting an evaluation or testing step to assess the presence, stage, evolution or rating of disease. Thus, a method for the treatment of an autoimmune or inflammatory disease in a patient may comprise: (a) conducting an evaluation of disease in the patient; and (b) if said patient has a disease suitable for treatment with an anti-KIR2DL1, 2 and/or 3 antibody of the invention, administering to said patient an effective dose of anti-KIR2DL1, 2 and/or 3 antibody. Optionally such evaluation step may involve obtaining a biological sample from a patient suspected of having an autoimmune or inflammatory disease. For example, the KIR and HLA-C genotype of an rheumatoid arthritis patient may provide predictive information for response to anti-TNF-α therapy. See McGeough, et al. (2011) Rheumatology International. Also, expression of KIR2DL isoforms are associated with susceptiblity to inflammatory bowel disease. Zhang, et al. (2008) Life Science Journal 5(4):17-22. Methods for evaluating disease (e.g. diagnosing, staging) can be achieved by any suitable technique known in the art, for example by performing a laboratory-based test. Examples of suitable techniques include conducting a PCR or RT-PCR based assay (e.g., to detect disease associated nucleic acids or genes, often referred to as "markers" or "biomarkers"), biopsy, endoscopy, stool studies, any noninvasive laboratory tests (e.g. anemia and infection, liver function tests to screen for liver and bile duct problems, tests for bacterial, viral and parasitic infections), ultrasound, CT, MRE, MRI and other imaging techniques, chromosomal analysis, immunoassay/immunocytochemical detection techniques (e.g. presence of autoantibodies), histological and/or histopathologic assays, serum protein electrophoresis, flow cytometry (e.g. detection of immune cells, T cells), arterial blood gas (ABG) analysis (in asthma or COPD), and physical examination techniques (e.g., for physical symptoms, numbers of joints with synovitis).

Further, subjects with activating KIR2DS1 and/or KIR2DS2 genes are susceptible to developing psoriatic arthritis, but only when HLA ligands for their homologous inhibitory receptors, KIR2DL1 and KIR2DL2/3, are missing. Absence of ligands for inhibitory KIRs could potentially lower the threshold for NK (and/or T) cell activation mediated through activating receptors, thereby contributing to pathogenesis of psoriatic arthritis. Martin, et al. (2002) The Journal of Immunology 169: 2818-2822. The methods comprise detecting the presence of auto-antibodies, for example detecting rheumatoid factor (RhF), anti-cyclic citrullinated peptide antibodies, anti-ssRNA, anti-dsRNA, anti-Smith, anti-phospholipid, anti-nuclear and/or anti-actin antibodies. In one embodiment, the methods comprise assessing levels of a proteolytic enzyme, an inflammatory mediator, a marker of ongoing inflammation or a proinflammatory cytokine. In one embodiment, the methods comprise determining c-reactive protein (CRP) level and/or erythrocyte sedimentation rate. A determination that an individual has abnormal results (indicative of disease, exacerbation, ongoing inflammation), for example abnormal levels of ABG, autoantibodies, CRP, any proteolytic enzyme, inflammatory mediator or marker of ongoing inflammation indicates the individual is suitable for treatment with an anti-KIR2DL1, 2 and/or 3 antibody. A biological sample from a patient is evaluated for the presence of T cells, preferably CD4+ T cells and/or activated and/or proliferation T cells).

Screening Assays

The invention provides a method for identifying modulators ("screening assay"), i.e., candidate or test compounds or agents (e.g., peptides, peptidomimetics, small molecules or other drugs) which bind to KIR2DL1, KIR2DL2, and KIR2DL3 polypeptides, have a stimulatory or inhibitory effect on, for example, KIR2DL1, KIR2DL2, and KIR2DL3 expression or KIR2DL1, KIR2DL2, and KIR2DL3 activity, or have a stimulatory or inhibitory effect on the interaction between KIR2DL1, KIR2DL2, and KIR2DL3 and its natural binding partner(s).

The invention provides assays for screening candidate or test compounds which bind to the KIR2DL1, KIR2DL2, and KIR2DL3 protein or polypeptide or biologically active portion thereof, e.g., modulate the ability of the KIR2DL1, KIR2DL2, and KIR2DL3 polypeptide to interact with its natural binding partner(s). In another embodiment, the invention provides assays for screening candidate or test compounds which bind to or modulate the activity of a KIR2DL1, KIR2DL2, and KIR2DL3 protein or polypeptide or biologically active portion thereof. In a embodiment, the invention provides assays for screening candidate or test compounds which have a stimulatory or inhibitory effect on immune functions negatively regulated by KIR2DL1, KIR2DL2, and KIR2DL3 such as are identified herein or based on its effect on the interaction of between KIR2DL1, KIR2DL2, and KIR2DL3 and its natural binding partner(s). These KIR2DL1, KIR2DL2, and KIR2DL3 related functions include by way of example inhibiting cytokine production (e.g., 11-2, gamma interferon by T cells, suppressing moderate CD28 costimulation, inhibiting CD4+ and CD8+ T cell proliferation, suppressing proliferation of naïve and memory CD4+ T cells, and suppressing TCR activation without inducing apoptosis.) The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. Lam (1997) Anticancer Drug Des. 12: 145.

In one embodiment, an assay is a cell-based assay in which a cell which expresses a KIR2DL1, KIR2DL2, and KIR2DL3 polypeptide or biologically active portion thereof is contacted with a test compound, and the ability of the test compound to modulate KIR2DL1, KIR2DL2, and KIR2DL3 activity is determined. Determining the ability of the test compound to modulate KIR2DL1, KIR2DL2, and KIR2DL3 activity can be accomplished by monitoring, for example, the ability of KIR2DL1, KIR2DL2, and KIR2DL3 to bind to its natural binding partner(s), and modulate immune cell activity. The immune cell can be a T cell, a B cell, or a myeloid cell. Determining the ability of the test compound to modulate KIR2DL1, KIR2DL2, and KIR2DL3 binding to its counter-receptor can be accomplished, for example, by coupling KIR2DL1, KIR2DL2, and KIR2DL3 with a radioisotope or enzymatic label to monitor the ability of a test compound to modulate KIR2DL1, KIR2DL2, and KIR2DL3 binding to T cells which express the KIR2DL1, KIR2DL2, and KIR2DL3 counter-receptor. Determining the ability of the test compound to bind KIR2DL1, KIR2DL2, and KIR2DL3 can be accomplished, for example, by coupling the compound with a radioisotope or enzymatic label such that binding of the compound to KIR2DL1, KIR2DL2, and KIR2DL3 can be determined by detecting the labeled KIR2DL1, KIR2DL2, and KIR2DL3 compound in a complex.

It is also within the scope of this invention to determine the ability of a compound to interact with KIR2DL1, KIR2DL2, and KIR2DL3 without the labeling of any of the interactants. For example, a microphysiometer can be used to detect the interaction of a compound with KIR2DL1, KIR2DL2, and KIR2DL3 without the labeling of either the compound or the KIR2DL1, KIR2DL2, and KIR2DL3. McConnell, H. M. et al. (1992) Science 257:1906-1912. A microphysiometer (e.g., Cytosensor) is an analytical instrument that measures the rate at which a cell acidifies its environment using a light-addressable potentiometric sensor (LAPS). Changes in this acidification rate can be used as an indicator of the interaction between a compound and KIR2DL1, KIR2DL2, and KIR2DL3.

An assay may be a cell-based assay comprising contacting a T cell expressing a KIR2DL1, KIR2DL2, and KIR2DL3 binding partner with a test compound and determining the ability of the test compound to modulate (e.g., stimulate or inhibit) the activity of the KIR2DL1, KIR2DL2, and KIR2DL3 binding partner. Determining the ability of the test compound to modulate the activity of a KIR2DL1, KIR2DL2, and KIR2DL3 binding partner can be accomplished, for example, by determining the ability of the KIR2DL1, KIR2DL2, and KIR2DL3 polypeptide to bind to or interact with the KIR2DL1, KIR2DL2, and KIR2DL3 binding partner.

Determining the ability of the KIR2DL1, KIR2DL2, and KIR2DL3 polypeptide, or a biologically active fragment thereof, to bind to or interact with a KIR2DL1, KIR2DL2, and KIR2DL3 binding partner, can be accomplished by one of the methods described above for determining direct binding. In a embodiment, determining the ability of the KIR2DL1, KIR2DL2, and KIR2DL3 polypeptide to bind to or interact with a KIR2DL1, KIR2DL2, and KIR2DL3 binding partner can be accomplished by determining the activity of the binding partner. For example, the activity of the binding partner can be determined by detecting induction of a cellular second messenger (e.g., tyrosine kinase or phosphatase activity), detecting catalytic/enzymatic activity of an appropriate substrate, detecting the induction of a reporter gene (comprising a target-responsive regulatory element operatively linked to a nucleic acid encoding a detectable marker, e.g., luciferase), or detecting a target-regulated cellular response. For example, determining the ability of the KIR2DL1, KIR2DL2, and KIR2DL3 polypeptide to bind to or interact with a natural KIR2DL1, KIR2DL2, and KIR2DL3 binding partner, can be accomplished by measuring the ability of a compound to modulate immune cell costimulation or inhibition in a proliferation assay, or by interfering with the ability of a KIR2DL1, KIR2DL2, and KIR2DL3 polypeptide to bind to antibodies that recognize a portion of the KIR2DL1, KIR2DL2, and KIR2DL3 polypeptide. In one embodiment, compounds that modulate T cell activation can be identified by determining the ability of a compound to modulate T cell proliferation or cytokine production. In a embodiment, compounds that modulate T cell activation can be identified by determining the ability of a compound to modulate T cell proliferation or cytokine production at more than one antigen concentration.

An assay may be a cell-free assay in which a KIR2DL1, KIR2DL2, and KIR2DL3 polypeptide or biologically active portion thereof is contacted with a test compound and the ability of the test compound to bind to the KIR2DL1, KIR2DL2, and KIR2DL3 polypeptide or biologically active portion thereof is determined. Preferred biologically active portions of the KIR2DL1, KIR2DL2, and KIR2DL3 polypeptides to be used in assays of the present invention include fragments which participate in interactions with non-KIR2DL1, KIR2DL2, and KIR2DL3 molecules, e.g., at least a portion of an extracellular domain which binds to a KIR2DL1, KIR2DL2, and KIR2DL3 binding partner. Binding of the test compound to the KIR2DL1, KIR2DL2, and KIR2DL3 polypeptide can be determined either directly or indirectly as described above.

The assay may be a cell-free assay in which a KIR2DL1, KIR2DL2, and KIR2DL3 polypeptide or biologically active portion thereof is contacted with a test compound and the ability of the test compound to modulate (e.g., stimulate or inhibit) the activity of the KIR2DL1, KIR2DL2, and KIR2DL3 polypeptide or biologically active portion thereof is determined. Determining the ability of the test compound to modulate the activity of a KIR2DL1, KIR2DL2, and KIR2DL3 polypeptide can be accomplished, for example, by determining the ability of the KIR2DL1, KIR2DL2, and KIR2DL3 polypeptide to bind to a KIR2DL1, KIR2DL2, and KIR2DL3 binding partner by one of the methods described above for determining direct binding. The cell-free assays of the present invention are amenable to use of both soluble and/or membrane-bound forms of polypeptides (e.g., KIR2DL1, KIR2DL2, and KIR2DL3 polypeptides or biologically active portions thereof, or binding partners to which KIR2DL1, KIR2DL2, and KIR2DL3 binds). In the case of cell-free assays in which a membrane-bound form a polypeptide is used (e.g., a cell-surface KIR2DL1, KIR2DL2, and KIR2DL3), it may be desirable to utilize a solubilizing agent such that the membrane-bound form of the polypeptide is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl.dbd.N,N-dimethyl-3-ammonio-1-propane sulfonate.

In assay methods, it may be desirable to immobilize either KIR2DL1, KIR2DL2, and KIR2DL3 or its binding partner to facilitate separation of complexed from uncomplexed forms of one or both of the polypeptides, as well as to accommodate automation of the assay. Binding of a test compound to a KIR2DL1, KIR2DL2, and KIR2DL3 polypeptide, or interaction of a KIR2DL1, KIR2DL2, and KIR2DL3 polypeptide with its binding partner in the presence and absence of a candidate compound, can be accomplished in any vessel suitable for containing the reactants. Examples of such vessels include microtitre plates, test tubes, and micro-centrifuge tubes. A fusion protein can be provided which adds a domain that allows one or both of the polypeptides to be bound to a matrix. For example, glutathione-S-transferase/KIR2DL1, KIR2DL2, and KIR2DL3 fusion proteins or glutathione-S-transferase/binding partner fusion proteins can be adsorbed onto glutathione SEPHAROSE® beads (Sigma Chemical, St. Louis, Mo.) or glutathione derivatized microtitre plates, which are then combined with the test compound or the test compound and either the non-adsorbed binding partner polypeptide or KIR2DL1, KIR2DL2, and KIR2DL3 polypeptide, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of KIR2DL1, KIR2DL2, and KIR2DL3 binding or activity determined using standard techniques. Other techniques for immobilizing polypeptides on matrices can also be used in the screening assays of the invention. In an alternative embodiment, determining the ability of the test compound to modulate the activity of a KIR2DL1, KIR2DL2, and KIR2DL3 polypeptide can be accomplished by determining the ability of the test compound to modulate the activity of a molecule that functions downstream of KIR2DL1, KIR2DL2, and KIR2DL3, e.g., by interacting with the cytoplasmic domain of a KIR2DL1, KIR2DL2, and KIR2DL3 binding partner. For example, levels of second messengers, the activity of the interacting molecule on an appropriate target, or the binding of the interactor to an appropriate target can be determined as previously described.

Modulators of KIR2DL1, KIR2DL2, and KIR2DL3 expression may be identified in a method wherein a cell is contacted with a candidate compound and the expression of KIR2DL1, KIR2DL2, and KIR2DL3 mRNA or polypeptide in the cell is determined. The level of expression of KIR2DL1, KIR2DL2, and KIR2DL3 mRNA or polypeptide in the presence of the candidate compound is compared to the level of expression of KIR2DL1, KIR2DL2, and KIR2DL3 mRNA or polypeptide in the absence of the candidate compound. The candidate compound can then be identified as a modulator of KIR2DL1, KIR2DL2, and KIR2DL3 expression based on this comparison if the change is statistically significant.

The KIR2DL1, KIR2DL2, and KIR2DL3 polypeptides may be used as "bait proteins" in a two-hybrid assay or three-hybrid assay (See, e.g., U.S. Pat. No. 5,283,317; Zervos, et al. (1993) Cell 72:223-232; Madura, et al. (1993) J. Biol. Chem. 268:12046-12054; Bartel, et al. (1993) Biotechniques 14:920-924; Iwabuchi, et al. (1993) Oncogene 8:1693-1696; and WO 94/10300), to identify other polypeptides which bind to or interact with KIR2DL1, KIR2DL2, and KIR2DL3 ("KIR2DL1, KIR2DL2, and KIR2DL3-binding proteins", "KIR2DL1, KIR2DL2, and KIR2DL3 binding partners", or "KIR2DL1, KIR2DL2, and KIR2DL3-bp") and are involved in KIR2DL1, KIR2DL2, and KIR2DL3 activity. Such KIR2DL1, KIR2DL2, and KIR2DL3-binding proteins are also likely to be involved in the propagation of signals by the KIR2DL1, KIR2DL2, and KIR2DL3 polypeptides or KIR2DL1, KIR2DL2, and KIR2DL3 targets as, for example, downstream elements of a KIR2DL1, KIR2DL2, and KIR2DL3-mediated signaling pathway. Alternatively, such KIR2DL1, KIR2DL2, and KIR2DL3-binding polypeptides may be KIR2DL1, KIR2DL2, and KIR2DL3 inhibitors. The two-hybrid system is based on the modular nature of most transcription factors, which consist of separable DNA-binding and activation domains. Briefly, the assay utilizes two different DNA constructs. In one construct, the gene that codes for a KIR2DL1, KIR2DL2, and KIR2DL3 polypeptide is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming a KIR2DL1, KIR2DL2, and KIR2DL3-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with the KIR2DL1, KIR2DL2, and KIR2DL3 polypeptide.

A combination of two or more of the assays described herein. For example, a modulating agent may be identified using a cell-based or a cell-free assay, and the ability of the agent to modulate the activity of a KIR2DL1, KIR2DL2, and KIR2DL3 polypeptide can be confirmed in vivo, e.g., in an animal such as an animal model for cellular transformation and/or tumorigenesis.

This invention further pertains to novel agents identified by the above-described screening assays. An agent as identified in the methods described herein in an appropriate animal model. For example, an agent identified as described herein (e.g., a KIR2DL1, KIR2DL2, and KIR2DL3 modulating agent, an antisense KIR2DL1, KIR2DL2, and KIR2DL3 nucleic acid molecule, a KIR2DL1, KIR2DL2, and KIR2DL3-specific antibody, or a KIR2DL1, KIR2DL2, and KIR2DL3 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the KIR2DL1, KIR2DL2, and KIR2DL3 nucleotide sequences, described herein, can be used to map the location of the KIR2DL1, KIR2DL2, and KIR2DL3 genes on a chromosome. The mapping of the KIR2DL1, KIR2DL2, and KIR2DL3 sequences to chromosomes is an important first step in correlating these sequences with genes associated with disease. Briefly, KIR2DL1, KIR2DL2, and KIR2DL3 genes can be mapped to chromosomes by preparing PCR primers (preferably 15-25 bp in length) from the KIR2DL1, KIR2DL2, and KIR2DL3 nucleotide sequences. Computer analysis of the KIR2DL1, KIR2DL2, and KIR2DL3 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the KIR2DL1, KIR2DL2, and KIR2DL3 sequences will yield an amplified fragment. Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. D'Eustachio, et al. (1983) Science 220: 919-924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the KIR2DL1, KIR2DL2, and KIR2DL3 nucleotide sequences to design oligonucleotide primers, sublocalization can be achieved with panels of fragments from specific chromosomes. Other mapping strategies which can similarly be used to map a KIR2DL1, KIR2DL2, and KIR2DL3 sequence to its chromosome include in situ hybridization (described in Fan, et al. (1990) Proc Natl. Acad. Sci. USA 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time. For a review of this technique, See Verma et al., Human Chromosomes: A Manual of basic Techniques (Pergamon Press, New York 1988). Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridization during chromosomal mapping.

Once a sequence has been mapped to a precise chromosomal location, the physical position of the sequence on the chromosome can be correlated with genetic map data Ultimately, complete sequencing of genes from several individuals can be performed to confirm the presence of a mutation and to distinguish mutations from polymorphisms.

Tissue Typing

The KIR2DL1, KIR2DL2, and KIR2DL3 sequences of the present invention can also be used to identify individuals from minute biological samples. Furthermore, the sequences of the present invention can be used to provide an alternative technique which determines the actual base-by-base DNA sequence of selected portions of an individual's genome. Thus, the KIR2DL1, KIR2DL2, and KIR2DL3 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The KIR2DL1, KIR2DL2, and KIR2DL3 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO: 1 or 4 can comfortably provide positive individual identification with a panel of perhaps 10 to 1,000 primers which each yield a noncoding amplified sequence of 100 bases. If predicted coding sequences, such as those in SEQ ID NO: 3 or 6 are used, a more appropriate number of primers for positive individual identification would be 500-2000.

If a panel of reagents from KIR2DL1, KIR2DL2, and KIR2DL3 nucleotide sequences described herein is used to generate a unique identification database for an individual, those same reagents can later be used to identify tissue from that individual. Using the unique identification database, positive identification of the individual, living or dead, can be made from extremely small tissue samples.

Use of KIR2DL1, KIR2DL2, and KIR2DL3 Sequences in Forensic Biology

DNA-based identification techniques can also be used in forensic biology. The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO: 1 or 3 are particularly appropriate for this use as greater numbers of polymorphisms occur in the noncoding regions, making it easier to differentiate individuals using this technique. Examples of polynucleotide reagents include the KIR2DL1, KIR2DL2, and KIR2DL3 nucleotide sequences or portions thereof, e.g., fragments derived from the noncoding regions of SEQ ID NO: 1 or 3 having a length of at least 20 bases, preferably at least 30 bases. The KIR2DL1, KIR2DL2, and KIR2DL3 nucleotide sequences described herein can further be used to provide polynucleotide reagents, e.g., labeled or labelable probes which can be used in, for example, an in situ hybridization technique, to identify a specific tissue, e.g., lymphocytes. This can be very useful in cases where a forensic pathologist is presented with a tissue of unknown origin. Panels of such KIR2DL1, KIR2DL2, and KIR2DL3 probes can be used to identify tissue by species and/or by organ type. In a similar fashion, these reagents, e.g., KIR2DL1, KIR2DL2, and KIR2DL3 primers or probes can be used to screen tissue culture for contamination (i.e., screen for the presence of a mixture of different types of cells in a culture).

Diagnostic Assays

An exemplary method for detecting the presence or absence of KIR2DL1, KIR2DL2, and KIR2DL3 polypeptide or nucleic acid in a biological sample involves obtaining a biological sample from a test subject and contacting the biological sample with a compound or an agent capable of detecting KIR2DL1, KIR2DL2, and KIR2DL3 polypeptide or nucleic acid (e.g., mRNA or genomic DNA) that encodes KIR2DL1, KIR2DL2, and KIR2DL3 polypeptide such that the presence of KIR2DL1, KIR2DL2, and KIR2DL3 polypeptide or nucleic acid is detected in the biological sample. A preferred agent for detecting KIR2DL1, KIR2DL2, and KIR2DL3 mRNA or genomic DNA is a labeled nucleic acid probe capable of hybridizing to KIR2DL1, KIR2DL2, and KIR2DL3 mRNA or genomic DNA. The nucleic acid probe can be, for example, the KIR2DL1, KIR2DL2, and KIR2DL3 nucleic acid set forth in SEQ ID NO: 1, or 3, or a portion thereof, such as an oligonucleotide of at least 15, 30, 50, 100, 250 or 500 nucleotides in length and sufficient to specifically hybridize under stringent conditions to KIR2DL1, KIR2DL2, and KIR2DL3 mRNA or genomic DNA. Other suitable probes for use in the diagnostic assays of the invention are described herein. A preferred agent for detecting KIR2DL1, KIR2DL2, and KIR2DL3 polypeptide is an antibody capable of binding to KIR2DL1, KIR2DL2, and KIR2DL3 polypeptide, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect KIR2DL1, KIR2DL2, and KIR2DL3 mRNA, polypeptide, or genomic DNA in a biological sample in vitro as well as in vivo. For example, in vitro techniques for detection of PD-L2 mRNA include Northern hybridizations and in situ hybridizations. In vitro techniques for detection of KIR2DL1, KIR2DL2, and KIR2DL3 polypeptide include enzyme linked immunosorbent assays (ELISAs), Western blots, immunoprecipitations and immunofluorescence. In vitro techniques for detection of KIR2DL1, KIR2DL2, and KIR2DL3 genomic DNA include Southern hybridizations. Furthermore, in vivo techniques for detection of KIR2DL1, KIR2DL2, and KIR2DL3 polypeptide include introducing into a subject a labeled anti-KIR2DL1, KIR2DL2, and KIR2DL3 antibody. For example, the antibody can be labeled with a radioactive marker whose presence and location in a subject can be detected by standard imaging techniques. The biological sample contains polypeptide molecules from the test subject. Alternatively, the biological sample can contain mRNA molecules from the test subject or genomic DNA molecules from the test subject. A preferred biological sample is a serum sample isolated by conventional means from a subject. In another embodiment, the methods further involve obtaining a control biological sample from a control subject, contacting the control sample with a compound or agent capable of detecting KIR2DL1, KIR2DL2, and KIR2DL3 polypeptide, mRNA, or genomic DNA, such that the presence of KIR2DL1, KIR2DL2, and KIR2DL3 polypeptide, mRNA or genomic DNA is detected in the biological sample, and comparing the presence of KIR2DL1, KIR2DL2, and KIR2DL3 polypeptide, mRNA or genomic DNA in the control sample with the presence of KIR2DL1, KIR2DL2, and KIR2DL3 polypeptide, mRNA or genomic DNA in the test sample.

The invention also encompasses kits for detecting the presence of KIR2DL1, KIR2DL2, and KIR2DL3 in a biological sample. For example, the kit can comprise a labeled compound or agent capable of detecting KIR2DL1, KIR2DL2, and KIR2DL3 polypeptide or mRNA in a biological sample; means for determining the amount of KIR2DL1, KIR2DL2, and KIR2DL3 in the sample; and means for comparing the amount of KIR2DL1, KIR2DL2, and KIR2DL3 in the sample with a standard. The compound or agent can be packaged in a suitable container. The kit can further comprise instructions for using the kit to detect KIR2DL1, KIR2DL2, and KIR2DL3 polypeptide or nucleic acid.

Prognostic Assays

The diagnostic methods described herein can furthermore be utilized to identify subjects having or at risk of developing a disease or disorder associated with aberrant or unwanted KIR2DL1, KIR2DL2, and KIR2DL3 expression or activity. As used herein, the term "aberrant" includes a KIR2DL1, KIR2DL2, and KIR2DL3 expression or activity which deviates from the wild type KIR2DL1, KIR2DL2, and KIR2DL3 expression or activity. Aberrant expression or activity includes increased or decreased expression or activity, as well as expression or activity which does not follow the wild type developmental pattern of expression or the subcellular pattern of expression. For example, aberrant KIR2DL1, KIR2DL2, and KIR2DL3 expression or activity is intended to include the cases in which a mutation in the KIR2DL1, KIR2DL2, and KIR2DL3 gene causes the KIR2DL1, KIR2DL2, and KIR2DL3 gene to be under-expressed or over-expressed and situations in which such mutations result in a non-functional KIR2DL1, KIR2DL2, and KIR2DL3 polypeptide or a polypeptide which does not function in a wild-type fashion, e.g., a polypeptide which does not interact with a KIR2DL1, KIR2DL2, and KIR2DL3 binding partner, or one which interacts with a non-KIR2DL1, KIR2DL2, and KIR2DL3 binding partner. As used herein, the term "unwanted" includes an unwanted phenomenon involved in a biological response such as immune cell activation. For example, the term unwanted includes a KIR2DL1, KIR2DL2, and KIR2DL3 expression or activity which is undesirable in a subject.

The assays described herein, such as the preceding diagnostic assays or the following assays, can be utilized to identify a subject having or at risk of developing a disorder associated with a misregulation in KIR2DL1, KIR2DL2, and KIR2DL3 polypeptide activity or nucleic acid expression, such as an autoimmune disorder, an immunodeficiency disorder, an immune system disorder such as autoimmunity, allergic or inflammatory disorder or cancer. Thus, the present invention provides a method for identifying a disease or disorder associated with aberrant or unwanted KIR2DL1, KIR2DL2, and KIR2DL3 expression or activity in which a test sample is obtained from a subject and KIR2DL1, KIR2DL2, and KIR2DL3 polypeptide or nucleic acid (e.g., mRNA or genomic DNA) is detected, wherein the presence of KIR2DL1, KIR2DL2, and KIR2DL3 polypeptide or nucleic acid is diagnostic for a subject having or at risk of developing a disease or disorder associated with aberrant or unwanted KIR2DL1, KIR2DL2, and KIR2DL3 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant or unwanted KIR2DL1, KIR2DL2, and KIR2DL3 expression or activity. For example, such methods can be used to determine whether a subject can be effectively treated with an agent for an autoimmune disorder, immunodeficiency disorder, immune system cancer, or allergic or inflammatory disorder. Thus, the present invention provides methods for determining whether a subject can be effectively treated with an agent for a disorder associated with aberrant or unwanted KIR2DL1, KIR2DL2, and KIR2DL3 expression or activity in which a test sample is obtained and KIR2DL1, KIR2DL2, and KIR2DL3 polypeptide or nucleic acid expression or activity is detected (e.g., wherein the abundance of KIR2DL1, KIR2DL2, and KIR2DL3 polypeptide or nucleic acid expression or activity is diagnostic for a subject that can be administered the agent to treat a disorder associated with aberrant or unwanted KIR2DL1, KIR2DL2, and KIR2DL3 expression or activity). The methods of the invention can also be used to detect genetic alterations in a KIR2DL1, KIR2DL2, and KIR2DL3 gene, thereby determining if a subject with the altered gene is at risk for a disorder characterized by misregulation in KIR2DL1, KIR2DL2, and KIR2DL3 polypeptide activity or nucleic acid expression, such as an autoimmune disorder, an immunodeficiency disorder, an immune system cancer, an allergic disorder, or an inflammatory disorder. The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a KIR2DL1, KIR2DL2, and KIR2DL3 gene. Furthermore, any cell type or tissue in which KIR2DL1, KIR2DL2, and KIR2DL3 is expressed may be utilized in the prognostic assays described herein.

Immunoassays

The KIR2DL1, KIR2DL2, and KIR2DL3, antibodies and antigen-binding fragments that bind the KIR2DL1, KIR2DL2, and KIR2DL3, may be used in immunoassays to qualitatively or quantitatively detect and analyze markers in a sample. This method comprises providing an antibody specifically binds to a KIR2DL1, KIR2DL2, and KIR2DL3; contacting a sample with the antibody; and detecting the presence of a complex of the antibody bound to the marker in the sample.

KIR2DL1, KIR2DL2, and KIR2DL3 may be detected and/or quantified using any of a number of well recognized immunological binding assays. Useful assays include, for example, an enzyme immune assay (EIA) such as enzyme-linked immunosorbent assay (ELISA), a radioimmunoassay (RIA), a Western blot assay, or a slot blot assay. See, e.g., U.S. Pat. Nos. 4,366,241; 4,376,110; 4,517,288; and 4,837,168. Generally, a sample obtained from a subject can be contacted with the antibody specifically binds the KIR2DL1, KIR2DL2, and KIR2DL3.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies may be attached to a solid support.

After incubating the sample with antibodies, the mixture is washed and the antibody-marker complex formed may be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations. Usually the assays will be carried out at ambient temperature, although they can be conducted over a range of temperatures (e.g., 10° C.-40° C.).

The immunoassay can be used to determine a test amount of a marker in a sample from a subject. First, a test amount of a marker in a sample may be detected using the immunoassay methods described above. If a marker is present in the sample, it will form an antibody-marker complex with an antibody specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal. Several immunoassays are known in the art and the KIR2DL1, KIR2DL2, and KIR2DL3 polypeptide described herein may used in such immunoassays including but not limited to radio-immunoassay (RIA), enzyme linked immunosorbent assay (ELISA), magnetic immunoassay, immunoblot, Western blot, immunoprecipitation assays, immunohistochemical analysis, and fluorescence activated cell sorting (FACS). See Wild, (2008) [Ed.] The Immunoassay Handbook [$3^{rd}$ Ed.] Elsevier.

Radio-Imaging Methods

The anti-KIR2DL1, KIR2DL2, and KIR2DL3 antibodies may be used in radio-imaging methods to diagnosis cancer including pancreatic and colorectal cancer, or monitor the progression of tumors. These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. SPECT may optionally be used with two labels simultaneously. See U.S. Pat. No. 6,696,686.

Commercial Applications And Methods

The present invention further provides for the production of anti-KIR2DL1, KIR2DL2, and KIR2DL3 antibodies to reach commercial quantities. The anti-KIR2DL1, KIR2DL2, and KIR2DL3 antibodies may be produced on a large scale, stored if necessary, and supplied to hospitals, clinicians or other healthcare facilities.

Methods of production, storage, and distribution of anti-KIR2DL1, KIR2DL2, and KIR2DL3 antibodies may be produced by the methods disclosed herein. Following production, the anti-KIR2DL1, KIR2DL2, and KIR2DL3 antibodies may be harvested, purified, and optionally stored prior to a patient's treatment. For example, once a patient presents with an indication such as, for example, cancer, autoimmune disease, or inflammatory condition, anti-KIR2DL1, KIR2DL2, and KIR2DL3 antibodies may be ordered and provided in a timely manner. Accordingly, the present invention relates to methods of producing KIR2DL1, KIR2DL2, and KIR2DL3 to attain antibodies on a commercial scale, pharmaceutical compositions comprising antibodies and antigen binding fragments thereof which selectively bind to KIR2DL1, KIR2DL2, and KIR2DL3, as well as methods of providing (i.e., producing, optionally storing, and selling) the anti-KIR2DL1, KIR2DL2, and KIR2DL3 antibodies to hospitals and clinicians. The production of anti-KIR2DL1, KIR2DL2, and KIR2DL3 antibodies may be scaled up for commercial use.

The present invention also provides for methods of conducting a pharmaceutical business comprising establishing a distribution system for distributing the preparation for sale or may include establishing a sales group for marketing the pharmaceutical preparation.

Library of Nucleic Acids

A variegated library of KIR2DL1, KIR2DL2, and KIR2DL3 variants may be generated by combinatorial mutagenesis at the nucleic acid level and is encoded by a variegated gene library. A variegated library of KIR2DL1, KIR2DL2, and KIR2DL3 variants may be produced by, for example, enzymatically ligating a mixture of synthetic oligonucleotides into gene sequences such that a degenerate set of potential KIR2DL1, KIR2DL2, and KIR2DL3 sequences expressible as individual polypeptides, or alternatively, as a set of larger fusion proteins (e.g., for phage display) containing the set of KIR2DL1, KIR2DL2, and KIR2DL3 sequences therein. There are a variety of methods which can be used to produce libraries of potential KIR2DL1, KIR2DL2, and KIR2DL3 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential KIR2DL1, KIR2DL2, and KIR2DL3 sequences. Methods for synthesizing degenerate oligonucleotides are known in the art. See, e.g., Narang (1983) Tetrahedron 39:3; Itakura, et al. (1984) Annu. Rev. Biochem. 53:323; Itakura, et al. (1984) Science 198:1056; Ike, et al. (1983) Nucleic Acids Res. 11:477.

In addition, libraries of fragments of a KIR2DL1, KIR2DL2, and KIR2DL3 polypeptide coding sequence may be used to generate a variegated population of KIR2DL1, KIR2DL2, and KIR2DL3 fragments for screening and subsequent selection of variants of a KIR2DL1, KIR2DL2, and KIR2DL3 polypeptide. A library of coding sequence fragments can be generated by treating a double stranded PCR fragment of a KIR2DL1, KIR2DL2, and KIR2DL3 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the KIR2DL1, KIR2DL2, and KIR2DL3 polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of KIR2DL1, KIR2DL2, and KIR2DL3 polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify KIR2DL1, KIR2DL2, and KIR2DL3 variants. Arkin and Youvan (1992) Proc Natl. Acad. Sci. USA 89:7811-7815; Delagrave et al. (1993) Protein Eng. 6(3):327-331.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

EXAMPLES

The invention now being generally described, it will be more readily understood by reference to the following examples, which are included merely for purposes of illustration of certain aspects and embodiments of the present invention, and are not intended to limit the invention.

Examples

Example 1

Pharmacokinetics in Patients

Plasma concentrations of anti-KIR (1-7F9) are determined by ELISA as briefly described below.

The plates are coated with KIR2DL3 coating solution (100 µl/well) and incubated overnight at about +4° C. The plates are then washed 3 times with wash buffer using an automated plate washer (400 µl/well). Blocking buffer is added (200 µl per well) and plates are incubated for approximately 2 hours on a plate shaker at room temperature. After this, the plates are once again washed 3 times with wash buffer (400 µl/well).

Standards, quality controls and samples are added to the plates (100 µl/well) before incubation for approximately 2 hours on the plate shaker at room temperature. Before adding mouse anti-human IgG4:peroxidase working solution (100 µl/well) the plates are washed another 3 times (as above). The plates are then again incubated for approximately 2 hours on a plate shaker at room temperature, after which they are washed once again.

TMB is added to the plates (100 µl/well), which are then incubated for approximately 30 minutes on a plate shaker at room temperature. The enzymatic reaction is terminated with addition of stop solution (50 µl/well). Absorbances are read at 450 nm (reference filter 650 nm). The lower limit of quantification for this study is 5.000 ng/mL and the upper limit of quantification for this study is 110.0 ng/mL.

Example 2

KIR Occupancy Assay

Receptor occupancy is evaluated on human whole blood samples by four-color fluorescence analysis. Briefly, free and bound KIR2D receptor levels are assessed on T and NK lymphocytes in EDTA anti-coagulated peripheral blood. Free site assay will assess unbound KIR2D by staining with PE-conjugated 1-7F9, which binds to the KIR2D molecule. Bound site assay will assess KIR2D receptors occupied by 1-7F9 by staining with a PE-conjugated mouse anti-human IgG4 monoclonal antibody that recognizes the 1-7F9 bound to the KIR2D receptors. The Free and Bound Assays will allow for assessment of both percentage positive staining as well as the fluorescence intensity [MESF] for 1-7F9-PE or anti-hIgG4-PE. The following combinations of conjugated antibodies are used in the following two assays:

Free Site Assay: CD3/1-7F9/CD45/CD56
Bound Assay: CD3/hIgG4/CD45/CD56.

Samples are analyzed on a Becton Dickinson FACScalibur using the Becton Dickinson Cellquest software. T cells are defined as CD45+CD3+ lymphocytes and NK cells are defined as CD45+CD3−CD56+ cells.

Example 3

Clinical Safety and Auto-Reactivity

A single dose escalation trial was conducted in elderly acute myeloid leukemia (AML) patients (>60 years), who are in first complete remission following induction and consolidation chemotherapy, and not eligible for bone-marrow transplantation. A standard 3+3 design is applied, and a total of 7 dose levels were explored: Doses range from 0.0003 mg/kg to 3 mg/kg. Following dosing, the patients were monitored for safety, PK and KIR occupancy until KIR occupancy was no longer detectable.

An extension trial was also conducted. AML patients who had completed the dose-escalation trial and who were still in complete remission could participate in the extension trial, in which the patients were dosed up to 6 times on a monthly basis. The patients are dosed with the same dose as they received in the previous trial.

Patients, Materials and Methods

In both trials, elderly AML patients (>60 years of age) in their first complete remission (CR) and not eligible for transplantation were eligible for the studies. AML was according to WHO Criteria. (Brunning R D, Matutes E, Harris N L et al.: Acute myeloid leukaemia: Introduction. In Jaffe E S, Harris N L, Stein H, et al. Eds.: Pathology and Genetics of Tumors of Haematopoietic and Lymphoid Tissues. Lyon, France: IARC Press, 2001. World Health Organization Classification of Tumors, 3, pp 77-80). Remission was morphological complete remission (CR) defined according to NCI criteria (Cheson et al. *JCO,* 21(24): 4642-4649 (2003)), or CRi with incomplete platelet count recovery only after 1 or 2 cycles of induction chemotherapy, and at least 1, and maximally 6 cycles of consolidation chemotherapy.

At screening in the dose-escalation trial, the time since last dose of chemotherapy was at least 30 days and no more than 120 days. Other eligibility criteria included (but were not limited to) expression of KIR2DL1 and 2/3 on NK-cells, ECOG (Oken, et al. Toxicity And Response Criteria Of The Eastern Cooperative Oncology Group. Am J Clin Oncol 5:649-655, 1982) status 0-2 and recovery from all toxicities from previous treatment.

For the extension trial, completion of the dose-escalation trial with an acceptable safety profile was an additional eligibility criterion.

Additional criteria included absolute neutrophil count>1× $10^9$/L, Platelets>80× $10^9$/L, no symptoms of disease, recovery from acute toxicities of all previous anti-leukemic therapies, KIR-expression on patient NK-cells (ability to bind Anti-KIR (1-7F9)), no major relevant organ dysfunction as judged by the Investigator, and clinical laboratory values as follows: (a) A Serum creatinine≤2 mg/dL, (b) Total bilirubin≤1.5× the upper limit of normal and (c) AST≤3× the upper limit of normal.

Study Design

The dose-escalation trial was a multi-centre, open-label, single dose-escalation safety and tolerability trial. Seven dose levels were explored; 0.0003 mg/kg, 0.003 mg/kg, 0.015 mg/kg, 0.075 mg/kg, 0.3 mg/kg, 1 mg/kg and 3 mg/kg. A general (3+3) design was chosen for this trial. Each patient was allocated to one dose, and monitored for safety, pharmacokinetics and pharmacodynamics until there is no detectable KIR-occupancy on the patients NK-cells. Safety, PK and KIR-occupancy are analyzed on an on-going basis, and the data obtained during the first 4 weeks post dosing from each dose group generally forms the foundation of the dose-escalation decision.

The extension trial was designed as a repeated dosing, multi-centre, open-label, safety and tolerability. The dose given to the individual patient was the same as the patient received in the single dose trial. The patient can receive 6 administrations at 4 week interval i.e. 6 dosing cycles with a maximal to duration of 6 months. Each dosing cycle consists of a dosing visit and a safety monitoring visit. Following the last dosing, the patient is monitored for safety until there is no detectable KIR-occupancy on the patients NK-cells. The duration of this safety follow-up period likely depends on the dose received, and is expected to be maximally 24 weeks post the last dosing.

Safety (i.e., any observed toxicity) to Anti-KIR (1-7F9) administration is assessed using the US National Cancer Institute Common Terminology Criteria for Adverse Events (CTCAE) version 3.0. Pharmacokinetic endpoints, KIR-occupancy, markers of NK- and T-cell activation, WT-1 tumour marker, progression-free survival and overall survival were also evaluated.

Results

Receptor saturation was evaluated in the dose escalation trial among the patients receiving each dose level of 0.0003 mg/kg, 0.003 mg/kg, 0.015 mg/kg, 0.075 mg/kg, 0.3 mg/kg, 1 mg/kg and 3 mg/kg. In summary, dose 0.0003 mg/kg resulted in partial KIR saturation (50% occupancy) for a period of about 2 hours; dose 0.003 mg/kg resulted in full KIR saturation (90% occupancy) for a period of less than 24 hours; dose 0.015 mg/kg resulted in full KIR saturation for a period of less than 7 days; dose 0.075 mg/kg resulted in full KIR saturation for a period of almost 7 days; dose 0.3 mg/kg resulted in full KIR saturation for a period of greater than 7 days and less than 14 days; dose 1 mg/kg resulted in full KIR saturation for a period of less than 3 weeks (between about 2 weeks and 3 weeks); dose 3 mg/kg resulted in full KIR saturation for a period of more than 4 weeks.

No adverse events related to auto-reactivity (such as skin rash and gastrointestinal symptoms), infusion (such as rash, pruritus, erythema, fatigue, headache, pyrexia) or cytokine release (such as pyrexia, fatigue, malaise, and headache) occurred to a degree that raised any safety concerns.

Example 4

In Vivo Efficacy in Elimination of conA Blasts in a Transgenic Mouse Model

Induction of NK-mediated in vivo killing of cw3-expressing conA blasts was evaluated in KIR2DL3 transgenic mice receiving anti-KIR2DL1, 2 and 3 antibody 1-7F9.

Materials and Methods

Antibodies: Fully human anti-KIR2DL1, 2 and 3 monoclonal antibody 1-7F9 was generated by immunization of mice bearing human genomic IgG loci (Medarex, Inc.) with BW5417 cells stably transfected with KIR2DL1, followed by 3 booster immunizations with the soluble, extracellular part of KIR2DL3 produced in *Escherichia coli* as described in WO 2006/003179. Antibodies were screened for binding to recombinant, soluble KIRs by enzyme-linked immunosorbent assay, and positive clones were tested for binding to YTS-KIR2DL1 cells by flow cytometry. Selected hybridomas were subcloned until stable lines were obtained.

Transgenic mice: Rag−/− mice and KIR2DL3 transgenic (tg) mice were crossed to obtain KIR2DL3tg, Rag−/− mice. HLA-Cw3 transgenic mice were crossed with KbDb−/− mice resulting in Cw3tg, KbDb−/−mice. The mice are described in Romagne et al., (2009) Blood 114: 2667-2677 as well as in Sola et al. (2009) P.N.A.S. U.S.A 106(31):12879-12884.

Fluorescence-based rejection assay: assays were carried our according to the methods described by K. Karr's laboratory (Oberg et al. Eur. J. Immunol (2004) 34: 1646; S. Johansson, et al. J. Exp. Med (2005) 201: 1145). Injection of CFSE-labelled target cells (target cell test and syngenic/control target cells, ratio 1:1) was followed by analysis of different organs after 1 or 2 days. Target cells were freshly isolated spleen cells, tumor cells or ConA blasts (48 h, ConA 2 µg/ml).

Results

The aim of the experiment was to test whether 1-7F9 induces NK killing of cw3-target ConA blasts in KIR2DL3 tg mice. Briefly, recipient mice and donor cells were as follows:
(1) Recipient mice: KIR2DL3tg B6, KIR2DL3 tg Rag−/− and C57/BL6 mice.
(2) Donor cells:
(a) naive spleen cells from KbDb KO mice, KbDb KO cw3 tg mice, C57/BL6 mice, and
(b) ConA blast from KbDb KO mice, KbDb KO cw3 tg mice, C57/BL6 mice.

Spleen cells from C57/BL6 and KbDb−/−cw3 tg mice were stimulated for 2 days with ConA (2 µg/$10^7$ cells/ml). Cells were labelled with 0.5 µM (B6) and 3 µM (KbDb−/−cw3) CFSE, mixed at a ratio of 1:1 and then injected in KIR2DL3tg B6 mice previously (or not) injected with 1-7F9 mAb (300 µg). Antibody 1-7F9 was thus administered about 6 hours prior cell injection) to induce cw3-target cell lysis. Anti-NK1.1 antibody PK136 (BD Biosciences), administered 24 h prior cell injection was used as a control to induce NK cell depletion.

Figure 1B:
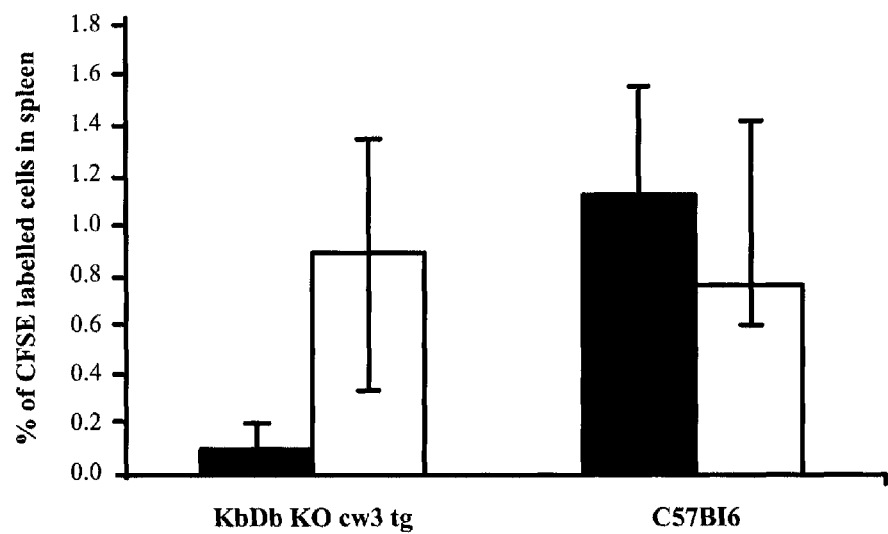
FIG. 1B depicts a decrease in percentage of CSFE-labelled spleen cells in KIR2DL3tg B6 mice when treated with antibody 1-7F9, compared to both untreated KIR2DL3tg B6 mice and treated and untreated C57Bl6 mice.
Figure 2:
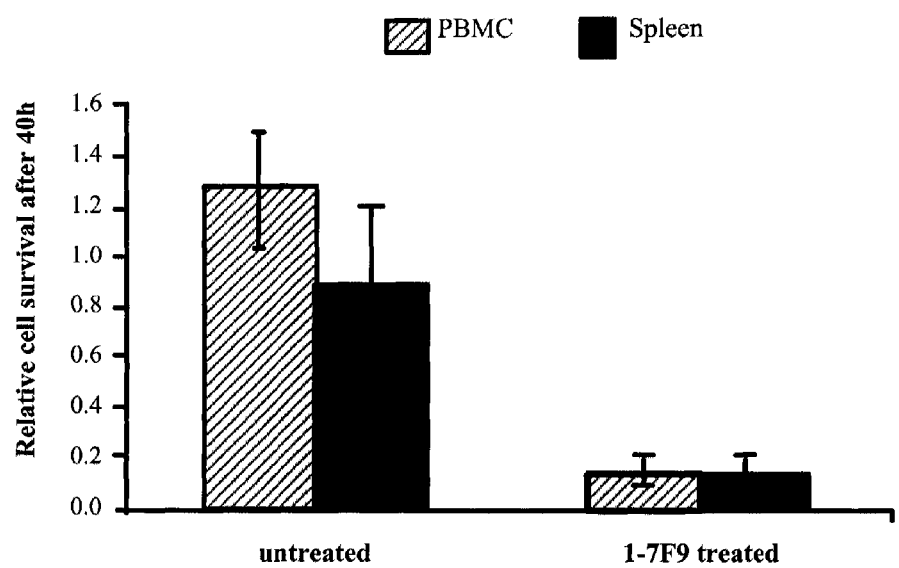
FIG. 2 depicts a decrease in survival of KbDb−/− cw3 ConA blasts in PBMC and spleen in KIR2DL3tg B6 mice when treated with antibody 1-7F9, compared to untreated KbDb KO cw3 tg mice.

Results are shown in FIGS. 1A, 1B and 2. FIGS. 1A and 1B examine percentage of CSFE-labelled cells at 40 hours after injection of cells. Similar results were obtained or CSFE-labelled cells at 20 hours after injection. FIG. 1A shows a dramatic decrease in percentage of CSFE-labelled cells in PBMC in KIR2DL3tg B6 mice when treated with antibody 1-7F9, compared to both untreated KIR2DL3tg B6 mice and treated and untreated C57B16 mice. FIG. 1B shows a dramatic decrease in percentage of CSFE-labelled spleen cells in spleen from KIR2DL3tg B6 mice when treated with antibody 1-7F9, compared to both untreated KIR2DL3tg B6 mice and treated and untreated C57B16 mice. FIG. 2 examines relative cell survival of CSFE-labelled cells at 40 hours after injection of cells. FIG. 2 shows a dramatic decrease in survival of KbDb−/− cw3 ConA blasts in PBMC and spleen in KIR2DL3tg B6 mice when treated with antibody 1-7F9, compared to untreated KbDb KO cw3 tg mice.

NK cells are generally known to have mechanisms to ensure self-tolerance. See Raulet and Vance (2006) Nature Immuno. Rev. 6: 520-531. In particular, all NK cells express an inhibitory KIR or the inhibitory CD94/NKG2A molecules. Blockade of KIR receptors, as observed in current Phase I clinical trials of anti-KIR antibody 1-7F9 in oncology, indicate that the antibody does not induce particular inflammation or autoimmunity other than that observed for monoclonal antibodies, generally. However, there have been no studies of the effect of KIR2DL1, 2 or 3 blockade on elimination of activated or proliferating T cells in vivo. The present results indicate that KIR2DL3-expressing NK cells are capable, in vivo, of reducing or eliminating activated T cells that would otherwise have been blocked by their HLA-cw3 ligand, so long as KIR2DL3 is blocked. Consequently, the KIR2DL1, 2 and/or population of cells have the potential to eliminate autologous activated pro-inflammatory cells when KIRs are blocked in vivo.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All publications, patents and patent applications are herein incorporated by reference in their entirety to the same extent as if each individual publication, patent or patent application was specifically and individually indicated to be incorporated by reference in its entirety.

Those skilled in the art will recognize, or be able to ascertain using no more than routine experimentation, many equivalents to the specific embodiments of the invention described herein. Such equivalents are intended to be encompassed by the following claims.

We claim:

1. A method for treating an autoimmune disorder mediated by T cells, comprising administering to an individual in need thereof an effective amount of an antibody or antigen-binding fragment thereof that potentiates the cytotoxic activity of NK cells by blocking or neutralizing NK cell inhibition mediated by a KIR2DL1, KIR2DL2, and/or KIR2DL3 polypeptide, thereby reducing the number of T cells involved in mediating the autoimmune disorder.

2. The method of claim 1, wherein the KIR2DL1, KIR2DL2, and/or KIR2DL3 polypeptide is/are expressed on NK cells.

3. The method of claim 1, wherein said T cells include one or more of pro-inflammatory, activated and/or proliferating T cells, CD4+ T cells, infiltrating T cells, and/or T cells which expresses express HLA-cw3 and/or HLA-cw4.

4. The method of claim 1, wherein said T cells exhibit one or more of the following properties: are in circulation; are comprised in a diseased or inflamed tissue; are infiltrating T cells; are T cells that have infiltrated into disease tissues; are comprised in synovial joint tissues or synovial fluid; and are comprised in the central nervous system, colon, or dermal tissue.

5. The method of claim 3, wherein said infiltrating T cells include one or more of the following: cells that have infiltrated into disease tissues; cells that have infiltrated into synovial joint tissues or synovial fluid; and cells that have infiltrated into the central nervous system, colon, or dermal tissue.

6. The method of claim 1, which further comprises evaluating the presence, stage and/or evolution of the autoimmune disorder in the treated individual by analyzing at least one of levels of autoantibodies, C-reactive protein (CRP), proteolytic enzyme, inflammatory mediator(s), and marker(s) of ongoing inflammation.

7. The method of claim 1, wherein the treated individual is experiencing an attack, crisis, exacerbation or flare of an autoimmune disorder.

8. The method of claim 7, wherein said attack, crisis, exacerbation, or flare of an autoimmune disorder is detected in the individual using a compound that detects a marker of inflammation or an autoimmune reaction.

9. The method of claim 1, wherein the autoimmune disorder is selected from acute sinusitis, chronic sinusitis, Addison's disease, autoimmune hepatitis, Behcet's disease, celiac disease, chronic active hepatitis, contact dermatitis, ulcerative colitis, Crohn's disease, dermatomyositis, eczema, Goodpasture's syndrome, Guillian-Barre syndrome, Hashimoto's encephalitis, Hashimoto's thyroiditis, juvenile diabetes, juvenile onset (Type I) diabetes mellitus, multiple sclerosis (MS), spino-optical MS, opsoclonus myoclonus syndrome (OMS), paraneoplastic cerebellar degeneration, pernicious anemia (anemia perniciosa), polymyositis, primary biliary cirrhosis, rheumatoid arthritis, sarcoidosis, scleroderma, lupus erythematosus, and temporal arteritis/giant cell arteritis.

10. The method of claim 1, wherein said antibody or antigen-binding fragment thereof is a human, chimeric, humanized, single-chain, or bifunctional antibody or an antigen-binding fragment thereof.

11. The method of claim 1, wherein the light chain of said antibody or antigen-binding fragment thereof comprises amino acids having the sequence set forth in SEQ ID NO:1, 3, or 5.

12. The method of claim 1, wherein the heavy chain of said antibody or antigen-binding fragment thereof comprises amino acids having the sequence set forth in SEQ ID NO:2, 4, or 6.

13. The method of claim 1, wherein the antibody or antigen-binding fragment thereof comprises (i) a light chain CDR1 having the amino acid sequence corresponding to residues 24-34 of SEQ ID NO: 1; a light chain CDR2 having the amino acid sequence corresponding to residues 50-56 of SEQ ID NO: 1; and a light chain CDR3 having the amino acid sequence corresponding to residues 89-97 of SEQ ID NO: 1; or (ii) a light chain CDR1 having the amino acid sequence corresponding to residues 24-34 of SEQ ID NO: 3; a light chain CDR2 having the amino acid sequence corresponding to residues 50-56 of SEQ ID NO: 3; and a light chain CDR3 having the amino acid sequence corresponding to residues 89-97 of SEQ ID NO: 3.

14. The method of claim 1, wherein the antibody or antigen-binding fragment thereof comprises (i) a heavy chain CDR1 having the amino acid sequence corresponding to residues 31-35 of SEQ ID NO: 2, a heavy chain CDR2 having the amino acid sequence corresponding to residues 50-65 of SEQ ID NO: 2, and a heavy chain CDR3 having the amino acid sequence corresponding to residues 99-112 of SEQ ID NO: 2, or (ii) a heavy chain CDR1 having the amino acid sequence corresponding to residues 31-35 of SEQ ID NO: 4, a heavy chain CDR2 having the amino acid sequence corresponding to residues 50-65 of SEQ ID NO: 4, and a heavy chain CDR3 having the amino acid sequence corresponding to residues 99-112 of SEQ ID NO: 4.

15. The method of claim 1, wherein the antibody or antigen-binding fragment thereof comprises a light chain variable region ($V_L$) and a heavy chain variable region ($V_H$) comprising:
   (a) amino acids having the sequences set forth in SEQ ID NO:1 and SEQ ID NO:2, respectively;
   (b) amino acids having the sequences set forth in SEQ ID NO:3 and SEQ ID NO:4, respectively; or a light chain and a heavy chain comprising:
   (c) amino acids having the sequences set forth in SEQ ID NO:5 and SEQ ID NO:6, respectively.

16. The method of claim 1, wherein said antibody or antigen-binding fragment thereof binds to an epitope within a region of KIR2DL1 and/or KIR2DL2/3 having the amino acid sequence set forth in SEQ ID NO:7, SEQ ID NO:8, SEQ ID NO:9, SEQ ID NO: 10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO: 24.

17. The method of claim 1, wherein said antibody binds to KIR2DL1and/or KIR2DL2/3 within a region defined by at least one of the amino acid residues selected from 105, 106, 107, 108, 109, 110, 111, 127, 129, 130, 131, 132, 133, 134, 135, 152, 153, 154, 155, 156, 157, 158, 159, 160, 161, 162, 163, 181, and 192.

18. The method of claim 1, wherein said antibody or antigen-binding fragment thereof binds to at least one of KIR2DL1 and/or KIR2DL2/3 and neutralizes KIR2DL1 and/or KIR2DL2/3-mediated inhibition of NK cell cytotoxicity.

19. The method of claim 1, wherein said antibody or antigen-binding fragment thereof results in at least about 20% increase in NK cell-mediated specific lysis of NK target cells.

20. The method of claim 1, wherein said antibody or antigen-binding fragment thereof competes with (i) an antibody comprising a light chain variable region having the amino acid sequence set forth in SEQ ID NO:1 and a heavy chain variable region having the amino acid sequence set forth in SEQ ID NO:2, or (ii) an antibody deposited as CNCM I-3224, for binding to the same antigenic determinant region of human KIR2DL 1, KIR2DL2 and/or KIR2DL3.

21. The method of claim 1, wherein said antibody or antigen-binding fragment thereof binds to at least two different inhibitory KIR receptors at the surface of NK cells.

22. The method of claim 1, wherein said antibody or fragment thereof binds to a common antigenic determinant region of human KIR2DL receptors.

23. The method of claim 1, wherein said antibody or antigen-binding fragment thereof cross-reacts with KIR2DL1 plus KIR2DL2/3, KIR3DL1 plus KIR3DL2, KIR2DL1 and KIR2DL2/3 plus KIR2DS4, and KIR2DL1 and KIR2DL2/3 but not KIR2D24.

24. The method of claim 1, wherein said antibody or antigen-binding fragment thereof is an antibody deposited as CNCM I-3224.

25. The method of claim 1, wherein the antibody or antigen-binding fragment thereof that inhibits a KIR2DL1, KIR2DL2 and/or KIR2DL3 polypeptide is administered as a monotherapy.

26. The method of claim 1, wherein the antibody or fragment thereof that inhibits a KIR2DL 1, KIR2DL2 and/or KIR2DL3 polypeptide is administered in combination with a second therapeutic agent.

27. The method of claim 26, wherein the second therapeutic agent is an agent that decreases inflammation, a DMARD, an anti-TNF-alpha antibody, a small molecule tyrosine kinase inhibitor, or methotrexate (MTX) or another therapeutic antibody.

28. The method of claim 1, wherein the anti-KIR2DL1, KIR2DL2 and/or KIR2DL3 antibody or antigen-binding fragment thereof is administered as a pharmaceutically acceptable composition comprising an effective amount of the anti-KIR2DL1, KIR2DL2 and/or KIR2DL3 antibody or antigen-binding fragment thereof.

29. The method of claim 1, wherein the anti-KIR2DL1, KIR2DL2 and/or KIR2DL3 antibody or antigen-binding fragment thereof is administered in an amount resulting in substantially complete saturation of the KIR2DL1, KIR2DL2 and/or KIR2DL3 polypeptide on NK cells for a period of at least about 1 week, 2 weeks, or 1 month.

30. The method of claim 1, wherein the anti-KIR2DL1, KIR2DL2 and/or KIR2DL3 antibody or antigen-binding fragment thereof is administered several times at a dosing frequency selected from once about every 2 weeks, once about every 1 month, once every 2 months, and once every period of more than 2 months.

31. The method of claim 1, wherein the antibody or antigen-binding fragment thereof is an IgG2 or IgG4 antibody.

32. The method of claim 1, wherein the antibody or antigen-binding fragment thereof comprises a heavy chain having the amino acid sequence set forth in SEQ ID NO:25 and a light chain comprising a light chain variable region having the amino acid sequence set forth in SEQ ID NO:1.

33. The method of claim 9, wherein the antibody or antigen-binding fragment thereof comprises a heavy chain having the amino acid sequence set forth in SEQ ID NO:25 and a light chain comprising a light chain variable region having the amino acid sequence set forth in SEQ ID NO:1.

34. The method of claim 1, wherein the antibody or antigen-binding fragment thereof comprises a heavy chain having the amino acid sequence set forth in SEQ ID NO:25 and a light chain having the amino acid sequence set forth in SEQ ID NO:5.

35. The method of claim 9, wherein the antibody or antigen-binding fragment thereof comprises a heavy chain having the amino acid sequence set forth in SEQ ID NO:25 and a light chain having the amino acid sequence set forth in SEQ ID NO:5.

* * * * *

SEQUENCE LISTING

```
<160> NUMBER OF SEQ ID NOS: 25

<210> SEQ ID NO 1
<211> LENGTH: 109
<212> TYPE: PRT
<213> ORGANISM: Homo sapiens

<400> SEQUENCE: 1

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr
                100                 105

<210> SEQ ID NO 2
<211> LENGTH: 123
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
                20                  25                  30

Ala Ile Ser Trp Val Arg Gln Ala Pro Gly Gln Gly Leu Glu Trp Met
            35                  40                  45

Gly Gly Phe Ile Pro Ile Phe Gly Ala Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
        115                 120
```

```
<210> SEQ ID NO 3
<211> LENGTH: 109
<212> TYPE: PRT
<213> ORGANISM: Homo sapiens
<220> FEATURE:
<221> NAME/KEY: Xaa
<222> LOCATION: (3)..(3)
<223> OTHER INFORMATION: Xaa can be Gln or Arg
<220> FEATURE:
<221> NAME/KEY: Xaa
<222> LOCATION: (4)..(4)
<223> OTHER INFORMATION: Xaa can be Leu or Met
<220> FEATURE:
<221> NAME/KEY: Xaa
<222> LOCATION: (9)..(9)
<223> OTHER INFORMATION: Xaa can be Ser or Phe
<220> FEATURE:
<221> NAME/KEY: Xaa
<222> LOCATION: (23)..(23)
<223> OTHER INFORMATION: Xaa can be any naturally occurring amino acid
<220> FEATURE:
<221> NAME/KEY: Xaa
<222> LOCATION: (24)..(24)
<223> OTHER INFORMATION: Xaa can be Arg or Trp
<220> FEATURE:
<221> NAME/KEY: Xaa
<222> LOCATION: (32)..(32)
<223> OTHER INFORMATION: Xaa can be Ala or Tyr
<220> FEATURE:
<221> NAME/KEY: Xaa
<222> LOCATION: (41)..(41)
<223> OTHER INFORMATION: Xaa can be Gly or Ala
<220> FEATURE:
<221> NAME/KEY: Xaa
<222> LOCATION: (47)..(47)
<223> OTHER INFORMATION: Xaa can be Leu or Phe
<220> FEATURE:
<221> NAME/KEY: Xaa
<222> LOCATION: (50)..(50)
<223> OTHER INFORMATION: Xaa can be Asp or Tyr
<220> FEATURE:
<221> NAME/KEY: Xaa
<222> LOCATION: (55)..(55)
<223> OTHER INFORMATION: Xaa can be Glu or Gln
<220> FEATURE:
<221> NAME/KEY: Xaa
<222> LOCATION: (71)..(71)
<223> OTHER INFORMATION: Xaa can be Phe or Tyr
<220> FEATURE:
<221> NAME/KEY: Xaa
<222> LOCATION: (74)..(74)
<223> OTHER INFORMATION: Xaa can be Ala or Thr

<400> SEQUENCE: 3

Ala Ile Xaa Xaa Thr Gln Ser Pro Xaa Ser Leu Ser Ala Ser Val Gly
1               5                   10                  15

Asp Arg Val Thr Ile Thr Xaa Xaa Ala Ser Gln Gly Ile Ser Ser Xaa
            20                  25                  30

Leu Ala Trp Tyr Gln Gln Lys Pro Xaa Lys Ala Pro Lys Leu Xaa Ile
        35                  40                  45

Tyr Xaa Ala Ser Ser Leu Xaa Ser Gly Val Pro Ser Arg Phe Ser Gly
    50                  55                  60

Ser Gly Ser Gly Thr Asp Xaa Thr Leu Xaa Ile Ser Ser Leu Gln Pro
65                  70                  75                  80
```

```
Glu Asp Phe Ala Thr Tyr Tyr Cys Gln Gln Tyr Tyr Ser Thr Pro Leu
                85                  90                  95

Thr Phe Gly Gly Gly Thr Lys Val Glu Ile Lys Arg Thr
            100                 105

<210> SEQ ID NO 4
<211> LENGTH: 124
<212> TYPE: PRT
<213> ORGANISM: HoJo virus

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Asn Ser Tyr
            20                  25                  30

Ser Ile Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Ser Ala Asp Glu Ser Thr Arg Thr Val Tyr
65                  70                  75                  80

Met Glu Leu Asn Ser Leu Arg Ser Glu Asp Thr Ala Val Tyr Tyr Cys
                85                  90                  95

Ala Arg Gly Tyr Tyr Asp Ile Phe Lys Asp Tyr Tyr Gly Met Asp
            100                 105                 110

Val Trp Gly Gln Gly Thr Thr Val Thr Val Ser Ser
        115                 120

<210> SEQ ID NO 5
<211> LENGTH: 214
<212> TYPE: PRT
<213> ORGANISM: Homo sapiens

<400> SEQUENCE: 5

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 450
<212> TYPE: PRT
<213> ORGANISM: Homo sapiens

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 7
<211> LENGTH: 224
<212> TYPE: PRT
<213> ORGANISM: Homo sapiens
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid

<400> SEQUENCE: 7

His Glu Gly Val His Arg Lys Pro Ser Leu Leu Ala His Pro Gly Xaa
1               5                   10                  15

Leu Val Lys Ser Glu Glu Thr Val Ile Leu Gln Cys Trp Ser Asp Val
            20                  25                  30

Met Phe Glu His Phe Leu Leu His Arg Glu Gly Met Phe Asn Asp Thr
        35                  40                  45

Leu Arg Leu Ile Gly Glu His His Asp Gly Val Ser Lys Ala Asn Phe
    50                  55                  60

Ser Ile Ser Arg Met Thr Gln Asp Leu Ala Gly Thr Tyr Arg Cys Tyr
65                  70                  75                  80

Gly Ser Val Thr His Ser Pro Tyr Gln Val Ser Ala Pro Ser Asp Pro
                85                  90                  95

Leu Asp Ile Val Ile Ile Gly Leu Tyr Glu Lys Pro Ser Leu Ser Ala
            100                 105                 110

Gln Xaa Gly Pro Thr Val Leu Ala Gly Glu Asn Val Thr Leu Ser Cys
        115                 120                 125

Ser Ser Arg Ser Ser Tyr Asp Met Tyr His Leu Ser Arg Glu Gly Glu
    130                 135                 140

Ala His Glu Arg Arg Leu Pro Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe His Asp Ser Pro Tyr Glu Trp Ser Lys Ser Ser
            180                 185                 190
```

```
Asp Pro Leu Leu Val Ser Val Thr Gly Asn Pro Ser Asn Ser Trp Pro
            195                 200                 205

Ser Pro Thr Glu Pro Ser Ser Lys Thr Gly Asn Pro Arg His Leu His
    210                 215                 220
```

<210> SEQ ID NO 8
<211> LENGTH: 224
<212> TYPE: PRT
<213> ORGANISM: Homo sapiens

<400> SEQUENCE: 8

```
His Glu Gly Val His Arg Lys Pro Ser Leu Leu Ala His Pro Gly Arg
1               5                   10                  15

Leu Val Lys Ser Glu Glu Thr Val Ile Leu Gln Cys Trp Ser Asp Val
            20                  25                  30

Arg Phe Glu His Phe Leu Leu His Arg Glu Gly Lys Phe Lys Asp Thr
        35                  40                  45

Leu His Leu Ile Gly Glu His His Asp Gly Val Ser Lys Ala Asn Phe
    50                  55                  60

Ser Ile Gly Pro Met Met Gln Asp Leu Ala Gly Thr Tyr Arg Cys Tyr
65                  70                  75                  80

Gly Ser Val Thr His Ser Pro Tyr Gln Leu Ser Ala Pro Ser Asp Pro
                85                  90                  95

Leu Asp Ile Val Ile Thr Gly Leu Tyr Glu Lys Pro Ser Leu Ser Ala
            100                 105                 110

Gln Pro Gly Pro Thr Val Leu Ala Gly Glu Ser Val Thr Leu Ser Cys
        115                 120                 125

Ser Ser Arg Ser Ser Tyr Asp Met Tyr His Leu Ser Arg Glu Gly Glu
    130                 135                 140

Ala His Glu Cys Arg Phe Ser Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe Arg Asp Ser Pro Tyr Glu Trp Ser Asn Ser Ser
            180                 185                 190

Asp Pro Leu Leu Val Ser Val Ile Gly Asn Pro Ser Asn Ser Trp Pro
        195                 200                 205

Ser Pro Thr Glu Pro Ser Ser Lys Thr Gly Asn Pro Arg His Leu His
    210                 215                 220
```

<210> SEQ ID NO 9
<211> LENGTH: 224
<212> TYPE: PRT
<213> ORGANISM: Homo sapiens

<400> SEQUENCE: 9

```
His Glu Gly Val His Arg Lys Pro Ser Leu Leu Ala His Pro Gly Pro
1               5                   10                  15

Leu Val Lys Ser Glu Glu Thr Val Ile Leu Gln Cys Trp Ser Asp Val
            20                  25                  30

Arg Phe Gln His Phe Leu Leu His Arg Glu Gly Lys Phe Lys Asp Thr
        35                  40                  45

Leu His Leu Ile Gly Glu His His Asp Gly Val Ser Lys Ala Asn Phe
    50                  55                  60

Ser Ile Gly Pro Met Met Gln Asp Leu Ala Gly Thr Tyr Arg Cys Tyr
65                  70                  75                  80
```

```
Gly Ser Val Thr His Ser Pro Tyr Gln Leu Ser Ala Pro Ser Asp Pro
                85                  90                  95

Leu Asp Ile Val Ile Thr Gly Leu Tyr Glu Lys Pro Ser Leu Ser Ala
            100                 105                 110

Gln Pro Gly Pro Thr Val Leu Ala Gly Glu Ser Val Thr Leu Ser Cys
        115                 120                 125

Ser Ser Arg Ser Ser Tyr Asp Met Tyr His Leu Ser Arg Glu Gly Glu
    130                 135                 140

Ala His Glu Arg Arg Phe Ser Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe Arg Asp Ser Pro Tyr Glu Trp Ser Asn Ser Ser
            180                 185                 190

Asp Pro Leu Leu Val Ser Val Thr Gly Asn Pro Ser Asn Ser Trp Pro
        195                 200                 205

Ser Pro Thr Glu Pro Ser Ser Glu Thr Gly Asn Pro Arg His Leu His
    210                 215                 220

<210> SEQ ID NO 10
<211> LENGTH: 100
<212> TYPE: PRT
<213> ORGANISM: Homo sapiens

<400> SEQUENCE: 10

Gln Glu Gly Val His Arg Lys Pro Ser Phe Leu Ala Leu Pro Gly His
1               5                   10                  15

Leu Val Lys Ser Glu Glu Thr Val Ile Leu Gln Cys Trp Ser Asp Val
            20                  25                  30

Met Phe Glu His Phe Leu Leu His Arg Glu Gly Lys Phe Asn Asn Thr
        35                  40                  45

Leu His Leu Ile Gly Glu His His Asp Gly Val Ser Lys Ala Asn Phe
    50                  55                  60

Ser Ile Gly Pro Met Met Pro Val Leu Ala Gly Thr Tyr Arg Cys Tyr
65                  70                  75                  80

Gly Ser Val Pro His Ser Pro Tyr Gln Leu Ser Ala Pro Ser Asp Pro
                85                  90                  95

Leu Asp Met Val
            100

<210> SEQ ID NO 11
<211> LENGTH: 348
<212> TYPE: PRT
<213> ORGANISM: Homo sapiens

<400> SEQUENCE: 11

Met Ser Leu Leu Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Pro Leu Val Lys Ser Glu Glu Thr Val Ile Leu Gln
        35                  40                  45

Cys Trp Ser Asp Val Met Phe Glu His Phe Leu Leu His Arg Glu Gly
    50                  55                  60

Met Phe Asn Asp Thr Leu Arg Leu Ile Gly Glu His His Asp Gly Val
65                  70                  75                  80
```

```
Ser Lys Ala Asn Phe Ser Ile Ser Arg Met Thr Gln Asp Leu Ala Gly
                     85                  90                  95

Thr Tyr Arg Cys Tyr Gly Ser Val Thr His Ser Pro Tyr Gln Val Ser
            100                 105                 110

Ala Pro Ser Asp Pro Leu Asp Ile Val Ile Gly Leu Tyr Glu Lys
        115                 120                 125

Pro Ser Leu Ser Ala Gln Pro Gly Pro Thr Val Leu Ala Gly Glu Asn
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Leu Pro Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe His Asp Ser Pro Tyr Glu
        195                 200                 205

Trp Ser Lys Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Ile Leu Ile Gly Thr Ser Val Val Ile Ile Leu
                245                 250                 255

Phe Ile Leu Leu Phe Phe Leu Leu His Arg Trp Cys Ser Asn Lys Lys
            260                 265                 270

Asn Ala Ala Val Met Asp Gln Glu Ser Ala Gly Asn Arg Thr Ala Asn
        275                 280                 285

Ser Glu Asp Ser Asp Glu Gln Asp Pro Gln Glu Val Thr Tyr Thr Gln
    290                 295                 300

Leu Asn His Cys Val Phe Thr Gln Arg Lys Ile Thr Arg Pro Ser Gln
305                 310                 315                 320

Arg Pro Lys Thr Pro Pro Thr Asp Ile Ile Val Tyr Thr Glu Leu Pro
                325                 330                 335

Asn Ala Glu Ser Arg Ser Lys Val Val Ser Cys Pro
        340                 345

<210> SEQ ID NO 12
<211> LENGTH: 348
<212> TYPE: PRT
<213> ORGANISM: Homo sapiens

<400> SEQUENCE: 12

Met Ser Leu Met Val Val Ser Met Ala Cys Val Gly Phe Phe Leu Leu
1               5                   10                  15

Gln Gly Ala Trp Pro His Glu Gly Val His Arg Lys Pro Ser Leu Leu
                20                  25                  30

Ala His Pro Gly Arg Leu Val Lys Ser Glu Glu Thr Val Ile Leu Gln
            35                  40                  45

Cys Trp Ser Asp Val Arg Phe Glu His Phe Leu Leu His Arg Glu Gly
        50                  55                  60

Lys Phe Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Tyr Gly Ser Val Thr His Ser Pro Tyr Gln Leu Ser
            100                 105                 110
```

```
Ala Pro Ser Asp Pro Leu Asp Ile Val Ile Thr Gly Leu Tyr Glu Lys
            115                 120                 125

Pro Ser Leu Ser Ala Gln Pro Gly Pro Thr Val Leu Ala Gly Glu Ser
        130                 135                 140

Val Thr Leu Ser Cys Ser Ser Arg Ser Ser Tyr Asp Met Tyr His Leu
145                 150                 155                 160

Ser Arg Glu Gly Glu Ala His Glu Cys Arg Phe Ser Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Asn Ser Ser Asp Pro Leu Leu Val Ser Val Ile Gly Asn Pro
210                 215                 220

Ser Asn Ser Trp Pro Ser Pro Thr Glu Pro Ser Ser Lys Thr Gly Asn
225                 230                 235                 240

Pro Arg His Leu His Ile Leu Ile Gly Thr Ser Val Val Ile Ile Leu
                245                 250                 255

Phe Ile Leu Leu Phe Phe Leu Leu His Arg Trp Cys Ser Asn Lys Lys
            260                 265                 270

Asn Ala Ala Val Met Asp Gln Glu Ser Ala Gly Asn Arg Thr Ala Asn
        275                 280                 285

Arg Gln Asp Ser Asp Glu Gln Asp Pro Gln Glu Val Thr Tyr Thr Gln
290                 295                 300

Leu Asn His Cys Val Phe Thr Gln Arg Lys Ile Thr Arg Pro Ser Gln
305                 310                 315                 320

Arg Pro Lys Thr Pro Pro Thr Asp Ile Ile Val Tyr Ala Glu Leu Pro
                325                 330                 335

Asn Ala Glu Ser Arg Ser Lys Val Val Ser Cys Pro
            340                 345

<210> SEQ ID NO 13
<211> LENGTH: 341
<212> TYPE: PRT
<213> ORGANISM: Homo sapiens

<400> SEQUENCE: 13

Met Ser Leu Met Val Val Ser Met Val Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Pro Leu Val Lys Ser Glu Glu Thr Val Ile Leu Gln
        35                  40                  45

Cys Trp Ser Asp Val Arg Phe Gln His Phe Leu Leu His Arg Glu Gly
50                  55                  60

Lys Phe Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
130                 135                 140
```

```
Val Thr Leu Ser Cys Ser Ser Arg Ser Ser Tyr Asp Met Tyr His Leu
145                 150                 155                 160

Ser Arg Glu Gly Glu Ala His Glu Arg Arg Phe Ser Ala Gly Pro Lys
            165                 170                 175

Val Asn Gly Thr Phe Gln Ala Asp Phe Pro Leu Gly Pro Ala Thr His
        180                 185                 190

Gly Gly Thr Tyr Arg Cys Phe Gly Ser Phe Arg Asp Ser Pro Tyr Glu
            195                 200                 205

Trp Ser Asn Ser Ser Asp Pro Leu Leu Val Ser Val Thr Gly Asn Pro
    210                 215                 220

Ser Asn Ser Trp Pro Ser Pro Thr Glu Pro Ser Ser Glu Thr Gly Asn
225                 230                 235                 240

Pro Arg His Leu His Val Leu Ile Gly Thr Ser Val Val Ile Ile Leu
            245                 250                 255

Phe Ile Leu Leu Leu Phe Phe Leu Leu His Arg Trp Cys Cys Asn Lys
        260                 265                 270

Lys Asn Ala Val Val Met Asp Gln Glu Pro Ala Gly Asn Arg Thr Val
            275                 280                 285

Asn Arg Glu Asp Ser Asp Glu Gln Asp Pro Gln Glu Val Thr Tyr Ala
        290                 295                 300

Gln Leu Asn His Cys Val Phe Thr Gln Arg Lys Ile Thr Arg Pro Ser
305                 310                 315                 320

Gln Arg Pro Lys Thr Pro Pro Thr Asp Ile Ile Val Tyr Thr Glu Leu
            325                 330                 335

Pro Asn Ala Glu Pro
            340

<210> SEQ ID NO 14
<211> LENGTH: 377
<212> TYPE: PRT
<213> ORGANISM: Homo sapiens

<400> SEQUENCE: 14

Met Ser Met Ser Pro Thr Val Ile Ile Leu Ala Cys Leu Gly Phe Phe
1               5                   10                  15

Leu Asp Gln Ser Val Trp Ala His Val Gly Gly Gln Asp Lys Pro Phe
            20                  25                  30

Cys Ser Ala Trp Pro Ser Ala Val Val Pro Gln Gly Gly His Val Thr
        35                  40                  45

Leu Arg Cys His Tyr Arg Arg Gly Phe Asn Ile Phe Thr Leu Tyr Lys
    50                  55                  60

Lys Asp Gly Val Pro Val Pro Glu Leu Tyr Asn Arg Ile Phe Trp Asn
65                  70                  75                  80

Ser Phe Leu Ile Ser Pro Val Thr Pro Ala His Ala Gly Thr Tyr Arg
            85                  90                  95

Cys Arg Gly Phe His Pro His Ser Pro Thr Glu Trp Ser Ala Pro Ser
            100                 105                 110

Asn Pro Leu Val Ile Met Val Thr Gly Leu Tyr Glu Lys Pro Ser Leu
            115                 120                 125

Thr Ala Arg Pro Gly Pro Thr Val Arg Ala Gly Glu Asn Val Thr Leu
        130                 135                 140

Ser Cys Ser Ser Gln Ser Ser Phe Asp Ile Tyr His Leu Ser Arg Glu
145                 150                 155                 160

Gly Glu Ala His Glu Leu Arg Leu Pro Ala Val Pro Ser Ile Asn Gly
            165                 170                 175
```

Thr Phe Gln Ala Asp Phe Pro Leu Gly Pro Ala Thr His Gly Glu Thr
            180                 185                 190

Tyr Arg Cys Phe Gly Ser Phe His Gly Ser Pro Tyr Glu Trp Ser Asp
        195                 200                 205

Pro Ser Asp Pro Leu Pro Val Ser Val Thr Gly Asn Pro Ser Ser Ser
    210                 215                 220

Trp Pro Ser Pro Thr Glu Pro Ser Phe Lys Thr Gly Ile Ala Arg His
225                 230                 235                 240

Leu His Ala Val Ile Arg Tyr Ser Val Ala Ile Ile Leu Phe Thr Ile
                245                 250                 255

Leu Pro Phe Phe Leu Leu His Arg Trp Cys Ser Lys Lys Lys Asn Ala
            260                 265                 270

Ala Val Met Asn Gln Glu Pro Ala Gly His Arg Thr Val Asn Arg Glu
        275                 280                 285

Asp Ser Asp Glu Gln Asp Pro Gln Glu Val Thr Tyr Ala Gln Leu Asp
    290                 295                 300

His Cys Ile Phe Thr Gln Arg Lys Ile Thr Gly Pro Ser Gln Arg Ser
305                 310                 315                 320

Lys Arg Pro Ser Thr Asp Thr Ser Val Cys Ile Glu Leu Pro Asn Ala
                325                 330                 335

Glu Pro Arg Ala Leu Ser Pro Ala His Glu His His Ser Gln Ala Leu
            340                 345                 350

Met Gly Ser Ser Arg Glu Thr Thr Ala Leu Ser Gln Thr Gln Leu Ala
        355                 360                 365

Ser Ser Asn Val Pro Ala Ala Gly Ile
    370                 375

<210> SEQ ID NO 15
<211> LENGTH: 375
<212> TYPE: PRT
<213> ORGANISM: Homo sapiens

<400> SEQUENCE: 15

Met Ser Leu Met Val Ile Ser Met Ala Cys Val Gly Phe Phe Leu Leu
1               5                   10                  15

Gln Gly Ala Trp Thr His Glu Gly Gly Gln Asp Lys Pro Leu Leu Ser
            20                  25                  30

Ala Trp Pro Ser Ala Val Val Pro Arg Gly Gly His Val Thr Leu Leu
        35                  40                  45

Cys Arg Ser Arg Leu Gly Phe Thr Ile Phe Ser Leu Tyr Lys Glu Asp
    50                  55                  60

Gly Val Pro Val Pro Glu Leu Tyr Asn Lys Ile Phe Trp Lys Ser Ile
65                  70                  75                  80

Leu Met Gly Pro Val Thr Pro Ala His Ala Gly Thr Tyr Arg Cys Arg
                85                  90                  95

Gly Ser His Pro Arg Ser Pro Ile Glu Trp Ser Ala Pro Ser Asn Pro
            100                 105                 110

Leu Val Ile Val Val Thr Gly Leu Phe Gly Lys Pro Ser Leu Ser Ala
        115                 120                 125

Gln Pro Gly Pro Thr Val Arg Thr Gly Glu Asn Val Thr Leu Ser Cys
    130                 135                 140

Ser Ser Arg Ser Ser Phe Asp Met Tyr His Leu Ser Arg Glu Gly Arg
145                 150                 155                 160

Ala His Glu Pro Arg Leu Pro Ala Val Pro Ser Val Asn Gly Thr Phe
                165                 170                 175

```
Gln Ala Asp Phe Pro Leu Gly Pro Ala Thr His Gly Thr Tyr Thr
            180                 185                 190

Cys Phe Gly Ser Leu His Asp Ser Pro Tyr Glu Trp Ser Asp Pro Ser
        195                 200                 205

Asp Pro Leu Leu Val Ser Val Thr Gly Asn Ser Ser Ser Ser Ser Ser
    210                 215                 220

Ser Pro Thr Glu Pro Ser Ser Lys Thr Gly Ile Arg Arg His Leu His
225                 230                 235                 240

Ile Leu Ile Gly Thr Ser Val Ala Ile Ile Leu Phe Ile Ile Leu Phe
                245                 250                 255

Phe Phe Leu Leu His Cys Cys Cys Ser Asn Lys Lys Asn Ala Ala Val
            260                 265                 270

Met Asp Gln Glu Pro Ala Gly Asp Arg Thr Val Asn Arg Glu Asp Ser
        275                 280                 285

Asp Asp Gln Asp Pro Gln Glu Val Thr Tyr Ala Gln Leu Asp His Cys
    290                 295                 300

Val Phe Thr Gln Thr Lys Ile Thr Ser Pro Ser Gln Arg Pro Lys Thr
305                 310                 315                 320

Pro Pro Thr Asp Thr Thr Met Tyr Met Glu Leu Pro Asn Ala Lys Pro
                325                 330                 335

Arg Ser Leu Ser Pro Ala His Lys His His Ser Gln Ala Leu Arg Gly
            340                 345                 350

Ser Ser Arg Glu Thr Thr Ala Leu Ser Gln Asn Arg Val Ala Ser Ser
        355                 360                 365

His Val Pro Ala Ala Gly Ile
    370                 375

<210> SEQ ID NO 16
<211> LENGTH: 304
<212> TYPE: PRT
<213> ORGANISM: Homo sapiens

<400> SEQUENCE: 16

Met Ser Leu Thr Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Arg Leu Val Lys Ser Glu Glu Thr Val Ile Leu Gln
        35                  40                  45

Cys Trp Ser Asp Val Met Phe Glu His Phe Leu Leu His Arg Glu Gly
    50                  55                  60

Met Phe Asn Asp Thr Leu Arg Leu Ile Gly Glu His His Asp Gly Val
65                  70                  75                  80

Ser Lys Ala Asn Phe Ser Ile Ser Arg Met Arg Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Ile Gly Leu Tyr Glu Lys
        115                 120                 125

Pro Ser Leu Ser Ala Gln Pro Gly Pro Thr Val Leu Ala Gly Glu Asn
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Leu Pro Ala Gly Thr Lys
                165                 170                 175
```

Val Asn Gly Thr Phe Gln Ala Asn Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Lys Ser Ser Asp Pro Leu Leu Val Ser Val Thr Gly Asn Pro
    210                 215                 220

Ser Asn Ser Trp Pro Ser Pro Thr Glu Pro Ser Ser Glu Thr Gly Asn
225                 230                 235                 240

Pro Arg His Leu His Val Leu Ile Gly Thr Ser Val Val Lys Ile Pro
                245                 250                 255

Phe Thr Ile Leu Leu Phe Phe Leu Leu His Arg Trp Cys Ser Asp Lys
            260                 265                 270

Lys Asn Ala Ala Val Met Asp Gln Glu Pro Ala Gly Asn Arg Thr Val
        275                 280                 285

Asn Ser Glu Asp Ser Asp Glu Gln Asp His Gln Glu Val Ser Tyr Ala
    290                 295                 300

<210> SEQ ID NO 17
<211> LENGTH: 206
<212> TYPE: PRT
<213> ORGANISM: Homo sapiens

<400> SEQUENCE: 17

Met Ser Leu Met Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Pro Leu Val Lys Ser Glu Glu Thr Val Ile Leu Gln
        35                  40                  45

Cys Trp Ser Asp Val Arg Phe Glu His Phe Leu Leu His Arg Glu Gly
    50                  55                  60

Lys Tyr Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Phe Gly Ser Phe Arg Asp Ser Pro Tyr Glu Trp Ser
            100                 105                 110

Asn Ser Ser Asp Pro Leu Leu Val Ser Val Thr Gly Asn Pro Ser Asn
        115                 120                 125

Ser Trp Pro Ser Pro Thr Glu Pro Ser Ser Lys Thr Gly Asn Pro Arg
    130                 135                 140

His Leu His Val Leu Ile Gly Thr Ser Val Val Lys Ile Pro Phe Thr
145                 150                 155                 160

Ile Leu Leu Phe Phe Leu Leu His Arg Trp Cys Ser Asn Lys Lys Asn
                165                 170                 175

Ala Ala Val Met Asp Gln Glu Pro Ala Gly Asn Arg Thr Val Asn Ser
            180                 185                 190

Glu Asp Ser Asp Glu Gln Asp His Gln Glu Val Ser Tyr Ala
        195                 200                 205

<210> SEQ ID NO 18
<211> LENGTH: 304
<212> TYPE: PRT
<213> ORGANISM: Homo sapiens -continued

```
<400> SEQUENCE: 18

Met Ser Leu Met Val Ile Ser Met Ala Cys Val Gly Phe Phe Trp Leu
1               5                   10                  15

Gln Gly Ala Trp Pro His Glu Gly Phe Arg Arg Lys Pro Ser Leu Leu
            20                  25                  30

Ala His Pro Gly Arg Leu Val Lys Ser Glu Glu Thr Val Ile Leu Gln
        35                  40                  45

Cys Trp Ser Asp Val Met Phe Glu His Phe Leu Leu His Arg Glu Gly
50                  55                  60

Thr Phe Asn Asp Thr Leu Arg Leu Ile Gly Glu His Ile Asp Gly Val
65                  70                  75                  80

Ser Lys Ala Asn Phe Ser Ile Gly Arg Met Arg Gln Asp Leu Ala Gly
                85                  90                  95

Thr Tyr Arg Cys Tyr Gly Ser Val Pro His Ser Pro Tyr Gln Phe Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140

Val Thr Leu Ser Cys Ser Ser Trp Ser Ser Tyr Asp Met Tyr His Leu
145                 150                 155                 160

Ser Thr Glu Gly Glu Ala His Glu Arg Arg Phe Ser Ala Gly Pro Lys
                165                 170                 175

Val Asn Gly Thr Phe Gln Ala Asp Phe Pro Leu Gly Pro Ala Thr Gln
            180                 185                 190

Gly Gly Thr Tyr Arg Cys Phe Gly Ser Phe His Asp Ser Pro Tyr Glu
        195                 200                 205

Trp Ser Lys Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Val Leu Ile Gly Thr Ser Val Val Lys Leu Pro
                245                 250                 255

Phe Thr Ile Leu Leu Phe Phe Leu Leu His Arg Trp Cys Ser Asp Lys
            260                 265                 270

Lys Asn Ala Ser Val Met Asp Gln Gly Pro Ala Gly Asn Arg Thr Val
        275                 280                 285

Asn Arg Glu Asp Ser Asp Glu Gln Asp His Gln Glu Val Ser Tyr Ala
    290                 295                 300

<210> SEQ ID NO 19
<211> LENGTH: 304
<212> TYPE: PRT
<213> ORGANISM: Homo sapiens

<400> SEQUENCE: 19

Met Ser Leu Met Val Ile Ile Met Ala Cys Val Gly Phe Phe Leu Leu
1               5                   10                  15

Gln Gly Ala Trp Pro Gln Glu Gly Val His Arg Lys Pro Ser Phe Leu
            20                  25                  30

Ala Leu Pro Gly His Leu Val Lys Ser Glu Glu Thr Val Ile Leu Gln
        35                  40                  45

Cys Trp Ser Asp Val Met Phe Glu His Phe Leu Leu His Arg Glu Gly
50                  55                  60
```

```
Lys Phe Asn Asn Thr Leu His Leu Ile Gly Glu His His Asp Gly Val
 65                  70                  75                  80

Ser Lys Ala Asn Phe Ser Ile Gly Pro Met Met Pro Val Leu Ala Gly
                 85                  90                  95

Thr Tyr Arg Cys Tyr Gly Ser Val Pro His Ser Pro Tyr Gln Leu Ser
            100                 105                 110

Ala Pro Ser Asp Pro Leu Asp Met Val Ile Ile Gly Leu Tyr Glu Lys
        115                 120                 125

Pro Ser Leu Ser Ala Gln Pro Gly Pro Thr Val Gln Ala Gly Glu Asn
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Leu Pro Ala Val Arg Ser
                165                 170                 175

Ile Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ala Pro Tyr Glu
        195                 200                 205

Trp Ser Asn Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Val Leu Ile Gly Thr Ser Val Val Lys Ile Pro
                245                 250                 255

Phe Thr Ile Leu Leu Phe Phe Leu Leu His Arg Trp Cys Ser Asp Lys
            260                 265                 270

Lys Asn Ala Ala Val Met Asp Gln Glu Pro Ala Gly Asn Arg Thr Val
        275                 280                 285

Asn Ser Glu Asp Ser Asp Glu Gln Asp His Gln Glu Val Ser Tyr Ala
    290                 295                 300

<210> SEQ ID NO 20
<211> LENGTH: 304
<212> TYPE: PRT
<213> ORGANISM: Homo sapiens

<400> SEQUENCE: 20

Met Leu Leu Met Val Ile Ser Met Ala Cys Val Ala Phe Phe Leu Leu
 1               5                  10                  15

Gln Gly Ala Trp Pro His Glu Gly Phe Arg Arg Lys Pro Ser Leu Leu
                20                  25                  30

Ala His Pro Gly Pro Leu Val Lys Ser Glu Glu Thr Val Ile Leu Gln
            35                  40                  45

Cys Trp Ser Asp Val Met Phe Glu His Phe Leu Leu His Arg Glu Gly
        50                  55                  60

Thr Phe Asn His Thr Leu Arg Leu Ile Gly Glu His Ile Asp Gly Val
 65                  70                  75                  80

Ser Lys Gly Asn Phe Ser Ile Gly Arg Met Thr Gln Asp Leu Ala Gly
                 85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Pro Ala Gln Pro Gly Pro Thr Val Leu Ala Gly Glu Ser
    130                 135                 140
```

-continued

```
Val Thr Leu Ser Cys Ser Arg Ser Ser Tyr Asp Met Tyr His Leu
145                 150                 155                 160

Ser Arg Glu Gly Glu Ala His Glu Arg Arg Leu Pro Ala Gly Pro Lys
                165                 170                 175

Val Asn Arg Thr Phe Gln Ala Asp Ser Pro Leu Asp Pro Ala Thr His
            180                 185                 190

Gly Gly Ala Tyr Arg Cys Phe Gly Ser Phe Arg Asp Ser Pro Tyr Glu
        195                 200                 205

Trp Ser Lys Ser Ser Asp Pro Leu Leu Val Ser Val Thr Gly Asn Ser
    210                 215                 220

Ser Asn Ser Trp Pro Ser Pro Thr Glu Pro Ser Ser Glu Thr Gly Asn
225                 230                 235                 240

Pro Arg His Leu His Val Leu Ile Gly Thr Ser Val Val Lys Leu Pro
                245                 250                 255

Phe Thr Ile Leu Leu Phe Phe Leu Leu His Arg Trp Cys Ser Asn Lys
            260                 265                 270

Lys Asn Ala Ser Val Met Asp Gln Gly Pro Ala Gly Asn Arg Thr Val
        275                 280                 285

Asn Arg Glu Asp Ser Asp Glu Gln Asp His Gln Glu Val Ser Tyr Ala
    290                 295                 300

<210> SEQ ID NO 21
<211> LENGTH: 443
<212> TYPE: PRT
<213> ORGANISM: Homo sapiens

<400> SEQUENCE: 21

Met Ser Leu Met Val Val Ser Met Ala Cys Val Gly Leu Phe Leu Val
1               5                   10                  15

Gln Arg Ala Gly Pro His Met Gly Gly Gln Asp Lys Pro Phe Leu Ser
                20                  25                  30

Ala Trp Pro Ser Ala Val Val Pro Arg Gly Gly His Val Thr Leu Arg
            35                  40                  45

Cys His Tyr Arg His Arg Phe Asn Asn Phe Met Leu Tyr Lys Glu Asp
        50                  55                  60

Arg Ile His Ile Pro Ile Phe His Gly Arg Ile Phe Gln Glu Ser Phe
65                  70                  75                  80

Asn Met Ser Pro Val Thr Thr Ala His Ala Gly Asn Tyr Thr Cys Arg
                85                  90                  95

Gly Ser His Pro His Ser Pro Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Val Lys Ser Gly Glu Arg Val Ile Leu Gln Cys
    130                 135                 140

Trp Ser Asp Ile Met Phe Glu His Phe Phe Leu His Lys Glu Gly Ile
145                 150                 155                 160

Ser Lys Asp Pro Ser Arg Leu Val Gly Gln Ile His Asp Gly Val Ser
                165                 170                 175

Lys Ala Asn Phe Ser Ile Gly Pro Met Met Leu Ala Leu Ala Gly Thr
            180                 185                 190

Tyr Arg Cys Tyr Gly Ser Val Thr His Thr Pro Tyr Gln Leu Ser Ala
        195                 200                 205

Pro Ser Asp Pro Leu Asp Ile Val Val Thr Gly Pro Tyr Glu Lys Pro
    210                 215                 220
```

-continued

Ser Leu Ser Ala Gln Pro Gly Pro Lys Val Gln Ala Gly Glu Ser Val
225                 230                 235                 240

Thr Leu Ser Cys Ser Ser Arg Ser Ser Tyr Asp Met Tyr His Leu Ser
            245                 250                 255

Arg Glu Gly Gly Ala His Glu Arg Arg Leu Pro Ala Val Arg Lys Val
        260                 265                 270

Asn Arg Thr Phe Gln Ala Asp Phe Pro Leu Gly Pro Ala Thr His Gly
    275                 280                 285

Gly Thr Tyr Arg Cys Phe Gly Ser Phe Arg His Ser Pro Tyr Glu Trp
290                 295                 300

Ser Asp Pro Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Asn Pro
            325                 330                 335

Arg His Leu His Ile Leu Ile Gly Thr Ser Val Val Ile Ile Leu Phe
        340                 345                 350

Ile Leu Leu Leu Phe Phe Leu Leu His Leu Trp Cys Ser Asn Lys Lys
    355                 360                 365

Asn Ala Ala Val Met Asp Gln Glu Pro Ala Gly Asn Arg Thr Ala Asn
370                 375                 380

Ser Glu Asp Ser Asp Glu Gln Asp Pro Glu Glu Val Thr Tyr Ala Gln
385                 390                 395                 400

Leu Asp His Cys Val Phe Thr Gln Arg Lys Ile Thr Arg Pro Ser Gln
            405                 410                 415

Arg Pro Lys Thr Pro Pro Thr Asp Thr Ile Leu Tyr Thr Glu Leu Pro
        420                 425                 430

Asn Ala Lys Pro Arg Ser Lys Val Val Ser Cys
    435                 440

<210> SEQ ID NO 22
<211> LENGTH: 455
<212> TYPE: PRT
<213> ORGANISM: Homo sapiens

<400> SEQUENCE: 22

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Leu Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Leu Leu His Arg Glu Gly Ile
145                 150                 155                 160

```
Ser Glu Asp Pro Ser Arg Leu Val Gly Gln Ile His Asp Gly Val Ser
            165                 170                 175

Lys Ala Asn Phe Ser Ile Gly Pro Leu Met Pro Val Leu Ala Gly Thr
        180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
            245                 250                 255

Arg Glu Gly Glu Ala His Glu Arg Arg Leu Arg Ala Val Pro Lys Val
        260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
            325                 330                 335

Arg His Leu His Val Leu Ile Gly Thr Ser Val Val Ile Phe Leu Phe
        340                 345                 350

Ile Leu Leu Leu Phe Phe Leu Leu Tyr Arg Trp Cys Ser Asn Lys Lys
        355                 360                 365

Asn Ala Ala Val Met Asp Gln Glu Pro Ala Gly Asp Arg Thr Val Asn
    370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
            405                 410                 415

Arg Pro Lys Thr Pro Leu Thr Asp Thr Ser Val Tyr Thr Glu Leu Pro
        420                 425                 430

Asn Ala Glu Pro Arg Ser Lys Val Val Ser Cys Pro Arg Ala Pro Gln
        435                 440                 445

Ser Gly Leu Glu Gly Val Phe
    450                 455

<210> SEQ ID NO 23
<211> LENGTH: 410
<212> TYPE: PRT
<213> ORGANISM: Homo sapiens

<400> SEQUENCE: 23

Met Ser Leu Met Val Val Ser Met Ala Cys Val Gly Phe Phe Leu Leu
1               5                   10                  15

Glu Gly Pro Trp Pro His Val Gly Gly Gln Asp Lys Pro Phe Leu Ser
            20                  25                  30

Ala Trp Pro Gly Thr Val Val Ser Glu Gly Gln His Val Thr Leu Gln
        35                  40                  45

Cys Arg Ser His Leu Gly Phe Asn Glu Phe Leu Ser Lys Glu Asp
    50                  55                  60

Gly Met Pro Val Pro Glu Leu Tyr Asn Arg Ile Phe Arg Asn Ser Phe
65                  70                  75                  80
```

```
Leu Met Gly Pro Val Thr Pro Ala His Ala Gly Thr Tyr Arg Cys Cys
                85                  90                  95

Ser Ser His Pro His Ser Pro Thr Gly Trp Ser Ala Pro Ser Asn Pro
            100                 105                 110

Val Val Ile Met Val Thr Gly Val His Arg Lys Pro Ser Leu Leu Ala
            115                 120                 125

His Pro Gly Pro Leu Val Lys Ser Gly Glu Thr Val Ile Leu Gln Cys
130                 135                 140

Trp Ser Asp Val Arg Phe Glu Arg Phe Leu Leu His Arg Glu Gly Ile
145                 150                 155                 160

Thr Glu Asp Pro Leu Arg Leu Val Gly Gln Leu His Asp Ala Gly Ser
                165                 170                 175

Gln Val Asn Tyr Ser Met Gly Pro Met Thr Pro Ala Leu Ala Gly Thr
            180                 185                 190

Tyr Arg Cys Phe Gly Ser Val Thr His Leu Pro Tyr Glu Leu Ser Ala
            195                 200                 205

Pro Ser Asp Pro Leu Asp Ile Val Val Val Gly Leu Tyr Gly Lys Pro
210                 215                 220

Ser Leu Ser Ala Gln Pro Gly Pro Thr Val Gln Ala Gly Glu Asn Val
225                 230                 235                 240

Thr Leu Ser Cys Ser Ser Arg Ser Leu Phe Asp Ile Tyr His Leu Ser
                245                 250                 255

Arg Glu Ala Glu Ala Gly Glu Leu Arg Leu Thr Ala Val Leu Arg Val
            260                 265                 270

Asn Gly Thr Phe Gln Ala Asn Phe Pro Leu Gly Pro Val Thr His Gly
            275                 280                 285

Gly Asn Tyr Arg Cys Phe Gly Ser Phe Arg Ala Leu Pro His Ala Trp
290                 295                 300

Ser Asp Pro Ser Asp Pro Leu Pro Val Ser Val Thr Gly Asn Ser Arg
305                 310                 315                 320

Tyr Leu His Ala Leu Ile Gly Thr Ser Val Val Ile Ile Pro Phe Ala
                325                 330                 335

Ile Leu Leu Phe Phe Leu Leu His Arg Trp Cys Ala Asn Lys Lys Asn
            340                 345                 350

Ala Val Val Met Asp Gln Glu Pro Ala Gly Asn Arg Thr Val Asn Arg
            355                 360                 365

Glu Asp Ser Asp Glu Gln Asp Pro Gln Glu Val Thr Tyr Ala Gln Leu
370                 375                 380

Asn His Cys Val Phe Thr Gln Arg Lys Ile Thr Arg Pro Ser Gln Arg
385                 390                 395                 400

Pro Lys Thr Pro Pro Thr Asp Thr Ser Val
                405                 410

<210> SEQ ID NO 24
<211> LENGTH: 387
<212> TYPE: PRT
<213> ORGANISM: Homo sapiens

<400> SEQUENCE: 24

Met Ser Leu Met Val Val Ser Met Ala Cys Val Gly Leu Phe Leu Val
1               5                   10                  15

Gln Arg Ala Gly Pro His Met Gly Gly Gln Asp Lys Pro Phe Leu Ser
            20                  25                  30

Ala Trp Pro Ser Ala Val Val Pro Arg Gly Gly His Val Thr Leu Arg
        35                  40                  45
```

Cys His Tyr Arg His Arg Phe Asn Asn Phe Met Leu Tyr Lys Glu Asp
 50                  55                  60

Arg Ile His Val Pro Ile Phe His Gly Arg Ile Phe Gln Glu Gly Phe
 65                  70                  75                  80

Asn Met Ser Pro Val Thr Thr Ala His Ala Gly Asn Tyr Thr Cys Arg
                 85                  90                  95

Gly Ser His Pro His Ser Pro Thr Gly Trp Ser Ala Pro Ser Asn Pro
             100                 105                 110

Met Val Ile Met Val Thr Gly Asn His Arg Lys Pro Ser Leu Leu Ala
         115                 120                 125

His Pro Gly Pro Leu Val Lys Ser Gly Glu Arg Val Ile Leu Gln Cys
130                 135                 140

Trp Ser Asp Ile Met Phe Glu His Phe Phe Leu His Lys Glu Trp Ile
145                 150                 155                 160

Ser Lys Asp Pro Ser Arg Leu Val Gly Gln Ile His Asp Gly Val Ser
                165                 170                 175

Lys Ala Asn Phe Ser Ile Gly Ser Met Met Arg Ala Leu Ala Gly Thr
            180                 185                 190

Tyr Arg Cys Tyr Gly Ser Val Thr His Thr Pro Tyr Gln Leu Ser Ala
        195                 200                 205

Pro Ser Asp Pro Leu Asp Ile Val Val Thr Gly Leu Tyr Glu Lys Pro
210                 215                 220

Ser Leu Ser Ala Gln Pro Gly Pro Lys Val Gln Ala Gly Glu Ser Val
225                 230                 235                 240

Thr Leu Ser Cys Ser Ser Arg Ser Ser Tyr Asp Met Tyr His Leu Ser
                245                 250                 255

Arg Glu Gly Gly Ala His Glu Arg Arg Leu Pro Ala Val Arg Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg His Ser Pro Tyr Glu Trp
290                 295                 300

Ser Asp Pro Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Asn Leu
                325                 330                 335

Arg His Leu His Ile Leu Ile Gly Thr Ser Val Val Lys Ile Pro Phe
            340                 345                 350

Thr Ile Leu Leu Phe Phe Leu Leu His Arg Trp Cys Ser Asn Lys Lys
        355                 360                 365

Asn Ala Ala Val Met Asp Gln Glu Pro Ala Gly Asn Arg Ser Glu Gln
370                 375                 380

Arg Gly Phe
385

<210> SEQ ID NO 25
<211> LENGTH: 469
<212> TYPE: PRT
<213> ORGANISM: Homo sapiens

<400> SEQUENCE: 25

Met Asp Trp Thr Trp Arg Phe Leu Phe Val Val Ala Ala Ser Thr Gly
 1               5                  10                  15

Val Gln Ser Gln Val Gln Leu Val Gln Ser Gly Ala Glu Val Lys Lys
                20                  25                  30

-continued

```
Pro Gly Ser Ser Val Lys Val Ser Cys Lys Ala Ser Gly Gly Thr Phe
            35                  40                  45
Ser Phe Tyr Ala Ile Ser Trp Val Arg Gln Ala Pro Gly Gln Gly Leu
 50                  55                  60
Glu Trp Met Gly Gly Phe Ile Pro Ile Phe Gly Ala Ala Asn Tyr Ala
 65                  70                  75                  80
Gln Lys Phe Gln Gly Arg Val Thr Ile Thr Ala Asp Glu Ser Thr Ser
                 85                  90                  95
Thr Ala Tyr Met Glu Leu Ser Ser Leu Arg Ser Asp Asp Thr Ala Val
                100                 105                 110
Tyr Tyr Cys Ala Arg Ile Pro Ser Gly Ser Tyr Tyr Asp Tyr Asp
                115                 120                 125
Met Asp Val Trp Gly Gln Gly Thr Thr Val Thr Val Ser Ser Ala Ser
            130                 135                 140
Thr Lys Gly Pro Ser Val Phe Pro Leu Ala Pro Cys Ser Arg Ser Thr
145                 150                 155                 160
Ser Glu Ser Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
                180                 185                 190
His Thr Phe Pro Ala Val Leu Gln Ser Ser Gly Leu Tyr Ser Leu Ser
            195                 200                 205
Ser Val Val Thr Val Pro Ser Ser Leu Gly Thr Lys Thr Tyr Thr
            210                 215                 220
Cys Asn Val Asp His Lys Pro Ser Asn Thr Lys Val Asp Lys Arg Val
225                 230                 235                 240
Glu Ser Lys Tyr Gly Pro Pro Cys Pro Pro Cys Pro Ala Pro Glu Phe
                245                 250                 255
Leu Gly Gly Pro Ser Val Phe Leu Phe Pro Pro Lys Pro Lys Asp Thr
                260                 265                 270
Leu Met Ile Ser Arg Thr Pro Glu Val Thr Cys Val Val Val Asp Val
            275                 280                 285
Ser Gln Glu Asp Pro Glu Val Gln Phe Asn Trp Tyr Val Asp Gly Val
            290                 295                 300
Glu Val His Asn Ala Lys Thr Lys Pro Arg Glu Glu Gln Phe Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Gly Leu Pro Ser
                340                 345                 350
Ser Ile Glu Lys Thr Ile Ser Lys Ala Lys Gly Gln Pro Arg Glu Pro
            355                 360                 365
Gln Val Tyr Thr Leu Pro Pro Ser Gln Glu Glu Met Thr Lys Asn Gln
            370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Arg Leu
                420                 425                 430
Thr Val Asp Lys Ser Arg Trp Gln Glu Gly Asn Val Phe Ser Cys Ser
            435                 440                 445
```

```
Val Met His Glu Ala Leu His Asn His Tyr Thr Gln Lys Ser Leu Ser
    450                 455                 460

Leu Ser Leu Gly Lys
465
```